US009187748B2

(12) United States Patent
Geisbert et al.

(10) Patent No.: US 9,187,748 B2
(45) Date of Patent: Nov. 17, 2015

(54) COMPOSITIONS AND METHODS FOR SILENCING EBOLA VIRUS GENE EXPRESSION

(71) Applicants: Protiva Biotherapeutics, Inc., Burnaby (CA); Trustees of Boston University, Boston, MA (US); United States Army Medical Research and Materiel Command, Frederick, MD (US)

(72) Inventors: Thomas W. Geisbert, Albany, TX (US); Amy C. H. Lee, Burnaby (CA); Marjorie Robbins, Vancouver (CA); Vandana Sood, Vancouver (CA); Adam Judge, Vancouver (CA); Lisa E. Hensley, Frederick, MD (US); Ian MacLachlan, Mission, CA (US)

( * ) Notice: Subject to any disclaimer, the term of this patent is extended or adjusted under 35 U.S.C. 154(b) by 0 days.

(21) Appl. No.: 14/229,675

(22) Filed: Mar. 28, 2014

(65) Prior Publication Data

US 2015/0111945 A1 Apr. 23, 2015

Related U.S. Application Data

(63) Continuation of application No. 12/840,226, filed on Jul. 20, 2010, now abandoned.

(60) Provisional application No. 61/226,959, filed on Jul. 20, 2009, provisional application No. 61/286,741, filed on Dec. 15, 2009.

(51) Int. Cl.
*C07H 21/04* (2006.01)
*C12N 15/113* (2010.01)
*A61K 9/127* (2006.01)
*A61K 31/713* (2006.01)

(52) U.S. Cl.
CPC ............ *C12N 15/1131* (2013.01); *A61K 9/127* (2013.01); *A61K 9/1271* (2013.01); *A61K 31/713* (2013.01); *C12N 2310/14* (2013.01); *C12N 2310/321* (2013.01); *C12N 2760/14111* (2013.01)

(58) Field of Classification Search
None
See application file for complete search history.

(56) References Cited

U.S. PATENT DOCUMENTS

| | | | |
|---|---|---|---|
| 5,334,761 | A | 8/1994 | Gebeyehu et al. |
| 5,578,475 | A | 11/1996 | Jessee |
| 5,627,159 | A | 5/1997 | Shih et al. |
| 5,674,908 | A | 10/1997 | Haces et al. |
| 5,705,385 | A | 1/1998 | Bally et al. |
| 5,736,392 | A | 4/1998 | Hawley-Nelson et al. |
| 5,877,220 | A | 3/1999 | Schwartz et al. |
| 5,958,901 | A | 9/1999 | Dwyer et al. |
| 5,976,567 | A | 11/1999 | Wheeler et al. |
| 5,981,501 | A | 11/1999 | Wheeler et al. |
| 6,020,202 | A | 2/2000 | Jessee |
| 6,020,526 | A | 2/2000 | Schwartz et al. |
| 6,034,135 | A | 3/2000 | Schwartz et al. |
| 6,051,429 | A | 4/2000 | Hawley-Nelson et al. |
| 6,075,012 | A | 6/2000 | Gebeyehu et al. |
| 6,172,049 | B1 | 1/2001 | Dwyer et al. |
| 6,251,939 | B1 | 6/2001 | Schwartz et al. |
| 6,339,173 | B1 | 1/2002 | Schwartz et al. |
| 6,376,248 | B1 | 4/2002 | Hawley-Nelson et al. |
| 6,534,484 | B1 | 3/2003 | Wheeler et al. |
| 6,586,410 | B1 | 7/2003 | Wheeler et al. |
| 6,638,529 | B2 | 10/2003 | Schwartz et al. |
| 6,671,393 | B2 | 12/2003 | Hays et al. |
| 6,680,068 | B2 | 1/2004 | Campbell et al. |
| 6,815,432 | B2 | 11/2004 | Wheeler et al. |
| 6,858,224 | B2 | 2/2005 | Wheeler et al. |
| 7,166,745 | B1 | 1/2007 | Chu et al. |
| 7,479,573 | B2 | 1/2009 | Chu et al. |
| 7,601,872 | B2 | 10/2009 | Chu et al. |
| 7,687,070 | B2 | 3/2010 | Gebeyehu et al. |
| 7,838,658 | B2 | 11/2010 | MacLachlan et al. |

(Continued)

FOREIGN PATENT DOCUMENTS

| | | | |
|---|---|---|---|
| WO | WO 02/087541 | A1 | 11/2002 |
| WO | WO 03/097805 | A2 | 11/2003 |

(Continued)

OTHER PUBLICATIONS

Arpicco, S., et al., "Preparation and Characterization of Novel Cationic Lipids Developed for Gene Transfection," Proceed. Int'l Symp. Control. Rel. Bioact. Mater. (Controlled Release Society, Inc.), 1999, vol. 26, pp. 759-760.
Arpicco, S., et al., "Synthesis, characterization and transfection activity of new saturated and unsaturated cationic lipids," IL Farmaco, 2004, vol. 59, pp. 869-878.
Beale, G., et al., "Gene Silencing Nucleic Acids Designed by Scanning Arrays: Anti-EGFR Activity of siRNA, Ribozyme and DNA Enzymes Targeting a Single Hybridization-accessible Region using the Same Delivery System," Journal of Drug Targeting, 2003, vol. 11, No. 7, pp. 449-456.
Cevc, G., "How Membrane Chain-Melting Phase-Transition Temperature is Affected by the Lipid Chain Asymmetry and Degree of Unsaturation: An Effective Chain-Length Model," Biochemistry, 1991, vol. 30, pp. 7186-7193.
Enterlein, Sven, et al., "VP35 Knockdown Inhibits Ebola Virus Amplification and Protects against Lethal Infection in Mice," Antimicrobial Agents and Chemotherapy, 2006, vol. 50, No. 3, pp. 984-993.

(Continued)

*Primary Examiner* — Kimberly Y Chong
(74) *Attorney, Agent, or Firm* — Kilpatrick Townsend & Stockton LLP

(57) ABSTRACT

The present invention provides compositions comprising therapeutic nucleic acids (e.g., interfering RNA such as siRNA) that target Ebola virus (EBOV) gene expression and methods of using such compositions to silence EBOV gene expression. More particularly, the invention provides unmodified and chemically modified interfering RNA which silence EBOV gene expression and methods of use thereof, e.g., for preventing or treating EBOV infections caused by one or more EBOV species such as Zaire EBOV. The invention also provides serum-stable nucleic acid-lipid particles comprising one or more interfering RNA molecules, a cationic lipid, and a non-cationic lipid, which can further comprise a conjugated lipid that inhibits aggregation of particles. Methods of silencing EBOV gene expression by administering one or more interfering RNA molecules to a mammalian subject are also provided.

23 Claims, 8 Drawing Sheets

(56) References Cited

U.S. PATENT DOCUMENTS

| | | | |
|---|---|---|---|
| 7,915,450 | B2 | 3/2011 | Chu et al. |
| 8,058,068 | B2 | 11/2011 | Hawley-Nelson et al. |
| 8,158,827 | B2 | 4/2012 | Chu et al. |
| 2003/0069173 | A1 | 4/2003 | Hawley-Nelson et al. |
| 2003/0143732 | A1 | 7/2003 | Fosnaugh et al. |
| 2004/0029275 | A1 | 2/2004 | Brown et al. |
| 2004/0142892 | A1 | 7/2004 | Finn et al. |
| 2004/0253723 | A1 | 12/2004 | Tachas et al. |
| 2004/0259247 | A1 | 12/2004 | Tuschl et al. |
| 2005/0064595 | A1 | 3/2005 | MacLachlan et al. |
| 2005/0260757 | A1 | 11/2005 | Gebeyehu et al. |
| 2005/0282188 | A1 | 12/2005 | Haeberli et al. |
| 2006/0008910 | A1 | 1/2006 | MacLachlan et al. |
| 2006/0147514 | A1 | 7/2006 | Gebeyehu et al. |
| 2006/0205693 | A1 | 9/2006 | Stein et al. |
| 2006/0228406 | A1 | 10/2006 | Chiou et al. |
| 2007/0135372 | A1 | 6/2007 | MacLachlan et al. |
| 2007/0202598 | A1 | 8/2007 | Chu et al. |
| 2007/0202600 | A1 | 8/2007 | Chu et al. |
| 2009/0143323 | A1 | 6/2009 | Bavari et al. |
| 2009/0143583 | A1 | 6/2009 | Chu et al. |
| 2010/0159593 | A1 | 6/2010 | Chu et al. |
| 2012/0136073 | A1 | 5/2012 | Yang et al. |
| 2012/0238747 | A1 | 9/2012 | Chu et al. |

FOREIGN PATENT DOCUMENTS

| | | | |
|---|---|---|---|
| WO | WO 2004/065546 | A2 | 8/2004 |
| WO | WO 2004/110499 | A1 | 12/2004 |
| WO | WO 2005/007196 | A2 | 1/2005 |
| WO | WO 2005/026372 | A1 | 3/2005 |
| WO | WO 2005/120152 | A2 | 12/2005 |
| WO | WO 2005/121348 | A1 | 12/2005 |
| WO | WO 2006/074546 | A1 | 7/2006 |
| WO | WO 2007/048046 | A2 | 4/2007 |
| WO | WO 2007/051303 | A1 | 5/2007 |
| WO | WO 2008/121604 | A2 | 10/2008 |

OTHER PUBLICATIONS

Feldmann, Heinz, et al., "Therapy and prophylaxis of Ebola virus infections," Current Opinion in Investigational Drugs, 2005, vol. 6, No. 8, pp. 823-830.

Fowler, Trent, et al., "Inhibition of Marburg virus protein expression and viral release by RNA interference," Journal of General Virology, 2005, vol. 86, pp. 1181-1188.

Geisbert, Thomas W., et al., "Postexposure Protection of Guinea Pigs against a Lethal Ebola Virus Challenge Is Conferred by RNA Interference," The Journal of Infectious Diseases, 2006, vol. 193, No. 12, pp. 1650-1657.

Geisbert, Thomas W., et al., "Postexposure Protection of non-human primates against a Lethal Ebola Virus Challenge with RNA Interference: a proof-of-concept study," Lancet, May 2010, vol. 193, No. 12, pp. 1650-1657.

Grimm, Dirk et al., "Combinatorial RNA1: a winning strategy for the race against evolving targets?," Molecular Therapy: The Journal of the American Society of Gene Therapy, May 2007, vol. 15, No. 5, pp. 878-888.

Jiang, L., et al., "Comparison of protein precipitation methods for sample preparation prior to proteomic analysis," Journal of Chromatography A, 2004, vol. 1023, pp. 317-320.

Keough, K., "Influence of chain unsaturation and chain position on thermotropism and intermolecular interactions in membranes," Biochem. Soc. Transactions, 1990, vol. 18, No. 5, pp. 835-837.

Paul, C., et al., "Effective expression of small interfering RNA in human cells," Nature Biotech., 2002, vol. 20, pp. 505-508.

Reynolds, A. et al., "Rational siRNA design for RNA interference," Nature Biotech., 2004, vol. 22, pp. 326-330.

Spagnou, S., et al., "Lipidic Carriers of siRNA: Differences in the Formulation, Cellular Uptake, and Delivery with Plasmid DNA," Biochemistry, 2004, vol. 43, pp. 13348-13356.

Spurgers, Kevin B. et al., "Toward RNA interferences-based therapy for filovirus infections," Drug Development Research, Jun. 2009, vol., 70, No. 4, 246-254.

Warfield, Kelly L., et al., "Gene-Specific Countermeasures against Ebola Virus Based on Antisense Phosphorodiamidate Morpholino Oligomers," PLoS Pathogens, 2006, vol. 2, No. 1, pp. 0005-0013.

FIG. 1A
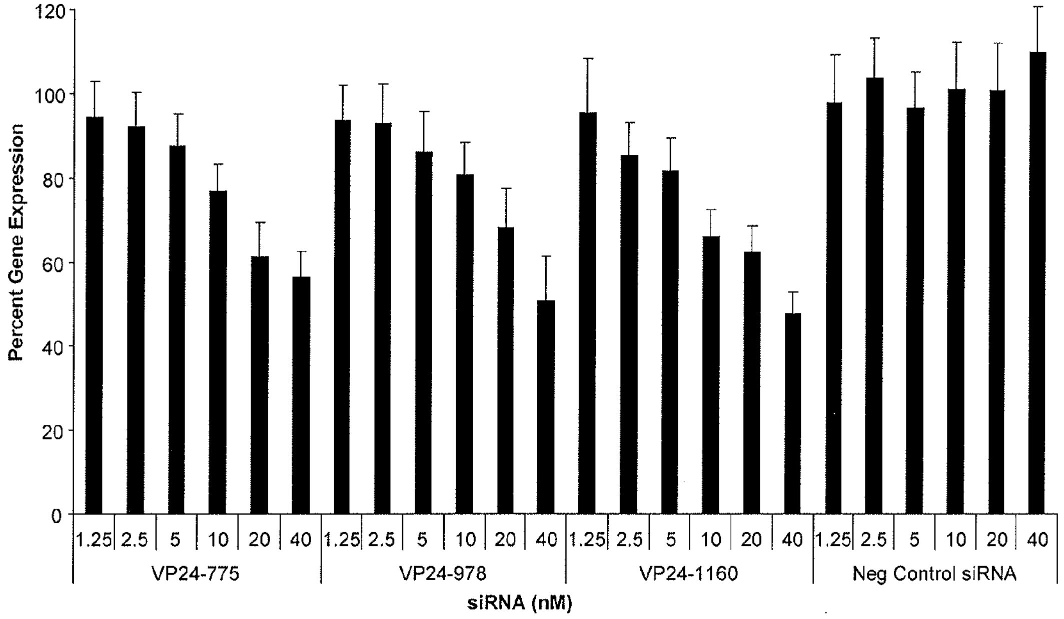
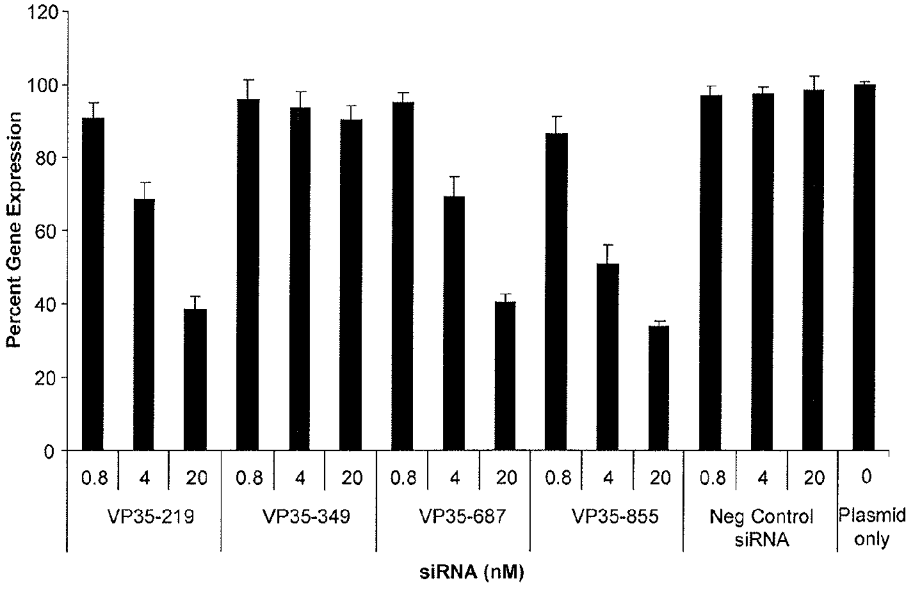
FIG. 1B

FIG. 2A
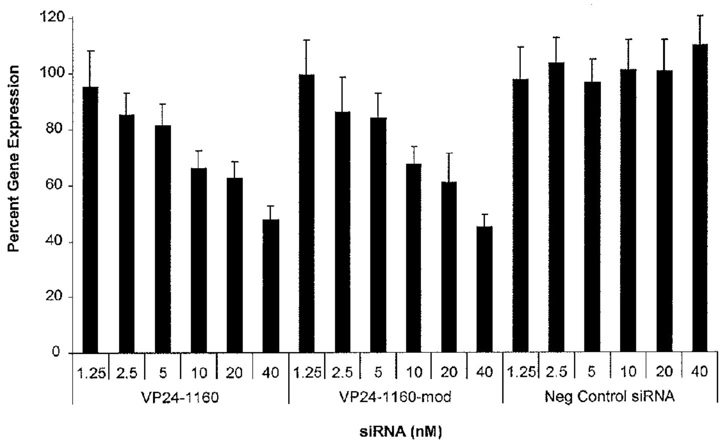
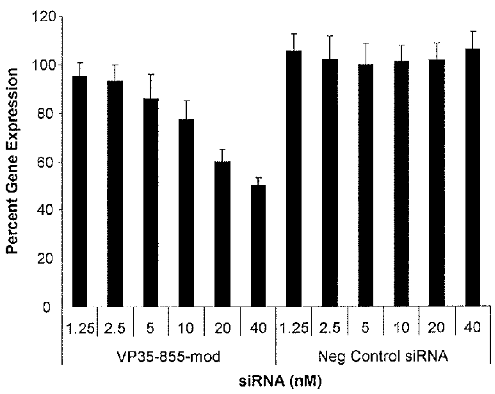
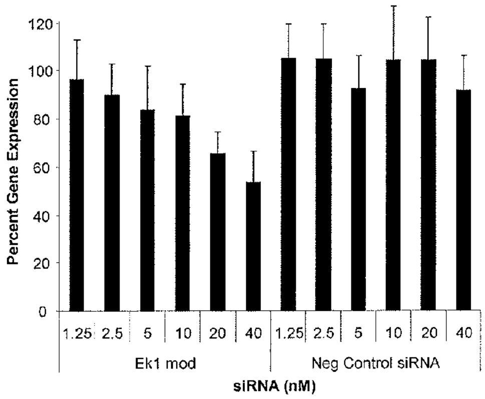
FIG. 2B
FIG. 2C

FIG. 3A
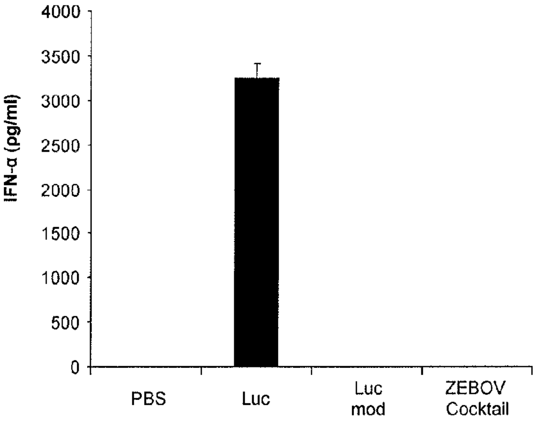
FIG. 3B
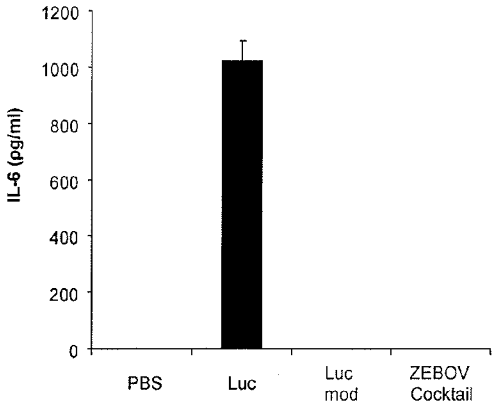
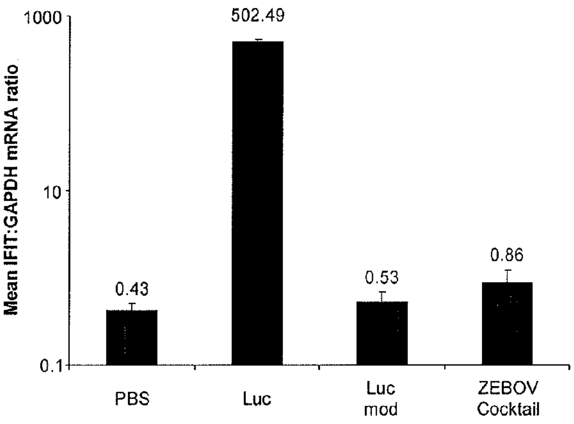
FIG. 3C

FIG. 5A
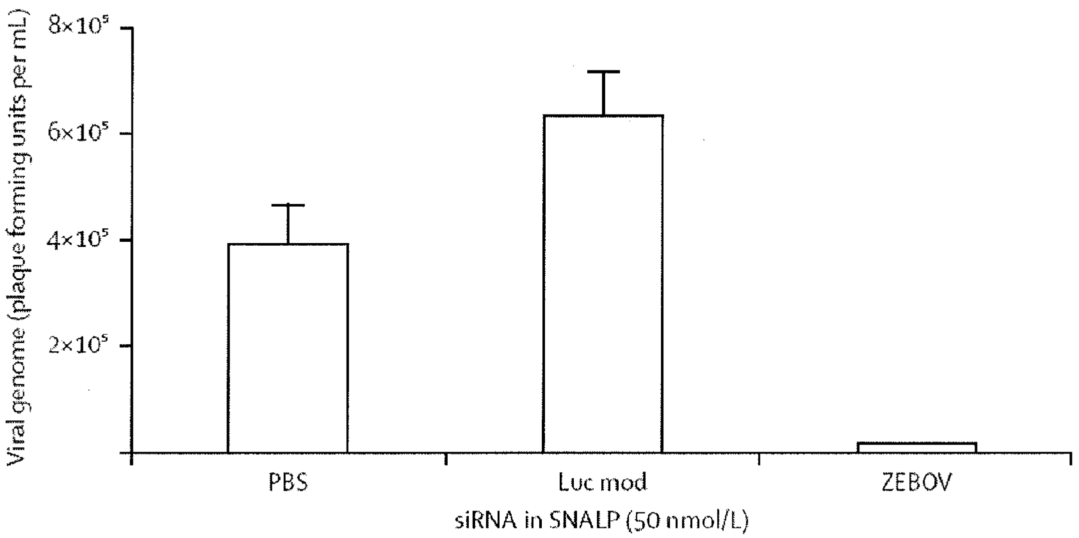
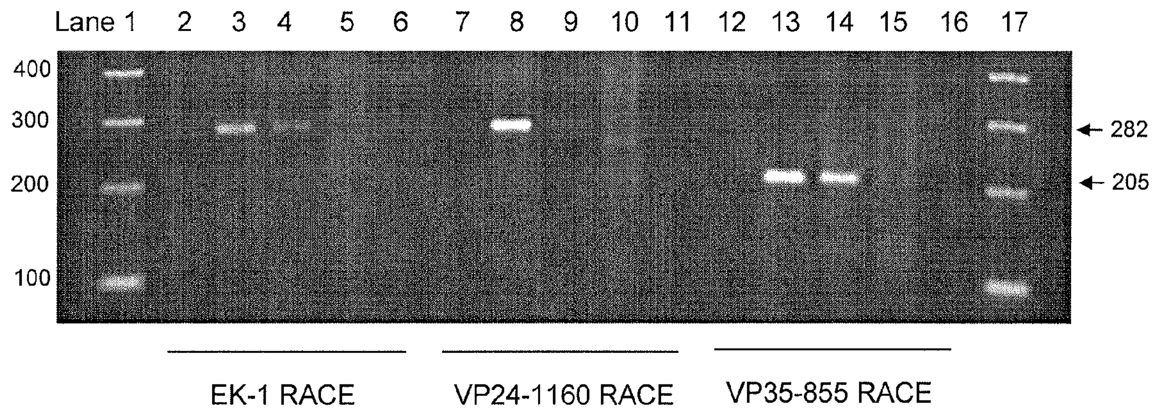
FIG. 5B
<!-- Bar chart: Viral genome (plaque forming units per mL) vs siRNA in SNALP (50 nmol/L). PBS ~4×10^5, Luc mod ~6.4×10^5, ZEBOV very low. Y-axis ranges 0 to 8×10^5. -->
<!-- Gel image with Lane 1-17, size markers 100, 200, 300, 400. Arrows indicate bands at 282 and 205. Labeled regions: EK-1 RACE, VP24-1160 RACE, VP35-855 RACE. -->

COMPOSITIONS AND METHODS FOR SILENCING EBOLA VIRUS GENE EXPRESSION

CROSS-REFERENCES TO RELATED APPLICATIONS

The present application is a continuation of U.S. patent application Ser. No. 12/840,226, filed Jul. 20, 2010, which application claims priority to U.S. Provisional Application No. 61/226,959, filed Jul. 20, 2009, and U.S. Provisional Application No. 61/286,741, filed Dec. 15, 2009, the disclosures of which are hereby incorporated by reference in their entirety for all purposes.

STATEMENT AS TO RIGHTS TO INVENTIONS MADE UNDER FEDERALLY SPONSORED RESEARCH AND DEVELOPMENT

This invention was made with Government support under Project No. 04-4-7J-012, awarded by the Defense Threat Reduction Agency. The Government has certain rights in this invention.

BACKGROUND OF THE INVENTION

Filoviruses (e.g., Ebola virus (EBOV) and Marburg virus (MARV)) are among the most lethal and destructive viruses. They cause severe, often fatal viral hemorrhagic fevers in humans and nonhuman primates (e.g., monkeys, gorillas, and chimpanzees). Filoviruses are of particular concern as possible biological weapons since they have the potential for aerosol dissemination and weaponization.

The incubation period for Filovirus infection ranges from 2 to 21 days. The onset of illness is abrupt and is characterized by high fever, headaches, joint and muscle aches, sore throat, fatigue, diarrhea, vomiting, and stomach pain. A rash, red eyes, hiccups and internal and external bleeding may be seen in some patients. Within one week of becoming infected with the virus, most patients experience chest pains and multiple organ failure, go into shock, and die. Some patients also experience blindness and extensive bleeding before dying.

Filoviridae are a family of RNA viruses. Two members of the Filoviridae family have been identified: EBOV and MARV. There is one identified strain of MARV and four identified subtypes (i.e., strains) of EBOV: Ebola-Zaire, Ebola-Sudan, Ebola-Ivory Coast (i.e., Ebola-Tai), and Ebola-Reston. The exact origin, locations, and natural habitat of Filoviridae are unknown. However, on the basis of available evidence and the nature of similar viruses, it is postulated that Filoviridae are zoonotic (i.e., animal-borne) and are normally maintained in an animal host that is native to the African continent.

For more than 30 years, EBOV has been associated with periodic episodes of hemorrhagic fever in Central Africa that produce severe disease in infected patients. Mortality rates in outbreaks have ranged from 50% for the Sudan species of EBOV (SEBOV) to up to 90% for the Zaire species of EBOV (ZEBOV) (Sanchez et al., Filoviridae: Marburg and Ebola Viruses, in *Fields Virology* (eds. Knipe, D. M. & Howley, P. M.) 1409-1448 (Lippincott Williams & Wilkins, Philadelphia)). An outbreak late in 2007 caused by an apparently new species of EBOV in Uganda resulted in a fatality rate of about 25% (Towner et al., *PLoS Pathog.,* 4:e1000212 (2008)). ZEBOV has also decimated populations of wild apes in this same region of Africa (Walsh et al., *Nature,* 422:611-614 (2003)).

Prevention and treatment of EBOV infections presents many challenges. In fact, there are no vaccines or postexposure treatment modalities available for preventing or managing EBOV infections. Patients instead receive supportive therapy, i.e., electrolyte and fluid balancing, oxygen, blood pressure maintenance, and treatment for any secondary infections.

Thus, there is a need for compositions and methods for treating and preventing EBOV infections, e.g., by specifically modulating EBOV gene expression. The present invention addresses these and other needs.

BRIEF SUMMARY OF THE INVENTION

The present invention provides compositions comprising therapeutic nucleic acids (e.g., interfering RNA such as siRNA) that target Ebola virus (EBOV) gene expression and methods of using such compositions to silence EBOV gene expression. More particularly, the invention provides unmodified and chemically modified interfering RNA (e.g., siRNA) which silence EBOV gene expression and methods of use thereof, e.g., for preventing or treating EBOV infections caused by one or more EBOV species such as Zaire EBOV. The invention also provides serum-stable nucleic acid-lipid particles (e.g., SNALP) comprising interfering RNA (e.g., siRNA), a cationic lipid, and a non-cationic lipid, which can further comprise a conjugated lipid that inhibits aggregation of particles. Methods of silencing EBOV gene expression by administering interfering RNA (e.g., siRNA) to a mammalian subject are also provided.

As explained herein, it has surprisingly been found that the SNALP formulations of the present invention containing a combination of interfering RNA (e.g., siRNA) molecules targeting at least two or all three of the EBOV L-pol, VP24, and VP35 genes were capable of providing complete postexposure protection of nonhuman primates against a lethal EBOV challenge. In particular embodiments, the SNALP formulations described herein comprising a cocktail of interfering RNAs (e.g., siRNAs) targeting any combination of at least two (or all three) of the EBOV L-pol, VP24, and VP35 genes demonstrate an increased potency (i.e., increased silencing activity) and/or an increased tolerability (e.g., a more favorable toxicity profile), e.g., when compared to other nucleic acid-lipid particle compositions previously described.

In one aspect, the present invention provides interfering RNA molecules such as siRNA that target EBOV L-polymerase (L-pol), VP24, VP30, VP35, VP40, nucleoprotein (NP), and/or glycoprotein (GP) expression. The interfering RNA (e.g., siRNA) molecules of the invention are capable of inactivating EBOV and/or inhibiting the replication of EBOV in vitro or in vivo.

In certain embodiments, the interfering RNA comprises at least one or a cocktail (e.g., at least two, three, four, five, six, seven, eight, nine, ten, or more) of unmodified and/or modified interfering RNA (e.g., siRNA) sequences that silence EBOV gene expression. In some instances, the cocktail of interfering RNA (e.g., siRNA) molecules may comprise sequences which target the same region of the EBOV genome. In other instances, the cocktail of interfering RNA (e.g., siRNA) molecules may comprise sequences which target different regions of the EBOV genome. In further instances, the cocktail of interfering RNA (e.g., siRNA) molecules may comprise sequences which target different EBOV species or subtypes. In certain instances, one or more (e.g., at least two, three, four, five, six, seven, eight, nine, ten, or more) modified interfering RNA (e.g., siRNA) that silence EBOV gene expression are present in a cocktail with one or more (e.g., at least two, three, four, five, six, seven, eight, nine, ten, or more) unmodified interfering RNA (e.g., siRNA) sequences that silence EBOV gene expression.

In some embodiments, the invention comprises an interfering RNA (e.g., siRNA) that silences EBOV L-pol expression, wherein the interfering RNA (e.g., siRNA) comprises an antisense strand comprising the following sequence: 5'-UUUAUAUACAGCUUCGUAC-3'. In other embodiments, the invention comprises an interfering RNA (e.g., siRNA) that silences EBOV VP24 expression, wherein the interfering RNA (e.g., siRNA) comprises an antisense strand comprising the following sequence: 5'-UUUGCAUUCGUGUCGAGGA-3'. In yet other embodiments, the invention comprises an interfering RNA (e.g., siRNA) that silences EBOV VP35 expression, wherein the interfering RNA (e.g., siRNA) comprises an antisense strand comprising the following sequence: 5'-AUGAUGUCCAAUGAGUUGC-3'. The interfering RNA (e.g., siRNA) may comprise at least one, two, three, four, five, six, seven, eight, nine, ten, or more modified nucleotides such as 2'OMe nucleotides, e.g., in the sense and/or antisense strand of the double-stranded region and optionally in one or both 3' overhangs if present.

In certain instances, the present invention provides a composition comprising a cocktail of two or all three of the EBOV L-pol, VP24, and VP35 interfering RNA (e.g., siRNA) molecules described herein. In other instances, the present invention provides a composition comprising a cocktail of one, two, or all three of these interfering RNA (e.g., siRNA) molecules, in combination with other interfering RNA (e.g., siRNA) molecules which target the same or different regions of the EBOV genome.

In particular embodiments, the present invention provides a composition comprising a cocktail of at least two interfering RNA molecules (e.g., siRNA molecules) targeting EBOV gene expression selected from the group consisting of:

(a) a first interfering RNA that silences EBOV L-pol expression, comprising the following antisense strand sequence: 5'-UUUAUAUACAGCUUCGUAC-3';

(b) a second interfering RNA that silences EBOV VP24 expression, comprising the following antisense strand sequence: 5'-UUUGCAUUCGUGUCGAGGA-3'; and (c) a third interfering RNA that silences EBOV VP35 expression, comprising the following antisense strand sequence: 5'-AUGAUGUCCAAUGAGUUGC-3'.

Each of the interfering RNA (e.g., siRNA) sequences present in the cocktail may independently comprise at least one, two, three, four, five, six, seven, eight, nine, ten, or more modified nucleotides such as 2'OMe nucleotides, e.g., in the sense and/or antisense strand of the double-stranded region. Preferably, uridine and/or guanosine nucleotides in one or more of the interfering RNA (e.g., siRNA) sequences present in the cocktail are modified with 2'OMe nucleotides. In particular embodiments, each of the interfering RNA (e.g., siRNA) sequences present in the cocktail comprises at least one 2'OMe-uridine nucleotide and at least one 2'OMe-guanosine nucleotide in the sense and/or antisense strands.

In some embodiments, each of the interfering RNA (e.g., siRNA) sequences present in the compositions of the invention may independently comprise a 3' overhang of at least 1, 2, 3, or 4 nucleotides in one or both strands of the interfering RNA or may comprise at least one blunt end. In certain instances, the 3' overhangs in one or both strands of the interfering RNA each independently comprise at least 1, 2, 3, or 4 of any combination of modified and unmodified deoxythymidine (dT) nucleotides, at least 1, 2, 3, or 4 of any combination of modified (e.g., 2'OMe) and unmodified uridine (U) ribonucleotides, or at least 1, 2, 3, or 4 of any combination of modified (e.g., 2'OMe) and unmodified ribonucleotides having complementarity to the target sequence (3' overhang in the antisense strand) or the complementary strand thereof (3' overhang in the sense strand).

In further embodiments, the present invention provides a composition comprising at least one or a cocktail (e.g., at least two, three, four, five, six, seven, eight, nine, ten, or more) of interfering RNAs (e.g., siRNAs) comprising sense and/or antisense sequences set forth in Tables 1-6 and/or interfering RNA (e.g., siRNA) duplexes set forth in Tables 11 and 12. In particular embodiments, the present invention provides a composition comprising a cocktail of at least two or all three of the EK-1, VP24-1160, and VP35-855 interfering RNAs (e.g., siRNAs) described herein. In certain embodiments, at least one, two, or all of three of these interfering RNAs (e.g., siRNAs) are chemically modified (e.g., 2'OMe-modified). In some preferred embodiments, the present invention provides a composition comprising a cocktail of at least two or all three of the modified EK-1, VP24-1160, and VP35-855 interfering RNA (e.g., siRNA) molecules described herein.

The present invention also provides a pharmaceutical composition comprising one or a cocktail of interfering RNA (e.g., siRNA) molecules that target EBOV gene expression and a pharmaceutically acceptable carrier.

In another aspect, the present invention provides a nucleic acid-lipid particle that targets EBOV gene expression. The nucleic acid-lipid particle typically comprises one or more unmodified and/or modified interfering RNA (e.g., siRNA) that silence EBOV gene expression, a cationic lipid, and a non-cationic lipid. In certain instances, the nucleic acid-lipid particle further comprises a conjugated lipid that inhibits aggregation of particles. In preferred embodiments, the nucleic acid-lipid particle comprises one or more unmodified and/or modified interfering RNA (e.g., siRNA) that silence EBOV gene expression, a cationic lipid, a non-cationic lipid, and a conjugated lipid that inhibits aggregation of particles.

In some embodiments, the nucleic acid-lipid particles comprise 1, 2, 3, 4, 5, 6, 7, 8, 9, 10, or more of the sense and/or antisense sequences set forth in Tables 1-6. In preferred embodiments, the nucleic acid-lipid particles comprise a cocktail of two or all three of the modified EK-1, VP24-1160, and VP35-855 siRNAs described herein (see, e.g., Tables 11-12 for exemplary modified EK-1 and VP35-855 siRNA duplexes).

In other embodiments, the cocktail of interfering RNAs (e.g., siRNAs) is fully encapsulated in the nucleic acid-lipid particle (e.g., SNALP). The interfering RNAs (e.g., siRNAs) may be co-encapsulated in the same nucleic acid-lipid particle, or each interfering RNA (e.g., siRNA) species present in the cocktail may be encapsulated in its own nucleic acid-lipid particle. The interfering RNA (e.g., siRNA) cocktail may be formulated in the nucleic acid-lipid particles (e.g., SNALP) using a mixture of individual interfering RNAs at identical, similar, or different concentrations. In one particular embodiment, a cocktail of two or three interfering RNAs may be formulated as a 1:1 mixture or as a 1:1:1 mixture of each interfering RNA species, respectively.

The nucleic acid-lipid particles of the present invention (e.g., SNALP) are useful for the therapeutic delivery of interfering RNA (e.g., siRNA) molecules that silence EBOV gene expression. In some embodiments, at least one or a cocktail of two, three, or more of the interfering RNA (e.g., siRNA) molecules described herein are formulated into nucleic acid-lipid particles, and the particles are administered to a mammal (e.g., a rodent such as a mouse or a primate such as a human, chimpanzee, or monkey) requiring such treatment. In certain instances, a therapeutically effective amount of the nucleic acid-lipid particle (e.g., SNALP) can be administered to the mammal, e.g., for preventing or treating EBOV infections caused by one or more EBOV species such as Zaire EBOV. The nucleic acid-lipid particles of the present invention are particularly useful for targeting cells, tissues, or organs infected and/or susceptible of being infected with EBOV, such as, for example, reticuloendothelial cells, fibroblast cells, endothelial cells, and/or platelets cells. Administration of the nucleic acid-lipid particle can be by any route known in the art, such as, e.g., oral, intranasal, intravenous, intraperitoneal, intramuscular, intra-articular, intralesional, intratracheal, subcutaneous, or intradermal. In particular embodiments, the nucleic acid-lipid particles (e.g., SNALP) are administered systemically, e.g., via enteral or parenteral routes of administration.

The present invention further provides pharmaceutical compositions comprising the nucleic acid-lipid particles described herein and a pharmaceutically acceptable carrier.

In yet another aspect, the interfering RNA (e.g., siRNA) molecules described herein are used in methods for silencing EBOV gene expression. In particular, it is an object of the present invention to provide in vitro and in vivo methods for inactivating EBOV and/or inhibiting the replication of EBOV to treat EBOV infections in a mammal by downregulating or silencing the transcription and/or translation of one or more EBOV genes. In certain embodiments, the present invention provides a method for introducing at least one or a cocktail of two, three, or more interfering RNA (e.g., siRNA) molecules capable of silencing EBOV gene expression (e.g., viral RNA and/or protein levels) into a cell by contacting the cell with the interfering RNA (e.g., siRNA) molecules described herein, e.g., formulated in a lipid particle such as a nucleic acid-lipid particle (e.g., SNALP). In another embodiment, the present invention provides a method for in vivo delivery of at least one or a cocktail of two, three, or more interfering RNA (e.g., siRNA) molecules capable of silencing EBOV gene expression by administering to a mammal the interfering RNA (e.g., siRNA) molecules described herein, e.g., formulated in a lipid particle such as a nucleic acid-lipid particle (e.g., SNALP). Administration of the interfering RNAs (e.g., siRNAs) can be by any route known in the art, such as, e.g., oral, intranasal, intravenous, intraperitoneal, intramuscular, intra-articular, intralesional, intratracheal, subcutaneous, or intradermal. In some embodiments, the nucleic acid-lipid particles (e.g., SNALP) are administered systemically, e.g., via enteral or parenteral routes of administration.

In certain embodiments, the mammal has an EBOV infection, e.g., a Zaire EBOV infection. In certain other embodiments, silencing of EBOV sequences that encode genes associated with viral infection and/or survival can conveniently be used in combination with the administration of conventional agents used to treat or ameliorate the viral condition or any of the symptoms associated therewith.

In certain other embodiments, the present invention provides a method for treating a mammal infected with EBOV (e.g., Zaire EBOV) comprising administering to the mammal at least one or a cocktail of two, three, or more of the interfering RNA (e.g., siRNA) molecules described herein, e.g., formulated in a lipid particle such as a nucleic acid-lipid particle. In some embodiments, the present invention provides a method for inactivating EBOV (e.g., Zaire EBOV) comprising administering to the mammal at least one or a cocktail of two, three, or more of the interfering RNA (e.g., siRNA) molecules described herein, e.g., formulated in a lipid particle such as a nucleic acid-lipid particle. In other embodiments, the present invention provides a method for inhibiting the replication of EBOV (e.g., Zaire EBOV) comprising administering to the mammal at least one or a cocktail of two, three, or more of the interfering RNA (e.g., siRNA) molecules described herein, e.g., formulated in a lipid particle such as a nucleic acid-lipid particle. In further embodiments, a mammal such as a human infected with EBOV may be administered at least one or a cocktail of two, three, or more of the interfering RNA (e.g., siRNA) molecules described herein, e.g., formulated in a lipid particle such as a nucleic acid-lipid particle, wherein the interfering RNA (e.g., siRNA) molecules target sequences that are conserved between two, three, or four EBOV subtypes or species.

Other objects, features, and advantages of the present invention will be apparent to one of skill in the art from the following detailed description and figures.

BRIEF DESCRIPTION OF THE DRAWINGS

FIGS. 1A-B illustrate the identification of lead VP24-1160 and VP35-855 siRNAs targeting VP24 and VP35 of ZEBOV using a nonviral plasmid-based expression system. HepG2 cells were transfected with 0.75 μg of psiCHECK2 plasmid expressing (1A) ZEBOV-p24 or (1B) ZEBOV-p35 in the presence of (1A) SNALP-formulated VP24-775, -978, -1160, or a nonspecific negative control siRNA at 1.25, 2.5, 5, 10, 20, or 40 nM, or (1B) SNALP-formulated VP35-219, -349, -687, -855, or a nonspecific negative control siRNA at 0.8, 4, or 20 nM. Data shown are the *Renilla* luciferase RLU signal normalized to the firefly luciferase RLU expressed as percent gene expression relative to a plasmid-only (0 nM siRNA) control treatment 48 h after start of transfection. Error bars represent standard deviation of triplicate tissue culture wells.

FIGS. 2A-C illustrate that modified ZEBOV siRNAs show similar activity to unmodified ZEBOV siRNAs. HepG2 cells were transfected using Lipofectamine 2000 complexed with (2A) 0.75 μg of ZEBOV-p24 expressing psiCHECK2 plasmid in the presence of VP24-1160 or VP24-1160-mod or a non-targeting negative control siRNA at 1.25, 2.5, 5, 10, 20, or 40 nM, or (2B) 0.75 μg of ZEBOV-p35 expressing psiCHECK2 plasmid in the presence of VP35-855-mod or a non-targeting negative control siRNA at 1.25, 2.5, 5, 10, 20, or 40 nM, or (2C) 0.75 m of ZEBOV-L-pol expressing psiCHECK2 plasmid in the presence of EK-1-mod or a non-targeting negative control siRNA at 1.25, 2.5, 5, 10, 20, or 40 nM. Data shown are the *Renilla* luciferase RLU normalized to the firefly luciferase RLU expressed as percent gene expression relative to a plasmid-only (0 nM siRNA) control 48 h after start of transfection. Error bars represent standard deviation of triplicate tissue culture wells.

FIGS. 3A-C illustrate that modified ZEBOV and Luc siRNAs cause no IFN-α or IL-6 protein or IFIT1 mRNA induction in vivo in mice. IFN-α and IL-6 protein and IFIT1 mRNA induction by SNALP-formulated Luc, Luc-mod, or ZEBOV cocktail (containing EK-1 mod, VP24-1160-mod, and VP35-855-mod siRNAs) in mice. SNALP-formulated siRNAs were injected i.v. at 5 mg/kg and plasma and livers harvested 4 h after treatment. Native (unmodified) Luc SNALP induced (3A) IFN-α and (3B) IL-6 protein in plasma and (3C) IFIT1 mRNA in liver, whereas no IFN-α or IL-6 or IFIT1 mRNA induction was detected in mice treated with SNALP containing 2'OMe-modified siRNA (Mean±SD, n=4 animals, lower limit of quantitation for IFN-α or IL-6 protein via ELISA was 15.6 pg/mL).

FIGS. 5A-B illustrate the rapid amplification of cDNA ends (RACE)-PCR of small interfering RNA (siRNA)-mediated cleavage of Zaire Ebola virus (ZEBOV) L polymerase, virion protein (VP24), and VP35 mRNAs in ZEBOV-infected Vero E6 cells. (5A) SNALPs containing ZEBOV siRNAs substantially reduced ZEBOV produced in supernatants of Vero E6 cells 48 h after infection. (5B) 5'RACE assays showing specific mRNA cleavage for the ZEBOV L-pol, VP24, and VP35 mRNAs in vitro on Vero E6 cells 24 hours after transfection with SNALP followed by ZEBOV infection. Vero E6 cells were treated with either EK-1-mod, VP24-1160-mod, VP35-855-mod, ZEBOV cocktail, or Luc mod SNALP or PBS and then 16 hours later infected with ZEBOV followed 24 hours later by lysis in Trizol. Total mRNA was examined for specific cleavage of the L-pol, VP24, or VP35 mRNAs via the respective siRNAs or the cocktail by performing a 5'RACE assay using specific primers designed for each RACE PCR product. The order of samples for each RACE PCR shown in the gel are (i) PBS, (ii) single gene-specific siRNA in SNALP (either EK-1-mod, VP24-1160-mod, or VP35-855-mod), (iii) ZEBOV cocktail SNALP, and (iv) Luc mod SNALP. Lanes 1 and 17 are the 100 bp ladder, lanes 2-5 are EK-1 RACE PCR, lanes 7-10 are VP24-1160 RACE, and lanes 12-15 are VP35-855 RACE. The predicted RACE PCR product for EK-1 and VP24-1160 RACE is 282 bp, while VP35-855 is 205 bp. Samples were processed from two separate transfections with similar results.

DETAILED DESCRIPTION OF THE INVENTION

I. Introduction

Figure 4:
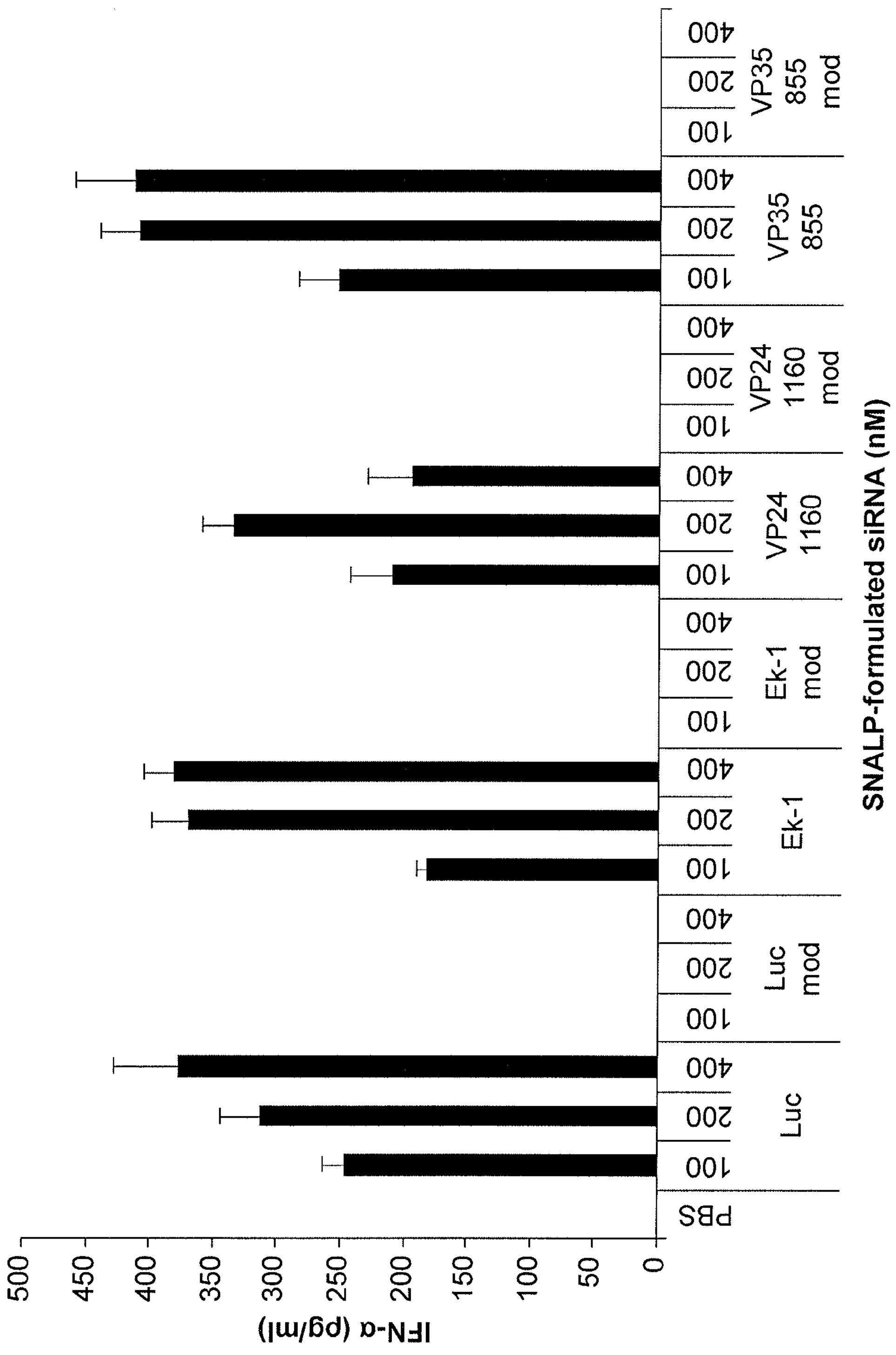
FIG. 4 illustrates that modified ZEBOV and Luc siRNAs show no IFN-α induction in human PBMC cultures, whereas unmodified versions induce significant IFN-α. IFN-α induction by SNALP-formulated Luc, Luc-mod, EK-1, EK-1 mod, VP24-1160, VP24-1160-mod, VP35-855, or VP35-855-mod siRNA in human PBMC cultures. Native (unmodified) or 2'OMe-modified siRNA were cultured with PBMC for 24 h at 100, 200, or 400 nM. Native Luc, EK-1, VP24-1160, and VP35-855 siRNA induced strong IFN-α in culture supernatants, whereas no IFN-α was detected in response to the 2'OMe-modified siRNAs (Mean±SD, n=3 culture wells, lower limit of quantitation=15.6 pg/mL).

Ebolavirus (EBOV) causes severe and often fatal hemorrhagic fever in humans and nonhuman primates. There are no vaccines or drugs approved for human use and no postexposure treatment has completely protected nonhuman primates from the most lethal EBOV species, Zaire ebolavirus (ZEBOV). It has been shown that siRNAs targeting the ZEBOV RNA polymerase L protein (L-pol) formulated in stable nucleic-acid-lipid particles (SNALP) completely protected guinea pigs when administered shortly after a lethal ZEBOV challenge (Geisbert et al., *J. Infect. Dis.,* 193:1650-1657 (2006)). Although rodent models of ZEBOV infection are useful for screening prospective countermeasures, it is desirable to use more stringent nonhuman primate models to predict efficacy. Example 1 provided herein describes an evaluation of the protective efficacy of a combination ("cocktail") of modified nonimmunostimulatory siRNAs targeting sequences of viral mRNAs encoding ZEBOV proteins in rhesus macaques. In particular, a cocktail of siRNA molecules targeting the ZEBOV L-pol, viral protein (VP) 24, and VP35 genes were formulated in SNALP. This cocktail of multiple siRNAs enables the targeting of potential RNAi escape mutants. As a result, by targeting three different viral gene products, the virus is inactivated in three different areas of its life cycle. Two different postexposure regimens were evaluated. In one study employing four postexposure treatments of the pooled anti-ZEBOV siRNAs, 66% of rhesus monkeys were protected from lethal ZEBOV infection, while in a second study employing seven postexposure treatments, 100% of macaques were protected from lethal ZEBOV challenge. Thus, Example 1 illustrates the applicability of RNAi as an effective postexposure treatment strategy for combating EBOV infections in humans.

II. Definitions

As used herein, the following terms have the meanings ascribed to them unless specified otherwise.

The term "Filovirus" or "Filoviridae" refers to single-stranded negative sense RNA viruses that typically infect primates. Filoviruses are able to multiply in virtually all cell types. The Filovirus antigens and virions are found primarily in fibroblasts and interstitium of an infected individual. There are two identified genera of Filoviruses: the Ebola virus (EBOV; four species) and the Marburg virus (MARV). The virions (viral particles) are characteristically shaped as long, cylindrical, filamentous particles which may be straight, curved, coiled, or found in a "6" or "U" shaped configuration. They are occasionally branched and the particles vary greatly in length, but the diameter (about 80 nm) is consistent. The filovirus genome comprises seven genes that encode 4 virion structural proteins (VP30, VP35, nucleoprotein (NP), and a polymerase protein (L-pol)) and 3 membrane-associated proteins (VP40, glycoprotein (GP), and VP24).

The term "interfering RNA" or "RNAi" or "interfering RNA sequence" as used herein includes single-stranded RNA (e.g., mature miRNA, ssRNAi oligonucleotides, ssDNAi oligonucleotides), double-stranded RNA (i.e., duplex RNA such as siRNA, Dicer-substrate dsRNA, shRNA, aiRNA, or pre-miRNA), a DNA-RNA hybrid (see, e.g., PCT Publication No. WO 2004/078941), or a DNA-DNA hybrid (see, e.g., PCT Publication No. WO 2004/104199) that is capable of reducing or inhibiting the expression of a target gene or sequence (e.g., by mediating the degradation or inhibiting the translation of mRNAs which are complementary to the interfering RNA sequence) when the interfering RNA is in the same cell as the target gene or sequence. Interfering RNA thus refers to the single-stranded RNA that is complementary to a target mRNA sequence or to the double-stranded RNA formed by two complementary strands or by a single, self-complementary strand. Interfering RNA may have substantial or complete identity to the target gene or sequence, or may comprise a region of mismatch (i.e., a mismatch motif). The sequence of the interfering RNA can correspond to the full-length target gene, or a subsequence thereof. Preferably, the interfering RNA molecules are chemically synthesized. The disclosures of each of the above patent documents are herein incorporated by reference in their entirety for all purposes.

Interfering RNA includes "small-interfering RNA" or "siRNA," e.g., interfering RNA of about 15-60, 15-50, or 15-40 (duplex) nucleotides in length, more typically about 15-30, 15-25, or 19-25 (duplex) nucleotides in length, and is preferably about 20-24, 21-22, or 21-23 (duplex) nucleotides in length (e.g., each complementary sequence of the double-stranded siRNA is 15-60, 15-50, 15-40, 15-30, 15-25, or 19-25 nucleotides in length, preferably about 20-24, 21-22, or 21-23 nucleotides in length, and the double-stranded siRNA is about 15-60, 15-50, 15-40, 15-30, 15-25, or 19-25 base pairs in length, preferably about 18-22, 19-20, or 19-21 base pairs in length). siRNA duplexes may comprise 3' overhangs of about 1 to about 4 nucleotides or about 2 to about 3 nucleotides and 5' phosphate termini. Examples of siRNA include, without limitation, a double-stranded polynucleotide molecule assembled from two separate stranded molecules, wherein one strand is the sense strand and the other is the complementary antisense strand; a double-stranded polynucleotide molecule assembled from a single stranded molecule, where the sense and antisense regions are linked by a nucleic acid-based or non-nucleic acid-based linker; a double-stranded polynucleotide molecule with a hairpin secondary structure having self-complementary sense and antisense regions; and a circular single-stranded polynucleotide molecule with two or more loop structures and a stem having self-complementary sense and antisense regions, where the circular polynucleotide can be processed in vivo or in vitro to generate an active double-stranded siRNA molecule. As used herein, the term "siRNA" includes RNA-RNA duplexes as well as DNA-RNA hybrids (see, e.g., PCT Publication No. WO 2004/078941).

Preferably, siRNA are chemically synthesized. siRNA can also be generated by cleavage of longer dsRNA (e.g., dsRNA greater than about 25 nucleotides in length) with the *E. coli* RNase III or Dicer. These enzymes process the dsRNA into biologically active siRNA (see, e.g., Yang et al., *Proc. Natl. Acad. Sci. USA,* 99:9942-9947 (2002); Calegari et al., *Proc. Natl. Acad. Sci. USA,* 99:14236 (2002); Byrom et al., *Ambion TechNotes,* 10(1):4-6 (2003); Kawasaki et al., *Nucleic Acids Res.,* 31:981-987 (2003); Knight et al., *Science,* 293:2269-2271 (2001); and Robertson et al., *J. Biol. Chem.,* 243:82 (1968)). Preferably, dsRNA are at least 50 nucleotides to about 100, 200, 300, 400, or 500 nucleotides in length. A dsRNA may be as long as 1000, 1500, 2000, 5000 nucleotides in length, or longer. The dsRNA can encode for an entire gene transcript or a partial gene transcript. In certain instances, siRNA may be encoded by a plasmid (e.g., transcribed as sequences that automatically fold into duplexes with hairpin loops).

As used herein, the term "mismatch motif" or "mismatch region" refers to a portion of an interfering RNA (e.g., siRNA) sequence that does not have 100% complementarity to its target sequence. An interfering RNA may have at least one, two, three, four, five, six, or more mismatch regions. The mismatch regions may be contiguous or may be separated by 1, 2, 3, 4, 5, 6, 7, 8, 9, 10, 11, 12, or more nucleotides. The mismatch motifs or regions may comprise a single nucleotide or may comprise two, three, four, five, or more nucleotides.

The phrase "inhibiting expression of a target gene" refers to the ability of an interfering RNA (e.g., siRNA) of the invention to silence, reduce, or inhibit the expression of a target gene (e.g., EBOV L-pol, VP24, VP30, VP35, VP40, NP, GP, or combinations thereof). To examine the extent of gene silencing, a test sample (e.g., a sample of cells in culture expressing the target gene) or a test mammal (e.g., a mammal such as a human or an animal model such as a rodent (e.g., mouse) or a non-human primate (e.g., monkey) model) is contacted with an interfering RNA (e.g., siRNA) that silences, reduces, or inhibits expression of the target gene. Expression of the target gene in the test sample or test animal is compared to expression of the target gene in a control sample (e.g., a sample of cells in culture expressing the target gene) or a control mammal (e.g., a mammal such as a human or an animal model such as a rodent (e.g., mouse) or non-human primate (e.g., monkey) model) that is not contacted with or administered the interfering RNA (e.g., siRNA). The expression of the target gene in a control sample or a control mammal may be assigned a value of 100%. In particular embodiments, silencing, inhibition, or reduction of expression of a target gene is achieved when the level of target gene expression in the test sample or the test mammal relative to the level of target gene expression in the control sample or the control mammal is about 95%, 90%, 85%, 80%, 75%, 70%, 65%, 60%, 55%, 50%, 45%, 40%, 35%, 30%, 25%, 20%, 15%, 10%, 5%, or 0%. In other words, the interfering RNAs (e.g., siRNAs) of the present invention are capable of silencing, reducing, or inhibiting the expression of a target gene (e.g., EBOV L-pol, VP24, VP30, VP35, VP40, NP, GP, or combinations thereof) by at least about 5%, 10%, 15%, 20%, 25%, 30%, 35%, 40%, 45%, 50%, 55%, 60%, 65%, 70%, 75%, 80%, 85%, 90%, 95%, or 100% in a test sample or a test mammal relative to the level of target gene expression in a control sample or a control mammal not contacted with or administered the interfering RNA. Suitable assays for determining the level of target gene expression include, without limitation, examination of protein or mRNA levels using techniques known to those of skill in the art, such as, e.g., dot blots, Northern blots, in situ hybridization, ELISA, immunoprecipitation, enzyme function, as well as phenotypic assays known to those of skill in the art.

An "effective amount" or "therapeutically effective amount" of a therapeutic nucleic acid such as an interfering RNA is an amount sufficient to produce the desired effect, e.g., an inhibition of expression of a target sequence in comparison to the normal expression level detected in the absence of an interfering RNA. Inhibition of expression of a target gene or target sequence is achieved when the value obtained with an interfering RNA relative to the control is about 95%, 90%, 85%, 80%, 75%, 70%, 65%, 60%, 55%, 50%, 45%, 40%, 35%, 30%, 25%, 20%, 15%, 10%, 5%, or 0%. Suitable assays for measuring expression of a target gene or target sequence include, e.g., examination of protein or RNA levels using techniques known to those of skill in the art such as dot blots, northern blots, in situ hybridization, ELISA, immunoprecipitation, enzyme function, as well as phenotypic assays known to those of skill in the art.

By "decrease," "decreasing," "reduce," or "reducing" of an immune response by an interfering RNA is intended to mean a detectable decrease of an immune response to a given interfering RNA (e.g., a modified interfering RNA). The amount of decrease of an immune response by a modified interfering RNA may be determined relative to the level of an immune response in the presence of an unmodified interfering RNA. A detectable decrease can be about 5%, 10%, 15%, 20%, 25%, 30%, 35%, 40%, 45%, 50%, 55%, 60%, 65%, 70%, 75%, 80%, 85%, 90%, 95%, 100%, or more lower than the immune response detected in the presence of the unmodified interfering RNA. A decrease in the immune response to interfering RNA is typically measured by a decrease in cytokine production (e.g., IFNγ, IFNα, TNFα, IL-6, IL-8, or IL-12) by a responder cell in vitro or a decrease in cytokine production in the sera of a mammalian subject after administration of the interfering RNA.

As used herein, the term "responder cell" refers to a cell, preferably a mammalian cell, that produces a detectable immune response when contacted with an immunostimulatory interfering RNA such as an unmodified siRNA. Exemplary responder cells include, e.g., dendritic cells, macrophages, peripheral blood mononuclear cells (PBMCs), splenocytes, and the like. Detectable immune responses include, e.g., production of cytokines or growth factors such as TNF-α, IFN-α, IFN-β, IFN-γ, IL-1, IL-2, IL-3, IL-4, IL-5, IL-6, IL-8, IL-10, IL-12, IL-13, TGF, and combinations thereof. Detectable immune responses also include, e.g., induction of interferon-induced protein with tetratricopeptide repeats 1 (IFIT1) mRNA.

"Substantial identity" refers to a sequence that hybridizes to a reference sequence under stringent conditions, or to a sequence that has a specified percent identity over a specified region of a reference sequence.

The phrase "stringent hybridization conditions" refers to conditions under which a nucleic acid will hybridize to its target sequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology-Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization.

Exemplary stringent hybridization conditions can be as follows: 50% formamide, 5×SSC, and 1% SDS, incubating at 42° C., or, 5×SSC, 1% SDS, incubating at 65° C., with wash in 0.2×SSC, and 0.1% SDS at 65° C. For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.-95° C. for 30 sec.-2 min., an annealing phase lasting 30 sec.-2 min., and an extension phase of about 72° C. for 1-2 min. Protocols and guidelines for low and high stringency amplification reactions are provided, e.g., in Innis et al., *PCR Protocols, A Guide to Methods and Applications*, Academic Press, Inc. N.Y. (1990).

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous references, e.g., Current Protocols in Molecular Biology, Ausubel et al., eds.

The terms "substantially identical" or "substantial identity," in the context of two or more nucleic acids, refer to two or more sequences or subsequences that are the same or have a specified percentage of nucleotides that are the same (i.e., at least about 60%, preferably at least about 65%, 70%, 75%, 80%, 85%, 90%, or 95% identity over a specified region), when compared and aligned for maximum correspondence over a comparison window, or designated region as measured using one of the following sequence comparison algorithms or by manual alignment and visual inspection. This definition, when the context indicates, also refers analogously to the complement of a sequence. Preferably, the substantial identity exists over a region that is at least about 5, 10, 15, 20, 25, 30, 35, 40, 45, 50, 55, or 60 nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window," as used herein, includes reference to a segment of any one of a number of contiguous positions selected from the group consisting of from about 5 to about 60, usually about 10 to about 45, more usually about 15 to about 30, in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman, *Adv. Appl. Math.,* 2:482 (1981), by the homology alignment algorithm of Needleman and Wunsch, *J. Mol. Biol.,* 48:443 (1970), by the search for similarity method of Pearson and Lipman, *Proc. Natl. Acad. Sci. USA,* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology*, Ausubel et al., eds. (1995 supplement)).

Non-limiting examples of algorithms that are suitable for determining percent sequence identity and sequence similarity are the BLAST and BLAST 2.0 algorithms, which are described in Altschul et al., *Nuc. Acids Res.,* 25:3389-3402 (1977) and Altschul et al., *J. Mol. Biol.,* 215:403-410 (1990), respectively. BLAST and BLAST 2.0 are used, with the parameters described herein, to determine percent sequence identity for the nucleic acids of the invention. Software for performing BLAST analyses is publicly available through the National Center for Biotechnology Information (http://www.ncbi.nlm.nih.gov/). Another example is a global alignment algorithm for determining percent sequence identify such as the Needleman-Wunsch algorithm for aligning protein or nucleotide (e.g., RNA) sequences.

The BLAST algorithm also performs a statistical analysis of the similarity between two sequences (see, e.g., Karlin and Altschul, *Proc. Natl. Acad. Sci. USA,* 90:5873-5787 (1993)). One measure of similarity provided by the BLAST algorithm is the smallest sum probability (P(N)), which provides an indication of the probability by which a match between two nucleotide sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The term "nucleic acid" as used herein refers to a polymer containing at least two deoxyribonucleotides or ribonucleotides in either single- or double-stranded form and includes DNA, RNA, and hybrids thereof. DNA may be in the form of, e.g., antisense molecules, plasmid DNA, DNA-DNA duplexes, pre-condensed DNA, PCR products, vectors (P1, PAC, BAC, YAC, artificial chromosomes), expression cassettes, chimeric sequences, chromosomal DNA, or derivatives and combinations of these groups. RNA may be in the form of small interfering RNA (siRNA), Dicer-substrate dsRNA, small hairpin RNA (shRNA), asymmetrical interfering RNA (aiRNA), microRNA (miRNA), mRNA, tRNA, rRNA, tRNA, viral RNA (vRNA), and combinations thereof. Nucleic acids include nucleic acids containing known nucleotide analogs or modified backbone residues or linkages, which are synthetic, naturally occurring, and non-naturally occurring, and which have similar binding properties as the reference nucleic acid. Examples of such analogs include, without limitation, phosphorothioates, phosphoramidates, methyl phosphonates, chiral-methyl phosphonates, 2'-O-methyl ribonucleotides, and peptide-nucleic acids (PNAs). Unless specifically limited, the term encompasses nucleic acids containing known analogues of natural nucleotides that have similar binding properties as the reference nucleic acid. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.,* 19:5081 (1991); Ohtsuka et al., *J Biol. Chem.,* 260:2605-2608 (1985); Rossolini et al., *Mol. Cell. Probes,* 8:91-98 (1994)). "Nucleotides" contain a sugar deoxyribose (DNA) or ribose (RNA), a base, and a phosphate group. Nucleotides are linked together through the phosphate groups. "Bases" include purines and pyrimidines, which further include natural compounds adenine, thymine, guanine, cytosine, uracil, inosine, and natural analogs, and synthetic derivatives of purines and pyrimidines, which include, but are not limited to, modifications which place new reactive groups such as, but not limited to, amines, alcohols, thiols, carboxylates, and alkylhalides.

The term "gene" refers to a nucleic acid (e.g., DNA or RNA) sequence that comprises partial length or entire length coding sequences necessary for the production of a polypeptide or precursor polypeptide.

"Gene product," as used herein, refers to a product of a gene such as an RNA transcript or a polypeptide.

The term "lipid" refers to a group of organic compounds that include, but are not limited to, esters of fatty acids and are characterized by being insoluble in water, but soluble in many organic solvents. They are usually divided into at least three classes: (1) "simple lipids," which include fats and oils as well as waxes; (2) "compound lipids," which include phospholipids and glycolipids; and (3) "derived lipids" such as steroids.

The term "lipid particle" includes a lipid formulation that can be used to deliver a therapeutic nucleic acid (e.g., interfering RNA) to a target site of interest (e.g., cell, tissue, organ, and the like). In preferred embodiments, the lipid particle of the invention is a nucleic acid-lipid particle, which is typically formed from a cationic lipid, a non-cationic lipid, and optionally a conjugated lipid that prevents aggregation of the particle. In other preferred embodiments, the therapeutic nucleic acid (e.g., interfering RNA) may be encapsulated in the lipid portion of the particle, thereby protecting it from enzymatic degradation.

As used herein, the term "SNALP" refers to a stable nucleic acid-lipid particle. A SNALP represents a particle made from lipids (e.g., a cationic lipid, a non-cationic lipid, and optionally a conjugated lipid that prevents aggregation of the particle), wherein the nucleic acid (e.g., an interfering RNA) is fully encapsulated within the lipid. In certain instances, SNALP are extremely useful for systemic applications, as they can exhibit extended circulation lifetimes following intravenous (i.v.) injection, they can accumulate at distal sites (e.g., sites physically separated from the administration site), and they can mediate silencing of target gene expression at these distal sites. The nucleic acid may be complexed with a condensing agent and encapsulated within a SNALP as set forth in PCT Publication No. WO 00/03683, the disclosure of which is herein incorporated by reference in its entirety for all purposes.

The lipid particles of the invention (e.g., SNALP) typically have a mean diameter of from about 30 nm to about 150 nm, from about 40 nm to about 150 nm, from about 50 nm to about 150 nm, from about 60 nm to about 130 nm, from about 70 nm to about 110 nm, from about 70 nm to about 100 nm, from about 80 nm to about 100 nm, from about 90 nm to about 100 nm, from about 70 to about 90 nm, from about 80 nm to about 90 nm, from about 70 nm to about 80 nm, or about 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, or 150 nm, and are substantially non-toxic. In addition, nucleic acids, when present in the lipid particles of the present invention, are resistant in aqueous solution to degradation with a nuclease. Nucleic acid-lipid particles and their method of preparation are disclosed in, e.g., U.S. Patent Publication Nos. 20040142025 and 20070042031, the disclosures of which are herein incorporated by reference in their entirety for all purposes.

As used herein, "lipid encapsulated" can refer to a lipid particle that provides a therapeutic nucleic acid, such as an interfering RNA (e.g., siRNA), with full encapsulation, partial encapsulation, or both. In a preferred embodiment, the nucleic acid (e.g., interfering RNA) is fully encapsulated in the lipid particle (e.g., to form a SNALP or other nucleic acid-lipid particle).

The term "lipid conjugate" refers to a conjugated lipid that inhibits aggregation of lipid particles. Such lipid conjugates include, but are not limited to, PEG-lipid conjugates such as, e.g., PEG coupled to dialkyloxypropyls (e.g., PEG-DAA conjugates), PEG coupled to diacylglycerols (e.g., PEG-DAG conjugates), PEG coupled to cholesterol, PEG coupled to phosphatidylethanolamines, and PEG conjugated to ceramides (see, e.g., U.S. Pat. No. 5,885,613), cationic PEG lipids, polyoxazoline (POZ)-lipid conjugates (e.g., POZ-DAA conjugates; see, e.g., U.S. Provisional Application No. 61/294, 828, filed Jan. 13, 2010, and U.S. Provisional Application No. 61/295,140, filed Jan. 14, 2010), polyamide oligomers (e.g., ATTA-lipid conjugates), and mixtures thereof. Additional examples of POZ-lipid conjugates are described in PCT Publication No. WO 2010/006282. PEG or POZ can be conjugated directly to the lipid or may be linked to the lipid via a linker moiety. Any linker moiety suitable for coupling the PEG or the POZ to a lipid can be used including, e.g., non-ester containing linker moieties and ester-containing linker moieties. In certain preferred embodiments, non-ester containing linker moieties, such as amides or carbamates, are used. The disclosures of each of the above patent documents are herein incorporated by reference in their entirety for all purposes.

The term "amphipathic lipid" refers, in part, to any suitable material wherein the hydrophobic portion of the lipid material orients into a hydrophobic phase, while the hydrophilic portion orients toward the aqueous phase. Hydrophilic characteristics derive from the presence of polar or charged groups such as carbohydrates, phosphate, carboxylic, sulfato, amino, sulfhydryl, nitro, hydroxyl, and other like groups. Hydrophobicity can be conferred by the inclusion of apolar groups that include, but are not limited to, long-chain saturated and unsaturated aliphatic hydrocarbon groups and such groups substituted by one or more aromatic, cycloaliphatic, or heterocyclic group(s). Examples of amphipathic compounds include, but are not limited to, phospholipids, aminolipids, and sphingolipids.

Representative examples of phospholipids include, but are not limited to, phosphatidylcholine, phosphatidylethanolamine, phosphatidylserine, phosphatidylinositol, phosphatidic acid, palmitoyloleoyl phosphatidylcholine, lysophosphatidylcholine, lysophosphatidylethanolamine, dipalmitoylphosphatidylcholine, dioleoylphosphatidylcholine, distearoylphosphatidylcholine, and dilinoleoylphosphatidylcholine. Other compounds lacking in phosphorus, such as sphingolipid, glycosphingolipid families, diacylglycerols, and β-acyloxyacids, are also within the group designated as amphipathic lipids. Additionally, the amphipathic lipids described above can be mixed with other lipids including triglycerides and sterols.

The term "neutral lipid" refers to any of a number of lipid species that exist either in an uncharged or neutral zwitterionic form at a selected pH. At physiological pH, such lipids include, for example, diacylphosphatidylcholine, diacylphosphatidylethanolamine, ceramide, sphingomyelin, cephalin, cholesterol, cerebrosides, and diacylglycerols.

The term "non-cationic lipid" refers to any amphipathic lipid as well as any other neutral lipid or anionic lipid.

The term "anionic lipid" refers to any lipid that is negatively charged at physiological pH. These lipids include, but are not limited to, phosphatidylglycerols, cardiolipins, diacylphosphatidylserines, diacylphosphatidic acids, N-dodecanoyl phosphatidylethanolamines, N-succinyl phosphatidylethanolamines, N-glutarylphosphatidylethanolamines, lysylphosphatidylglycerols, palmitoyloleyolphosphatidylglycerol (POPG), and other anionic modifying groups joined to neutral lipids.

The term "hydrophobic lipid" refers to compounds having apolar groups that include, but are not limited to, long-chain saturated and unsaturated aliphatic hydrocarbon groups and such groups optionally substituted by one or more aromatic, cycloaliphatic, or heterocyclic group(s). Suitable examples include, but are not limited to, diacylglycerol, dialkylglycerol, N—N-dialkylamino, 1,2-diacyloxy-3-aminopropane, and 1,2-dialkyl-3-aminopropane.

The term "fusogenic" refers to the ability of a lipid particle, such as a SNALP, to fuse with the membranes of a cell. The membranes can be either the plasma membrane or membranes surrounding organelles, e.g., endosome, nucleus, etc.

As used herein, the term "aqueous solution" refers to a composition comprising in whole, or in part, water.

As used herein, the term "organic lipid solution" refers to a composition comprising in whole, or in part, an organic solvent having a lipid.

"Distal site," as used herein, refers to a physically separated site, which is not limited to an adjacent capillary bed, but includes sites broadly distributed throughout an organism.

"Serum-stable" in relation to nucleic acid-lipid particles such as SNALP means that the particle is not significantly degraded after exposure to a serum or nuclease assay that would significantly degrade free DNA or RNA. Suitable assays include, for example, a standard serum assay, a DNAse assay, or an RNAse assay.

"Systemic delivery," as used herein, refers to delivery of lipid particles that leads to a broad biodistribution of an active agent such as an interfering RNA (e.g., siRNA) within an organism. Some techniques of administration can lead to the systemic delivery of certain agents, but not others. Systemic delivery means that a useful, preferably therapeutic, amount of an agent is exposed to most parts of the body. To obtain broad biodistribution generally requires a blood lifetime such that the agent is not rapidly degraded or cleared (such as by first pass organs (liver, lung, etc.) or by rapid, nonspecific cell binding) before reaching a disease site distal to the site of administration. Systemic delivery of lipid particles can be by any means known in the art including, for example, intravenous, subcutaneous, and intraperitoneal. In a preferred embodiment, systemic delivery of lipid particles is by intravenous delivery.

"Local delivery," as used herein, refers to delivery of an active agent such as an interfering RNA (e.g., siRNA) directly to a target site within an organism. For example, an agent can be locally delivered by direct injection into a disease site, other target site, or a target organ such as the liver, heart, pancreas, kidney, and the like.

The term "mammal" refers to any mammalian species such as a human, mouse, rat, dog, cat, hamster, guinea pig, rabbit, livestock, and the like.

The term "reticuloendothelial system" or "RES" refers to the part of the immune system that contains reticuloendothelial cells, including the phagocytic cells located in reticular connective tissue such as monocytes and macrophages. These cells typically accumulate in lymph nodes and the spleen. The Kupffer cells of the liver and tissue histiocytes are also part of the RES. The RES is divided into primary and secondary lymphoid organs. Primary ("central") lymphoid organs are the sites where the cells of the RES are produced. The cells of the RES are produced in the bone marrow. The thymus is also included as it is the required site for T cell maturation. Secondary ("peripheral") lymphoid organs are the sites where the cells of the RES function. This includes the lymph nodes, tonsils, spleen, and "MALT" (mucosa-associated lymphoid tissue). MALT is further divided into "GALT" (gut-associated lymphoid tissue) and "BALT" (bronchus-associated lymphoid tissue). The Kupffer cells of the liver act as part of this system, but are not organized into a tissue; rather, they are dispersed throughout the liver sinusoids. The microglia of the central nervous system (CNS) can be considered a part of the RES. They are scavenger cells that proliferate in response to CNS injury.

III. Description of the Embodiments

The present invention provides therapeutic nucleic acids such as interfering RNA that target Ebola virus (EBOV) gene expression, lipid particles comprising one or more (e.g., a cocktail) of the therapeutic nucleic acids, methods of making the lipid particles, and methods of delivering and/or administering the lipid particles (e.g., for the prevention or treatment of EBOV infections).

In one aspect, the present invention provides interfering RNA molecules that target EBOV L-pol, VP24, VP30, VP35, VP40, NP, and/or GP expression. Non-limiting examples of interfering RNA molecules include siRNA, Dicer-substrate dsRNA, shRNA, aiRNA, miRNA, and mixtures thereof. In preferred embodiments, the present invention provides compositions comprising a combination (e.g., a cocktail, pool, or mixture) of siRNAs that target multiple genes (e.g., at least two, three, four, five, six, or all seven of the genes) in the EBOV genome. The interfering RNA (e.g., siRNA) molecules of the invention are capable of inactivating EBOV and/or inhibiting the replication of EBOV in vitro or in vivo.

In some embodiments, the interfering RNA (e.g., siRNA) comprises a sense strand and a complementary antisense strand. In certain embodiments, the sense strand comprises or consists of a sequence that is at least about 80%, 85%, 86%, 87%, 88%, 89%, 90%, 91%, 92%, 93%, 94%, 95%, 96%, 97%, 98%, 99%, or 100% identical to the target sequence or a portion thereof. In certain other embodiments, the sense strand comprises or consists of at least about 15 contiguous nucleotides (e.g., at least about 15, 16, 17, 18, or 19 contiguous nucleotides) of a sequence that is identical to the target sequence or a portion thereof. In preferred embodiments, the interfering RNA (e.g., siRNA) comprising such a sense strand sequence is capable of mediating target-specific RNAi (e.g., silencing EBOV L-pol, VP24, VP30, VP35, VP40, NP, and/or GP expression).

In other embodiments, the antisense strand comprises or consists of a sequence that is at least about 80%, 85%, 86%, 87%, 88%, 89%, 90%, 91%, 92%, 93%, 94%, 95%, 96%, 97%, 98%, 99%, or 100% complementary to the target sequence or a portion thereof. In certain other embodiments, the antisense strand comprises or consists of at least about 15 contiguous nucleotides (e.g., at least about 15, 16, 17, 18, or 19 contiguous nucleotides) of a sequence that is complementary to the target sequence or a portion thereof. In further embodiments, the antisense strand comprises or consists of a sequence that specifically hybridizes to the target sequence or a portion thereof. In preferred embodiments, the interfering RNA (e.g., siRNA) comprising such an antisense strand sequence is capable of mediating target-specific RNAi (e.g., silencing EBOV L-pol, VP24, VP30, VP35, VP40, NP, and/or GP expression).

In particular embodiments, the present invention provides a composition comprising a cocktail of at least two interfering RNA molecules (e.g., siRNA molecules) targeting EBOV gene expression selected from the group consisting of:

(a) a first interfering RNA that silences EBOV L-pol expression, comprising the following antisense strand sequence: 5'-UUUAUAUACAGCUUCGUAC-3';
(b) a second interfering RNA that silences EBOV VP24 expression, comprising the following antisense strand sequence: 5'-UUUGCAUUCGUGUCGAGGA-3'; and
(c) a third interfering RNA that silences EBOV VP35 expression, comprising the following antisense strand sequence: 5'-AUGAUGUCCAAUGAGUUGC-3'.

The compositions of the present invention may comprise any pairwise combination of the first, second, and third interfering RNA (e.g., siRNA) molecules, or may comprise all three of the first, second, and third interfering RNAs (e.g., siRNAs). In some embodiments, the composition comprises the first and second interfering RNAs (e.g., siRNAs) targeting EBOV L-pol and VP24 expression. In other embodiments, the composition comprises the first and third interfering RNAs (e.g., siRNAs) targeting EBOV L-pol and VP35 expression. In yet other embodiments, the composition comprises the second and third interfering RNAs (e.g., siRNAs) targeting EBOV VP24 and VP35 expression. In further embodiments, the composition comprises the first, second, and third (i.e., all three) interfering RNAs (e.g., siRNAs) targeting EBOV L-pol, VP24, and VP35 expression.

In some embodiments, one, two, or all three of the first, second, and third interfering RNAs (e.g., siRNAs) comprise a sense strand and a complementary antisense strand, and each of the first, second, and third interfering RNAs (e.g., siRNAs) independently comprises a double-stranded region of about 15 to about 60 nucleotides in length (e.g., about 15-60, 15-30, 15-25, 19-30, 19-25, 20-60, 20-55, 20-50, 20-45, 20-40, 20-35, 20-30, 20-25, 21-30, 21-29, 22-30, 22-29, 22-28, 23-30, 23-28, 24-30, 24-28, 25-60, 25-55, 25-50, 25-45, 25-40, 25-35, or 25-30 nucleotides in length, or about 15, 16, 17, 18, 19, 20, 21, 22, 23, 24, 25, 26, 27, 28, 29, 30, 31, 32, 33, 34, or 35 nucleotides in length). In other embodiments, one, two, or all three of the first, second, and third interfering RNAs are chemically synthesized.

In certain embodiments, each of the first, second, and third interfering RNAs (e.g., siRNAs) may independently comprise at least one, two, three, four, five, six, seven, eight, nine, ten, or more modified nucleotides such as 2'OMe nucleotides, e.g., in the sense and/or antisense strand of the double-stranded region of the interfering RNA. Preferably, uridine and/or guanosine nucleotides in the interfering RNA are modified with 2'OMe nucleotides. In certain instances, the interfering RNA contains 2'OMe nucleotides in both the sense and antisense strands and comprises at least one 2'OMe-uridine nucleotide and at least one 2'OMe-guanosine nucleotide in the double-stranded region. In some embodiments, the sense and/or antisense strand of the interfering RNA may further comprise modified (e.g., 2'OMe-modified) adenosine and/or modified (e.g., 2'OMe-modified) cytosine nucleotides, e.g., in the double-stranded region of the interfering RNA.

In some embodiments, the sense and/or antisense strand sequences may comprise at least one, two, three, four, five, six, seven, eight, nine, ten, or more modified nucleotides such as 2'OMe nucleotides. In certain embodiments, the sense and/or antisense strand sequences may each independently comprise or consist of a modified (e.g., 2'OMe) and/or unmodified 3' overhang of 1, 2, 3, or 4 nucleotides, or one or both ends of the double-stranded molecule may be blunt-ended.

One of skill in the art will understand that unmodified sense and/or antisense strand sequences can be modified in accordance with the selective modification patterns described herein (e.g., at selective uridine and/or guanosine nucleotides, and optionally at adenosine and/or cytosine nucleotides, within the RNA duplex), and screened for RNAi activity as well as immune stimulation, such that the degree of chemical modifications introduced into the interfering RNA molecule strikes a balance between reduction or abrogation of the immunostimulatory properties of the interfering RNA and retention of RNAi activity.

In particular embodiments, each of the first, second, and third interfering RNAs (e.g., siRNAs) may independently comprise a 3' overhang of 1, 2, 3, or 4 nucleotides in one or both strands. In certain instances, the interfering RNA may contain at least one blunt end. In particular embodiments, the 3' overhangs in one or both strands of the interfering RNA (e.g., siRNA) may each independently comprise 1, 2, 3, or 4 modified and/or unmodified deoxythymidine (“t” or “dT”) nucleotides, 1, 2, 3, or 4 modified (e.g., 2'OMe) and/or unmodified uridine (“U”) ribonucleotides, or 1, 2, 3, or 4 modified (e.g., 2'OMe) and/or unmodified ribonucleotides or deoxyribonucleotides having complementarity to the target sequence or the complementary strand thereof.

In another embodiment, the compositions of the present invention comprise at least about 1, 2, 3, 4, 5, 6, 7, 8, 9, 10, 11, 12, 13, 14, 15, 16, 17, 18, 19, 20, or more additional unmodified and/or modified interfering RNA (e.g., siRNA) sequences that target EBOV L-pol, VP24, VP30, VP35, VP40, NP, and/or GP expression. The additional interfering RNA (e.g., siRNA) molecules may comprise sequences which are directed to the same region or domain (e.g., a “hot spot”) and/or to different regions or domains of one or more target genes. In certain instances, at least about 1, 2, 3, 4, 5, 6, 7, 8, 9, 10, 11, 12, 13, 14, 15, 16, 17, 18, 19, 20, or more additional unmodified and/or modified interfering RNA (e.g., siRNA) sequences that target EBOV L-pol, VP24, and/or VP35 are included in the compositions of the present invention. In particular embodiments, at least about 1, 2, 3, 4, 5, 6, 7, 8, 9, 10, 11, 12, 13, 14, 15, 16, 17, 18, 19, 20, or more (e.g., all) of the additional interfering RNA (e.g., siRNA) sequences are chemically modified (e.g., 2'OMe-modified) as described herein.

In some embodiments, the first interfering RNA (e.g., siRNA) further comprises a sense strand comprising the following sequence: 5'-GUACGAAGCUGUAUAUAAA-3'. In some aspects of these embodiments, the first interfering RNA (e.g., siRNA) comprises at least one 2'OMe nucleotide, e.g., at least one 2'OMe-guanosine and/or 2'OMe-uridine nucleotide. In certain instances, the first interfering RNA comprises an antisense strand comprising at least one, at least two, at least three, at least four, at least five, at least six, at least seven, or more 2'OMe nucleotides, e.g., 2'OMe-guanosine and/or 2'OMe-uridine nucleotides. In certain other instances, the first interfering RNA comprises a sense strand comprising at least one, at least two, at least three, at least four, at least five, at least six, at least seven, or more 2'OMe nucleotides, e.g., 2'OMe-guanosine and/or 2'OMe-uridine nucleotides. In further instances, the antisense strand and/or sense strand may further comprise at least one, at least two, at least three, at least four, at least five, at least six, at least seven, or more 2'OMe-adenosine and/or 2'OMe-cytosine nucleotides.

In particular embodiments, from about 20%-40%, 25%-40%, 30%-40%, 20%-35%, 25%-35%, 20%-30%, 25%-30%, 26%-34%, 27%-33%, 28%-32%, or about 20%, 21%, 22%, 23%, 24%, 25%, 26%, 27%, 28%, 29%, 30%, 31%, 32%, 33%, 34%, 35%, 36%, 37%, 38%, 39%, or 40% of the nucleotides in the double-stranded region of the first interfering RNA (e.g., siRNA) comprise modified nucleotides such as, e.g., 2'OMe nucleotides (e.g., 2'OMe-guanosine and/or 2'OMe-uridine nucleotides).

In certain embodiments, the first interfering RNA (e.g., siRNA) of the invention comprises a 3' overhang in one or both strands of the interfering RNA. In one particular embodiment, the antisense strand comprises a 5'-dTdT-3' (i.e., 5'-TT-3') overhang or a 5'-AA-3' overhang and the sense strand comprises a 5'-dTdT-3' (i.e., 5'-TT-3') overhang or a 5'-UU-3' overhang. In certain instances, the 3' overhangs on one or both strands of the interfering RNA (e.g., siRNA) comprise at least one 2'OMe nucleotide, e.g., at least one 2'OMe-guanosine and/or 2'OMe-uridine nucleotide. In other embodiments, the 3' overhangs on one or both strands of the interfering RNA (e.g., siRNA) comprise 1-4 deoxythymidine (dT) nucleotides, 1-4 modified and/or unmodified uridine (U) ribonucleotides, or 1-2 additional ribonucleotides having complementarity to the target sequence or the complementary strand thereof.

In some embodiments, the first interfering RNA (e.g., siRNA) that silences EBOV L-pol expression comprises one of the following sense strand sequences set forth in Table 1, wherein the underlined nucleotides are 2'OMe nucleotides.

TABLE 1

| Name | Sense Strand Sequence |
|---|---|
| S-1 | 5'-GUACGAAGCUGUAUAUAAATT-3' |
| S-2 | 5'-GUACGAAGCUGUAUAUAAATT-3' |
| S-3 | 5'-GUACGAAGCUGUAUAUAAATT-3' |
| S-4 | 5'-GUACGAAGCUGUAUAUAAATT-3' |
| S-5 | 5'-GUACGAAGCUGUAUAUAAATT-3' |
| S-6 | 5'-GUACGAAGCUGUAUAUAAATT-3' |
| S-7 | 5'-GUACGAAGCUGUAUAUAAATT-3' |
| S-8 | 5'-GUACGAAGCUGUAUAUAAATT-3' |
| S-9 | 5'-GUACGAAGCUGUAUAUAAATT-3' |
| S-10 | 5'-GUACGAAGCUGUAUAUAAATT-3' |
| S-11 | 5'-GUACGAAGCUGUAUAUAAATT-3' |
| S-12 | 5'-GUACGAAGCUGUAUAUAAATT-3' |
| S-13 | 5'-GUACGAAGCUGUAUAUAAATT-3' |
| S-14 | 5'-GUACGAAGCUGUAUAUAAATT-3' |
| S-15 | 5'-GUACGAAGCUGUAUAUAAATT-3' |
| S-16 | 5'-GUACGAAGCUGUAUAUAAATT-3' |
| S-17 | 5'-GUACGAAGCUGUAUAUAAATT-3' |
| S-18 | 5'-GUACGAAGCUGUAUAUAAATT-3' |
| S-19 | 5'-GUACGAAGCUGUAUAUAAATT-3' |
| S-20 | 5'-GUACGAAGCUGUAUAUAAATT-3' |
| S-21 | 5'-GUACGAAGCUGUAUAUAAATT-3' |
| S-22 | 5'-GUACGAAGCUGUAUAUAAATT-3' |
| S-23 | 5'-GUACGAAGCUGUAUAUAAATT-3' |
| S-24 | 5'-GUACGAAGCUGUAUAUAAATT-3' |
| S-25 | 5'-GUACGAAGCUGUAUAUAAATT-3' |
| S-26 | 5'-GUACGAAGCUGUAUAUAAATT-3' |
| S-27 | 5'-GUACGAAGCUGUAUAUAAATT-3' |
| S-28 | 5'-GUACGAAGCUGUAUAUAAATT-3' |
| S-29 | 5'-GUACGAAGCUGUAUAUAAATT-3' |
| S-30 | 5'-GUACGAAGCUGUAUAUAAATT-3' |
| S-31 | 5'-GUACGAAGCUGUAUAUAAATT-3' |
| S-32 | 5'-GUACGAAGCUGUAUAUAAATT-3' |
| S-33 | 5'-GUACGAAGCUGUAUAUAAATT-3' |
| S-34 | 5'-GUACGAAGCUGUAUAUAAATT-3' |

TABLE 1-continued

| Name | Sense Strand Sequence |
|---|---|
| S-35 | 5'-GUACGAAGCUGUAUAUAAATT-3' |
| S-36 | 5'-GUACGAAGCUGUAUAUAAATT-3' |
| S-37 | 5'-GUACGAAGCUGUAUAUAAATT-3' |
| S-38 | 5'-GUACGAAGCUGUAUAUAAATT-3' |
| S-39 | 5'-GUACGAAGCUGUAUAUAAATT-3' |
| S-40 | 5'-GUACGAAGCUGUAUAUAAATT-3' |
| S-41 | 5'-GUACGAAGCUGUAUAUAAATT-3' |
| S-42 | 5'-GUACGAAGCUGUAUAUAAATT-3' |
| S-43 | 5'-GUACGAAGCUGUAUAUAAATT-3' |
| S-44 | 5'-GUACGAAGCUGUAUAUAAATT-3' |
| S-45 | 5'-GUACGAAGCUGUAUAUAAATT-3' |
| S-46 | 5'-GUACGAAGCUGUAUAUAAATT-3' |
| S-47 | 5'-GUACGAAGCUGUAUAUAAATT-3' |
| S-48 | 5'-GUACGAAGCUGUAUAUAAATT-3' |
| S-49 | 5'-GUACGAAGCUGUAUAUAAATT-3' |
| S-50 | 5'-GUACGAAGCUGUAUAUAAATT-3' |
| S-51 | 5'-GUACGAAGCUGUAUAUAAATT-3' |
| S-52 | 5'-GUACGAAGCUGUAUAUAAATT-3' |
| S-53 | 5'-GUACGAAGCUGUAUAUAAATT-3' |
| S-54 | 5'-GUACGAAGCUGUAUAUAAATT-3' |
| S-55 | 5'-GUACGAAGCUGUAUAUAAATT-3' |
| S-56 | 5'-GUACGAAGCUGUAUAUAAATT-3' |
| S-57 | 5'-GUACGAAGCUGUAUAUAAATT-3' |
| S-58 | 5'-GUACGAAGCUGUAUAUAAATT-3' |
| S-59 | 5'-GUACGAAGCUGUAUAUAAATT-3' |
| S-60 | 5'-GUACGAAGCUGUAUAUAAATT-3' |
| S-61 | 5'-GUACGAAGCUGUAUAUAAATT-3' |
| S-62 | 5'-GUACGAAGCUGUAUAUAAATT-3' |
| S-63 | 5'-GUACGAAGCUGUAUAUAAATT-3' |
| S-64 | 5'-GUACGAAGCUGUAUAUAAATT-3' |
| S-65 | 5'-GUACGAAGCUGUAUAUAAATT-3' |
| S-66 | 5'-GUACGAAGCUGUAUAUAAATT-3' |
| S-67 | 5'-GUACGAAGCUGUAUAUAAATT-3' |
| S-68 | 5'-GUACGAAGCUGUAUAUAAATT-3' |
| S-69 | 5'-GUACGAAGCUGUAUAUAAATT-3' |
| S-70 | 5'-GUACGAAGCUGUAUAUAAATT-3' |
| S-71 | 5'-GUACGAAGCUGUAUAUAAATT-3' |
| S-72 | 5'-GUACGAAGCUGUAUAUAAATT-3' |
| S-73 | 5'-GUACGAAGCUGUAUAUAAATT-3' |
| S-74 | 5'-GUACGAAGCUGUAUAUAAATT-3' |
| S-75 | 5'-GUACGAAGCUGUAUAUAAATT-3' |
| S-76 | 5'-GUACGAAGCUGUAUAUAAATT-3' |
| S-77 | 5'-GUACGAAGCUGUAUAUAAATT-3' |
| S-78 | 5'-GUACGAAGCUGUAUAUAAATT-3' |
| S-79 | 5'-GUACGAAGCUGUAUAUAAATT-3' |
| S-80 | 5'-GUACGAAGCUGUAUAUAAATT-3' |
| S-81 | 5'-GUACGAAGCUGUAUAUAAATT-3' |
| S-82 | 5'-GUACGAAGCUGUAUAUAAATT-3' |
| S-83 | 5'-GUACGAAGCUGUAUAUAAATT-3' |
| S-84 | 5'-GUACGAAGCUGUAUAUAAATT-3' |
| S-85 | 5'-GUACGAAGCUGUAUAUAAATT-3' |
| S-86 | 5'-GUACGAAGCUGUAUAUAAATT-3' |
| S-87 | 5'-GUACGAAGCUGUAUAUAAATT-3' |
| S-88 | 5'-GUACGAAGCUGUAUAUAAATT-3' |
| S-89 | 5'-GUACGAAGCUGUAUAUAAATT-3' |
| S-90 | 5'-GUACGAAGCUGUAUAUAAATT-3' |
| S-91 | 5'-GUACGAAGCUGUAUAUAAATT-3' |
| S-92 | 5'-GUACGAAGCUGUAUAUAAATT-3' |
| S-93 | 5'-GUACGAAGCUGUAUAUAAATT-3' |
| S-94 | 5'-GUACGAAGCUGUAUAUAAATT-3' |
| S-95 | 5'-GUACGAAGCUGUAUAUAAATT-3' |
| S-96 | 5'-GUACGAAGCUGUAUAUAAATT-3' |
| S-97 | 5'-GUACGAAGCUGUAUAUAAATT-3' |
| S-98 | 5'-GUACGAAGCUGUAUAUAAATT-3' |
| S-99 | 5'-GUACGAAGCUGUAUAUAAATT-3' |
| S-100 | 5'-GUACGAAGCUGUAUAUAAATT-3' |
| S-101 | 5'-GUACGAAGCUGUAUAUAAATT-3' |
| S-102 | 5'-GUACGAAGCUGUAUAUAAATT-3' |
| S-103 | 5'-GUACGAAGCUGUAUAUAAATT-3' |
| S-104 | 5'-GUACGAAGCUGUAUAUAAATT-3' |
| S-105 | 5'-GUACGAAGCUGUAUAUAAATT-3' |
| S-106 | 5'-GUACGAAGCUGUAUAUAAATT-3' |
| S-107 | 5'-GUACGAAGCUGUAUAUAAATT-3' |
| S-108 | 5'-GUACGAAGCUGUAUAUAAATT-3' |
| S-109 | 5'-GUACGAAGCUGUAUAUAAATT-3' |
| S-110 | 5'-GUACGAAGCUGUAUAUAAATT-3' |
| S-111 | 5'-GUACGAAGCUGUAUAUAAATT-3' |
| S-112 | 5'-GUACGAAGCUGUAUAUAAATT-3' |

TABLE 1-continued

| Name | Sense Strand Sequence |
| --- | --- |
| S-113 | 5'-GUACGAAGCUGUAUAUAAATT-3' |
| S-114 | 5'-GUACGAAGCUGUAUAUAAATT-3' |
| S-115 | 5'-GUACGAAGCUGUAUAUAAATT-3' |
| S-116 | 5'-GUACGAAGCUGUAUAUAAATT-3' |
| S-117 | 5'-GUACGAAGCUGUAUAUAAATT-3' |
| S-118 | 5'-GUACGAAGCUGUAUAUAAATT-3' |
| S-119 | 5'-GUACGAAGCUGUAUAUAAATT-3' |
| S-120 | 5'-GUACGAAGCUGUAUAUAAATT-3' |
| S-121 | 5'-GUACGAAGCUGUAUAUAAATT-3' |
| S-122 | 5'-GUACGAAGCUGUAUAUAAATT-3' |
| S-123 | 5'-GUACGAAGCUGUAUAUAAATT-3' |
| S-124 | 5'-GUACGAAGCUGUAUAUAAATT-3' |
| S-125 | 5'-GUACGAAGCUGUAUAUAAATT-3' |
| S-126 | 5'-GUACGAAGCUGUAUAUAAATT-3' |
| S-127 | 5'-GUACGAAGCUGUAUAUAAATT-3' |
| S-128 | 5'-GUACGAAGCUGUAUAUAAATT-3' |
| S-129 | 5'-GUACGAAGCUGUAUAUAAATT-3' |
| S-130 | 5'-GUACGAAGCUGUAUAUAAATT-3' |
| S-131 | 5'-GUACGAAGCUGUAUAUAAATT-3' |
| S-132 | 5'-GUACGAAGCUGUAUAUAAATT-3' |
| S-133 | 5'-GUACGAAGCUGUAUAUAAATT-3' |
| S-134 | 5'-GUACGAAGCUGUAUAUAAATT-3' |
| S-135 | 5'-GUACGAAGCUGUAUAUAAATT-3' |
| S-136 | 5'-GUACGAAGCUGUAUAUAAATT-3' |
| S-137 | 5'-GUACGAAGCUGUAUAUAAATT-3' |
| S-138 | 5'-GUACGAAGCUGUAUAUAAATT-3' |
| S-139 | 5'-GUACGAAGCUGUAUAUAAATT-3' |
| S-140 | 5'-GUACGAAGCUGUAUAUAAATT-3' |
| S-141 | 5'-GUACGAAGCUGUAUAUAAATT-3' |
| S-142 | 5'-GUACGAAGCUGUAUAUAAATT-3' |
| S-143 | 5'-GUACGAAGCUGUAUAUAAATT-3' |
| S-144 | 5'-GUACGAAGCUGUAUAUAAATT-3' |
| S-145 | 5'-GUACGAAGCUGUAUAUAAATT-3' |
| S-146 | 5'-GUACGAAGCUGUAUAUAAATT-3' |
| S-147 | 5'-GUACGAAGCUGUAUAUAAATT-3' |
| S-148 | 5'-GUACGAAGCUGUAUAUAAATT-3' |
| S-149 | 5'-GUACGAAGCUGUAUAUAAATT-3' |
| S-150 | 5'-GUACGAAGCUGUAUAUAAATT-3' |
| S-151 | 5'-GUACGAAGCUGUAUAUAAATT-3' |
| S-152 | 5'-GUACGAAGCUGUAUAUAAATT-3' |
| S-153 | 5'-GUACGAAGCUGUAUAUAAATT-3' |
| S-154 | 5'-GUACGAAGCUGUAUAUAAATT-3' |
| S-155 | 5'-GUACGAAGCUGUAUAUAAATT-3' |
| S-156 | 5'-GUACGAAGCUGUAUAUAAATT-3' |
| S-157 | 5'-GUACGAAGCUGUAUAUAAATT-3' |
| S-158 | 5'-GUACGAAGCUGUAUAUAAATT-3' |
| S-159 | 5'-GUACGAAGCUGUAUAUAAATT-3' |
| S-160 | 5'-GUACGAAGCUGUAUAUAAATT-3' |
| S-161 | 5'-GUACGAAGCUGUAUAUAAATT-3' |
| S-162 | 5'-GUACGAAGCUGUAUAUAAATT-3' |
| S-163 | 5'-GUACGAAGCUGUAUAUAAATT-3' |
| S-164 | 5'-GUACGAAGCUGUAUAUAAATT-3' |
| S-165 | 5'-GUACGAAGCUGUAUAUAAATT-3' |
| S-166 | 5'-GUACGAAGCUGUAUAUAAATT-3' |
| S-167 | 5'-GUACGAAGCUGUAUAUAAATT-3' |
| S-168 | 5'-GUACGAAGCUGUAUAUAAATT-3' |
| S-169 | 5'-GUACGAAGCUGUAUAUAAATT-3' |
| S-170 | 5'-GUACGAAGCUGUAUAUAAATT-3' |
| S-171 | 5'-GUACGAAGCUGUAUAUAAATT-3' |
| S-172 | 5'-GUACGAAGCUGUAUAUAAATT-3' |
| S-173 | 5'-GUACGAAGCUGUAUAUAAATT-3' |
| S-174 | 5'-GUACGAAGCUGUAUAUAAATT-3' |
| S-175 | 5'-GUACGAAGCUGUAUAUAAATT-3' |
| S-176 | 5'-GUACGAAGCUGUAUAUAAATT-3' |
| S-177 | 5'-GUACGAAGCUGUAUAUAAATT-3' |
| S-178 | 5'-GUACGAAGCUGUAUAUAAATT-3' |
| S-179 | 5'-GUACGAAGCUGUAUAUAAATT-3' |
| S-180 | 5'-GUACGAAGCUGUAUAUAAATT-3' |
| S-181 | 5'-GUACGAAGCUGUAUAUAAATT-3' |
| S-182 | 5'-GUACGAAGCUGUAUAUAAATT-3' |
| S-183 | 5'-GUACGAAGCUGUAUAUAAATT-3' |
| S-184 | 5'-GUACGAAGCUGUAUAUAAATT-3' |
| S-185 | 5'-GUACGAAGCUGUAUAUAAATT-3' |
| S-186 | 5'-GUACGAAGCUGUAUAUAAATT-3' |
| S-187 | 5'-GUACGAAGCUGUAUAUAAATT-3' |
| S-188 | 5'-GUACGAAGCUGUAUAUAAATT-3' |
| S-189 | 5'-GUACGAAGCUGUAUAUAAATT-3' |
| S-190 | 5'-GUACGAAGCUGUAUAUAAATT-3' |

TABLE 1-continued

| Name | Sense Strand Sequence |
|---|---|
| S-191 | 5'-GUACGAAGCUGUAUAUAAATT-3' |
| S-192 | 5'-GUACGAAGCUGUAUAUAAATT-3' |
| S-193 | 5'-GUACGAAGCUGUAUAUAAATT-3' |
| S-194 | 5'-GUACGAAGCUGUAUAUAAATT-3' |
| S-195 | 5'-GUACGAAGCUGUAUAUAAATT-3' |
| S-196 | 5'-GUACGAAGCUGUAUAUAAATT-3' |
| S-197 | 5'-GUACGAAGCUGUAUAUAAATT-3' |
| S-198 | 5'-GUACGAAGCUGUAUAUAAATT-3' |
| S-199 | 5'-GUACGAAGCUGUAUAUAAATT-3' |
| S-200 | 5'-GUACGAAGCUGUAUAUAAATT-3' |
| S-201 | 5'-GUACGAAGCUGUAUAUAAATT-3' |
| S-202 | 5'-GUACGAAGCUGUAUAUAAATT-3' |
| S-203 | 5'-GUACGAAGCUGUAUAUAAATT-3' |
| S-204 | 5'-GUACGAAGCUGUAUAUAAATT-3' |
| S-205 | 5'-GUACGAAGCUGUAUAUAAATT-3' |
| S-206 | 5'-GUACGAAGCUGUAUAUAAATT-3' |
| S-207 | 5'-GUACGAAGCUGUAUAUAAATT-3' |
| S-208 | 5'-GUACGAAGCUGUAUAUAAATT-3' |
| S-209 | 5'-GUACGAAGCUGUAUAUAAATT-3' |
| S-210 | 5'-GUACGAAGCUGUAUAUAAATT-3' |
| S-211 | 5'-GUACGAAGCUGUAUAUAAATT-3' |
| S-212 | 5'-GUACGAAGCUGUAUAUAAATT-3' |
| S-213 | 5'-GUACGAAGCUGUAUAUAAATT-3' |
| S-214 | 5'-GUACGAAGCUGUAUAUAAATT-3' |
| S-215 | 5'-GUACGAAGCUGUAUAUAAATT-3' |
| S-216 | 5'-GUACGAAGCUGUAUAUAAATT-3' |
| S-217 | 5'-GUACGAAGCUGUAUAUAAATT-3' |
| S-218 | 5'-GUACGAAGCUGUAUAUAAATT-3' |
| S-219 | 5'-GUACGAAGCUGUAUAUAAATT-3' |
| S-220 | 5'-GUACGAAGCUGUAUAUAAATT-3' |
| S-221 | 5'-GUACGAAGCUGUAUAUAAATT-3' |
| S-222 | 5'-GUACGAAGCUGUAUAUAAATT-3' |
| S-223 | 5'-GUACGAAGCUGUAUAUAAATT-3' |
| S-224 | 5'-GUACGAAGCUGUAUAUAAATT-3' |
| S-225 | 5'-GUACGAAGCUGUAUAUAAATT-3' |
| S-226 | 5'-GUACGAAGCUGUAUAUAAATT-3' |
| S-227 | 5'-GUACGAAGCUGUAUAUAAATT-3' |
| S-228 | 5'-GUACGAAGCUGUAUAUAAATT-3' |
| S-229 | 5'-GUACGAAGCUGUAUAUAAATT-3' |
| S-230 | 5'-GUACGAAGCUGUAUAUAAATT-3' |
| S-231 | 5'-GUACGAAGCUGUAUAUAAATT-3' |
| S-232 | 5'-GUACGAAGCUGUAUAUAAATT-3' |
| S-233 | 5'-GUACGAAGCUGUAUAUAAATT-3' |
| S-234 | 5'-GUACGAAGCUGUAUAUAAATT-3' |
| S-235 | 5'-GUACGAAGCUGUAUAUAAATT-3' |
| S-236 | 5'-GUACGAAGCUGUAUAUAAATT-3' |
| S-237 | 5'-GUACGAAGCUGUAUAUAAATT-3' |
| S-238 | 5'-GUACGAAGCUGUAUAUAAATT-3' |
| S-239 | 5'-GUACGAAGCUGUAUAUAAATT-3' |
| S-240 | 5'-GUACGAAGCUGUAUAUAAATT-3' |
| S-241 | 5'-GUACGAAGCUGUAUAUAAATT-3' |
| S-242 | 5'-GUACGAAGCUGUAUAUAAATT-3' |
| S-243 | 5'-GUACGAAGCUGUAUAUAAATT-3' |
| S-244 | 5'-GUACGAAGCUGUAUAUAAATT-3' |
| S-245 | 5'-GUACGAAGCUGUAUAUAAATT-3' |
| S-246 | 5'-GUACGAAGCUGUAUAUAAATT-3' |
| S-247 | 5'-GUACGAAGCUGUAUAUAAATT-3' |
| S-248 | 5'-GUACGAAGCUGUAUAUAAATT-3' |
| S-249 | 5'-GUACGAAGCUGUAUAUAAATT-3' |
| S-250 | 5'-GUACGAAGCUGUAUAUAAATT-3' |
| S-251 | 5'-GUACGAAGCUGUAUAUAAATT-3' |
| S-252 | 5'-GUACGAAGCUGUAUAUAAATT-3' |
| S-253 | 5'-GUACGAAGCUGUAUAUAAATT-3' |
| S-254 | 5'-GUACGAAGCUGUAUAUAAATT-3' |
| S-255 | 5'-GUACGAAGCUGUAUAUAAATT-3' |
| S-256 | 5'-GUACGAAGCUGUAUAUAAATT-3' |
| S-257 | 5'-GUACGAAGCUGUAUAUAAATT-3' |
| S-258 | 5'-GUACGAAGCUGUAUAUAAATT-3' |
| S-259 | 5'-GUACGAAGCUGUAUAUAAATT-3' |
| S-260 | 5'-GUACGAAGCUGUAUAUAAATT-3' |
| S-261 | 5'-GUACGAAGCUGUAUAUAAATT-3' |
| S-262 | 5'-GUACGAAGCUGUAUAUAAATT-3' |
| S-263 | 5'-GUACGAAGCUGUAUAUAAATT-3' |
| S-264 | 5'-GUACGAAGCUGUAUAUAAATT-3' |
| S-265 | 5'-GUACGAAGCUGUAUAUAAATT-3' |
| S-266 | 5'-GUACGAAGCUGUAUAUAAATT-3' |
| S-267 | 5'-GUACGAAGCUGUAUAUAAATT-3' |
| S-268 | 5'-GUACGAAGCUGUAUAUAAATT-3' |

TABLE 1-continued

| Name | Sense Strand Sequence |
|---|---|
| S-269 | 5'-GUACGAAGCUGUAUAUAAATT-3' |
| S-270 | 5'-GUACGAAGCUGUAUAUAAATT-3' |
| S-271 | 5'-GUACGAAGCUGUAUAUAAATT-3' |
| S-272 | 5'-GUACGAAGCUGUAUAUAAATT-3' |
| S-273 | 5'-GUACGAAGCUGUAUAUAAATT-3' |
| S-274 | 5'-GUACGAAGCUGUAUAUAAATT-3' |
| S-275 | 5'-GUACGAAGCUGUAUAUAAATT-3' |
| S-276 | 5'-GUACGAAGCUGUAUAUAAATT-3' |
| S-277 | 5'-GUACGAAGCUGUAUAUAAATT-3' |
| S-278 | 5'-GUACGAAGCUGUAUAUAAATT-3' |
| S-279 | 5'-GUACGAAGCUGUAUAUAAATT-3' |
| S-280 | 5'-GUACGAAGCUGUAUAUAAATT-3' |
| S-281 | 5'-GUACGAAGCUGUAUAUAAATT-3' |
| S-282 | 5'-GUACGAAGCUGUAUAUAAATT-3' |
| S-283 | 5'-GUACGAAGCUGUAUAUAAATT-3' |
| S-284 | 5'-GUACGAAGCUGUAUAUAAATT-3' |
| S-285 | 5'-GUACGAAGCUGUAUAUAAATT-3' |
| S-286 | 5'-GUACGAAGCUGUAUAUAAATT-3' |
| S-287 | 5'-GUACGAAGCUGUAUAUAAATT-3' |
| S-288 | 5'-GUACGAAGCUGUAUAUAAATT-3' |
| S-289 | 5'-GUACGAAGCUGUAUAUAAATT-3' |
| S-290 | 5'-GUACGAAGCUGUAUAUAAATT-3' |
| S-291 | 5'-GUACGAAGCUGUAUAUAAATT-3' |
| S-292 | 5'-GUACGAAGCUGUAUAUAAATT-3' |
| S-293 | 5'-GUACGAAGCUGUAUAUAAATT-3' |
| S-294 | 5'-GUACGAAGCUGUAUAUAAATT-3' |
| S-295 | 5'-GUACGAAGCUGUAUAUAAATT-3' |
| S-296 | 5'-GUACGAAGCUGUAUAUAAATT-3' |
| S-297 | 5'-GUACGAAGCUGUAUAUAAATT-3' |
| S-298 | 5'-GUACGAAGCUGUAUAUAAATT-3' |
| S-299 | 5'-GUACGAAGCUGUAUAUAAATT-3' |
| S-300 | 5'-GUACGAAGCUGUAUAUAAATT-3' |
| S-301 | 5'-GUACGAAGCUGUAUAUAAATT-3' |
| S-302 | 5'-GUACGAAGCUGUAUAUAAATT-3' |
| S-303 | 5'-GUACGAAGCUGUAUAUAAATT-3' |
| S-304 | 5'-GUACGAAGCUGUAUAUAAATT-3' |
| S-305 | 5'-GUACGAAGCUGUAUAUAAATT-3' |
| S-306 | 5'-GUACGAAGCUGUAUAUAAATT-3' |
| S-307 | 5'-GUACGAAGCUGUAUAUAAATT-3' |

In other embodiments, the first interfering RNA (e.g., siRNA) that silences EBOV L-pol expression comprises one of the following antisense strand sequences set forth in Table 2, wherein the underlined nucleotides are 2'OMe nucleotides.

TABLE 2

| Name | Antisense Strand Sequence |
|---|---|
| AS-1 | 5'-UUUAUAUACAGCUUCGUACTT-3' |
| AS-2 | 5'-UUUAUAUACAGCUUCGUACTT-3' |
| AS-3 | 5'-UUUAUAUACAGCUUCGUACTT-3' |
| AS-4 | 5'-UUUAUAUACAGCUUCGUACTT-3' |
| AS-5 | 5'-UUUAUAUACAGCUUCGUACTT-3' |
| AS-6 | 5'-UUUAUAUACAGCUUCGUACTT-3' |
| AS-7 | 5'-UUUAUAUACAGCUUCGUACTT-3' |
| AS-8 | 5'-UUUAUAUACAGCUUCGUACTT-3' |
| AS-9 | 5'-UUUAUAUACAGCUUCGUACTT-3' |
| AS-10 | 5'-UUUAUAUACAGCUUCGUACTT-3' |
| AS-11 | 5'-UUUAUAUACAGCUUCGUACTT-3' |
| AS-12 | 5'-UUUAUAUACAGCUUCGUACTT-3' |
| AS-13 | 5'-UUUAUAUACAGCUUCGUACTT-3' |
| AS-14 | 5'-UUUAUAUACAGCUUCGUACTT-3' |
| AS-15 | 5'-UUUAUAUACAGCUUCGUACTT-3' |
| AS-16 | 5'-UUUAUAUACAGCUUCGUACTT-3' |
| AS-17 | 5'-UUUAUAUACAGCUUCGUACTT-3' |
| AS-18 | 5'-UUUAUAUACAGCUUCGUACTT-3' |
| AS-19 | 5'-UUUAUAUACAGCUUCGUACTT-3' |
| AS-20 | 5'-UUUAUAUACAGCUUCGUACTT-3' |
| AS-21 | 5'-UUUAUAUACAGCUUCGUACTT-3' |
| AS-22 | 5'-UUUAUAUACAGCUUCGUACTT-3' |
| AS-23 | 5'-UUUAUAUACAGCUUCGUACTT-3' |
| AS-24 | 5'-UUUAUAUACAGCUUCGUACTT-3' |
| AS-25 | 5'-UUUAUAUACAGCUUCGUACTT-3' |
| AS-26 | 5'-UUUAUAUACAGCUUCGUACTT-3' |
| AS-27 | 5'-UUUAUAUACAGCUUCGUACTT-3' |
| AS-28 | 5'-UUUAUAUACAGCUUCGUACTT-3' |
| AS-29 | 5'-UUUAUAUACAGCUUCGUACTT-3' |
| AS-30 | 5'-UUUAUAUACAGCUUCGUACTT-3' |
| AS-31 | 5'-UUUAUAUACAGCUUCGUACTT-3' |
| AS-32 | 5'-UUUAUAUACAGCUUCGUACTT-3' |
| AS-33 | 5'-UUUAUAUACAGCUUCGUACTT-3' |
| AS-34 | 5'-UUUAUAUACAGCUUCGUACTT-3' |
| AS-35 | 5'-UUUAUAUACAGCUUCGUACTT-3' |
| AS-36 | 5'-UUUAUAUACAGCUUCGUACTT-3' |

TABLE 2-continued

| Name | Antisense Strand Sequence |
|---|---|
| AS-37 | 5'-UUUAUAUACAGCUUCGUACTT-3' |
| AS-38 | 5'-UUUAUAUACAGCUUCGUACTT-3' |
| AS-39 | 5'-UUUAUAUACAGCUUCGUACTT-3' |
| AS-40 | 5'-UUUAUAUACAGCUUCGUACTT-3' |
| AS-41 | 5'-UUUAUAUACAGCUUCGUACTT-3' |
| AS-42 | 5'-UUUAUAUACAGCUUCGUACTT-3' |
| AS-43 | 5'-UUUAUAUACAGCUUCGUACTT-3' |
| AS-44 | 5'-UUUAUAUACAGCUUCGUACTT-3' |
| AS-45 | 5'-UUUAUAUACAGCUUCGUACTT-3' |
| AS-46 | 5'-UUUAUAUACAGCUUCGUACTT-3' |
| AS-47 | 5'-UUUAUAUACAGCUUCGUACTT-3' |
| AS-48 | 5'-UUUAUAUACAGCUUCGUACTT-3' |
| AS-49 | 5'-UUUAUAUACAGCUUCGUACTT-3' |
| AS-50 | 5'-UUUAUAUACAGCUUCGUACTT-3' |
| AS-51 | 5'-UUUAUAUACAGCUUCGUACTT-3' |
| AS-52 | 5'-UUUAUAUACAGCUUCGUACTT-3' |
| AS-53 | 5'-UUUAUAUACAGCUUCGUACTT-3' |
| AS-54 | 5'-UUUAUAUACAGCUUCGUACTT-3' |
| AS-55 | 5'-UUUAUAUACAGCUUCGUACTT-3' |
| AS-56 | 5'-UUUAUAUACAGCUUCGUACTT-3' |
| AS-57 | 5'-UUUAUAUACAGCUUCGUACTT-3' |
| AS-58 | 5'-UUUAUAUACAGCUUCGUACTT-3' |
| AS-59 | 5'-UUUAUAUACAGCUUCGUACTT-3' |
| AS-60 | 5'-UUUAUAUACAGCUUCGUACTT-3' |
| AS-61 | 5'-UUUAUAUACAGCUUCGUACTT-3' |
| AS-62 | 5'-UUUAUAUACAGCUUCGUACTT-3' |
| AS-63 | 5'-UUUAUAUACAGCUUCGUACTT-3' |
| AS-64 | 5'-UUUAUAUACAGCUUCGUACTT-3' |
| AS-65 | 5'-UUUAUAUACAGCUUCGUACTT-3' |
| AS-66 | 5'-UUUAUAUACAGCUUCGUACTT-3' |
| AS-67 | 5'-UUUAUAUACAGCUUCGUACTT-3' |
| AS-68 | 5'-UUUAUAUACAGCUUCGUACTT-3' |
| AS-69 | 5'-UUUAUAUACAGCUUCGUACTT-3' |
| AS-70 | 5'-UUUAUAUACAGCUUCGUACTT-3' |
| AS-71 | 5'-UUUAUAUACAGCUUCGUACTT-3' |
| AS-72 | 5'-UUUAUAUACAGCUUCGUACTT-3' |
| AS-73 | 5'-UUUAUAUACAGCUUCGUACTT-3' |
| AS-74 | 5'-UUUAUAUACAGCUUCGUACTT-3' |
| AS-75 | 5'-UUUAUAUACAGCUUCGUACTT-3' |
| AS-76 | 5'-UUUAUAUACAGCUUCGUACTT-3' |
| AS-77 | 5'-UUUAUAUACAGCUUCGUACTT-3' |
| AS-78 | 5'-UUUAUAUACAGCUUCGUACTT-3' |
| AS-79 | 5'-UUUAUAUACAGCUUCGUACTT-3' |
| AS-80 | 5'-UUUAUAUACAGCUUCGUACTT-3' |
| AS-81 | 5'-UUUAUAUACAGCUUCGUACTT-3' |
| AS-82 | 5'-UUUAUAUACAGCUUCGUACTT-3' |
| AS-83 | 5'-UUUAUAUACAGCUUCGUACTT-3' |
| AS-84 | 5'-UUUAUAUACAGCUUCGUACTT-3' |
| AS-85 | 5'-UUUAUAUACAGCUUCGUACTT-3' |
| AS-86 | 5'-UUUAUAUACAGCUUCGUACTT-3' |
| AS-87 | 5'-UUUAUAUACAGCUUCGUACTT-3' |
| AS-88 | 5'-UUUAUAUACAGCUUCGUACTT-3' |
| AS-89 | 5'-UUUAUAUACAGCUUCGUACTT-3' |
| AS-90 | 5'-UUUAUAUACAGCUUCGUACTT-3' |
| AS-91 | 5'-UUUAUAUACAGCUUCGUACTT-3' |
| AS-92 | 5'-UUUAUAUACAGCUUCGUACTT-3' |
| AS-93 | 5'-UUUAUAUACAGCUUCGUACTT-3' |
| AS-94 | 5'-UUUAUAUACAGCUUCGUACTT-3' |
| AS-95 | 5'-UUUAUAUACAGCUUCGUACTT-3' |
| AS-96 | 5'-UUUAUAUACAGCUUCGUACTT-3' |
| AS-97 | 5'-UUUAUAUACAGCUUCGUACTT-3' |
| AS-98 | 5'-UUUAUAUACAGCUUCGUACTT-3' |
| AS-99 | 5'-UUUAUAUACAGCUUCGUACTT-3' |
| AS-100 | 5'-UUUAUAUACAGCUUCGUACTT-3' |
| AS-101 | 5'-UUUAUAUACAGCUUCGUACTT-3' |
| AS-102 | 5'-UUUAUAUACAGCUUCGUACTT-3' |
| AS-103 | 5'-UUUAUAUACAGCUUCGUACTT-3' |
| AS-104 | 5'-UUUAUAUACAGCUUCGUACTT-3' |
| AS-105 | 5'-UUUAUAUACAGCUUCGUACTT-3' |
| AS-106 | 5'-UUUAUAUACAGCUUCGUACTT-3' |
| AS-107 | 5'-UUUAUAUACAGCUUCGUACTT-3' |
| AS-108 | 5'-UUUAUAUACAGCUUCGUACTT-3' |
| AS-109 | 5'-UUUAUAUACAGCUUCGUACTT-3' |
| AS-110 | 5'-UUUAUAUACAGCUUCGUACTT-3' |
| AS-111 | 5'-UUUAUAUACAGCUUCGUACTT-3' |
| AS-112 | 5'-UUUAUAUACAGCUUCGUACTT-3' |
| AS-113 | 5'-UUUAUAUACAGCUUCGUACTT-3' |
| AS-114 | 5'-UUUAUAUACAGCUUCGUACTT-3' |

TABLE 2-continued

| Name | Antisense Strand Sequence |
|---|---|
| AS-115 | 5'-UUUAUAUACAGCUUCGUACTT-3' |
| AS-116 | 5'-UUUAUAUACAGCUUCGUACTT-3' |
| AS-117 | 5'-UUUAUAUACAGCUUCGUACTT-3' |
| AS-118 | 5'-UUUAUAUACAGCUUCGUACTT-3' |
| AS-119 | 5'-UUUAUAUACAGCUUCGUACTT-3' |
| AS-120 | 5'-UUUAUAUACAGCUUCGUACTT-3' |
| AS-121 | 5'-UUUAUAUACAGCUUCGUACTT-3' |
| AS-122 | 5'-UUUAUAUACAGCUUCGUACTT-3' |
| AS-123 | 5'-UUUAUAUACAGCUUCGUACTT-3' |
| AS-124 | 5'-UUUAUAUACAGCUUCGUACTT-3' |
| AS-125 | 5'-UUUAUAUACAGCUUCGUACTT-3' |
| AS-126 | 5'-UUUAUAUACAGCUUCGUACTT-3' |
| AS-127 | 5'-UUUAUAUACAGCUUCGUACTT-3' |
| AS-128 | 5'-UUUAUAUACAGCUUCGUACTT-3' |
| AS-129 | 5'-UUUAUAUACAGCUUCGUACTT-3' |
| AS-130 | 5'-UUUAUAUACAGCUUCGUACTT-3' |
| AS-131 | 5'-UUUAUAUACAGCUUCGUACTT-3' |
| AS-132 | 5'-UUUAUAUACAGCUUCGUACTT-3' |
| AS-133 | 5'-UUUAUAUACAGCUUCGUACTT-3' |
| AS-134 | 5'-UUUAUAUACAGCUUCGUACTT-3' |
| AS-135 | 5'-UUUAUAUACAGCUUCGUACTT-3' |
| AS-136 | 5'-UUUAUAUACAGCUUCGUACTT-3' |
| AS-137 | 5'-UUUAUAUACAGCUUCGUACTT-3' |
| AS-138 | 5'-UUUAUAUACAGCUUCGUACTT-3' |
| AS-139 | 5'-UUUAUAUACAGCUUCGUACTT-3' |
| AS-140 | 5'-UUUAUAUACAGCUUCGUACTT-3' |
| AS-141 | 5'-UUUAUAUACAGCUUCGUACTT-3' |
| AS-142 | 5'-UUUAUAUACAGCUUCGUACTT-3' |
| AS-143 | 5'-UUUAUAUACAGCUUCGUACTT-3' |
| AS-144 | 5'-UUUAUAUACAGCUUCGUACTT-3' |
| AS-145 | 5'-UUUAUAUACAGCUUCGUACTT-3' |
| AS-146 | 5'-UUUAUAUACAGCUUCGUACTT-3' |
| AS-147 | 5'-UUUAUAUACAGCUUCGUACTT-3' |
| AS-148 | 5'-UUUAUAUACAGCUUCGUACTT-3' |
| AS-149 | 5'-UUUAUAUACAGCUUCGUACTT-3' |
| AS-150 | 5'-UUUAUAUACAGCUUCGUACTT-3' |
| AS-151 | 5'-UUUAUAUACAGCUUCGUACTT-3' |
| AS-152 | 5'-UUUAUAUACAGCUUCGUACTT-3' |
| AS-153 | 5'-UUUAUAUACAGCUUCGUACTT-3' |
| AS-154 | 5'-UUUAUAUACAGCUUCGUACTT-3' |
| AS-155 | 5'-UUUAUAUACAGCUUCGUACTT-3' |
| AS-156 | 5'-UUUAUAUACAGCUUCGUACTT-3' |
| AS-157 | 5'-UUUAUAUACAGCUUCGUACTT-3' |
| AS-158 | 5'-UUUAUAUACAGCUUCGUACTT-3' |
| AS-159 | 5'-UUUAUAUACAGCUUCGUACTT-3' |
| AS-160 | 5'-UUUAUAUACAGCUUCGUACTT-3' |
| AS-161 | 5'-UUUAUAUACAGCUUCGUACTT-3' |
| AS-162 | 5'-UUUAUAUACAGCUUCGUACTT-3' |
| AS-163 | 5'-UUUAUAUACAGCUUCGUACTT-3' |
| AS-164 | 5'-UUUAUAUACAGCUUCGUACTT-3' |
| AS-165 | 5'-UUUAUAUACAGCUUCGUACTT-3' |
| AS-166 | 5'-UUUAUAUACAGCUUCGUACTT-3' |
| AS-167 | 5'-UUUAUAUACAGCUUCGUACTT-3' |
| AS-168 | 5'-UUUAUAUACAGCUUCGUACTT-3' |
| AS-169 | 5'-UUUAUAUACAGCUUCGUACTT-3' |
| AS-170 | 5'-UUUAUAUACAGCUUCGUACTT-3' |
| AS-171 | 5'-UUUAUAUACAGCUUCGUACTT-3' |
| AS-172 | 5'-UUUAUAUACAGCUUCGUACTT-3' |
| AS-173 | 5'-UUUAUAUACAGCUUCGUACTT-3' |
| AS-174 | 5'-UUUAUAUACAGCUUCGUACTT-3' |
| AS-175 | 5'-UUUAUAUACAGCUUCGUACTT-3' |
| AS-176 | 5'-UUUAUAUACAGCUUCGUACTT-3' |
| AS-177 | 5'-UUUAUAUACAGCUUCGUACTT-3' |
| AS-178 | 5'-UUUAUAUACAGCUUCGUACTT-3' |
| AS-179 | 5'-UUUAUAUACAGCUUCGUACTT-3' |
| AS-180 | 5'-UUUAUAUACAGCUUCGUACTT-3' |
| AS-181 | 5'-UUUAUAUACAGCUUCGUACTT-3' |
| AS-182 | 5'-UUUAUAUACAGCUUCGUACTT-3' |
| AS-183 | 5'-UUUAUAUACAGCUUCGUACTT-3' |
| AS-184 | 5'-UUUAUAUACAGCUUCGUACTT-3' |
| AS-185 | 5'-UUUAUAUACAGCUUCGUACTT-3' |
| AS-186 | 5'-UUUAUAUACAGCUUCGUACTT-3' |
| AS-187 | 5'-UUUAUAUACAGCUUCGUACTT-3' |
| AS-188 | 5'-UUUAUAUACAGCUUCGUACTT-3' |
| AS-189 | 5'-UUUAUAUACAGCUUCGUACTT-3' |
| AS-190 | 5'-UUUAUAUACAGCUUCGUACTT-3' |
| AS-191 | 5'-UUUAUAUACAGCUUCGUACTT-3' |
| AS-192 | 5'-UUUAUAUACAGCUUCGUACTT-3' |

TABLE 2-continued

| Name | Antisense Strand Sequence |
|---|---|
| AS-193 | 5'-UUUAUAUACAGCUUCGUACTT-3' |
| AS-194 | 5'-UUUAUAUACAGCUUCGUACTT-3' |
| AS-195 | 5'-UUUAUAUACAGCUUCGUACTT-3' |
| AS-196 | 5'-UUUAUAUACAGCUUCGUACTT-3' |
| AS-197 | 5'-UUUAUAUACAGCUUCGUACTT-3' |
| AS-198 | 5'-UUUAUAUACAGCUUCGUACTT-3' |
| AS-199 | 5'-UUUAUAUACAGCUUCGUACTT-3' |
| AS-200 | 5'-UUUAUAUACAGCUUCGUACTT-3' |
| AS-201 | 5'-UUUAUAUACAGCUUCGUACTT-3' |
| AS-202 | 5'-UUUAUAUACAGCUUCGUACTT-3' |
| AS-203 | 5'-UUUAUAUACAGCUUCGUACTT-3' |
| AS-204 | 5'-UUUAUAUACAGCUUCGUACTT-3' |
| AS-205 | 5'-UUUAUAUACAGCUUCGUACTT-3' |
| AS-206 | 5'-UUUAUAUACAGCUUCGUACTT-3' |
| AS-207 | 5'-UUUAUAUACAGCUUCGUACTT-3' |
| AS-208 | 5'-UUUAUAUACAGCUUCGUACTT-3' |
| AS-209 | 5'-UUUAUAUACAGCUUCGUACTT-3' |
| AS-210 | 5'-UUUAUAUACAGCUUCGUACTT-3' |
| AS-211 | 5'-UUUAUAUACAGCUUCGUACTT-3' |
| AS-212 | 5'-UUUAUAUACAGCUUCGUACTT-3' |
| AS-213 | 5'-UUUAUAUACAGCUUCGUACTT-3' |
| AS-214 | 5'-UUUAUAUACAGCUUCGUACTT-3' |
| AS-215 | 5'-UUUAUAUACAGCUUCGUACTT-3' |
| AS-216 | 5'-UUUAUAUACAGCUUCGUACTT-3' |
| AS-217 | 5'-UUUAUAUACAGCUUCGUACTT-3' |
| AS-218 | 5'-UUUAUAUACAGCUUCGUACTT-3' |
| AS-219 | 5'-UUUAUAUACAGCUUCGUACTT-3' |
| AS-220 | 5'-UUUAUAUACAGCUUCGUACTT-3' |
| AS-221 | 5'-UUUAUAUACAGCUUCGUACTT-3' |
| AS-222 | 5'-UUUAUAUACAGCUUCGUACTT-3' |
| AS-223 | 5'-UUUAUAUACAGCUUCGUACTT-3' |
| AS-224 | 5'-UUUAUAUACAGCUUCGUACTT-3' |
| AS-225 | 5'-UUUAUAUACAGCUUCGUACTT-3' |
| AS-226 | 5'-UUUAUAUACAGCUUCGUACTT-3' |
| AS-227 | 5'-UUUAUAUACAGCUUCGUACTT-3' |
| AS-228 | 5'-UUUAUAUACAGCUUCGUACTT-3' |
| AS-229 | 5'-UUUAUAUACAGCUUCGUACTT-3' |
| AS-230 | 5'-UUUAUAUACAGCUUCGUACTT-3' |
| AS-231 | 5'-UUUAUAUACAGCUUCGUACTT-3' |

TABLE 2-continued

| Name | Antisense Strand Sequence |
|---|---|
| AS-232 | 5'-UUUAUAUACAGCUUCGUACTT-3' |
| AS-233 | 5'-UUUAUAUACAGCUUCGUACTT-3' |
| AS-234 | 5'-UUUAUAUACAGCUUCGUACTT-3' |
| AS-235 | 5'-UUUAUAUACAGCUUCGUACTT-3' |
| AS-236 | 5'-UUUAUAUACAGCUUCGUACTT-3' |
| AS-237 | 5'-UUUAUAUACAGCUUCGUACTT-3' |
| AS-238 | 5'-UUUAUAUACAGCUUCGUACTT-3' |
| AS-239 | 5'-UUUAUAUACAGCUUCGUACTT-3' |
| AS-240 | 5'-UUUAUAUACAGCUUCGUACTT-3' |
| AS-241 | 5'-UUUAUAUACAGCUUCGUACTT-3' |
| AS-242 | 5'-UUUAUAUACAGCUUCGUACTT-3' |
| AS-243 | 5'-UUUAUAUACAGCUUCGUACTT-3' |
| AS-244 | 5'-UUUAUAUACAGCUUCGUACTT-3' |
| AS-245 | 5'-UUUAUAUACAGCUUCGUACTT-3' |
| AS-246 | 5'-UUUAUAUACAGCUUCGUACTT-3' |
| AS-247 | 5'-UUUAUAUACAGCUUCGUACTT-3' |
| AS-248 | 5'-UUUAUAUACAGCUUCGUACTT-3' |
| AS-249 | 5'-UUUAUAUACAGCUUCGUACTT-3' |
| AS-250 | 5'-UUUAUAUACAGCUUCGUACTT-3' |
| AS-251 | 5'-UUUAUAUACAGCUUCGUACTT-3' |
| AS-252 | 5'-UUUAUAUACAGCUUCGUACTT-3' |
| AS-253 | 5'-UUUAUAUACAGCUUCGUACTT-3' |
| AS-254 | 5'-UUUAUAUACAGCUUCGUACTT-3' |
| AS-255 | 5'-UUUAUAUACAGCUUCGUACTT-3' |
| AS-256 | 5'-UUUAUAUACAGCUUCGUACTT-3' |
| AS-257 | 5'-UUUAUAUACAGCUUCGUACTT-3' |
| AS-258 | 5'-UUUAUAUACAGCUUCGUACTT-3' |
| AS-259 | 5'-UUUAUAUACAGCUUCGUACTT-3' |
| AS-260 | 5'-UUUAUAUACAGCUUCGUACTT-3' |
| AS-261 | 5'-UUUAUAUACAGCUUCGUACTT-3' |
| AS-262 | 5'-UUUAUAUACAGCUUCGUACTT-3' |
| AS-263 | 5'-UUUAUAUACAGCUUCGUACTT-3' |
| AS-264 | 5'-UUUAUAUACAGCUUCGUACTT-3' |
| AS-265 | 5'-UUUAUAUACAGCUUCGUACTT-3' |
| AS-266 | 5'-UUUAUAUACAGCUUCGUACTT-3' |
| AS-267 | 5'-UUUAUAUACAGCUUCGUACTT-3' |
| AS-268 | 5'-UUUAUAUACAGCUUCGUACTT-3' |
| AS-269 | 5'-UUUAUAUACAGCUUCGUACTT-3' |
| AS-270 | 5'-UUUAUAUACAGCUUCGUACTT-3' |

TABLE 2-continued

| Name | Antisense Strand Sequence |
|---|---|
| AS-271 | 5'-UUUAUAUACAGCUUCGUACTT-3' |
| AS-272 | 5'-UUUAUAUACAGCUUCGUACTT-3' |
| AS-273 | 5'-UUUAUAUACAGCUUCGUACTT-3' |
| AS-274 | 5'-UUUAUAUACAGCUUCGUACTT-3' |
| AS-275 | 5'-UUUAUAUACAGCUUCGUACTT-3' |
| AS-276 | 5'-UUUAUAUACAGCUUCGUACTT-3' |
| AS-277 | 5'-UUUAUAUACAGCUUCGUACTT-3' |
| AS-278 | 5'-UUUAUAUACAGCUUCGUACTT-3' |
| AS-279 | 5'-UUUAUAUACAGCUUCGUACTT-3' |
| AS-280 | 5'-UUUAUAUACAGCUUCGUACTT-3' |
| AS-281 | 5'-UUUAUAUACAGCUUCGUACTT-3' |
| AS-282 | 5'-UUUAUAUACAGCUUCGUACTT-3' |
| AS-283 | 5'-UUUAUAUACAGCUUCGUACTT-3' |
| AS-284 | 5'-UUUAUAUACAGCUUCGUACTT-3' |
| AS-285 | 5'-UUUAUAUACAGCUUCGUACTT-3' |
| AS-286 | 5'-UUUAUAUACAGCUUCGUACTT-3' |
| AS-287 | 5'-UUUAUAUACAGCUUCGUACTT-3' |
| AS-288 | 5'-UUUAUAUACAGCUUCGUACTT-3' |
| AS-289 | 5'-UUUAUAUACAGCUUCGUACTT-3' |
| AS-290 | 5'-UUUAUAUACAGCUUCGUACTT-3' |
| AS-291 | 5'-UUUAUAUACAGCUUCGUACTT-3' |
| AS-292 | 5'-UUUAUAUACAGCUUCGUACTT-3' |
| AS-293 | 5'-UUUAUAUACAGCUUCGUACTT-3' |
| AS-294 | 5'-UUUAUAUACAGCUUCGUACTT-3' |
| AS-295 | 5'-UUUAUAUACAGCUUCGUACTT-3' |
| AS-296 | 5'-UUUAUAUACAGCUUCGUACTT-3' |
| AS-297 | 5'-UUUAUAUACAGCUUCGUACTT-3' |
| AS-298 | 5'-UUUAUAUACAGCUUCGUACTT-3' |
| AS-299 | 5'-UUUAUAUACAGCUUCGUACTT-3' |
| AS-300 | 5'-UUUAUAUACAGCUUCGUACTT-3' |
| AS-301 | 5'-UUUAUAUACAGCUUCGUACTT-3' |
| AS-302 | 5'-UUUAUAUACAGCUUCGUACTT-3' |
| AS-303 | 5'-UUUAUAUACAGCUUCGUACTT-3' |
| AS-304 | 5'-UUUAUAUACAGCUUCGUACTT-3' |
| AS-305 | 5'-UUUAUAUACAGCUUCGUACTT-3' |
| AS-306 | 5'-UUUAUAUACAGCUUCGUACTT-3' |
| AS-307 | 5'-UUUAUAUACAGCUUCGUACTT-3' |
| AS-308 | 5'-UUUAUAUACAGCUUCGUACTT-3' |
| AS-309 | 5'-UUUAUAUACAGCUUCGUACTT-3' |

TABLE 2-continued

| Name | Antisense Strand Sequence |
|---|---|
| AS-310 | 5'-UUUAUAUACAGCUUCGUACTT-3' |
| AS-311 | 5'-UUUAUAUACAGCUUCGUACTT-3' |
| AS-312 | 5'-UUUAUAUACAGCUUCGUACTT-3' |
| AS-313 | 5'-UUUAUAUACAGCUUCGUACTT-3' |
| AS-314 | 5'-UUUAUAUACAGCUUCGUACTT-3' |
| AS-315 | 5'-UUUAUAUACAGCUUCGUACTT-3' |
| AS-316 | 5'-UUUAUAUACAGCUUCGUACTT-3' |
| AS-317 | 5'-UUUAUAUACAGCUUCGUACTT-3' |
| AS-318 | 5'-UUUAUAUACAGCUUCGUACTT-3' |
| AS-319 | 5'-UUUAUAUACAGCUUCGUACTT-3' |
| AS-320 | 5'-UUUAUAUACAGCUUCGUACTT-3' |
| AS-321 | 5'-UUUAUAUACAGCUUCGUACTT-3' |
| AS-322 | 5'-UUUAUAUACAGCUUCGUACTT-3' |
| AS-323 | 5'-UUUAUAUACAGCUUCGUACTT-3' |
| AS-324 | 5'-UUUAUAUACAGCUUCGUACTT-3' |
| AS-325 | 5'-UUUAUAUACAGCUUCGUACTT-3' |
| AS-326 | 5'-UUUAUAUACAGCUUCGUACTT-3' |
| AS-327 | 5'-UUUAUAUACAGCUUCGUACTT-3' |
| AS-328 | 5'-UUUAUAUACAGCUUCGUACTT-3' |
| AS-329 | 5'-UUUAUAUACAGCUUCGUACTT-3' |
| AS-330 | 5'-UUUAUAUACAGCUUCGUACTT-3' |
| AS-331 | 5'-UUUAUAUACAGCUUCGUACTT-3' |

In one preferred embodiment, the first interfering RNA (e.g., siRNA) that silences EBOV L-pol expression comprises: an antisense strand comprising the sequence 5'-UUUAUAUACAGCUUCGUAC-3' and at least one, two, three, four, five, six, seven, or more 2'OMe nucleotides, e.g., at least one, two, three, four, five, six, seven, or more 2'OMe-guanosine and/or 2'OMe-uridine nucleotides; and a sense strand comprising the sequence 5'-GUACGAAGCU-GUAUAUAAA-3' and at least one, two, three, four, five, six, seven, or more 2'OMe nucleotides, e.g., at least one, two, three, four, five, six, seven, or more 2'OMe-guanosine and/or 2'OMe-uridine nucleotides. In another preferred embodiment, the first interfering RNA (e.g., siRNA) that silences EBOV L-pol expression comprises: a sense strand comprising nucleotides 1-19 of any one of S-1 to S-307 set forth in Table 1; and an antisense strand comprising nucleotides 1-19 of any one of AS-1 to AS-331 set forth in Table 2. In a particularly preferred embodiment, the first interfering RNA (e.g., siRNA) that silences EBOV L-pol expression consists of: a sense strand selected from any one of S-1 to S-307 set forth in Table 1; and an antisense strand selected from any one of AS-1 to AS-331 set forth in Table 2. In additional embodiments, the sense strand and/or antisense strand of the first interfering RNA (e.g., siRNA) may further comprise at least 1, 2, 3, 4, 5, 6, 7, 8, 9, or 10 2'OMe-adenosine and/or 2'OMe-cytosine nucleotides.

In particular embodiments, the compositions of the present invention comprise the first interfering RNA (e.g., siRNA)

comprising any one of the sense strand sequences set forth in Table 1 (or nucleotides 1-19 thereof) and any one of the antisense strand sequences set forth in Table 2 (or nucleotides 1-19 thereof) in combination with (1) the second interfering RNA (e.g., siRNA) comprising any one of the sense strand sequences set forth in Table 3 (or nucleotides 1-19 thereof) and any one of the antisense strand sequences set forth in Table 4 (or nucleotides 1-19 thereof), (2) the third interfering RNA (e.g., siRNA) comprising any one of the sense strand sequences set forth in Table 5 (or nucleotides 1-19 thereof) and any one of the antisense strand sequences set forth in Table 6 (or nucleotides 1-19 thereof), or (3) both the second and third interfering RNA (e.g., siRNA) described in (1) and (2).

In one particular embodiment, the first interfering RNA (e.g., siRNA) that silences EBOV L-pol expression consists of the following sense and antisense strand sequences:

5'-GUACGAAGCUGUAUAUAAATT-3'

3'-TTCAUGCUUCGACAUAUAUUU-5', ("S-1+AS-1" or "EK-1 S1/AS1"), wherein the bolded and underlined nucleotides are 2'OMe nucleotides.

In another particular embodiment, the first interfering RNA (e.g., siRNA) that silences EBOV L-pol expression consists of the following sense and antisense strand sequences:

5'-GUACGAAGCUGUAUAUAAATT-3'

3'-TTCAUGCUUCGACAUAUAUUU-5', ("S-1+AS-2" or "EK-1 S1/AS2"), wherein the bolded and underlined nucleotides are 2'OMe nucleotides.

In yet another particular embodiment, the first interfering RNA (e.g., siRNA) that silences EBOV L-pol expression consists of the following sense and antisense strand sequences:

5'-GUACGAAGCUGUAUAUAAATT-3'

3'-TTCAUGCUUCGACAUAUAUUU-5', ("S-1+AS-3" or "EK-1 S1/AS3"), wherein the bolded and underlined nucleotides are 2'OMe nucleotides.

In still yet another particular embodiment, the first interfering RNA (e.g., siRNA) that silences EBOV L-pol expression consists of the following sense and antisense strand sequences:

5'-GUACGAAGCUGUAUAUAAATT-3'

3'-TTCAUGCUUCGACAUAUAUUU-5', ("S-1+AS-4" or "EK-1 S1/AS4"), wherein the bolded and underlined nucleotides are 2'OMe nucleotides.

In another particular embodiment, the first interfering RNA (e.g., siRNA) that silences EBOV L-pol expression consists of the following sense and antisense strand sequences:

5'-GUACGAAGCUGUAUAUAAATT-3'

3'-TTCAUGCUUCGACAUAUAUUU-5', ("S-1+AS-5" or "EK-1 S1/AS5"), wherein the bolded and underlined nucleotides are 2'OMe nucleotides.

In yet another particular embodiment, the first interfering RNA (e.g., siRNA) that silences EBOV L-pol expression consists of the following sense and antisense strand sequences:

5'-GUACGAAGCUGUAUAUAAATT-3'

3'-TTCAUGCUUCGACAUAUAUUU-5', ("S-1+AS-6" or "EK-1 S1/AS6"), wherein the bolded and underlined nucleotides are 2'OMe nucleotides.

In still yet another particular embodiment, the first interfering RNA (e.g., siRNA) that silences EBOV L-pol expression consists of the following sense and antisense strand sequences:

5'-GUACGAAGCUGUAUAUAAATT-3'

3'-TTCAUGCUUCGACAUAUAUUU-5', ("S-2+AS-1" or "EK-1 S2/AS1"), wherein the bolded and underlined nucleotides are 2'OMe nucleotides.

In another particular embodiment, the first interfering RNA (e.g., siRNA) that silences EBOV L-pol expression consists of the following sense and antisense strand sequences:

5'-GUACGAAGCUGUAUAUAAATT-3'

3'-TTCAUGCUUCGACAUAUAUUU-5', ("S-2+AS-2" or "EK-1 S2/AS2"), wherein the bolded and underlined nucleotides are 2'OMe nucleotides.

In yet another particular embodiment, the first interfering RNA (e.g., siRNA) that silences EBOV L-pol expression consists of the following sense and antisense strand sequences:

5'-GUACGAAGCUGUAUAUAAATT-3'

3'-TTCAUGCUUCGACAUAUAUUU-5', ("S-2+AS-3" or "EK-1 S2/AS3"), wherein the bolded and underlined nucleotides are 2'OMe nucleotides.

In still yet another particular embodiment, the first interfering RNA (e.g., siRNA) that silences EBOV L-pol expression consists of the following sense and antisense strand sequences:

5'-GUACGAAGCUGUAUAUAAATT-3'

3'-TTCAUGCUUCGACAUAUAUUU-5', ("S-2+AS-4" or "EK-1 S2/AS4"), wherein the bolded and underlined nucleotides are 2'OMe nucleotides.

In another particular embodiment, the first interfering RNA (e.g., siRNA) that silences EBOV L-pol expression consists of the following sense and antisense strand sequences:

5'-GUACGAAGCUGUAUAUAAATT-3'

3'-TTCAUGCUUCGACAUAUAUUU-5', ("S-2+AS-5" or "EK-1 S2/AS5"), wherein the bolded and underlined nucleotides are 2'OMe nucleotides.

In yet another particular embodiment, the first interfering RNA (e.g., siRNA) that silences EBOV L-pol expression consists of the following sense and antisense strand sequences:

```
5'-GUACGAAGCUGUAUAUAAATT-3'

3'-TTCAUGCUUCGACAUAUAUUU-5',
```

("S-2+AS-6" or "EK-1 S2/AS6"), wherein the bolded and underlined nucleotides are 2'OMe nucleotides.

In still yet another particular embodiment, the first interfering RNA (e.g., siRNA) that silences EBOV L-pol expression consists of the following sense and antisense strand sequences:

```
5'-GUACGAAGCUGUAUAUAAATT-3'

3'-TTCAUGCUUCGACAUAUAUUU-5',
```

("S-3+AS-1" or "EK-1 S3/AS1"), wherein the bolded and underlined nucleotides are 2'OMe nucleotides.

In another particular embodiment, the first interfering RNA (e.g., siRNA) that silences EBOV L-pol expression consists of the following sense and antisense strand sequences:

```
5'-GUACGAAGCUGUAUAUAAATT-3'

3'-TTCAUGCUUCGACAUAUAUUU-5',
```

("S-3+AS-2" or "EK-1 S3/AS2"), wherein the bolded and underlined nucleotides are 2'OMe nucleotides.

In yet another particular embodiment, the first interfering RNA (e.g., siRNA) that silences EBOV L-pol expression consists of the following sense and antisense strand sequences:

```
5'-GUACGAAGCUGUAUAUAAATT-3'

3'-TTCAUGCUUCGACAUAUAUUU-5',
```

("S-3+AS-3" or "EK-1 S3/AS3"), wherein the bolded and underlined nucleotides are 2'OMe nucleotides.

In still yet another particular embodiment, the first interfering RNA (e.g., siRNA) that silences EBOV L-pol expression consists of the following sense and antisense strand sequences:

```
5'-GUACGAAGCUGUAUAUAAATT-3'

3'-TTCAUGCUUCGACAUAUAUUU-5',
```

("S-3+AS-4" or "EK-1 S3/AS4"), wherein the bolded and underlined nucleotides are 2'OMe nucleotides.

In another particular embodiment, the first interfering RNA (e.g., siRNA) that silences EBOV L-pol expression consists of the following sense and antisense strand sequences:

```
5'-GUACGAAGCUGUAUAUAAATT-3'

3'-TTCAUGCUUCGACAUAUAUUU-5',
```

("S-3+AS-5" or "EK-1 S3/AS5"), wherein the bolded and underlined nucleotides are 2'OMe nucleotides.

In yet another particular embodiment, the first interfering RNA (e.g., siRNA) that silences EBOV L-pol expression consists of the following sense and antisense strand sequences:

```
5'-GUACGAAGCUGUAUAUAAATT-3'

3'-TTCAUGCUUCGACAUAUAUUU-5',
```

("S-3+AS-6" or "EK-1 S3/AS6"), wherein the bolded and underlined nucleotides are 2'OMe nucleotides.

In some embodiments, the second interfering RNA (e.g., siRNA) further comprises a sense strand comprising the following sequence: 5'-UCCUCGACACGAAUGCAAA-3'. In some aspects of these embodiments, the second interfering RNA (e.g., siRNA) comprises at least one 2'OMe nucleotide, e.g., at least one 2'OMe-guanosine and/or 2'OMe-uridine nucleotide. In certain instances, the second interfering RNA comprises an antisense strand comprising at least one, at least two, at least three, at least four, at least five, at least six, at least seven, or more 2'OMe nucleotides, e.g., 2'OMe-guanosine and/or 2'OMe-uridine nucleotides. In certain other instances, the second interfering RNA comprises a sense strand comprising at least one, at least two, at least three, at least four, at least five, at least six, at least seven, or more 2'OMe nucleotides, e.g., 2'OMe-guanosine and/or 2'OMe-uridine nucleotides. In further instances, the antisense strand and/or sense strand may further comprise at least one, at least two, at least three, at least four, at least five, at least six, at least seven, or more 2'OMe-adenosine and/or 2'OMe-cytosine nucleotides.

In particular embodiments, from about 20%-40%, 25%-40%, 30%-40%, 20%-35%, 25%-35%, 20%-30%, 25%-30%, 26%-34%, 27%-33%, 28%-32%, or about 20%, 21%, 22%, 23%, 24%, 25%, 26%, 27%, 28%, 29%, 30%, 31%, 32%, 33%, 34%, 35%, 36%, 37%, 38%, 39%, or 40% of the nucleotides in the double-stranded region of the second interfering RNA (e.g., siRNA) comprise modified nucleotides such as, e.g., 2'OMe nucleotides (e.g., 2'OMe-guanosine and/or 2'OMe-uridine nucleotides).

In certain embodiments, the second interfering RNA (e.g., siRNA) of the invention comprises a 3' overhang in one or both strands of the interfering RNA. In one particular embodiment, the antisense strand comprises a 5'-dTdT-3' (i.e., 5'-TT-3') overhang or a 5'-UC-3' overhang and the sense strand comprises a 5'-dTdT-3' (i.e., 5'-TT-3') overhang or a 5'-GU-3' overhang. In certain instances, the 3' overhangs on one or both strands of the interfering RNA (e.g., siRNA) comprise at least one 2'OMe nucleotide, e.g., at least one 2'OMe-guanosine and/or 2'OMe-uridine nucleotide. In other embodiments, the 3' overhangs on one or both strands of the interfering RNA (e.g., siRNA) comprise 1-4 deoxythymidine (dT) nucleotides, 1-4 modified and/or unmodified uridine (U) ribonucleotides, or 1-2 additional ribonucleotides having complementarity to the target sequence or the complementary strand thereof.

In some embodiments, the second interfering RNA (e.g., siRNA) that silences EBOV VP24 expression comprises a modified sense strand having the following sequence: 5'-UCCUCGACACGAAUGCAAA-3', wherein the underlined nucleotides indicate potential sites for the introduction of modified nucleotides such as 2'OMe nucleotides. As such, in certain instances, any one or a combination of 2, 3, 4, 5, or all 6 of the underlined nucleotides in the sense strand can be modified, e.g., 2'OMe modified. In certain other instances, the sense strand may further comprise at least 1, 2, 3, 4, 5, 6, 7, 8, 9, 10, 11, 12, or 13 modified adenosine and/or cytosine nucleotides, e.g., 2'OMe-adenosine and/or 2'OMe-cytosine nucleotides. In further instances, the sense strand may comprise a 5'-GU-3' overhang, wherein any one or both of the nucleotides in the overhang can be modified, e.g., 2'OMe modified.

In one particular embodiment, the sense strand of the second interfering RNA (e.g., siRNA) comprises the following sequence: 5'-UCCUCGACACGAAUGCAAA-3', wherein the bolded and underlined nucleotides are 2'OMe nucleotides. In certain instances, the sense strand may further comprise 2'OMe-adenosine and/or 2'OMe-cytosine nucleotides. In certain other instances, the sense strand may comprise a 5'-GU-3' overhang, wherein any one or both of the nucleotides in the overhang can be modified, e.g., 2'OMe modified. Table 3 below sets forth exemplary sense strand sequences for the second interfering RNA (e.g., siRNA) that silences EBOV VP24 expression, wherein the underlined nucleotides are 2'OMe nucleotides.

TABLE 3

| | |
|---|---|
| 5'-UCC**U**CGACACGAA**U**GCAAAGU-3' | 5'-UCC**U**CGACAC**G**AA**U**GCAAAGU-3' |
| 5'-UCC**U**CGACACGAA**U**GCAAA**G**U-3' | 5'-UCC**U**CGACAC**G**AA**U**GCAAA**G**U-3' |
| 5'-UCC**U**CGACACGAA**U**GCAAAG**U**-3' | 5'-UCC**U**CGACAC**G**AA**U**GCAAAG**U**-3' |
| 5'-UCC**U**CGACACGAA**U**GCAAA**GU**-3' | 5'-UCC**U**CGACACGAAU**G**CAAAGU-3' |
| 5'-**U**CC**U**CGACACGAA**U**GCAAAGU-3' | 5'-UCC**U**CGACACGAAU**G**CAAA**G**U-3' |
| 5'-**U**CC**U**CGACACGAA**U**GCAAA**G**U-3' | 5'-UCC**U**CGACACGAAU**G**CAAAG**U**-3' |
| 5'-**U**CC**U**CGACACGAA**U**GCAAAG**U**-3' | 5'-**U**CCUC**G**ACACGAAU**G**CAAAGU-3' |
| 5'-**U**CC**U**CGACACGAAUGCAAAGU-3' | 5'-**U**CCUC**G**ACACGAAU**G**CAAA**G**U-3' |
| 5'-**U**CC**U**CGACACGAAUGCAAA**G**U-3' | 5'-**U**CCUC**G**ACACGAAU**G**CAAAG**U**-3' |
| 5'-**U**CC**U**CGACACGAAUGCAAAG**U**-3' | 5'-**U**CCUCGACAC**G**AAU**G**CAAAGU-3' |
| 5'-**U**CC**U**CGACACGAAUGCAAAGU-3' | 5'-**U**CCUCGACAC**G**AAU**G**CAAA**G**U-3' |
| 5'-**U**CC**U**CGACACGAAUGCAAA**G**U-3' | 5'-**U**CCUCGACAC**G**AAU**G**CAAAG**U**-3' |
| 5'-**U**CC**U**CGACACGAAUGCAAAG**U**-3' | 5'-UCCUC**G**ACACGAA**U**GCAAAGU-3' |
| 5'-**U**CCUCGACACGAA**U**GCAAAGU-3' | 5'-UCCUC**G**ACACGAA**U**GCAAA**G**U-3' |
| 5'-**U**CCUCGACACGAA**U**GCAAA**G**U-3' | 5'-UCCUC**G**ACACGAA**U**GCAAAG**U**-3' |
| 5'-**U**CCUCGACACGAA**U**GCAAAG**U**-3' | 5'-UCCUC**G**ACAC**G**AA**U**GCAAAGU-3' |
| 5'-UCCUC**G**ACAC**G**AAU**G**CAAAGU-3' | 5'-UCCUC**G**ACAC**G**AA**U**GCAAA**G**U-3' |
| 5'-UCCUC**G**ACAC**G**AAU**G**CAAA**G**U-3' | 5'-UCCUC**G**ACAC**G**AA**U**GCAAAG**U**-3' |
| 5'-UCCUC**G**ACAC**G**AAU**G**CAAAG**U**-3' | 5'-UCC**U**C**G**ACAC**G**AAUGCAAAGU-3' |

TABLE 3-continued

| | |
|---|---|
| 5'-UCCUC**G**ACAC**G**AAUGCAAAGU-3' | 5'-UCC**U**C**G**ACAC**G**AAUGCAAA**G**U-3' |
| 5'-UCCUC**G**ACAC**G**AAUGCAAA**G**U-3' | 5'-UCC**U**C**G**ACAC**G**AAUGCAAAG**U**-3' |
| 5'-UCCUC**G**ACAC**G**AAUGCAAAG**U**-3' | 5'-UCC**U**C**G**ACAC**G**AAUGCAAAGU-3' |
| 5'-UCCUC**G**ACACGAAU**G**CAAAGU-3' | 5'-UCC**U**C**G**ACACGAAU**G**CAAA**G**U-3' |
| 5'-UCCUC**G**ACACGAAU**G**CAAA**G**U-3' | 5'-UCC**U**C**G**ACACGAAU**G**CAAAG**U**-3' |
| 5'-UCCUC**G**ACACGAAU**G**CAAAG**U**-3' | 5'-**U**CC**U**CGACAC**G**AAUGCAAAGU-3' |
| 5'-UCCUCGACAC**G**AAU**G**CAAAGU-3' | 5'-**U**CC**U**CGACAC**G**AAUGCAAA**G**U-3' |
| 5'-UCCUCGACAC**G**AAU**G**CAAA**G**U-3' | 5'-**U**CC**U**CGACAC**G**AAUGCAAAG**U**-3' |
| 5'-UCCUCGACAC**G**AAU**G**CAAAG**U**-3' | 5'-**U**CC**U**CGACACGAAU**G**CAAAGU-3' |
| 5'-UCC**U**CGACAC**G**AAUGCAAAGU-3' | 5'-**U**CC**U**CGACACGAAU**G**CAAA**G**U-3' |
| 5'-UCC**U**CGACAC**G**AAUGCAAA**G**U-3' | 5'-**U**CC**U**CGACACGAAU**G**CAAAG**U**-3' |
| 5'-UCC**U**CGACAC**G**AAUGCAAAG**U**-3' | 5'-UCC**U**CGACAC**G**AA**UG**CAAAGU-3' |
| 5'-UCC**U**CGACACGAAU**G**CAAAGU-3' | 5'-UCC**U**CGACAC**G**AA**UG**CAAA**G**U-3' |
| 5'-UCC**U**CGACACGAAU**G**CAAA**G**U-3' | 5'-UCC**U**CGACAC**G**AA**UG**CAAAG**U**-3' |
| 5'-UCC**U**CGACACGAAU**G**CAAAG**U**-3' | 5'-UCC**U**C**G**ACACGAA**UG**CAAAGU-3' |
| 5'-UCC**U**C**G**ACACGAAUGCAAAGU-3' | 5'-UCC**U**C**G**ACACGAA**UG**CAAA**G**U-3' |
| 5'-UCC**U**C**G**ACACGAAUGCAAA**G**U-3' | 5'-UCC**U**C**G**ACACGAA**UG**CAAAG**U**-3' |
| 5'-UCC**U**C**G**ACACGAAUGCAAAG**U**-3' | 5'-**U**CC**U**CGACACGAA**UG**CAAAGU-3' |
| 5'-UCC**U**CGACAC**G**AAU**G**CAAAGU-3' | 5'-**U**CC**U**CGACACGAA**UG**CAAA**G**U-3' |
| 5'-UCC**U**CGACAC**G**AAU**G**CAAA**G**U-3' | 5'-**U**CC**U**CGACACGAA**UG**CAAAG**U**-3' |
| 5'-UCC**U**CGACAC**G**AAU**G**CAAAG**U**-3' | 5'-**U**CC**U**C**G**ACACGAA**UG**CAAAGU-3' |
| 5'-UCC**U**C**G**ACAC**G**AA**U**GCAAAGU-3' | 5'-**U**CC**U**C**G**ACACGAA**UG**CAAA**G**U-3' |
| 5'-UCC**U**C**G**ACAC**G**AA**U**GCAAA**G**U-3' | 5'-**U**CC**U**C**G**ACACGAA**UG**CAAAG**U**-3' |
| 5'-UCC**U**C**G**ACAC**G**AA**U**GCAAAG**U**-3' | 5'-**U**CC**U**C**G**ACAC**G**AA**UG**CAAAGU-3' |

In other embodiments, the second interfering RNA (e.g., siRNA) that silences EBOV VP24 expression comprises a modified antisense strand having the following sequence: 5'-UUUGCAUUCGUGUCGAGGA-3', wherein the underlined nucleotides indicate potential sites for the introduction of modified nucleotides such as 2'OMe nucleotides. As such, in certain instances, any one or a combination of 2, 3, 4, 5, 6, 7, 8, 9, 10, 11, 12, or all 13 of the underlined nucleotides in the antisense strand can be modified, e.g., 2'OMe modified. In certain other instances, the antisense strand may further comprise at least 1, 2, 3, 4, 5, or 6 modified adenosine and/or cytosine nucleotides, e.g., 2'OMe-adenosine and/or 2'OMe-cytosine nucleotides. In further instances, the antisense strand may comprise a 5'-UC-3' overhang, wherein any one or both of the nucleotides in the overhang can be modified, e.g., 2'OMe modified.

In one particular embodiment, the antisense strand of the second interfering RNA (e.g., siRNA) comprises the following sequence: 5'-UUUGCAUUCGUGUCGAGGA-3', wherein the bolded and underlined nucleotides are 2'OMe nucleotides. In certain instances, the antisense strand may further comprise 2'OMe-adenosine and/or 2'OMe-cytosine nucleotides. In certain other instances, the antisense strand may comprise a 5'-UC-3' overhang, wherein any one or both of the nucleotides in the overhang can be modified, e.g., 2'OMe modified. Table 4 below sets forth exemplary antisense strand sequences for the second interfering RNA (e.g., siRNA) that silences EBOV VP24 expression, wherein the underlined nucleotides are 2'OMe nucleotides.

TABLE 4

| | |
|---|---|
| 5'-UU**U**GCAUUCGUGUC**G**AG**G**AUC-3' | 5'-U**U**UGCAU**U**CGUGUC**G**AGGAUC-3' |
| 5'-UU**U**GCAUUCGUGUC**G**AG**G**A**U**C-3' | 5'-U**U**UGCAU**U**CGUGUC**G**AGGA**U**C-3' |
| 5'-U**U**UGCAU**U**CGUG**U**CGAGGAUC-3' | 5'-U**U**UGCAUUC**G**UG**U**CGAGGAUC-3' |
| 5'-U**U**UGCAU**U**CGUG**U**CGAGGA**U**C-3' | 5'-U**U**UGCAUUC**G**UG**U**CGAGGA**U**C-3' |
| 5'-**U**U**U**GCAUUCGUG**U**CGAGGAUC-3' | 5'-U**U**UGCA**U**UCG**U**GUCGA**G**GAUC-3' |
| 5'-**U**U**U**GCAUUCGUG**U**CGAGGA**U**C-3' | 5'-U**U**UGCA**U**UCG**U**GUCGA**G**GA**U**C-3' |
| 5'-U**U**UGCA**U**UCG**U**GUCGAGGAUC-3' | 5'-UUU**G**CAU**U**CGU**G**UCGAGGAUC-3' |
| 5'-U**U**UGCA**U**UCG**U**GUCGAGGA**U**C-3' | 5'-UUU**G**CAU**U**CGU**G**UCGAGGA**U**C-3' |
| 5'-UU**U**GCAUUCGUG**U**CGAGGAUC-3' | 5'-UUUGCAU**U**CGUGUC**G**AG**G**AUC-3' |
| 5'-UU**U**GCAUUCGUG**U**CGAGGA**U**C-3' | 5'-UUUGCAU**U**CGUGUC**G**AG**G**A**U**C-3' |
| 5'-U**U**UGCAUUCG**U**GUCGAGGAUC-3' | 5'-U**U**UGCAUUCGUGUC**G**AG**G**AUC-3' |
| 5'-U**U**UGCAUUCG**U**GUCGAGGA**U**C-3' | 5'-U**U**UGCAUUCGUGUC**G**AG**G**A**U**C-3' |
| 5'-**U**UUGCAU**U**CGUGUCGAGGAUC-3' | 5'-UUUGCA**U**UCGUGUC**G**AG**G**AUC-3' |
| 5'-**U**UUGCAU**U**CGUGUCGAGGA**U**C-3' | 5'-UUUGCA**U**UCGUGUC**G**AG**G**A**U**C-3' |
| 5'-U**U**UGCA**U**UCGUGUCGAGGAUC-3' | 5'-U**UU**GCAUUCGUGUC**G**AG**G**AUC-3' |
| 5'-U**U**UGCA**U**UCGUGUCGAGGA**U**C-3' | 5'-**UUU**GCAUUCGUGUC**G**AG**G**A**U**C-3' |
| 5'-U**U**UGCAU**U**CG**U**G**U**CGAGGAUC-3' | 5'-**UU**UGCAUUCGUGUC**G**AG**G**AUC-3' |

TABLE 4-continued

| | |
|---|---|
| 5'-U**U**UGCAU**U**CG**U**G**U**CGAGGA**U**C-3' | 5'-**UU**UGCAUUCGUGUC**G**AG**G**A**U**C-3' |
| 5'-**U**U**U**GCA**U**UCG**U**GUCGAGGAUC-3' | 5'-UUUGCA**UU**CGUGUC**G**AG**G**AUC-3' |
| 5'-**U**U**U**GCA**U**UCG**U**GUCGAGGA**U**C-3' | 5'-UUUGCA**UU**CGUGUC**G**AG**G**A**U**C-3' |
| 5'-UUU**G**CAUUC**G**U**G**UCGAG**G**AUC-3' | 5'-UU**U**GCAUUCG**UG**UC**G**AG**G**AUC-3' |
| 5'-UUU**G**CAUUC**G**U**G**UCGAG**G**A**U**C-3' | 5'-UU**U**GCAUUCG**UG**UC**G**AG**G**A**U**C-3' |
| 5'-UUU**G**CAUUC**G**U**G**UC**G**AGGAUC-3' | 5'-UU**U**GCAUUC**GU**GUC**G**AG**G**AUC-3' |
| 5'-UUU**G**CAUUC**G**U**G**UC**G**AGGA**U**C-3' | 5'-UU**U**GCAUUC**GU**GUC**G**AG**G**A**U**C-3' |
| 5'-UUU**G**CAUUC**G**U**G**UCGAGGAUC-3' | 5'-UU**U**GCAUUCGU**GU**C**G**AG**G**AUC-3' |
| 5'-UUU**G**CAUUC**G**U**G**UCGAGGA**U**C-3' | 5'-UU**U**GCAUUCGU**GU**C**G**AG**G**A**U**C-3' |
| 5'-UUUGCAUUC**G**UGUCGA**G**GAUC-3' | 5'-UU**U**GCAUUCG**UGU**C**G**AG**G**AUC-3' |
| 5'-UUUGCAUUC**G**UGUCGA**G**GA**U**C-3' | 5'-UU**U**GCAUUCG**UGU**C**G**AG**G**A**U**C-3' |
| 5'-UUUGCAUUC**G**UGUCGA**G**GAUC-3' | 5'-UU**U**GCAUUCGUGUC**G**A**GG**AUC-3' |
| 5'-UUUGCAUUC**G**UGUCGA**G**GA**U**C-3' | 5'-UU**U**GCAUUCGUGUC**G**A**GG**A**U**C-3' |
| 5'-UUU**G**CAUUCGU**G**UCGAG**G**AUC-3' | 5'-**UUU**GCAUUCGUGUC**G**AG**G**AUC-3' |
| 5'-UUU**G**CAUUCGU**G**UCGAG**G**A**U**C-3' | 5'-**UUU**GCAUUCGUGUC**G**AG**G**A**U**C-3' |
| 5'-UUU**G**CAUUCGUGUC**G**AGGAUC-3' | 5'-UU**UG**CAUUCGUGUC**G**AG**G**AUC-3' |
| 5'-UUU**G**CAUUCGUGUC**G**AGGA**U**C-3' | 5'-UU**UG**CAUUCGUGUC**G**AG**G**A**U**C-3' |
| 5'-UUU**G**CAUUCG**U**GUCGAG**G**AUC-3' | 5'-U**UUG**CAUUCGUGUC**G**AG**G**AUC-3' |
| 5'-UUU**G**CAUUCG**U**GUCGAG**G**A**U**C-3' | 5'-**UUUG**CA**UU**C**GUGU**C**G**A**GG**AUC-3' |

In one preferred embodiment, the second interfering RNA (e.g., siRNA) that silences EBOV VP24 expression comprises: an antisense strand comprising the sequence 5'-UUUGCAUUCGUGUCGAGGA-3' and at least one, two, three, four, five, six, seven, or more 2'OMe nucleotides, e.g., at least one, two, three, four, five, six, seven, or more 2'OMe-guanosine and/or 2'OMe-uridine nucleotides; and a sense strand comprising the sequence 5'-UCCUCGACACGAAUGCAAAGU-3' and at least one, two, three, four, five, six, seven, or more 2'OMe nucleotides, e.g., at least one, two, three, four, five, six, seven, or more 2'OMe-guanosine and/or 2'OMe-uridine nucleotides. In another preferred embodiment, the second interfering RNA (e.g., siRNA) that silences EBOV VP24 expression comprises: a sense strand comprising nucleotides 1-19 of any one of the sense strand sequences set forth in Table 3; and an antisense strand comprising nucleotides 1-19 of any one of the antisense strand sequences set forth in Table 4. In a particularly preferred embodiment, the second interfering RNA (e.g., siRNA) that silences EBOV VP24 expression consists of: a sense strand selected from any one of the sense strand sequences set forth in Table 3; and an antisense strand selected from any one of the antisense strand sequences set forth in Table 4. In additional embodiments, the sense strand and/or antisense strand of the second interfering RNA (e.g., siRNA) molecule may further comprise at least 1, 2, 3, 4, 5, 6, 7, 8, 9, 10, 11, 12, or 13 2'OMe-adenosine and/or 2'OMe-cytosine nucleotides.

In particular embodiments, the compositions of the present invention comprise the second interfering RNA (e.g., siRNA) comprising any one of the sense strand sequences set forth in Table 3 (or nucleotides 1-19 thereof) and any one of the antisense strand sequences set forth in Table 4 (or nucleotides 1-19 thereof) in combination with (1) the first interfering RNA (e.g., siRNA) comprising any one of the sense strand sequences set forth in Table 1 (or nucleotides 1-19 thereof) and any one of the antisense strand sequences set forth in Table 2 (or nucleotides 1-19 thereof), (2) the third interfering RNA (e.g., siRNA) comprising any one of the sense strand sequences set forth in Table 5 (or nucleotides 1-19 thereof) and any one of the antisense strand sequences set forth in Table 6 (or nucleotides 1-19 thereof), or (3) both the first and third interfering RNA (e.g., siRNA) described in (1) and (2).

In one particular embodiment, the second interfering RNA (e.g., siRNA) that silences EBOV VP24 expression consists of the following sense and antisense strand sequences:

5'-UCCUCGACACGAAUGCAAAGU-3'

3'-CUAGGAGCUGUGCUUACGUUU-5', ("VP24-1160 mod"), wherein the bolded and underlined nucleotides are 2'OMe nucleotides.

In some embodiments, the third interfering RNA (e.g., siRNA) further comprises a sense strand comprising the following sequence: 5'-GCAACUCAUUGGACAUCAU-3'. In some aspects of these embodiments, the third interfering RNA (e.g., siRNA) comprises at least one 2'OMe nucleotide, e.g., at least one 2'OMe-guanosine and/or 2'OMe-uridine nucleotide. In certain instances, the third interfering RNA comprises an antisense strand comprising at least one, at least two, at least three, at least four, at least five, at least six, at least seven, or more 2'OMe nucleotides, e.g., 2'OMe-guanosine and/or 2'OMe-uridine nucleotides. In certain other instances, the third interfering RNA comprises a sense strand comprising at least one, at least two, at least three, at least four, at least five, at least six, at least seven, or more 2'OMe nucleotides, e.g., 2'OMe-guanosine and/or 2'OMe-uridine nucleotides. In further instances, the antisense strand and/or sense strand may further comprise at least one, at least two, at least three, at least four, at least five, at least six, at least seven, or more 2'OMe-adenosine and/or 2'OMe-cytosine nucleotides.

In particular embodiments, from about 20%-40%, 25%-40%, 30%-40%, 20%-35%, 25%-35%, 20%-30%, 25%-30%, 26%-34%, 27%-33%, 28%-32%, or about 20%, 21%, 22%, 23%, 24%, 25%, 26%, 27%, 28%, 29%, 30%, 31%, 32%, 33%, 34%, 35%, 36%, 37%, 38%, 39%, or 40% of the nucleotides in the double-stranded region of the third interfering RNA (e.g., siRNA) comprise modified nucleotides such as, e.g., 2'OMe nucleotides (e.g., 2'OMe-guanosine and/or 2'OMe-uridine nucleotides).

In certain embodiments, the third interfering RNA (e.g., siRNA) of the invention comprises a 3' overhang in one or both strands of the interfering RNA. In one particular embodiment, the antisense strand comprises a 5'-dTdT-3' (i.e., 5'-TT-3') overhang or a 5'-UA-3' overhang and the sense strand comprises a 5'-dTdT-3' (i.e., 5'-TT-3') overhang or a 5'-UC-3' overhang. In certain instances, the 3' overhangs on one or both strands of the interfering RNA (e.g., siRNA) comprise at least one 2'OMe nucleotide, e.g., at least one 2'OMe-guanosine and/or 2'OMe-uridine nucleotide. In other embodiments, the 3' overhangs on one or both strands of the interfering RNA (e.g., siRNA) comprise 1-4 deoxythymidine (dT) nucleotides, 1-4 modified and/or unmodified uridine (U) ribonucleotides, or 1-2 additional ribonucleotides having complementarity to the target sequence or the complementary strand thereof.

In some embodiments, the third interfering RNA (e.g., siRNA) that silences EBOV VP35 expression comprises one of the following sense strand sequences set forth in Table 5, wherein the underlined nucleotides are 2'OMe nucleotides.

TABLE 5

| Name | Sense Strand Sequence |
|---|---|
| S-1 | 5'-GCAAC**U**CAUUG**G**ACA**U**CAUUC-3' |
| S-2 | 5'-**G**CAAC**U**CAU**U**G**G**ACA**U**CA**UU**C-3' |
| S-3 | 5'-GCAAC**U**CAU**U**G**G**ACA**U**CAU**U**C-3' |
| S-4 | 5'-**G**CAAC**U**CA**UU**G**G**ACA**U**CAUUC-3' |
| S-5 | 5'-**G**CAAC**U**CA**U**U**GG**ACA**U**CAUUC-3' |
| S-6 | 5'-**G**CAAC**U**CA**U**UG**G**ACA**U**CA**U**UC-3' |
| S-7 | 5'-**G**CAAC**U**CA**U**UG**G**ACA**U**CAU**U**C-3' |
| S-8 | 5'-**G**CAAC**U**CAU**UGG**ACA**U**CAUUC-3' |
| S-9 | 5'-**G**CAAC**U**CAU**U**G**G**ACA**U**CA**U**UC-3' |
| S-10 | 5'-**G**CAAC**U**CAU**U**G**G**ACA**U**CAU**U**C-3' |
| S-11 | 5'-**G**CAAC**U**CAUU**GG**ACA**U**CA**U**UC-3' |
| S12 | 5'-**G**CAAC**U**CAUU**GG**ACA**U**CAU**U**C-3' |
| S-13 | 5'-**G**CAAC**U**CAUUG**G**ACA**U**CA**UU**C-3' |
| S-14 | 5'-GCAAC**U**CA**UUGG**ACA**U**CAUUC-3' |
| S-15 | 5'-GCAAC**U**CA**UU**G**G**ACA**U**CA**U**UC-3' |
| S-16 | 5'-GCAAC**U**CA**UU**G**G**ACA**U**CAU**U**C-3' |
| S-17 | 5'-GCAAC**U**CA**U**U**GG**ACA**U**CA**U**UC-3' |
| S-18 | 5'-GCAAC**U**CA**U**U**GG**ACA**U**CAU**U**C-3' |
| S-19 | 5'-GCAAC**U**CA**U**UG**G**ACA**U**CA**UU**C-3' |
| S-20 | 5'-GCAAC**U**CAU**UGG**ACA**U**CA**U**UC-3' |
| S-21 | 5'-GCAAC**U**CAU**UGG**ACA**U**CAU**U**C-3' |
| S-22 | 5'-GCAAC**U**CAU**U**G**G**ACA**U**CA**UU**C-3' |
| S-23 | 5'-GCAAC**U**CAUU**GG**ACA**U**CA**UU**C-3' |
| S-24 | 5'-**G**CAAC**U**CA**UUGG**ACA**U**CAUUC-3' |
| S-25 | 5'-**G**CAAC**U**CA**UU**G**G**ACA**U**CA**U**UC-3' |
| S-26 | 5'-**G**CAAC**U**CA**UU**G**G**ACA**U**CAU**U**C-3' |
| S-27 | 5'-**G**CAAC**U**CA**U**U**GG**ACA**U**CA**U**UC-3' |
| S-28 | 5'-**G**CAAC**U**CA**U**U**GG**ACA**U**CAU**U**C-3' |
| S-29 | 5'-**G**CAAC**U**CA**U**UG**G**ACA**U**CA**UU**C-3' |

TABLE 5-continued

| Name | Sense Strand Sequence |
|---|---|
| S-30 | 5'-GCAACUCAUUGGACAUCAUUC-3' |
| S-31 | 5'-GCAACUCAUUGGACAUCAUUC-3' |
| S-32 | 5'-GCAACUCAUUGGACAUCAUUC-3' |
| S-33 | 5'-GCAACUCAUUGGACAUCAUUC-3' |
| S-34 | 5'-GCAACUCAUUGGACAUCAUUC-3' |
| S-35 | 5'-GCAACUCAUUGGACAUCAUUC-3' |
| S-36 | 5'-GCAACUCAUUGGACAUCAUUC-3' |
| S-37 | 5'-GCAACUCAUUGGACAUCAUUC-3' |

In other embodiments, the third interfering RNA (e.g., siRNA) that silences EBOV VP35 expression comprises one of the following antisense strand sequences set forth in Table 6, wherein the underlined nucleotides are 2'OMe nucleotides.

TABLE 6

| Name | Antisense Strand Sequence |
|---|---|
| AS-1 | 5'-AUGAUGUCCAAUGAGUUGCUA-3' |
| AS-2 | 5'-AUGAUGUCCAAUGAGUUGCUA-3' |
| AS-3 | 5'-AUGAUGUCCAAUGAGUUGCUA-3' |
| AS-4 | 5'-AUGAUGUCCAAUGAGUUGCUA-3' |
| AS-5 | 5'-AUGAUGUCCAAUGAGUUGCUA-3' |
| AS-6 | 5'-AUGAUGUCCAAUGAGUUGCUA-3' |
| AS-7 | 5'-AUGAUGUCCAAUGAGUUGCUA-3' |
| AS-8 | 5'-AUGAUGUCCAAUGAGUUGCUA-3' |
| AS-9 | 5'-AUGAUGUCCAAUGAGUUGCUA-3' |
| AS-10 | 5'-AUGAUGUCCAAUGAGUUGCUA-3' |
| AS-11 | 5'-AUGAUGUCCAAUGAGUUGCUA-3' |
| AS-12 | 5'-AUGAUGUCCAAUGAGUUGCUA-3' |
| AS-13 | 5'-AUGAUGUCCAAUGAGUUGCUA-3' |
| AS-14 | 5'-AUGAUGUCCAAUGAGUUGCUA-3' |
| AS-15 | 5'-AUGAUGUCCAAUGAGUUGCUA-3' |
| AS-16 | 5'-AUGAUGUCCAAUGAGUUGCUA-3' |
| AS-17 | 5'-AUGAUGUCCAAUGAGUUGCUA-3' |
| AS-18 | 5'-AUGAUGUCCAAUGAGUUGCUA-3' |
| AS-19 | 5'-AUGAUGUCCAAUGAGUUGCUA-3' |
| AS-20 | 5'-AUGAUGUCCAAUGAGUUGCUA-3' |
| AS-21 | 5'-AUGAUGUCCAAUGAGUUGCUA-3' |
| AS-22 | 5'-AUGAUGUCCAAUGAGUUGCUA-3' |
| AS-23 | 5'-AUGAUGUCCAAUGAGUUGCUA-3' |
| AS-24 | 5'-AUGAUGUCCAAUGAGUUGCUA-3' |
| AS-25 | 5'-AUGAUGUCCAAUGAGUUGCUA-3' |

TABLE 6-continued

| Name | Antisense Strand Sequence |
|---|---|
| AS-26 | 5'-AUGAUGUCCAAUGAGUUGCUA-3' |
| AS-27 | 5'-AUGAUGUCCAAUGAGUUGCUA-3' |
| AS-28 | 5'-AUGAUGUCCAAUGAGUUGCUA-3' |
| AS-29 | 5'-AUGAUGUCCAAUGAGUUGCUA-3' |
| AS-30 | 5'-AUGAUGUCCAAUGAGUUGCUA-3' |
| AS-31 | 5'-AUGAUGUCCAAUGAGUUGCUA-3' |
| AS-32 | 5'-AUGAUGUCCAAUGAGUUGCUA-3' |
| AS-33 | 5'-AUGAUGUCCAAUGAGUUGCUA-3' |
| AS-34 | 5'-AUGAUGUCCAAUGAGUUGCUA-3' |
| AS-35 | 5'-AUGAUGUCCAAUGAGUUGCUA-3' |
| AS-36 | 5'-AUGAUGUCCAAUGAGUUGCUA-3' |
| AS-37 | 5'-AUGAUGUCCAAUGAGUUGCUA-3' |
| AS-38 | 5'-AUGAUGUCCAAUGAGUUGCUA-3' |
| AS-39 | 5'-AUGAUGUCCAAUGAGUUGCUA-3' |
| AS-40 | 5'-AUGAUGUCCAAUGAGUUGCUA-3' |
| AS-41 | 5'-AUGAUGUCCAAUGAGUUGCUA-3' |
| AS-42 | 5'-AUGAUGUCCAAUGAGUUGCUA-3' |
| AS-43 | 5'-AUGAUGUCCAAUGAGUUGCUA-3' |
| AS-44 | 5'-AUGAUGUCCAAUGAGUUGCUA-3' |
| AS-45 | 5'-AUGAUGUCCAAUGAGUUGCUA-3' |
| AS-46 | 5'-AUGAUGUCCAAUGAGUUGCUA-3' |
| AS-47 | 5'-AUGAUGUCCAAUGAGUUGCUA-3' |
| AS-48 | 5'-AUGAUGUCCAAUGAGUUGCUA-3' |
| AS-49 | 5'-AUGAUGUCCAAUGAGUUGCUA-3' |
| AS-50 | 5'-AUGAUGUCCAAUGAGUUGCUA-3' |

In one preferred embodiment, the third interfering RNA (e.g., siRNA) that silences EBOV VP35 expression comprises: an antisense strand comprising the sequence 5'-AUGAUGUCCAAUGAGUUGC-3' and at least one, two, three, four, five, six, seven, or more 2'OMe nucleotides, e.g., at least one, two, three, four, five, six, seven, or more 2'OMe-guanosine and/or 2'OMe-uridine nucleotides; and a sense strand comprising the sequence 5'-GCAACUCAUUGGACAUCAU-3' and at least one, two, three, four, five, six, seven, or more 2'OMe nucleotides, e.g., at least one, two, three, four, five, six, seven, or more 2'OMe-guanosine and/or 2'OMe-uridine nucleotides. In another preferred embodiment, the third interfering RNA (e.g., siRNA) that silences EBOV VP35 expression comprises: a sense strand comprising nucleotides 1-19 of any one of S-1 to S-37 set forth in Table 5; and an antisense strand comprising nucleotides 1-19 of any one of AS-1 to AS-50 set forth in Table 6. In a particularly preferred embodiment, the third interfering RNA (e.g., siRNA) that silences EBOV VP35 expression consists of: a sense strand selected from any one of S-1 to S-37 set forth in Table 5; and an antisense strand selected from any one of AS-1 to AS-50 set forth in Table 6. In additional embodiments, the sense strand and/or antisense strand of the third interfering RNA (e.g., siRNA) may further comprise at least 1, 2, 3, 4, 5, 6, 7, 8, 9, 10, or 11 2'OMe-adenosine and/or 2'OMe-cytosine nucleotides.

In particular embodiments, the compositions of the present invention comprise the third interfering RNA (e.g., siRNA) comprising any one of the sense strand sequences set forth in Table 5 (or nucleotides 1-19 thereof) and any one of the antisense strand sequences set forth in Table 6 (or nucleotides 1-19 thereof) in combination with (1) the first interfering RNA (e.g., siRNA) comprising any one of the sense strand sequences set forth in Table 1 (or nucleotides 1-19 thereof) and any one of the antisense strand sequences set forth in Table 2 (or nucleotides 1-19 thereof), (2) the second interfering RNA (e.g., siRNA) comprising any one of the sense strand sequences set forth in Table 3 (or nucleotides 1-19 thereof) and any one of the antisense strand sequences set forth in Table 4 (or nucleotides 1-19 thereof), or (3) both the first and second interfering RNA (e.g., siRNA) molecules described in (1) and (2).

In one particular embodiment, the third interfering RNA (e.g., siRNA) that silences EBOV VP35 expression consists of the following sense and antisense strand sequences:

5'-GCAACUCAUUGGACAUCAUUC-3'

3'-AUCGUUGAGUAACCUGUAGUA-5', ("S-1+AS-1" or "VP35-855 S1/AS1"), wherein the bolded and underlined nucleotides are 2'OMe nucleotides.

In another particular embodiment, the third interfering RNA (e.g., siRNA) that silences EBOV VP35 expression consists of the following sense and antisense strand sequences:

5'-GCAACUCAUUGGACAUCAUUC-3'

3'-AUCGUUGAGUAACCUGUAGUA-5', ("S-1+AS-2" or "VP35-855 S1/AS2"), wherein the bolded and underlined nucleotides are 2'OMe nucleotides.

In yet another particular embodiment, the third interfering RNA (e.g., siRNA) that silences EBOV VP35 expression consists of the following sense and antisense strand sequences:

5'-GCAACUCAUUGGACAUCAUUC-3'

3'-AUCGUUGAGUAACCUGUAGUA-5', ("S-1+AS-3" or "VP35-855 S1/AS3"), wherein the bolded and underlined nucleotides are 2'OMe nucleotides.

In still yet another particular embodiment, the third interfering RNA (e.g., siRNA) that silences EBOV VP35 expression consists of the following sense and antisense strand sequences:

5'-GCAACUCAUUGGACAUCAUUC-3'

3'-AUCGUUGAGUAACCUGUAGUA-5', ("S-1+AS-4" or "VP35-855 S1/AS4"), wherein the bolded and underlined nucleotides are 2'OMe nucleotides.

In another particular embodiment, the third interfering RNA (e.g., siRNA) that silences EBOV VP35 expression consists of the following sense and antisense strand sequences:

5'-GCAACUCAUUGGACAUCAUUC-3'

3'-AUCGUUGAGUAACCUGUAGUA-5', ("S-1+AS-5" or "VP35-855 S1/AS5"), wherein the bolded and underlined nucleotides are 2'OMe nucleotides.

In yet another particular embodiment, the third interfering RNA (e.g., siRNA) that silences EBOV VP35 expression consists of the following sense and antisense strand sequences:

5'-GCAACUCAUUGGACAUCAUUC-3'

3'-AUCGUUGAGUAACCUGUAGUA-5', ("S-2+AS-1" or "VP35-855 S2/AS1"), wherein the bolded and underlined nucleotides are 2'OMe nucleotides.

In still yet another particular embodiment, the third interfering RNA (e.g., siRNA) that silences EBOV VP35 expression consists of the following sense and antisense strand sequences:

5'-GCAACUCAUUGGACAUCAUUC-3'

3'-AUCGUUGAGUAACCUGUAGUA-5', ("S-2+AS-2" or "VP35-855 S2/AS2"), wherein the bolded and underlined nucleotides are 2'OMe nucleotides.

In another particular embodiment, the third interfering RNA (e.g., siRNA) that silences EBOV VP35 expression consists of the following sense and antisense strand sequences:

5'-GCAACUCAUUGGACAUCAUUC-3'

3'-AUCGUUGAGUAACCUGUAGUA-5', ("S-2+AS-3" or "VP35-855 S2/AS3"), wherein the bolded and underlined nucleotides are 2'OMe nucleotides.

In yet another particular embodiment, the third interfering RNA (e.g., siRNA) that silences EBOV VP35 expression consists of the following sense and antisense strand sequences:

5'-GCAACUCAUUGGACAUCAUUC-3'

3'-AUCGUUGAGUAACCUGUAGUA-5', ("S-2+AS-4" or "VP35-855 S2/AS4"), wherein the bolded and underlined nucleotides are 2'OMe nucleotides.

In still yet another particular embodiment, the third interfering RNA (e.g., siRNA) that silences EBOV VP35 expression consists of the following sense and antisense strand sequences:

5'-GCAACUCAUUGGACAUCAUUC-3'

3'-AUCGUUGAGUAACCUGUAGUA-5', ("S-2+AS-5" or "VP35-855 S2/AS5"), wherein the bolded and underlined nucleotides are 2'OMe nucleotides.

In another particular embodiment, the third interfering RNA (e.g., siRNA) that silences EBOV VP35 expression consists of the following sense and antisense strand sequences:

5'-GCAACUCAUUGGACAUCAUUC-3'

3'-AUCGUUGAGUAACCUGUAGUA-5', ("S-3+AS-1" or "VP35-855 S3/AS1"), wherein the bolded and underlined nucleotides are 2'OMe nucleotides.

In yet another particular embodiment, the third interfering RNA (e.g., siRNA) that silences EBOV VP35 expression consists of the following sense and antisense strand sequences:

5'-GCAACUCAUUGGACAUCAUUC-3'

3'-AUCGUUGAGUAACCUGUAGUA-5', ("S-3+AS-2" or "VP35-855 S3/AS2"), wherein the bolded and underlined nucleotides are 2'OMe nucleotides.

In still yet another particular embodiment, the third interfering RNA (e.g., siRNA) that silences EBOV VP35 expression consists of the following sense and antisense strand sequences:

5'-GCAACUCAUUGGACAUCAUUC-3'

3'-AUCGUUGAGUAACCUGUAGUA-5', ("S-3+AS-3" or "VP35-855 S3/AS3"), wherein the bolded and underlined nucleotides are 2'OMe nucleotides.

In another particular embodiment, the third interfering RNA (e.g., siRNA) that silences EBOV VP35 expression consists of the following sense and antisense strand sequences:

5'-GCAACUCAUUGGACAUCAUUC-3'

3'-AUCGUUGAGUAACCUGUAGUA-5', ("S-3+AS-4" or "VP35-855 S3/AS4"), wherein the bolded and underlined nucleotides are 2'OMe nucleotides.

In yet another particular embodiment, the third interfering RNA (e.g., siRNA) that silences EBOV VP35 expression consists of the following sense and antisense strand sequences:

5'-GCAACUCAUUGGACAUCAUUC-3'

3'-AUCGUUGAGUAACCUGUAGUA-5', ("S-3+AS-5" or "VP35-855 S3/AS5"), wherein the bolded and underlined nucleotides are 2'OMe nucleotides.

In particular embodiments, the present invention provides a composition comprising a cocktail (e.g., at least two, three, four, five, six, seven, eight, nine, ten, or more) of siRNAs comprising different double-stranded siRNA sequences based upon mix-and-match annealing of the modified siRNA sequences set forth in Tables 1-6 (e.g., mix-and-match annealing of sequences in Tables 1 and 2, mix-and-match annealing of sequences in Tables 3 and 4; and/or mix-and-match annealing of sequences in Tables 5 and 6). In some embodiments, the present invention provides a composition comprising one of the double-stranded EK-1 siRNAs set forth in Table 11 in combination with one of the double-stranded VP35-855 siRNAs set forth in Table 12. In one aspect of this embodiment, the composition further comprises a double-stranded VP24-1160 siRNA comprising a sense strand sequence set forth in Table 3 and an antisense strand sequence set forth in Table 4.

In other embodiments, the present invention provides a composition comprising at least one or a cocktail of at least two siRNAs selected from unmodified and/or modified EK-1, VP24-1160, and VP35-855 siRNAs. In certain instances, at least one, two, or all three of these EK-1, VP24-1160, and VP35-855 siRNA sequences are chemically modified (e.g., 2'OMe-modified). In preferred embodiments, the present invention provides a composition comprising a cocktail of at least two or all three of the siRNAs selected from modified EK-1, VP24-1160, and VP35-855 siRNAs as described herein.

The present invention also provides a pharmaceutical composition comprising a cocktail of interfering RNA (e.g., siRNA) molecules that target EBOV gene expression (e.g., silence two or all three of L-pol, VP24, and VP35) and a pharmaceutically acceptable carrier.

In another aspect, the present invention provides a nucleic acid-lipid particle (e.g., SNALP) that targets EBOV gene expression. The nucleic acid-lipid particle (e.g., SNALP) typically comprises a cocktail of interfering RNA (e.g., siRNA) molecules that silences multiple EBOV genes (e.g., silences two or all three of the EBOV L-pol, VP24, and VP35 genes), a cationic lipid, and a non-cationic lipid. In certain instances, the nucleic acid-lipid particle (e.g., SNALP) further comprises a conjugated lipid that inhibits aggregation of particles. Preferably, the nucleic acid-lipid particle (e.g., SNALP) comprises a cocktail of unmodified and/or modified interfering RNA (e.g., siRNA) molecules that silences at least two, three, or more EBOV genes, a cationic lipid, a non-cationic lipid, and a conjugated lipid that inhibits aggregation of particles. In one particular embodiment, the nucleic acid-lipid particle (e.g., SNALP) comprises a cocktail of any combination of at least two or all three of the first, second, and third interfering RNA (e.g., siRNA) described above, a cationic lipid, a non-cationic lipid, and a conjugated lipid that inhibits aggregation of particles. In preferred embodiments, the nucleic acid-lipid particle (e.g., SNALP) comprises a cocktail of at least two or all three interfering RNAs (e.g., siRNAs) selected from modified EK-1, VP24-1160, and VP35-855 interfering RNAs (e.g., siRNAs).

In some embodiments, the interfering RNAs (e.g., siRNAs) of the present invention are fully encapsulated in the nucleic acid-lipid particle (e.g., SNALP). With respect to formulations comprising an interfering RNA cocktail, the different types of interfering RNA species present in the cocktail (e.g., interfering RNA compounds with different sequences) may be co-encapsulated in the same particle, or each type of interfering RNA species present in the cocktail may be encapsulated in a separate particle. The interfering RNA cocktail may be formulated in the particles described herein using a mixture of two or more individual interfering RNAs (each having a unique sequence) at identical, similar, or different concentrations or molar ratios. In one embodiment, a cocktail of interfering RNAs (corresponding to a plurality of interfering RNAs with different sequences) is formulated using identical, similar, or different concentrations or molar ratios of each interfering RNA species, and the different types of interfering RNAs are co-encapsulated in the same particle. In another embodiment, each type of interfering RNA species present in the cocktail is encapsulated in different particles at identical, similar, or different interfering RNA concentrations or molar ratios, and the particles thus formed (each containing a different interfering RNA payload) are administered separately (e.g., at different times in accordance with a therapeutic regimen), or are combined and administered together as a single unit dose (e.g., with a pharmaceutically acceptable carrier). In one particular embodiment, a cocktail of two interfering RNAs (e.g., siRNAs) may be formulated as a 1:1 mixture of each interfering RNA species. In another particular embodiment, a cocktail of three interfering RNAs (e.g., siRNAs) may be formulated as a 1:1:1 mixture of each interfering RNA species. The particles described herein are serum-stable, are resistant to nuclease degradation, and are substantially non-toxic to mammals such as humans.

The cationic lipid in the nucleic acid-lipid particles of the present invention (e.g., SNALP) may comprise, e.g., one or more cationic lipids of Formula I-XVI described herein or any other cationic lipid species. In one particular embodiment, the cationic lipid comprises 1,2-dilinoleyloxy-N,N-dimethylaminopropane (DLinDMA), 1,2-dilinolenyloxy-N,N-dimethylaminopropane (DLenDMA), 1,2-di-γ-linolenyloxy-N,N-dimethylaminopropane (γ-DLenDMA), 2,2-dilinoleyl-4-(2-dimethylaminoethyl)-[1,3]-dioxolane (DLin-K-C2-DMA), 2,2-dilinoleyl-4-dimethylaminomethyl-[1,3]-dioxolane (DLin-K-DMA), salts thereof, or a mixture thereof.

The non-cationic lipid in the nucleic acid-lipid particles of the present invention (e.g., SNALP) may comprise, e.g., one or more anionic lipids and/or neutral lipids. In some embodiments, the non-cationic lipid comprises one of the following neutral lipid components: (1) a mixture of a phospholipid and cholesterol or a derivative thereof; (2) cholesterol or a derivative thereof; or (3) a phospholipid. In certain preferred embodiments, the phospholipid comprises dipalmitoylphosphatidylcholine (DPPC), distearoylphosphatidylcholine (DSPC), or a mixture thereof. In a particularly preferred embodiment, the non-cationic lipid is a mixture of DPPC and cholesterol.

The lipid conjugate in the nucleic acid-lipid particles of the invention (e.g., SNALP) inhibits aggregation of particles and may comprise, e.g., one or more of the lipid conjugates described herein. In one particular embodiment, the lipid conjugate comprises a PEG-lipid conjugate. Examples of PEG-lipid conjugates include, but are not limited to, PEG-DAG conjugates, PEG-DAA conjugates, and mixtures thereof. In certain embodiments, the PEG-DAA conjugate in the lipid particle may comprise a PEG-didecyloxypropyl ($C_{10}$) conjugate, a PEG-dilauryloxypropyl ($C_{12}$) conjugate, a PEG-dimyristyloxypropyl ($C_{14}$) conjugate, a PEG-dipalmityloxypropyl ($C_{16}$) conjugate, a PEG-distearyloxypropyl ($C_{18}$) conjugate, or mixtures thereof. In another embodiment, the lipid conjugate comprises a POZ-lipid conjugate such as a POZ-DAA conjugate.

In some embodiments, the present invention provides nucleic acid-lipid particles (e.g., SNALP) comprising: (a) a cocktail of interfering RNAs (e.g., siRNAs) (e.g., two or three siRNAs each independently targeting EBOV L-pol, VP24, or VP35); (b) one or more cationic lipids (e.g., cationic lipids of Formula I-XVI) or salts thereof comprising from about 50 mol % to about 85 mol % of the total lipid present in the particle; (c) one or more non-cationic lipids comprising from about 13 mol % to about 49.5 mol % of the total lipid present in the particle; and (d) one or more conjugated lipids that inhibit aggregation of particles comprising from about 0.5 mol % to about 2 mol % of the total lipid present in the particle.

In one aspect of this embodiment, the nucleic acid-lipid particle comprises: (a) a cocktail of interfering RNAs (e.g., siRNAs) (e.g., two or three siRNAs each independently targeting EBOV L-pol, VP24, or VP35); (b) a cationic lipid (e.g., cationic lipid of Formula I-XVI) or a salt thereof comprising from about 52 mol % to about 62 mol % of the total lipid present in the particle; (c) a mixture of a phospholipid and cholesterol or a derivative thereof comprising from about 36 mol % to about 47 mol % of the total lipid present in the particle; and (d) a PEG-lipid conjugate comprising from about 1 mol % to about 2 mol % of the total lipid present in the particle. This embodiment of nucleic acid-lipid particle is generally referred to herein as the "1:57" formulation. In one particular embodiment, the 1:57 formulation is a four-component system comprising about 1.4 mol % PEG-lipid conjugate (e.g., PEG2000-C-DMA), about 57.1 mol % cationic lipid (e.g., cationic lipid of Formula I-XVI) or a salt thereof, about 7.1 mol % DPPC (or DSPC), and about 34.3 mol % cholesterol (or derivative thereof).

In another aspect of this embodiment, the nucleic acid-lipid particle comprises: (a) a cocktail of interfering RNAs (e.g., siRNAs) (e.g., two or three siRNAs each independently targeting EBOV L-pol, VP24, or VP35); (b) a cationic lipid (e.g., cationic lipid of Formula I-XVI) or a salt thereof comprising from about 56.5 mol % to about 66.5 mol % of the total lipid present in the particle; (c) cholesterol or a derivative thereof comprising from about 31.5 mol % to about 42.5 mol % of the total lipid present in the particle; and (d) a PEG-lipid conjugate comprising from about 1 mol % to about 2 mol % of the total lipid present in the particle. This embodiment of nucleic acid-lipid particle is generally referred to herein as the "1:62" formulation. In one particular embodiment, the 1:62 formulation is a three-component system which is phospholipid-free and comprises about 1.5 mol % PEG-lipid conjugate (e.g., PEG2000-C-DMA), about 61.5 mol % cationic lipid (e.g., cationic lipid of Formula I-XVI) or a salt thereof, and about 36.9 mol % cholesterol (or derivative thereof).

Additional embodiments related to the 1:57 and 1:62 formulations are described in PCT Publication No. WO 09/127060 and U.S. application Ser. No. 12/794,701, filed Jun. 4, 2010, the disclosures of which are herein incorporated by reference in their entirety for all purposes.

In other embodiments, the present invention provides nucleic acid-lipid particles (e.g., SNALP) comprising: (a) a cocktail of interfering RNAs (e.g., siRNAs) (e.g., two or three siRNAs each independently targeting EBOV L-pol, VP24, or VP35); (b) one or more cationic lipids (e.g., cationic lipids of Formula I-XVI) or salts thereof comprising from about 2 mol % to about 50 mol % of the total lipid present in the particle; (c) one or more non-cationic lipids comprising from about 5 mol % to about 90 mol % of the total lipid present in the particle; and (d) one or more conjugated lipids that inhibit aggregation of particles comprising from about 0.5 mol % to about 20 mol % of the total lipid present in the particle.

In one aspect of this embodiment, the nucleic acid-lipid particle comprises: (a) a cocktail of interfering RNAs (e.g., siRNAs) (e.g., two or three siRNAs each independently targeting EBOV L-pol, VP24, or VP35); (b) a cationic lipid (e.g., cationic lipid of Formula I-XVI) or a salt thereof comprising from about 30 mol % to about 50 mol % of the total lipid present in the particle; (c) a mixture of a phospholipid and cholesterol or a derivative thereof comprising from about 47 mol % to about 69 mol % of the total lipid present in the particle; and (d) a PEG-lipid conjugate comprising from about 1 mol % to about 3 mol % of the total lipid present in the particle. This embodiment of nucleic acid-lipid particle is generally referred to herein as the "2:40" formulation. In one particular embodiment, the 2:40 formulation is a four-component system which comprises about 2 mol % PEG-lipid conjugate (e.g., PEG2000-C-DMA), about 40 mol % cationic lipid (e.g., cationic lipid of Formula I-XVI) or a salt thereof, about 10 mol % DPPC (or DSPC), and about 48 mol % cholesterol (or derivative thereof).

In further embodiments, the present invention provides nucleic acid-lipid particles (e.g., SNALP) comprising: (a) a cocktail of interfering RNAs (e.g., siRNAs) (e.g., two or three siRNAs each independently targeting EBOV L-pol, VP24, or VP35); (b) one or more cationic lipids (e.g., cationic lipids of Formula I-XVI) or salts thereof comprising from about 50 mol % to about 65 mol % of the total lipid present in the particle; (c) one or more non-cationic lipids comprising from about 25 mol % to about 45 mol % of the total lipid present in the particle; and (d) one or more conjugated lipids that inhibit aggregation of particles comprising from about 5 mol % to about 10 mol % of the total lipid present in the particle.

In one aspect of this embodiment, the nucleic acid-lipid particle comprises: (a) a cocktail of interfering RNAs (e.g., siRNAs) (e.g., two or three siRNAs each independently targeting EBOV L-pol, VP24, or VP35); (b) a cationic lipid (e.g., cationic lipid of Formula I-XVI) or a salt thereof comprising from about 50 mol % to about 60 mol % of the total lipid present in the particle; (c) a mixture of a phospholipid and cholesterol or a derivative thereof comprising from about 35 mol % to about 45 mol % of the total lipid present in the particle; and (d) a PEG-lipid conjugate comprising from about 5 mol % to about 10 mol % of the total lipid present in the particle. This embodiment of nucleic acid-lipid particle is generally referred to herein as the "7:54" formulation. In certain instances, the non-cationic lipid mixture in the 7:54 formulation comprises: (i) a phospholipid of from about 5 mol % to about 10 mol % of the total lipid present in the particle; and (ii) cholesterol or a derivative thereof of from about 25 mol % to about 35 mol % of the total lipid present in the particle. In one particular embodiment, the 7:54 formulation is a four-component system comprising about 7 mol % PEG-lipid conjugate (e.g., PEG750-C-DMA), about 54 mol % cationic lipid (e.g., cationic lipid of Formula I-XVI) or a salt thereof, about 7 mol % DPPC (or DSPC), and about 32 mol % cholesterol (or derivative thereof).

In another aspect of this embodiment, the nucleic acid-lipid particle comprises: (a) a cocktail of interfering RNAs (e.g., siRNAs) (e.g., two or three siRNAs each independently targeting EBOV L-pol, VP24, or VP35); (b) a cationic lipid (e.g., cationic lipid of Formula I-XVI) or a salt thereof comprising from about 55 mol % to about 65 mol % of the total lipid present in the particle; (c) cholesterol or a derivative thereof comprising from about 30 mol % to about 40 mol % of the total lipid present in the particle; and (d) a PEG-lipid conjugate comprising from about 5 mol % to about 10 mol % of the total lipid present in the particle. This embodiment of nucleic acid-lipid particle is generally referred to herein as the "7:58" formulation. In one particular embodiment, the 7:58 formulation is a three-component system which is phospholipid-free and comprises about 7 mol % PEG-lipid conjugate (e.g., PEG750-C-DMA), about 58 mol % cationic lipid (e.g., cationic lipid of Formula I-XVI) or a salt thereof, and about 35 mol % cholesterol (or derivative thereof).

Additional embodiments related to the 7:54 and 7:58 formulations are described in U.S. application Ser. No. 12/828,189, filed Jun. 30, 2010, the disclosure of which is herein incorporated by reference in its entirety for all purposes.

The present invention also provides pharmaceutical compositions comprising a nucleic acid-lipid particle such as a SNALP and a pharmaceutically acceptable carrier.

The nucleic acid-lipid particles of the invention are useful for the therapeutic delivery of interfering RNA (e.g., siRNA) molecules that silence EBOV gene expression. In some embodiments, a cocktail of interfering RNAs (e.g., siRNAs) (e.g., two or three siRNAs each independently targeting EBOV L-pol, VP24, or VP35) are formulated into nucleic acid-lipid particles, and the particles are administered to a mammal (e.g., a human) requiring such treatment. In certain instances, a therapeutically effective amount of the nucleic acid-lipid particle can be administered to the mammal, e.g., for treating, preventing, reducing the risk of developing, and/or delaying the onset of EBOV infections caused by one or more EBOV species such as Zaire EBOV.

In some embodiments, the interfering RNA (e.g., siRNA) molecules described herein are used in methods for silencing EBOV gene expression, e.g., in a cell such as a reticuloendothelial cell (e.g., monocyte or macrophage), fibroblast cell, endothelial cell, and/or platelet cell. In particular, it is an object of the present invention to provide in vitro and in vivo methods for inactivating EBOV and/or inhibiting the replication of EBOV to treat EBOV infections in a mammal by downregulating or silencing the transcription and/or translation of multiple (e.g., two, three, four, five, or more) EBOV genes. In certain embodiments, the present invention provides a method for introducing a cocktail of interfering RNAs (e.g., siRNAs) (e.g., two or three siRNAs each independently targeting EBOV L-pol, VP24, or VP35) capable of silencing EBOV expression (e.g., viral RNA and/or protein levels) into a cell by contacting the cell with a nucleic acid-lipid particle described herein (e.g., SNALP). In one particular embodiment, the cell is a reticuloendothelial cell (e.g., monocyte or macrophage), fibroblast cell, endothelial cell, or platelet cell. In another embodiment, the present invention provides a method for the in vivo delivery of a cocktail of interfering RNAs (e.g., siRNAs) (e.g., two or three siRNAs each independently targeting EBOV L-pol, VP24, or VP35) to a cell, tissue, or organ infected and/or susceptible of being infected with EBOV by administering to a mammal (e.g., human) a nucleic acid-lipid particle described herein (e.g., a SNALP formulation).

The nucleic acid-lipid particles of the invention (e.g., SNALP) are particularly useful for targeting cells (e.g., reticuloendothelial cells, fibroblast cells, endothelial cells, and/or platelets cells), tissues, or organs infected and/or susceptible of being infected with EBOV. Administration of the nucleic acid-lipid particle can be by any route known in the art, such as, e.g., oral, intranasal, intravenous, intraperitoneal, intramuscular, intra-articular, intralesional, intratracheal, subcutaneous, or intradermal. In particular embodiments, the nucleic acid-lipid particles (e.g., SNALP) are administered systemically, e.g., via enteral or parenteral routes of administration.

In certain aspects, the present invention provides methods for silencing EBOV gene expression in a mammal (e.g., human) in need thereof, the method comprising administering to the mammal a therapeutically effective amount of a nucleic acid-lipid particle described herein (e.g., a SNALP formulation) comprising a cocktail of interfering RNAs (e.g., siRNAs) (e.g., two or three siRNAs each independently targeting the EBOV L-pol, VP24, or VP35 genes). In some embodiments, administration of nucleic acid-lipid particles comprising a cocktail of interfering RNAs (e.g., siRNAs) reduces EBOV viral RNA levels by at least about 5%, 10%, 15%, 20%, 25%, 30%, 35%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or 100% (or any range therein) relative to EBOV viral RNA levels detected in the absence of the interfering RNA (e.g., buffer control or irrelevant non-EBOV targeting interfering RNA control). In other embodiments, administration of nucleic acid-lipid particles comprising one or more EBOV-targeting interfering RNAs reduces EBOV viral RNA levels for at least about 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, or 100 days or more (or any range therein) relative to a negative control such as, e.g., a buffer control or an irrelevant non-EBOV targeting interfering RNA control. In preferred embodiments, the EBOV-targeting interfering RNA (e.g., siRNA) molecules comprise a cocktail of at least two or all three interfering RNAs selected from the modified EK-1, VP24-1160, and VP35-855 interfering RNAs described herein.

In other aspects, the present invention provides methods for treating, preventing, reducing the risk or likelihood of developing (e.g., reducing the susceptibility to), delaying the onset of, and/or ameliorating one or more symptoms associated with an EBOV infection in a mammal (e.g., human) in need thereof, the method comprising administering to the mammal a therapeutically effective amount of a nucleic acid-lipid particle (e.g., a SNALP formulation) comprising a cocktail of interfering RNAs (e.g., siRNAs) (e.g., two or three siRNAs each independently targeting the EBOV L-pol, VP24, or VP35 genes). In preferred embodiments, the EBOV-targeting interfering RNAs (e.g., siRNAs) comprise a cocktail of at least two or all three interfering RNAs selected from the modified EK-1, VP24-1160, and VP35-855 interfering RNAs described herein.

In further aspects, the present invention provides methods for treating, preventing, reducing the risk or likelihood of developing (e.g., reducing the susceptibility to), delaying the onset of, and/or ameliorating one or more symptoms associated with hemorrhagic fever, the method comprising administering to the mammal a therapeutically effective amount of a nucleic acid-lipid particle (e.g., a SNALP formulation) comprising a cocktail of interfering RNAs (e.g., siRNAs) (e.g., two or three siRNAs each independently targeting the EBOV L-pol, VP24, or VP35 genes). In preferred embodiments, the EBOV-targeting interfering RNAs (e.g., siRNAs) comprise a cocktail of at least two or all three interfering RNAs selected from the modified EK-1, VP24-1160, and VP35-855 interfering RNAs described herein.

In further aspects, the present invention provides a method for inactivating EBOV and/or inhibiting the replication of EBOV in a mammal (e.g., human) in need thereof (e.g., a mammal with an EBOV infection), the method comprising administering to the mammal a therapeutically effective amount of a nucleic acid-lipid particle (e.g., a SNALP formulation) comprising a cocktail of interfering RNAs (e.g., siRNAs) (e.g., two or three siRNAs each independently targeting the EBOV L-pol, VP24, or VP35 genes). In some embodiments, administration of nucleic acid-lipid particles (e.g., SNALP) comprising a cocktail of EBOV-targeting interfering RNAs lowers, reduces, or decreases EBOV viral load or titer by at least about 5%, 10%, 15%, 20%, 25%, 30%, 35%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or 100% (or any range therein) relative to the EBOV viral load or titer detected in the absence of the interfering RNA (e.g., buffer control or irrelevant non-EBOV targeting interfering RNA control). In preferred embodiments, the EBOV-targeting interfering RNAs (e.g., siRNAs) comprise a cocktail of at least two or all three interfering RNAs selected from the modified EK-1, VP24-1160, and VP35-855 interfering RNAs described herein.

In certain embodiments, the mammal has an EBOV infection, e.g., a Zaire EBOV infection. In certain other embodiments, silencing of EBOV sequences that encode genes associated with viral infection and/or survival can conveniently be used in combination with the administration of conventional agents used to treat or ameliorate the viral condition or any of the symptoms associated therewith.

Examples of anti-viral drugs include, but are not limited to, abacavir, aciclovir, acyclovir, adefovir, amantadine, amprenavir, arbidol, atazanavir, atripla, cidofovir, combivir, darunavir, delavirdine, didanosine, docosanol, edoxudine, efavirenz, emtricitabine, enfuvirtide, entecavir, entry inhibitors, famciclovir, fixed dose combinations, fomivirsen, fosamprenavir, foscarnet, fosfonet, fusion inhibitors, ganciclovir, ibacitabine, imunovir, idoxuridine, imiquimod, indinavir, inosine, integrase inhibitors, interferon type III (e.g., IFN-λ, molecules such as IFN-λ1, IFN-λ2, and IFN-λ3), interferon type II (e.g., IFN-γ), interferon type I (e.g., IFN-α such as PEGylated IFN-α, IFN-β, IFN-κ, IFN-δ, IFN-ε, IFN-τ, IFN-ω, and IFN-ζ), interferon, lamivudine, lopinavir, loviride, MK-0518, maraviroc, moroxydine, nelfinavir, nevirapine, nexavir, nucleoside analogues, oseltamivir, penciclovir, peramivir, pleconaril, podophyllotoxin, protease inhibitors, reverse transcriptase inhibitors, ribavirin, rimantadine, ritonavir, saquinavir, stavudine, synergistic enhancers, tenofovir, tenofovir disoproxil, tipranavir, trifluridine, trizivir, tromantadine, truvada, valaciclovir, valganciclovir, vicriviroc, vidarabine, viramidine, zalcitabine, zanamivir, zidovudine, pharmaceutically acceptable salts thereof, stereoisomers thereof, derivatives thereof, analogs thereof, and mixtures thereof.

As non-limiting examples, the dose of one or more nucleic acid-lipid particles can be administered about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, or 24 hours, or about 1, 2, 3, 4, 5, 6, 7, 8, 9, 10, 11, 12, 13, or 14 days, or about 1, 2, 3, 4, 5, 6, 7, 8, 9, or 10 weeks, or about 1, 2, 3, 4, 5, or 6 months, or any interval thereof, after EBOV (e.g., Zaire EBOV) infection. In one particular embodiment, more than one dose of nucleic acid-lipid particles containing an siRNA cocktail can be administered at different times following EBOV infection. In certain instances, the EBOV-infected mammal can be treated with a second, third, fourth, fifth, sixth, seventh, eighth, ninth, tenth, or more dose of the same or different nucleic acid-lipid particles containing an EBOV siRNA cocktail. In another embodiment, the EBOV-infected mammal can be treated with a daily dose of the same or different particles containing a cocktail of EBOV siRNA and assessed for a reduction in EBOV viremia and/or severity of clinical symptoms of EBOV infection. In some embodiments, a mammal susceptible to being infected with EBOV may be pretreated with one or more doses of nucleic acid-lipid particles containing an siRNA cocktail described herein as a prophylactic measure for preventing an EBOV infection.

IV. Therapeutic Nucleic Acids

The term "nucleic acid" includes any oligonucleotide or polynucleotide, with fragments containing up to 60 nucleotides generally termed oligonucleotides, and longer fragments termed polynucleotides. In particular embodiments, oligonucleotides of the invention are from about 15 to about 60 nucleotides in length. In some embodiments, nucleic acid is associated with a carrier system such as the lipid particles described herein. In certain embodiments, the nucleic acid is fully encapsulated in the lipid particle. Nucleic acid may be administered alone in the lipid particles of the invention, or in combination (e.g., co-administered) with lipid particles comprising peptides, polypeptides, or small molecules such as conventional drugs.

In the context of this invention, the terms "polynucleotide" and "oligonucleotide" refer to a polymer or oligomer of nucleotide or nucleoside monomers consisting of naturally-occurring bases, sugars and intersugar (backbone) linkages. The terms "polynucleotide" and "oligonucleotide" also include polymers or oligomers comprising non-naturally occurring monomers, or portions thereof, which function similarly. Such modified or substituted oligonucleotides are often preferred over native forms because of properties such as, for example, enhanced cellular uptake, reduced immunogenicity, and increased stability in the presence of nucleases.

Oligonucleotides are generally classified as deoxyribooligonucleotides or ribooligonucleotides. A deoxyribooligonucleotide consists of a 5-carbon sugar called deoxyribose joined covalently to phosphate at the 5' and 3' carbons of this sugar to form an alternating, unbranched polymer. A ribooligonucleotide consists of a similar repeating structure where the 5-carbon sugar is ribose.

The nucleic acid according to this invention includes any form of nucleic acid that is known. The nucleic acids used herein can be single-stranded DNA or RNA, or double-stranded DNA or RNA, or DNA-RNA hybrids. Examples of double-stranded DNA are described herein and include, e.g., structural genes, genes including control and termination regions, and self-replicating systems such as viral or plasmid DNA. Examples of double-stranded RNA are described herein and include, e.g., siRNA and other RNAi agents such as Dicer-substrate dsRNA, shRNA, aiRNA, and pre-miRNA. Single-stranded nucleic acids include, e.g., antisense oligonucleotides, ribozymes, mature miRNA, and triplex-forming oligonucleotides. In further embodiments, the nucleic acids are double-stranded DNA. Examples of double-stranded DNA include, e.g., DNA-DNA hybrids comprising a DNA sense strand and a DNA antisense strand as described in PCT Publication No. WO 2004/104199, the disclosure of which is herein incorporated by reference in its entirety for all purposes.

Nucleic acids of the invention may be of various lengths, generally dependent upon the particular form of nucleic acid. For example, in particular embodiments, plasmids or genes may be from about 1,000 to about 100,000 nucleotide residues in length. In particular embodiments, oligonucleotides may range from about 10 to about 100 nucleotides in length. In various related embodiments, oligonucleotides, both single-stranded, double-stranded, and triple-stranded, may range in length from about 10 to about 60 nucleotides, from about 15 to about 60 nucleotides, from about 20 to about 50 nucleotides, from about 15 to about 30 nucleotides, or from about 20 to about 30 nucleotides in length.

In particular embodiments, an oligonucleotide (or a strand thereof) of the invention specifically hybridizes to or is complementary to a target polynucleotide sequence. The terms "specifically hybridizable" and "complementary" as used herein indicate a sufficient degree of complementarity such that stable and specific binding occurs between the DNA or RNA target and the oligonucleotide. It is understood that an oligonucleotide need not be 100% complementary to its target nucleic acid sequence to be specifically hybridizable. In preferred embodiments, an oligonucleotide is specifically hybridizable when binding of the oligonucleotide to the target sequence interferes with the normal function of the target sequence to cause a loss of utility or expression therefrom, and there is a sufficient degree of complementarity to avoid non-specific binding of the oligonucleotide to non-target sequences under conditions in which specific binding is desired, i.e., under physiological conditions in the case of in vivo assays or therapeutic treatment, or, in the case of in vitro assays, under conditions in which the assays are conducted. Thus, the oligonucleotide may include 1, 2, 3, or more base substitutions as compared to the region of a gene or mRNA sequence that it is targeting or to which it specifically hybridizes.

A. siRNA

The unmodified and modified siRNA molecules of the invention are capable of silencing EBOV gene expression, e.g., to inhibit EBOV replication and/or to inactivate EBOV. Each strand of the siRNA duplex is typically about 15 to about 60 nucleotides in length, preferably about 15 to about 30 nucleotides in length. In certain embodiments, the siRNA comprises at least one modified nucleotide. The modified siRNA is generally less immunostimulatory than a corresponding unmodified siRNA sequence and retains RNAi activity against the target gene of interest. In some embodiments, the modified siRNA contains at least one 2'OMe purine or pyrimidine nucleotide such as a 2'OMe-guanosine, 2'OMe-uridine, 2'OMe-adenosine, and/or 2'OMe-cytosine nucleotide. The modified nucleotides can be present in one strand (i.e., sense or antisense) or both strands of the siRNA. In some preferred embodiments, one or more of the uridine and/or guanosine nucleotides are modified (e.g., 2'OMe-modified) in one strand (i.e., sense or antisense) or both strands of the siRNA. In these embodiments, the modified siRNA can further comprise one or more modified (e.g., 2'OMe-modified) adenosine and/or modified (e.g., 2'OMe-modified) cytosine nucleotides. In other preferred embodiments, only uridine and/or guanosine nucleotides are modified (e.g., 2'OMe-modified) in one strand (i.e., sense or antisense) or both strands of the siRNA. The siRNA sequences may have overhangs (e.g., 3' or 5' overhangs as described in Elbashir et al., *Genes Dev.,* 15:188 (2001) or Nykänen et al., *Cell,* 107:309 (2001)), or may lack overhangs (i.e., have blunt ends).

In particular embodiments, the selective incorporation of modified nucleotides such as 2'OMe uridine and/or guanosine nucleotides into the double-stranded region of either or both strands of the siRNA reduces or completely abrogates the immune response to that siRNA molecule. In certain instances, the immunostimulatory properties of specific siRNA sequences and their ability to silence gene expression can be balanced or optimized by the introduction of minimal and selective 2'OMe modifications within the double-stranded region of the siRNA duplex. This can be achieved at therapeutically viable siRNA doses without cytokine induction, toxicity, and off-target effects associated with the use of unmodified siRNA.

The modified siRNA generally comprises from about 1% to about 100% (e.g., about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 55%, 60%, 65%, 70%, 75%, 80%, 85%, 90%, 95%, or 100%) modified nucleotides in the double-stranded region of the siRNA duplex. In certain embodiments, one, two, three, four, five, six, seven, eight, nine, ten, or more of the nucleotides in the double-stranded region of the siRNA comprise modified nucleotides. In certain other embodiments, some or all of the modified nucleotides in the double-stranded region of the siRNA are 1, 2, 3, 4, 5, 6, 7, 8, 9, 10, or more nucleotides apart from each other. In one preferred embodiment, none of the modified nucleotides in the double-stranded region of the siRNA are adjacent to each other (e.g., there is a gap of at least 1, 2, 3, 4, 5, 6, 7, 8, 9, or 10 unmodified nucleotides between each modified nucleotide).

In some embodiments, less than about 50% (e.g., less than about 49%, 48%, 47%, 46%, 45%, 44%, 43%, 42%, 41%, 40%, 39%, 38%, 37%, or 36%, preferably less than about 35%, 34%, 33%, 32%, 31%, or 30%) of the nucleotides in the double-stranded region of the siRNA comprise modified (e.g., 2'OMe) nucleotides. In one aspect of these embodiments, less than about 50% of the uridine and/or guanosine nucleotides in the double-stranded region of one or both strands of the siRNA are selectively (e.g., only) modified. In another aspect of these embodiments, less than about 50% of the nucleotides in the double-stranded region of the siRNA comprise 2'OMe nucleotides, wherein the siRNA comprises 2'OMe nucleotides in both strands of the siRNA, wherein the siRNA comprises at least one 2'OMe-guanosine nucleotide and at least one 2'OMe-uridine nucleotide, and wherein 2'OMe-guanosine nucleotides and 2'OMe-uridine nucleotides are the only 2'OMe nucleotides present in the double-stranded region. In yet another aspect of these embodiments, less than about 50% of the nucleotides in the double-stranded region of the siRNA comprise 2'OMe nucleotides, wherein the siRNA comprises 2'OMe nucleotides in both strands of the modified siRNA, wherein the siRNA comprises 2'OMe nucleotides selected from the group consisting of 2'OMe-guanosine nucleotides, 2'OMe-uridine nucleotides, 2'OMe-adenosine nucleotides, and mixtures thereof, and wherein the siRNA does not comprise 2'OMe-cytosine nucleotides in the double-stranded region. In a further aspect of these embodiments, less than about 50% of the nucleotides in the double-stranded region of the siRNA comprise 2'OMe nucleotides, wherein the siRNA comprises 2'OMe nucleotides in both strands of the siRNA, wherein the siRNA comprises at least one 2'OMe-guanosine nucleotide and at least one 2'OMe-uridine nucleotide, and wherein the siRNA does not comprise 2'OMe-cytosine nucleotides in the double-stranded region. In another aspect of these embodiments, less than about 50% of the nucleotides in the double-stranded region of the siRNA comprise 2'OMe nucleotides, wherein the siRNA comprises 2'OMe nucleotides in both strands of the modified siRNA, wherein the siRNA comprises 2'OMe nucleotides selected from the group consisting of 2'OMe-guanosine nucleotides, 2'OMe-uridine nucleotides, 2'OMe-adenosine nucleotides, and mixtures thereof, and wherein the 2'OMe nucleotides in the double-stranded region are not adjacent to each other.

In other embodiments, from about 1% to about 50% (e.g., from about 5%-50%, 10%-50%, 15%-50%, 20%-50%, 25%-50%, 30%-50%, 35%-50%, 40%-50%, 45%-50%, 5%-45%, 10%-45%, 15%-45%, 20%-45%, 25%-45%, 30%-45%, 35%-45%, 40%-45%, 5%-40%, 10%-40%, 15%-40%, 20%-40%, 25%-40%, 25%-39%, 25%-38%, 25%-37%, 25%-36%, 26%-39%, 26%-38%, 26%-37%, 26%-36%, 27%-39%, 27%-38%, 27%-37%, 27%-36%, 28%-39%, 28%-38%, 28%-37%, 28%-36%, 29%-39%, 29%-38%, 29%-37%, 29%-36%, 30%-40%, 30%-39%, 30%-38%, 30%-37%, 30%-36%, 31%-39%, 31%-38%, 31%-37%, 31%-36%, 32%-39%, 32%-38%, 32%-37%, 32%-36%, 33%-39%, 33%-38%, 33%-37%, 33%-36%, 34%-39%, 34%-38%, 34%-37%, 34%-36%, 35%-40%, 5%-35%, 10%-35%, 15%-35%, 20%-35%, 21%-35%, 22%-35%, 23%-35%, 24%-35%, 25%-35%, 26%-35%, 27%-35%, 28%-35%, 29%-35%, 30%-35%, 31%-35%, 32%-35%, 33%-35%, 34%-35%, 30%-34%, 31%-34%, 32%-34%, 33%-34%, 30%-33%, 31%-33%, 32%-33%, 30%-32%, 31%-32%, 25%-34%, 25%-33%, 25%-32%, 25%-31%, 26%-34%, 26%-33%, 26%-32%, 26%-31%, 27%-34%, 27%-33%, 27%-32%, 27%-31%, 28%-34%, 28%-33%, 28%-32%, 28%-31%, 29%-34%, 29%-33%, 29%-32%, 29%-31%, 5%-30%, 10%-30%, 15%-30%, 20%-34%, 20%-33%, 20%-32%, 20%-31%, 20%-30%, 21%-30%, 22%-30%, 23%-30%, 24%-30%, 25%-30%, 25%-29%, 25%-28%, 25%-27%, 25%-26%, 26%-30%, 26%-29%, 26%-28%, 26%-27%, 27%-30%, 27%-29%, 27%-28%, 28%-30%, 28%-29%, 29%-30%, 5%-25%, 10%-25%, 15%-25%, 20%-29%, 20%-28%, 20%-27%, 20%-26%, 20%-25%, 5%-20%, 10%-20%, 15%-20%, 5%-15%, 10%-15%, or 5%-10%) of the nucleotides in the double-stranded region of the siRNA comprise modified nucleotides. In one aspect of these embodiments, from about 1% to about 50% of the uridine and/or guanosine nucleotides in the double-stranded region of one or both strands of the siRNA are selectively (e.g., only) modified. In another aspect of these embodiments, from about 1% to about 50% of the nucleotides in the double-stranded region of the siRNA comprise 2'OMe nucleotides, wherein the siRNA comprises 2'OMe nucleotides in both strands of the siRNA, wherein the siRNA comprises at least one 2'OMe-guanosine nucleotide and at least one 2'OMe-uridine nucleotide, and wherein 2'OMe-guanosine nucleotides and 2'OMe-uridine nucleotides are the only 2'OMe nucleotides present in the double-stranded region. In yet another aspect of these embodiments, from about 1% to about 50% of the nucleotides in the double-stranded region of the siRNA comprise 2'OMe nucleotides, wherein the siRNA comprises 2'OMe nucleotides in both strands of the modified siRNA, wherein the siRNA comprises 2'OMe nucleotides selected from the group consisting of 2'OMe-guanosine nucleotides, 2'OMe-uridine nucleotides, 2'OMe-adenosine nucleotides, and mixtures thereof, and wherein the siRNA does not comprise 2'OMe-cytosine nucleotides in the double-stranded region. In a further aspect of these embodiments, from about 1% to about 50% of the nucleotides in the double-stranded region of the siRNA comprise 2'OMe nucleotides, wherein the siRNA comprises 2'OMe nucleotides in both strands of the siRNA, wherein the siRNA comprises at least one 2'OMe-guanosine nucleotide and at least one 2'OMe-uridine nucleotide, and wherein the siRNA does not comprise 2'OMe-cytosine nucleotides in the double-stranded region. In another aspect of these embodiments, from about 1% to about 50% of the nucleotides in the double-stranded region of the siRNA comprise 2'OMe nucleotides, wherein the siRNA comprises 2'OMe nucleotides in both strands of the modified siRNA, wherein the siRNA comprises 2'OMe nucleotides selected from the group consisting of 2'OMe-guanosine nucleotides, 2'OMe-uridine nucleotides, 2'OMe-adenosine nucleotides, and mixtures thereof, and wherein the 2'OMe nucleotides in the double-stranded region are not adjacent to each other.

In certain embodiments, the siRNA molecules of the present invention comprise an asymmetric siRNA duplex as described in PCT Publication No. WO 2004/078941, which comprises a double-stranded region consisting of a DNA sense strand and an RNA antisense strand (e.g., a DNA-RNA hybrid), wherein a blocking agent is located on the siRNA duplex. In some instances, the asymmetric siRNA duplex can be chemically modified as described herein. Other non-limiting examples of asymmetric siRNA duplexes are described in PCT Publication No. WO 2006/074108, which discloses self-protected oligonucleotides comprising a region having a sequence complementary to one, two, three, or more same or different target mRNA sequences (e.g., multivalent siRNAs) and one or more self-complementary regions. Yet other non-limiting examples of asymmetric siRNA duplexes are described in PCT Publication No. WO 2009/076321, which discloses self-forming asymmetric precursor polynucleotides comprising a targeting region comprising a polynucleotide sequence complementary to a region of one, two, three, or more same or different target mRNA sequences (e.g., multivalent siRNAs); a first self-complementary region; and a second self-complementary region, wherein the first and second self-complementary regions are located one at each end of the targeting region and both self-complementary regions form stem-loop structures, wherein the first self-complementary region is capable of being cleaved by a RNase III endoribonuclease that is not a class IV DICER endoribonuclease, and wherein both self-complementary regions comprise a nucleotide sequence that is complementary to a region of the target gene sequence, but wherein a portion of the target sequence present in the targeting region does not have a complementary sequence in either of the self-complementary regions. The disclosures of each of the above patent documents are herein incorporated by reference in their entirety for all purposes.

Additional ranges, percentages, and patterns of modifications that may be introduced into siRNA are described in U.S. Patent Publication No. 20070135372, the disclosure of which is herein incorporated by reference in its entirety for all purposes.

1. Selection of siRNA Sequences

Suitable siRNA sequences can be identified using any means known in the art. Typically, the methods described in Elbashir et al., *Nature,* 411:494-498 (2001) and Elbashir et al., *EMBO J.,* 20:6877-6888 (2001) are combined with rational design rules set forth in Reynolds et al., *Nature Biotech.,* 22(3):326-330 (2004).

As a non-limiting example, the nucleotide sequence 3' of the AUG start codon of a transcript from the target gene of interest may be scanned for dinucleotide sequences (e.g., AA, NA, CC, GG, or UU, wherein N=C, G, or U) (see, e.g., Elbashir et al., *EMBO J.,* 20:6877-6888 (2001)). The nucleotides immediately 3' to the dinucleotide sequences are identified as potential siRNA sequences (i.e., a target sequence or a sense strand sequence). Typically, the 19, 21, 23, 25, 27, 29, 31, 33, 35, or more nucleotides immediately 3' to the dinucleotide sequences are identified as potential siRNA sequences. In some embodiments, the dinucleotide sequence is an AA or NA sequence and the 19 nucleotides immediately 3' to the AA or NA dinucleotide are identified as potential siRNA sequences. siRNA sequences are usually spaced at different positions along the length of the target gene. To further enhance silencing efficiency of the siRNA sequences, potential siRNA sequences may be analyzed to identify sites that do not contain regions of homology to other coding sequences, e.g., in the target cell or organism. For example, a suitable siRNA sequence of about 21 base pairs typically will not have more than 16-17 contiguous base pairs of homology to coding sequences in the target cell or organism. If the siRNA sequences are to be expressed from an RNA Pol III promoter, siRNA sequences lacking more than 4 contiguous A's or T's are selected.

Once a potential siRNA sequence has been identified, a complementary sequence (i.e., an antisense strand sequence) can be designed. A potential siRNA sequence can also be analyzed using a variety of criteria known in the art. For example, to enhance their silencing efficiency, the siRNA sequences may be analyzed by a rational design algorithm to identify sequences that have one or more of the following features: (1) G/C content of about 25% to about 60% G/C; (2) at least 3 A/Us at positions 15-19 of the sense strand; (3) no internal repeats; (4) an A at position 19 of the sense strand; (5) an A at position 3 of the sense strand; (6) a U at position 10 of the sense strand; (7) no G/C at position 19 of the sense strand; and (8) no G at position 13 of the sense strand. siRNA design tools that incorporate algorithms that assign suitable values of each of these features and are useful for selection of siRNA can be found at, e.g., http://ihome.ust.hk/~bokcmho/siRNA/siRNA.html. One of skill in the art will appreciate that sequences with one or more of the foregoing characteristics may be selected for further analysis and testing as potential siRNA sequences.

Additionally, potential siRNA sequences with one or more of the following criteria can often be eliminated as siRNA: (1) sequences comprising a stretch of 4 or more of the same base in a row; (2) sequences comprising homopolymers of Gs (i.e., to reduce possible non-specific effects due to structural characteristics of these polymers; (3) sequences comprising triple base motifs (e.g., GGG, CCC, AAA, or TTT); (4) sequences comprising stretches of 7 or more G/Cs in a row; and (5) sequences comprising direct repeats of 4 or more bases within the candidates resulting in internal fold-back structures. However, one of skill in the art will appreciate that sequences with one or more of the foregoing characteristics may still be selected for further analysis and testing as potential siRNA sequences.

In some embodiments, potential siRNA sequences may be further analyzed based on siRNA duplex asymmetry as described in, e.g., Khvorova et al., *Cell,* 115:209-216 (2003); and Schwarz et al., *Cell,* 115:199-208 (2003). In other embodiments, potential siRNA sequences may be further analyzed based on secondary structure at the target site as described in, e.g., Luo et al., *Biophys. Res. Commun.,* 318: 303-310 (2004). For example, secondary structure at the target site can be modeled using the Mfold algorithm (available at http://mfold.burnet.edu.au/rna_form) to select siRNA sequences which favor accessibility at the target site where less secondary structure in the form of base-pairing and stem-loops is present.

Once a potential siRNA sequence has been identified, the sequence can be analyzed for the presence of any immunostimulatory properties, e.g., using an in vitro cytokine assay or an in vivo animal model. Motifs in the sense and/or antisense strand of the siRNA sequence such as GU-rich motifs (e.g., 5'-GU-3', 5'-UGU-3', 5'-GUGU-3', 5'-UGUGU-3', etc.) can also provide an indication of whether the sequence may be immunostimulatory. Once an siRNA molecule is found to be immunostimulatory, it can then be modified to decrease its immunostimulatory properties as described herein. As a non-limiting example, an siRNA sequence can be contacted with a mammalian responder cell under conditions such that the cell produces a detectable immune response to determine whether the siRNA is an immunostimulatory or a non-immunostimulatory siRNA. The mammalian responder cell may be from a naïve mammal (i.e., a mammal that has not previously been in contact with the gene product of the siRNA sequence). The mammalian responder cell may be, e.g., a peripheral blood mononuclear cell (PBMC), a macrophage, and the like. The detectable immune response may comprise production of a cytokine or growth factor such as, e.g., TNF-$\alpha$, IFN-$\alpha$, IFN-$\beta$, IL-$\gamma$, IL-6, IL-8, IL-12, or a combination thereof. An siRNA molecule identified as being immunostimulatory can then be modified to decrease its immunostimulatory properties by replacing at least one of the nucleotides on the sense and/or antisense strand with modified nucleotides. For example, less than about 30% (e.g., less than about 30%, 25%, 20%, 15%, 10%, or 5%) of the nucleotides in the double-stranded region of the siRNA duplex can be replaced with modified nucleotides such as 2'OMe nucleotides. The modified siRNA can then be contacted with a mammalian responder cell as described above to confirm that its immunostimulatory properties have been reduced or abrogated.

Suitable in vitro assays for detecting an immune response include, but are not limited to, the double monoclonal antibody sandwich immunoassay technique of David et al. (U.S. Pat. No. 4,376,110); monoclonal-polyclonal antibody sandwich assays (Wide et al., in Kirkham and Hunter, eds., *Radioimmunoassay Methods*, E. and S. Livingstone, Edinburgh (1970)); the "Western blot" method of Gordon et al. (U.S. Pat. No. 4,452,901); immunoprecipitation of labeled ligand (Brown et al., *J. Biol. Chem.,* 255:4980-4983 (1980)); enzyme-linked immunosorbent assays (ELISA) as described, for example, by Raines et al., *J. Biol. Chem.,* 257:5154-5160 (1982); immunocytochemical techniques, including the use of fluorochromes (Brooks et al., *Clin. Exp. Immunol.,* 39:477 (1980)); and neutralization of activity (Bowen-Pope et al., *Proc. Natl. Acad. Sci. USA,* 81:2396-2400 (1984)). In addition to the immunoassays described above, a number of other immunoassays are available, including those described in U.S. Pat. Nos. 3,817,827; 3,850,752; 3,901,654; 3,935,074; 3,984,533; 3,996,345; 4,034,074; and 4,098,876. The disclosures of these references are herein incorporated by reference in their entirety for all purposes.

A non-limiting example of an in vivo model for detecting an immune response includes an in vivo mouse cytokine induction assay as described in, e.g., Judge et al., *Mol. Ther.,* 13:494-505 (2006). In certain embodiments, the assay that can be performed as follows: (1) siRNA can be administered by standard intravenous injection in the lateral tail vein; (2) blood can be collected by cardiac puncture about 6 hours after administration and processed as plasma for cytokine analysis; and (3) cytokines can be quantified using sandwich ELISA kits according to the manufacturer's instructions (e.g., mouse and human IFN-α (PBL Biomedical; Piscataway, N.J.); human IL-6 and TNF-α (eBioscience; San Diego, Calif.); and mouse IL-6, TNF-α, and IFN-γ (BD Biosciences; San Diego, Calif.)).

Monoclonal antibodies that specifically bind cytokines and growth factors are commercially available from multiple sources and can be generated using methods known in the art (see, e.g., Kohler et al., *Nature,* 256: 495-497 (1975) and Harlow and Lane, ANTIBODIES, A LABORATORY MANUAL, Cold Spring Harbor Publication, New York (1999)). Generation of monoclonal antibodies has been previously described and can be accomplished by any means known in the art (Buhring et al., in Hybridoma, Vol. 10, No. 1, pp. 77-78 (1991)). In some methods, the monoclonal antibody is labeled (e.g., with any composition detectable by spectroscopic, photochemical, biochemical, electrical, optical, or chemical means) to facilitate detection.

2. Generating siRNA Molecules siRNA can be provided in several forms including, e.g., as one or more isolated small-interfering RNA (siRNA) duplexes, as longer double-stranded RNA (dsRNA), or as siRNA or dsRNA transcribed from a transcriptional cassette in a DNA plasmid. In some embodiments, siRNA may be produced enzymatically or by partial/total organic synthesis, and modified ribonucleotides can be introduced by in vitro enzymatic or organic synthesis. In certain instances, each strand is prepared chemically. Methods of synthesizing RNA molecules are known in the art, e.g., the chemical synthesis methods as described in Verma and Eckstein (1998) or as described herein.

An RNA population can be used to provide long precursor RNAs, or long precursor RNAs that have substantial or complete identity to a selected target sequence can be used to make the siRNA. The RNAs can be isolated from cells or tissue, synthesized, and/or cloned according to methods well known to those of skill in the art. The RNA can be a mixed population (obtained from cells or tissue, transcribed from cDNA, subtracted, selected, etc.), or can represent a single target sequence. RNA can be naturally occurring (e.g., isolated from tissue or cell samples), synthesized in vitro (e.g., using T7 or SP6 polymerase and PCR products or a cloned cDNA), or chemically synthesized.

To form a long dsRNA, for synthetic RNAs, the complement is also transcribed in vitro and hybridized to form a dsRNA. If a naturally occurring RNA population is used, the RNA complements are also provided (e.g., to form dsRNA for digestion by *E. coli* RNAse III or Dicer), e.g., by transcribing cDNAs corresponding to the RNA population, or by using RNA polymerases. The precursor RNAs are then hybridized to form double stranded RNAs for digestion. The dsRNAs can be directly administered to a subject or can be digested in vitro prior to administration.

Methods for isolating RNA, synthesizing RNA, hybridizing nucleic acids, making and screening cDNA libraries, and performing PCR are well known in the art (see, e.g., Gubler and Hoffman, *Gene,* 25:263-269 (1983); Sambrook et al., supra; Ausubel et al., supra), as are PCR methods (see, U.S. Pat. Nos. 4,683,195 and 4,683,202*; PCR Protocols: A Guide to Methods and Applications* (Innis et al., eds, 1990)). Expression libraries are also well known to those of skill in the art. Additional basic texts disclosing the general methods of use in this invention include Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994). The disclosures of these references are herein incorporated by reference in their entirety for all purposes.

Preferably, siRNA are chemically synthesized. The oligonucleotides that comprise the siRNA molecules of the invention can be synthesized using any of a variety of techniques known in the art, such as those described in Usman et al., *J. Am. Chem. Soc.,* 109:7845 (1987); Scaringe et al., *Nucl. Acids Res.,* 18:5433 (1990); Wincott et al., *Nucl. Acids Res.,* 23:2677-2684 (1995); and Wincott et al., *Methods Mol. Bio.,* 74:59 (1997). The synthesis of oligonucleotides makes use of common nucleic acid protecting and coupling groups, such as dimethoxytrityl at the 5'-end and phosphoramidites at the 3'-end. As a non-limiting example, small scale syntheses can be conducted on an Applied Biosystems synthesizer using a 0.2 μmol scale protocol. Alternatively, syntheses at the 0.2 μmol scale can be performed on a 96-well plate synthesizer from Protogene (Palo Alto, Calif.). However, a larger or smaller scale of synthesis is also within the scope of this invention. Suitable reagents for oligonucleotide synthesis, methods for RNA deprotection, and methods for RNA purification are known to those of skill in the art.

siRNA molecules can also be synthesized via a tandem synthesis technique, wherein both strands are synthesized as a single continuous oligonucleotide fragment or strand separated by a cleavable linker that is subsequently cleaved to provide separate fragments or strands that hybridize to form the siRNA duplex. The linker can be a polynucleotide linker or a non-nucleotide linker. The tandem synthesis of siRNA can be readily adapted to both multiwell/multiplate synthesis platforms as well as large scale synthesis platforms employing batch reactors, synthesis columns, and the like. Alternatively, siRNA molecules can be assembled from two distinct oligonucleotides, wherein one oligonucleotide comprises the sense strand and the other comprises the antisense strand of the siRNA. For example, each strand can be synthesized separately and joined together by hybridization or ligation following synthesis and/or deprotection. In certain other instances, siRNA molecules can be synthesized as a single continuous oligonucleotide fragment, where the self-complementary sense and antisense regions hybridize to form an siRNA duplex having hairpin secondary structure.

3. Modifying siRNA Sequences

In certain aspects, siRNA molecules comprise a duplex having two strands and at least one modified nucleotide in the double-stranded region, wherein each strand is about 15 to about 60 nucleotides in length. Advantageously, the modified siRNA is less immunostimulatory than a corresponding unmodified siRNA sequence, but retains the capability of silencing the expression of a target sequence. In preferred embodiments, the degree of chemical modifications introduced into the siRNA molecule strikes a balance between reduction or abrogation of the immunostimulatory properties of the siRNA and retention of RNAi activity. As a non-limiting example, an siRNA molecule that targets a gene of interest can be minimally modified (e.g., less than about 30%, 25%, 20%, 15%, 10%, or 5% modified) at selective uridine and/or guanosine nucleotides within the siRNA duplex to eliminate the immune response generated by the siRNA while retaining its capability to silence target gene expression.

Examples of modified nucleotides suitable for use in the invention include, but are not limited to, ribonucleotides having a 2'-O-methyl (2'OMe), 2'-deoxy-2'-fluoro (2'F), 2'-deoxy, 5-C-methyl, 2'-O-(2-methoxyethyl) (MOE), 4'-thio, 2'-amino, or 2'-C-allyl group. Modified nucleotides having a Northern conformation such as those described in, e.g., Saenger, *Principles of Nucleic Acid Structure*, Springer-Verlag Ed. (1984), are also suitable for use in siRNA molecules. Such modified nucleotides include, without limitation, locked nucleic acid (LNA) nucleotides (e.g., 2'-O, 4'-C-methylene-(D-ribofuranosyl) nucleotides), 2'-O-(2-methoxyethyl) (MOE) nucleotides, 2'-methyl-thio-ethyl nucleotides, 2'-deoxy-2'-fluoro (2'F) nucleotides, 2'-deoxy-2'-chloro (2'Cl) nucleotides, and 2'-azido nucleotides. In certain instances, the siRNA molecules described herein include one or more G-clamp nucleotides. A G-clamp nucleotide refers to a modified cytosine analog wherein the modifications confer the ability to hydrogen bond both Watson-Crick and Hoogsteen faces of a complementary guanine nucleotide within a duplex (see, e.g., Lin et al., *J. Am. Chem. Soc.*, 120:8531-8532 (1998)). In addition, nucleotides having a nucleotide base analog such as, for example, C-phenyl, C-naphthyl, other aromatic derivatives, inosine, azole carboxamides, and nitroazole derivatives such as 3-nitropyrrole, 4-nitroindole, 5-nitroindole, and 6-nitroindole (see, e.g., Loakes, *Nucl. Acids Res.*, 29:2437-2447 (2001)) can be incorporated into siRNA molecules.

In certain embodiments, siRNA molecules may further comprise one or more chemical modifications such as terminal cap moieties, phosphate backbone modifications, and the like. Examples of terminal cap moieties include, without limitation, inverted deoxy abasic residues, glyceryl modifications, 4',5'-methylene nucleotides, 1-(β-D-erythrofuranosyl) nucleotides, 4'-thio nucleotides, carbocyclic nucleotides, 1,5-anhydrohexitol nucleotides, L-nucleotides, α-nucleotides, modified base nucleotides, threo-pentofuranosyl nucleotides, acyclic 3',4'-seco nucleotides, acyclic 3,4-dihydroxybutyl nucleotides, acyclic 3,5-dihydroxypentyl nucleotides, 3'-3'-inverted nucleotide moieties, 3'-3'-inverted abasic moieties, 3'-2'-inverted nucleotide moieties, 3'-2'-inverted abasic moieties, 5'-5'-inverted nucleotide moieties, 5'-5'-inverted abasic moieties, 3'-5'-inverted deoxy abasic moieties, 5'-amino-alkyl phosphate, 1,3-diamino-2-propyl phosphate, 3-aminopropyl phosphate, 6-aminohexyl phosphate, 1,2-aminododecyl phosphate, hydroxypropyl phosphate, 1,4-butanediol phosphate, 3'-phosphoramidate, 5'-phosphoramidate, hexylphosphate, aminohexyl phosphate, 3'-phosphate, 5'-amino, 3'-phosphorothioate, 5'-phosphorothioate, phosphorodithioate, and bridging or non-bridging methylphosphonate or 5'-mercapto moieties (see, e.g., U.S. Pat. No. 5,998,203; Beaucage et al., *Tetrahedron* 49:1925 (1993)). Non-Limiting Examples of Phosphate Backbone modifications (i.e., resulting in modified internucleotide linkages) include phosphorothioate, phosphorodithioate, methylphosphonate, phosphotriester, morpholino, amidate, carbamate, carboxymethyl, acetamidate, polyamide, sulfonate, sulfonamide, sulfamate, formacetal, thioformacetal, and alkylsilyl substitutions (see, e.g., Hunziker et al., *Nucleic Acid Analogues: Synthesis and Properties*, in *Modern Synthetic Methods*, VCH, 331-417 (1995); Mesmaeker et al., *Novel Backbone Replacements for Oligonucleotides*, in *Carbohydrate Modifications in Antisense Research*, ACS, 24-39 (1994)). Such chemical modifications can occur at the 5'-end and/or 3'-end of the sense strand, antisense strand, or both strands of the siRNA. The disclosures of these references are herein incorporated by reference in their entirety for all purposes.

In some embodiments, the sense and/or antisense strand of the siRNA molecule can further comprise a 3'-terminal overhang having about 1 to about 4 (e.g., 1, 2, 3, or 4) 2'-deoxy ribonucleotides, modified (e.g., 2'OMe) and/or unmodified uridine ribonucleotides, and/or any other combination of modified (e.g., 2'OMe) and unmodified nucleotides.

Additional examples of modified nucleotides and types of chemical modifications that can be introduced into siRNA molecules are described, e.g., in UK Patent No. GB 2,397,818 B and U.S. Patent Publication Nos. 20040192626, 20050282188, and 20070135372, the disclosures of which are herein incorporated by reference in their entirety for all purposes.

The siRNA molecules described herein can optionally comprise one or more non-nucleotides in one or both strands of the siRNA. As used herein, the term "non-nucleotide" refers to any group or compound that can be incorporated into a nucleic acid chain in the place of one or more nucleotide units, including sugar and/or phosphate substitutions, and allows the remaining bases to exhibit their activity. The group or compound is abasic in that it does not contain a commonly recognized nucleotide base such as adenosine, guanine, cytosine, uracil, or thymine and therefore lacks a base at the 1'-position.

In other embodiments, chemical modification of the siRNA comprises attaching a conjugate to the siRNA molecule. The conjugate can be attached at the 5' and/or 3'-end of the sense and/or antisense strand of the siRNA via a covalent attachment such as, e.g., a biodegradable linker. The conjugate can also be attached to the siRNA, e.g., through a carbamate group or other linking group (see, e.g., U.S. Patent Publication Nos. 20050074771, 20050043219, and 20050158727). In certain instances, the conjugate is a molecule that facilitates the delivery of the siRNA into a cell. Examples of conjugate molecules suitable for attachment to siRNA include, without limitation, steroids such as cholesterol, glycols such as polyethylene glycol (PEG), human serum albumin (HSA), fatty acids, carotenoids, terpenes, bile acids, folates (e.g., folic acid, folate analogs and derivatives thereof), sugars (e.g., galactose, galactosamine, N-acetyl galactosamine, glucose, mannose, fructose, fucose, etc.), phospholipids, peptides, ligands for cellular receptors capable of mediating cellular uptake, and combinations thereof (see, e.g., U.S. Patent Publication Nos. 20030130186, 20040110296, and 20040249178; U.S. Pat. No. 6,753,423). Other examples include the lipophilic moiety, vitamin, polymer, peptide, protein, nucleic acid, small molecule, oligosaccharide, carbohydrate cluster, intercalator, minor groove binder, cleaving agent, and cross-linking agent conjugate molecules described in U.S. Patent Publication Nos. 20050119470 and 20050107325. Yet other examples include the 2'-O-alkyl amine, 2'-O-alkoxyalkyl amine, polyamine, C5-cationic modified pyrimidine, cationic peptide, guanidinium group, amidininium group, cationic amino acid conjugate molecules described in U.S. Patent Publication No. 20050153337. Additional examples include the hydrophobic group, membrane active compound, cell penetrating compound, cell targeting signal, interaction modifier, and steric stabilizer conjugate molecules described in U.S. Patent Publication No. 20040167090. Further examples include the conjugate molecules described in U.S. Patent Publication No. 20050239739. The type of conjugate used and the extent of conjugation to the siRNA molecule can be evaluated for improved pharmacokinetic profiles, bioavailability, and/or stability of the siRNA while retaining RNAi activity. As such, one skilled in the art can screen siRNA molecules having various conjugates attached thereto to identify ones having improved properties and full RNAi activity using any of a variety of well-known in vitro cell culture or in vivo animal models. The disclosures of the above-described patent documents are herein incorporated by reference in their entirety for all purposes.

4. Target Genes

The siRNA molecules of the invention can be used to downregulate or silence the translation (i.e., expression) of one or more EBOV genes of interest, such as L-pol, VP24, VP30, VP35, VP40, nucleoprotein (NP), glycoprotein (GP), or combinations thereof. In particular embodiments, the present invention provides a cocktail of siRNA molecules that silences the expression of at least two of the following genes: EBOV L-pol, EBOV VP24, and/or EBOV VP35 (e.g., the siRNA cocktail targets L-pol+VP35, L-pol+VP24, VP24+VP35, or L-pol+VP24+VP35). In some embodiments, the cocktail of siRNA molecules is fully encapsulated in a lipid particle such as a nucleic acid-lipid particle (e.g., SNALP). The siRNA molecules may be co-encapsulated in the same lipid particle, or each siRNA species present in the cocktail may be formulated in separate particles. As described herein, it has been unexpectedly found that the nucleic acid-lipid particles of the present invention (i.e., SNALP formulations) containing a cocktail of siRNA molecules as disclosed herein show increased potency (i.e., increased silencing) and/or increased tolerability (e.g., decreased toxicity) when targeting one or more EBOV genes of interest, when compared to other nucleic acid-lipid particle compositions previously described.

The EBOV genome comprises seven genes that encode 4 virion structural proteins (VP30, VP35, NP, and L-pol) and 3 membrane-associated proteins (VP40, GP, and VP24). The GP gene is found fourth from the 3' end of the 7 linearly arranged genes. The NP, VP30, VP35, and L-pol genes are required for viral replication and RNA translation. Complete genome sequences for EBOV are set forth in, e.g., Genbank Accession Nos. NC_002549; AY769362; NC_006432; NC_004161; AY729654; AY354458; AY142960; AB050936; AF522874; AF499101; AF272001; and AF086833. EBOV VP24 sequences are set forth in, e.g., Genbank Accession Nos. U77385 and AY058897. EBOV L-pol sequences are set forth in, e.g., Genbank Accession No. X67110. EBOV VP40 sequences are set forth in, e.g., Genbank Accession No. AY058896. EBOV NP sequences are set forth in, e.g., Genbank Accession No. AY058895. EBOV GP sequences are set forth in, e.g., Genbank Accession No. AY058898; Sanchez et al., *Virus Res.,* 29: 215-240 (1993); Will et al., *J. Virol.,* 67: 1203-1210 (1993); Volchkov et al., *FEBS Lett.,* 305:181-184 (1992); and U.S. Pat. No. 6,713,069. Additional EBOV sequences are set forth in, e.g., Genbank Accession Nos. L11365 and X61274. Non-limiting examples of siRNA molecules targeting EBOV nucleic acid sequences are set forth herein as well as in U.S. Patent Publication No. 20070135370 and Geisbert et al., *J. Infect. Dis.,* 193:1650-7 (2006), the disclosures of which are herein incorporated by reference in their entirety for all purposes.

In certain embodiments, the compositions of the present invention further comprise one or more siRNA molecules that downregulate or silence the translation (i.e., expression) of one or more additional genes associated with viral infection and survival.

Examples of additional genes associated with viral infection and survival include those expressed by a host (e.g., a host factor such as tissue factor (TF)) or a virus in order to bind, enter, and replicate in a cell. Of particular interest are viral sequences associated with chronic viral diseases. Additional viral sequences of particular interest include sequences of other Filoviruses such as Marburg virus (see, e.g., Geisbert et al., *J. Infect. Dis.,* 193:1650-1657 (2006)) and Arenaviruses such as Lassa virus, Junin virus, Machupo virus, Guanarito virus, and Sabia virus (Buchmeier et al., Arenaviridae: the viruses and their replication, In: Fields Virology, Knipe et al. (eds.), 4th ed., Lippincott-Raven, Philadelphia, (2001)).

Complete genome sequences for Marburg virus are set forth in, e.g., Genbank Accession Nos. NC_001608; AY430365; AY430366; and AY358025. Marburg virus GP sequences are set forth in, e.g., Genbank Accession Nos. AF005734; AF005733; and AF005732. Marburg virus VP35 sequences are set forth in, e.g., Genbank Accession Nos. AF005731 and AF005730. Additional Marburg virus sequences are set forth in, e.g., Genbank Accession Nos. X64406; Z29337; AF005735; and Z12132. Non-limiting examples of siRNA molecules targeting Marburg virus nucleic acid sequences include those described in U.S. Patent Publication No. 20070135370, the disclosure of which is herein incorporated by reference in its entirety for all purposes.

Exemplary Arenavirus nucleic acid sequences that can be silenced include, but are not limited to, nucleic acid sequences encoding nucleoprotein (NP), glycoprotein (GP), L-polymerase (L), and Z protein (Z). Complete genome sequences for Lassa virus are set forth in, e.g., Genbank Accession Nos. NC_004296 (LASV segment S) and NC_004297 (LASV segment L). Non-limiting examples of siRNA molecules targeting Lassa virus nucleic acid sequences include those described in U.S. Provisional Application No. 61/319,855, filed Mar. 31, 2010, the disclosure of which is herein incorporated by reference in its entirety for all purposes.

Exemplary host nucleic acid sequences that can be silenced include, but are not limited to, nucleic acid sequences encoding host factors such as tissue factor (TF) that are known to play a role in the pathogenisis of hemorrhagic fever viruses. The mRNA sequence of TF is set forth in Genbank Accession No. NM_001993. Those of skill in the art will appreciate that TF is also known as F3, coagulation factor III, thromboplastin, and CD142. Non-limiting examples of siRNA molecules targeting TF nucleic acid sequences include those described in U.S. Provisional Application No. 61/319,855, filed Mar. 31, 2010, the disclosure of which is herein incorporated by reference in its entirety for all purposes.

In addition to its utility in silencing the expression of any of the above-described EBOV genes and/or other viral-associated genes for therapeutic purposes, the siRNA described herein are also useful in research and development applications as well as diagnostic, prophylactic, prognostic, clinical, and other healthcare applications. As a non-limiting example, the siRNA can be used in target validation studies directed at testing whether a gene of interest has the potential to be a therapeutic target. The siRNA can also be used in target identification studies aimed at discovering genes as potential therapeutic targets.

5. Exemplary siRNA Embodiments

In some embodiments, each strand of the siRNA molecule comprises from about 15 to about 60 nucleotides in length (e.g., about 15-60, 15-50, 15-40, 15-30, 15-25, or 19-25 nucleotides in length, or 15, 16, 17, 18, 19, 20, 21, 22, 23, 24, or 25 nucleotides in length). In one particular embodiment, the siRNA is chemically synthesized. The siRNA molecules of the invention are capable of silencing the expression of a target sequence in vitro and/or in vivo.

In other embodiments, the siRNA comprises at least one modified nucleotide. In certain embodiments, the siRNA comprises one, two, three, four, five, six, seven, eight, nine, ten, or more modified nucleotides in the double-stranded region. In particular embodiments, less than about 50% (e.g., less than about 50%, 45%, 40%, 35%, 30%, 25%, 20%, 15%, 10%, or 5%) of the nucleotides in the double-stranded region of the siRNA comprise modified nucleotides. In preferred embodiments, from about 1% to about 50% (e.g., from about 5%-50%, 10%-50%, 15%-50%, 20%-50%, 25%-50%, 30%-50%, 35%-50%, 40%-50%, 45%-50%, 5%-45%, 10%-45%, 15%-45%, 20%-45%, 25%-45%, 30%-45%, 35%-45%, 40%-45%, 5%-40%, 10%-40%, 15%-40%, 20%-40%, 25%-40%, 30%-40%, 35%-40%, 5%-35%, 10%-35%, 15%-35%, 20%-35%, 25%-35%, 30%-35%, 5%-30%, 10%-30%, 15%-30%, 20%-30%, 25%-30%, 5%-25%, 10%-25%, 15%-25%, 20%-25%, 5%-20%, 10%-20%, 15%-20%, 5%-15%, 10%-15%, or 5%-10%) of the nucleotides in the double-stranded region of the siRNA comprise modified nucleotides.

In further embodiments, the siRNA comprises modified nucleotides including, but not limited to, 2'-O-methyl (2'OMe) nucleotides, 2'-deoxy-2'-fluoro (2'F) nucleotides, 2'-deoxy nucleotides, 2'-O-(2-methoxyethyl) (MOE) nucleotides, locked nucleic acid (LNA) nucleotides, and mixtures thereof. In preferred embodiments, the siRNA comprises 2'OMe nucleotides (e.g., 2'OMe purine and/or pyrimidine nucleotides) such as, e.g., 2'OMe-guanosine nucleotides, 2'OMe-uridine nucleotides, 2'OMe-adenosine nucleotides, 2'OMe-cytosine nucleotides, or mixtures thereof. In one particular embodiment, the siRNA comprises at least one 2'OMe-guanosine nucleotide, 2'OMe-uridine nucleotide, or mixtures thereof. In certain instances, the siRNA does not comprise 2'OMe-cytosine nucleotides. In other embodiments, the siRNA comprises a hairpin loop structure.

In certain embodiments, the siRNA comprises modified nucleotides in one strand (i.e., sense or antisense) or both strands of the double-stranded region of the siRNA molecule. Preferably, uridine and/or guanosine nucleotides are modified at selective positions in the double-stranded region of the siRNA duplex. With regard to uridine nucleotide modifications, at least one, two, three, four, five, six, or more of the uridine nucleotides in the sense and/or antisense strand can be a modified uridine nucleotide such as a 2'OMe-uridine nucleotide. In some embodiments, every uridine nucleotide in the sense and/or antisense strand is a 2'OMe-uridine nucleotide. With regard to guanosine nucleotide modifications, at least one, two, three, four, five, six, or more of the guanosine nucleotides in the sense and/or antisense strand can be a modified guanosine nucleotide such as a 2'OMe-guanosine nucleotide. In some embodiments, every guanosine nucleotide in the sense and/or antisense strand is a 2'OMe-guanosine nucleotide.

In certain embodiments, at least one, two, three, four, five, six, seven, or more 5'-GU-3' motifs in an siRNA sequence may be modified, e.g., by introducing mismatches to eliminate the 5'-GU-3' motifs and/or by introducing modified nucleotides such as 2'OMe nucleotides. The 5'-GU-3' motif can be in the sense strand, the antisense strand, or both strands of the siRNA sequence. The 5'-GU-3' motifs may be adjacent to each other or, alternatively, they may be separated by 1, 2, 3, 4, 5, 6, 7, 8, 9, 10, 11, 12, or more nucleotides.

In some embodiments, a modified siRNA molecule is less immunostimulatory than a corresponding unmodified siRNA sequence. In such embodiments, the modified siRNA molecule with reduced immunostimulatory properties advantageously retains RNAi activity against the target sequence. In another embodiment, the immunostimulatory properties of the modified siRNA molecule and its ability to silence target gene expression can be balanced or optimized by the introduction of minimal and selective 2'OMe modifications within the siRNA sequence such as, e.g., within the double-stranded region of the siRNA duplex. In certain instances, the modified siRNA is at least about 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 100% less immunostimulatory than the corresponding unmodified siRNA. It will be readily apparent to those of skill in the art that the immunostimulatory properties of the modified siRNA molecule and the corresponding unmodified siRNA molecule can be determined by, for example, measuring INF-α and/or IL-6 levels from about two to about twelve hours after systemic administration in a mammal or transfection of a mammalian responder cell using an appropriate lipid-based delivery system (such as the SNALP delivery system disclosed herein).

In other embodiments, a modified siRNA molecule has an $IC_{50}$ (i.e., half-maximal inhibitory concentration) less than or equal to ten-fold that of the corresponding unmodified siRNA (i.e., the modified siRNA has an $IC_{50}$ that is less than or equal to ten-times the $IC_{50}$ of the corresponding unmodified siRNA). In other embodiments, the modified siRNA has an $IC_{50}$ less than or equal to three-fold that of the corresponding unmodified siRNA sequence. In yet other embodiments, the modified siRNA has an $IC_{50}$ less than or equal to two-fold that of the corresponding unmodified siRNA. It will be readily apparent to those of skill in the art that a dose-response curve can be generated and the $IC_{50}$ values for the modified siRNA and the corresponding unmodified siRNA can be readily determined using methods known to those of skill in the art.

In another embodiment, an unmodified or modified siRNA molecule is capable of silencing at least about 5%, 10%, 15%, 20%, 25%, 30%, 35%, 40%, 45%, 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% of the expression of the target sequence relative to a negative control (e.g., buffer only, an siRNA sequence that targets a different gene, a scrambled siRNA sequence, etc.).

In yet another embodiment, a modified siRNA molecule is capable of silencing at least about 5%, 10%, 15%, 20%, 25%, 30%, 35%, 40%, 45%, 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% of the expression of the target sequence relative to the corresponding unmodified siRNA sequence.

In some embodiments, the siRNA molecule does not comprise phosphate backbone modifications, e.g., in the sense and/or antisense strand of the double-stranded region. In other embodiments, the siRNA comprises one, two, three, four, or more phosphate backbone modifications, e.g., in the sense and/or antisense strand of the double-stranded region. In preferred embodiments, the siRNA does not comprise phosphate backbone modifications.

In further embodiments, the siRNA does not comprise 2'-deoxy nucleotides, e.g., in the sense and/or antisense strand of the double-stranded region. In yet further embodiments, the siRNA comprises one, two, three, four, or more 2'-deoxy nucleotides, e.g., in the sense and/or antisense strand of the double-stranded region. In preferred embodiments, the siRNA does not comprise 2'-deoxy nucleotides.

In certain instances, the nucleotide at the 3'-end of the double-stranded region in the sense and/or antisense strand is not a modified nucleotide. In certain other instances, the nucleotides near the 3'-end (e.g., within one, two, three, or four nucleotides of the 3'-end) of the double-stranded region in the sense and/or antisense strand are not modified nucleotides.

The siRNA molecules described herein may have 3' overhangs of one, two, three, four, or more nucleotides on one or both sides of the double-stranded region, or may lack overhangs (i.e., have blunt ends) on one or both sides of the double-stranded region. In certain embodiments, the 3' overhang on the sense and/or antisense strand independently comprises one, two, three, four, or more modified nucleotides such as 2'OMe nucleotides and/or any other modified nucleotide described herein or known in the art.

In particular embodiments, siRNAs targeting EBOV RNA are administered using a carrier system such as a nucleic acid-lipid particle. In a preferred embodiment, the nucleic acid-lipid particle comprises: (a) a combination of siRNA molecules targeting at least two (or all three) of the following genes: EBOV L-pol, EBOV VP24, and/or EBOV VP35; (b) a cationic lipid of Formula I-XVI or a salt thereof; and (c) a non-cationic lipid (e.g., DPPC, DSPC, DSPE, and/or cholesterol). In certain instances, the nucleic acid-lipid particle may further comprise a conjugated lipid that prevents aggregation of particles (e.g., PEG-DAA).

B. Dicer-Substrate dsRNA

As used herein, the term "Dicer-substrate dsRNA" or "precursor RNAi molecule" is intended to include any precursor molecule that is processed in vivo by Dicer to produce an active siRNA which is incorporated into the RISC complex for RNA interference of a target gene.

In one embodiment, the Dicer-substrate dsRNA has a length sufficient such that it is processed by Dicer to produce an siRNA. According to this embodiment, the Dicer-substrate dsRNA comprises (i) a first oligonucleotide sequence (also termed the sense strand) that is between about 25 and about 60 nucleotides in length (e.g., about 25-60, 25-55, 25-50, 25-45, 25-40, 25-35, or 25-30 nucleotides in length), preferably between about 25 and about 30 nucleotides in length (e.g., 25, 26, 27, 28, 29, or 30 nucleotides in length), and (ii) a second oligonucleotide sequence (also termed the antisense strand) that anneals to the first sequence under biological conditions, such as the conditions found in the cytoplasm of a cell. The second oligonucleotide sequence may be between about 25 and about 60 nucleotides in length (e.g., about 25-60, 25-55, 25-50, 25-45, 25-40, 25-35, or 25-30 nucleotides in length), and is preferably between about 25 and about 30 nucleotides in length (e.g., 25, 26, 27, 28, 29, or 30 nucleotides in length). In addition, a region of one of the sequences, particularly of the antisense strand, of the Dicer-substrate dsRNA has a sequence length of at least about 19 nucleotides, for example, from about 19 to about 60 nucleotides (e.g., about 19-60, 19-55, 19-50, 19-45, 19-40, 19-35, 19-30, or 19-25 nucleotides), preferably from about 19 to about 23 nucleotides (e.g., 19, 20, 21, 22, or 23 nucleotides) that are sufficiently complementary to a nucleotide sequence of the RNA produced from the target gene to trigger an RNAi response.

In a second embodiment, the Dicer-substrate dsRNA has several properties which enhance its processing by Dicer. According to this embodiment, the dsRNA has a length sufficient such that it is processed by Dicer to produce an siRNA and has at least one of the following properties: (i) the dsRNA is asymmetric, e.g., has a 3'-overhang on the antisense strand; and/or (ii) the dsRNA has a modified 3'-end on the sense strand to direct orientation of Dicer binding and processing of the dsRNA to an active siRNA. According to this latter embodiment, the sense strand comprises from about 22 to about 28 nucleotides and the antisense strand comprises from about 24 to about 30 nucleotides.

In one embodiment, the Dicer-substrate dsRNA has an overhang on the 3'-end of the antisense strand. In another embodiment, the sense strand is modified for Dicer binding and processing by suitable modifiers located at the 3'-end of the sense strand. Suitable modifiers include nucleotides such as deoxyribonucleotides, acyclonucleotides, and the like, and sterically hindered molecules such as fluorescent molecules and the like. When nucleotide modifiers are used, they replace ribonucleotides in the dsRNA such that the length of the dsRNA does not change. In another embodiment, the Dicer-substrate dsRNA has an overhang on the 3'-end of the antisense strand and the sense strand is modified for Dicer processing. In another embodiment, the 5'-end of the sense strand has a phosphate. In another embodiment, the 5'-end of the antisense strand has a phosphate. In another embodiment, the antisense strand or the sense strand or both strands have one or more 2'-O-methyl (2'OMe) modified nucleotides. In another embodiment, the antisense strand contains 2'OMe modified nucleotides. In another embodiment, the antisense stand contains a 3'-overhang that is comprised of 2'OMe modified nucleotides. The antisense strand could also include additional 2'OMe modified nucleotides. The sense and antisense strands anneal under biological conditions, such as the conditions found in the cytoplasm of a cell. In addition, a region of one of the sequences, particularly of the antisense strand, of the Dicer-substrate dsRNA has a sequence length of at least about 19 nucleotides, wherein these nucleotides are in the 21-nucleotide region adjacent to the 3'-end of the antisense strand and are sufficiently complementary to a nucleotide sequence of the RNA produced from the target gene. Further, in accordance with this embodiment, the Dicer-substrate dsRNA may also have one or more of the following additional properties: (a) the antisense strand has a right shift from the typical 21-mer (i.e., the antisense strand includes nucleotides on the right side of the molecule when compared to the typical 21-mer); (b) the strands may not be completely complementary, i.e., the strands may contain simple mismatch pairings; and (c) base modifications such as locked nucleic acid(s) may be included in the 5'-end of the sense strand.

In a third embodiment, the sense strand comprises from about 25 to about 28 nucleotides (e.g., 25, 26, 27, or 28 nucleotides), wherein the 2 nucleotides on the 3'-end of the sense strand are deoxyribonucleotides. The sense strand contains a phosphate at the 5'-end. The antisense strand comprises from about 26 to about 30 nucleotides (e.g., 26, 27, 28, 29, or 30 nucleotides) and contains a 3'-overhang of 1-4 nucleotides. The nucleotides comprising the 3'-overhang are modified with 2'OMe modified ribonucleotides. The antisense strand contains alternating 2'OMe modified nucleotides beginning at the first monomer of the antisense strand adjacent to the 3'-overhang, and extending 15-19 nucleotides from the first monomer adjacent to the 3'-overhang. For example, for a 27-nucleotide antisense strand and counting the first base at the 5'-end of the antisense strand as position number 1, 2'OMe modifications would be placed at bases 9, 11, 13, 15, 17, 19, 21, 23, 25, 26, and 27. In one embodiment, the Dicer-substrate dsRNA has the following structure:

5'-pXXXXXXXXXXXXXXXXXXXXXXXDD-3'

3'-YX̲XX̲XX̲XX̲XX̲XX̲XX̲XX̲XX̲XXXXXXXXp-5' wherein "X"=RNA, "p"=a phosphate group, "X̲"=2'OMe RNA, "Y" is an overhang domain comprised of 1, 2, 3, or 4 RNA monomers that are optionally 2'OMe RNA monomers, and "D"=DNA. The top strand is the sense strand, and the bottom strand is the antisense strand.

In a fourth embodiment, the Dicer-substrate dsRNA has several properties which enhance its processing by Dicer. According to this embodiment, the dsRNA has a length sufficient such that it is processed by Dicer to produce an siRNA and at least one of the following properties: (i) the dsRNA is asymmetric, e.g., has a 3'-overhang on the sense strand; and (ii) the dsRNA has a modified 3'-end on the antisense strand to direct orientation of Dicer binding and processing of the dsRNA to an active siRNA. According to this embodiment, the sense strand comprises from about 24 to about 30 nucleotides (e.g., 24, 25, 26, 27, 28, 29, or 30 nucleotides) and the antisense strand comprises from about 22 to about 28 nucleotides (e.g., 22, 23, 24, 25, 26, 27, or 28 nucleotides). In one embodiment, the Dicer-substrate dsRNA has an overhang on the 3'-end of the sense strand. In another embodiment, the antisense strand is modified for Dicer binding and processing by suitable modifiers located at the 3'-end of the antisense strand. Suitable modifiers include nucleotides such as deoxyribonucleotides, acyclonucleotides, and the like, and sterically hindered molecules such as fluorescent molecules and the like. When nucleotide modifiers are used, they replace ribonucleotides in the dsRNA such that the length of the dsRNA does not change. In another embodiment, the dsRNA has an overhang on the 3'-end of the sense strand and the antisense strand is modified for Dicer processing. In one embodiment, the antisense strand has a 5'-phosphate. The sense and antisense strands anneal under biological conditions, such as the conditions found in the cytoplasm of a cell. In addition, a region of one of the sequences, particularly of the antisense strand, of the dsRNA has a sequence length of at least 19 nucleotides, wherein these nucleotides are adjacent to the 3'-end of antisense strand and are sufficiently complementary to a nucleotide sequence of the RNA produced from the target gene. Further, in accordance with this embodiment, the Dicer-substrate dsRNA may also have one or more of the following additional properties: (a) the antisense strand has a left shift from the typical 21-mer (i.e., the antisense strand includes nucleotides on the left side of the molecule when compared to the typical 21-mer); and (b) the strands may not be completely complementary, i.e., the strands may contain simple mismatch pairings.

In a preferred embodiment, the Dicer-substrate dsRNA has an asymmetric structure, with the sense strand having a 25-base pair length, and the antisense strand having a 27-base pair length with a 2 base 3'-overhang. In certain instances, this dsRNA having an asymmetric structure further contains 2 deoxynucleotides at the 3'-end of the sense strand in place of two of the ribonucleotides. In certain other instances, this dsRNA having an asymmetric structure further contains 2'OMe modifications at positions 9, 11, 13, 15, 17, 19, 21, 23, and 25 of the antisense strand (wherein the first base at the 5'-end of the antisense strand is position 1). In certain additional instances, this dsRNA having an asymmetric structure further contains a 3'-overhang on the antisense strand comprising 1, 2, 3, or 4 2'OMe nucleotides (e.g., a 3'-overhang of 2'OMe nucleotides at positions 26 and 27 on the antisense strand).

In another embodiment, Dicer-substrate dsRNAs may be designed by first selecting an antisense strand siRNA sequence having a length of at least 19 nucleotides. In some instances, the antisense siRNA is modified to include about 5 to about 11 ribonucleotides on the 5'-end to provide a length of about 24 to about 30 nucleotides. When the antisense strand has a length of 21 nucleotides, 3-9, preferably 4-7, or more preferably 6 nucleotides may be added on the 5'-end. Although the added ribonucleotides may be complementary to the target gene sequence, full complementarity between the target sequence and the antisense siRNA is not required. That is, the resultant antisense siRNA is sufficiently complementary with the target sequence. A sense strand is then produced that has about 22 to about 28 nucleotides. The sense strand is substantially complementary with the antisense strand to anneal to the antisense strand under biological conditions. In one embodiment, the sense strand is synthesized to contain a modified 3'-end to direct Dicer processing of the antisense strand. In another embodiment, the antisense strand of the dsRNA has a 3'-overhang. In a further embodiment, the sense strand is synthesized to contain a modified 3'-end for Dicer binding and processing and the antisense strand of the dsRNA has a 3'-overhang.

In a related embodiment, the antisense siRNA may be modified to include about 1 to about 9 ribonucleotides on the 5'-end to provide a length of about 22 to about 28 nucleotides. When the antisense strand has a length of 21 nucleotides, 1-7, preferably 2-5, or more preferably 4 ribonucleotides may be added on the 3'-end. The added ribonucleotides may have any sequence. Although the added ribonucleotides may be complementary to the target gene sequence, full complementarity between the target sequence and the antisense siRNA is not required. That is, the resultant antisense siRNA is sufficiently complementary with the target sequence. A sense strand is then produced that has about 24 to about 30 nucleotides. The sense strand is substantially complementary with the antisense strand to anneal to the antisense strand under biological conditions. In one embodiment, the antisense strand is synthesized to contain a modified 3'-end to direct Dicer processing. In another embodiment, the sense strand of the dsRNA has a 3'-overhang. In a further embodiment, the antisense strand is synthesized to contain a modified 3'-end for Dicer binding and processing and the sense strand of the dsRNA has a 3'-overhang.

Suitable Dicer-substrate dsRNA sequences can be identified, synthesized, and modified using any means known in the art for designing, synthesizing, and modifying siRNA sequences. In certain embodiments, Dicer-substrate dsRNAs may silence one or more EBOV genes of interest, and preferably silence the expression of any combination of at least two of the EBOV L-pol, VP24, and VP35 genes. In particular embodiments, Dicer-substrate dsRNAs targeting EBOV RNA are administered using a carrier system such as a nucleic acid-lipid particle (e.g., SNALP). In a preferred embodiment, the nucleic acid-lipid particle comprises: (a) a combination of Dicer-substrate dsRNA molecules targeting at least two (or all three) of the following genes: EBOV L-pol, EBOV VP24, and/or EBOV VP35; (b) a cationic lipid of Formula I-XVI or a salt thereof; and (c) a non-cationic lipid (e.g., DPPC, DSPC, DSPE, and/or cholesterol). In certain instances, the nucleic acid-lipid particle may further comprise a conjugated lipid that prevents aggregation of particles (e.g., PEG-DAA).

Additional embodiments related to the Dicer-substrate dsRNAs of the invention, as well as methods of designing and synthesizing such dsRNAs, are described in U.S. Patent Publication Nos. 20050244858, 20050277610, and 20070265220, and U.S. Application Ser. No. 12/794,701, filed Jun. 4, 2010, the disclosures of which are herein incorporated by reference in their entirety for all purposes.

C. Small Hairpin RNA (shRNA)

A "small hairpin RNA" or "short hairpin RNA" or "shRNA" includes a short RNA sequence that makes a tight hairpin turn that can be used to silence gene expression via RNA interference. The shRNAs of the invention may be chemically synthesized or transcribed from a transcriptional cassette in a DNA plasmid. The shRNA hairpin structure is cleaved by the cellular machinery into siRNA, which is then bound to the RNA-induced silencing complex (RISC).

The shRNAs of the invention are typically about 15-60, 15-50, or 15-40 (duplex) nucleotides in length, more typically about 15-30, 15-25, or 19-25 (duplex) nucleotides in length, and are preferably about 20-24, 21-22, or 21-23 (duplex) nucleotides in length (e.g., each complementary sequence of the double-stranded shRNA is 15-60, 15-50, 15-40, 15-30, 15-25, or 19-25 nucleotides in length, preferably about 20-24, 21-22, or 21-23 nucleotides in length, and the double-stranded shRNA is about 15-60, 15-50, 15-40, 15-30, 15-25, or 19-25 base pairs in length, preferably about 18-22, 19-20, or 19-21 base pairs in length). shRNA duplexes may comprise 3' overhangs of about 1 to about 4 nucleotides or about 2 to about 3 nucleotides on the antisense strand and/or 5'-phosphate termini on the sense strand. In some embodiments, the shRNA comprises a sense strand and/or antisense strand sequence of from about 15 to about 60 nucleotides in length (e.g., about 15-60, 15-55, 15-50, 15-45, 15-40, 15-35, 15-30, or 15-25 nucleotides in length), preferably from about 19 to about 40 nucleotides in length (e.g., about 19-40, 19-35, 19-30, or 19-25 nucleotides in length), more preferably from about 19 to about 23 nucleotides in length (e.g., 19, 20, 21, 22, or 23 nucleotides in length).

Non-limiting examples of shRNA include a double-stranded polynucleotide molecule assembled from a single-stranded molecule, where the sense and antisense regions are linked by a nucleic acid-based or non-nucleic acid-based linker; and a double-stranded polynucleotide molecule with a hairpin secondary structure having self-complementary sense and antisense regions. In preferred embodiments, the sense and antisense strands of the shRNA are linked by a loop structure comprising from about 1 to about 25 nucleotides, from about 2 to about 20 nucleotides, from about 4 to about 15 nucleotides, from about 5 to about 12 nucleotides, or 1, 2, 3, 4, 5, 6, 7, 8, 9, 10, 11, 12, 13, 14, 15, 16, 17, 18, 19, 20, 21, 22, 23, 24, 25, or more nucleotides.

Additional shRNA sequences include, but are not limited to, asymmetric shRNA precursor polynucleotides such as those described in PCT Publication Nos. WO 2006/074108 and WO 2009/076321, the disclosures of which are herein incorporated by reference in their entirety for all purposes. For example, PCT Publication No. WO 2006/074108 discloses self-protected oligonucleotides comprising a region having a sequence complementary to one, two, three, or more same or different target mRNA sequences (e.g., multivalent shRNAs) and one or more self-complementary regions. Similarly, PCT Publication No. WO 2009/076321 discloses self-forming asymmetric precursor polynucleotides comprising a targeting region comprising a polynucleotide sequence complementary to a region of one, two, three, or more same or different target mRNA sequences (e.g., multivalent shRNAs); a first self-complementary region; and a second self-complementary region, wherein the first and second self-complementary regions are located one at each end of the targeting region and both self-complementary regions form stem-loop structures, wherein the first self-complementary region is capable of being cleaved by a RNase III endoribonuclease that is not a class IV DICER endoribonuclease, and wherein both self-complementary regions comprise a nucleotide sequence that is complementary to a region of the target gene sequence, but wherein a portion of the target sequence present in the targeting region does not have a complementary sequence in either of the self-complementary regions.

Suitable shRNA sequences can be identified, synthesized, and modified using any means known in the art for designing, synthesizing, and modifying siRNA sequences. In certain embodiments, shRNAs may silence one or more EBOV genes of interest, and preferably silence the expression of any combination of at least two of the EBOV L-pol, VP24, and VP35 genes. In particular embodiments, shRNAs targeting EBOV RNA are administered using a carrier system such as a nucleic acid-lipid particle (e.g., SNALP). In a preferred embodiment, the nucleic acid-lipid particle comprises: (a) a combination of shRNA molecules targeting at least two (or all three) of the following genes: EBOV L-pol, EBOV VP24, and/or EBOV VP35; (b) a cationic lipid of Formula I-XVI or a salt thereof; and (c) a non-cationic lipid (e.g., DPPC, DSPC, DSPE, and/or cholesterol). In certain instances, the nucleic acid-lipid particle may further comprise a conjugated lipid that prevents aggregation of particles (e.g., PEG-DAA).

Additional embodiments related to the shRNAs of the invention, as well as methods of designing and synthesizing such shRNAs, are described in U.S. patent application Ser. No. 12/794,701, filed Jun. 4, 2010, the disclosure of which is herein incorporated by reference in its entirety for all purposes.

D. aiRNA

Like siRNA, asymmetrical interfering RNA (aiRNA) can recruit the RNA-induced silencing complex (RISC) and lead to effective silencing of a variety of genes in mammalian cells by mediating sequence-specific cleavage of the target sequence between nucleotide 10 and 11 relative to the 5' end of the antisense strand (Sun et al., *Nat. Biotech.,* 26:1379-1382 (2008)). Typically, an aiRNA molecule comprises a short RNA duplex having a sense strand and an antisense strand, wherein the duplex contains overhangs at the 3' and 5' ends of the antisense strand. The aiRNA is generally asymmetric because the sense strand is shorter on both ends when compared to the complementary antisense strand. In some aspects, aiRNA molecules may be designed, synthesized, and annealed under conditions similar to those used for siRNA molecules. As a non-limiting example, aiRNA sequences may be selected and generated using the methods described above for selecting siRNA sequences.

In another embodiment, aiRNA duplexes of various lengths (e.g., about 10-25, 12-20, 12-19, 12-18, 13-17, or 14-17 base pairs, more typically 12, 13, 14, 15, 16, 17, 18, 19, or 20 base pairs) may be designed with overhangs at the 3' and 5' ends of the antisense strand to target an mRNA of interest. In certain instances, the sense strand of the aiRNA molecule is about 10-25, 12-20, 12-19, 12-18, 13-17, or 14-17 nucleotides in length, more typically 12, 13, 14, 15, 16, 17, 18, 19, or 20 nucleotides in length. In certain other instances, the antisense strand of the aiRNA molecule is about 15-60, 15-50, or 15-40 nucleotides in length, more typically about 15-30, 15-25, or 19-25 nucleotides in length, and is preferably about 20-24, 21-22, or 21-23 nucleotides in length.

In some embodiments, the 5' antisense overhang contains one, two, three, four, or more nontargeting nucleotides (e.g., "AA", "UU", "dTdT", etc.). In other embodiments, the 3' antisense overhang contains one, two, three, four, or more nontargeting nucleotides (e.g., "AA", "UU", "dTdT", etc.). In certain aspects, the aiRNA molecules described herein may comprise one or more modified nucleotides, e.g., in the double-stranded (duplex) region and/or in the antisense overhangs. As a non-limiting example, aiRNA sequences may comprise one or more of the modified nucleotides described above for siRNA sequences. In a preferred embodiment, the aiRNA molecule comprises 2'OMe nucleotides such as, for example, 2'OMe-guanosine nucleotides, 2'OMe-uridine nucleotides, or mixtures thereof.

In certain embodiments, aiRNA molecules may comprise an antisense strand which corresponds to the antisense strand of an siRNA molecule, e.g., one of the siRNA molecules described herein. In other embodiments, aiRNA molecules may be used to silence one or more EBOV genes of interest, and preferably silence the expression of any combination of at least two of the EBOV L-pol, VP24, and VP35 genes.

In particular embodiments, aiRNAs targeting EBOV RNA are administered using a carrier system such as a nucleic acid-lipid particle (e.g., SNALP). In preferred embodiments, the nucleic acid-lipid particle comprises: (a) a combination of aiRNA molecules targeting at least two (or all three) of the following genes: EBOV L-pol, EBOV VP24, and/or EBOV VP35; (b) a cationic lipid of Formula I-XVI or a salt thereof; and (c) a non-cationic lipid (e.g., DPPC, DSPC, DSPE, and/or cholesterol). In certain instances, the nucleic acid-lipid particle may further comprise a conjugated lipid that prevents aggregation of particles (e.g., PEG-DAA).

Suitable aiRNA sequences can be identified, synthesized, and modified using any means known in the art for designing, synthesizing, and modifying siRNA sequences. Additional embodiments related to the aiRNA molecules of the invention are described in U.S. Patent Publication No. 20090291131 and PCT Publication No. WO 09/127060, the disclosures of which are herein incorporated by reference in their entirety for all purposes.

E. miRNA

Generally, microRNAs (miRNA) are single-stranded RNA molecules of about 21-23 nucleotides in length which regulate gene expression. miRNAs are encoded by genes from whose DNA they are transcribed, but miRNAs are not translated into protein (non-coding RNA); instead, each primary transcript (a pri-miRNA) is processed into a short stem-loop structure called a pre-miRNA and finally into a functional mature miRNA. Mature miRNA molecules are either partially or completely complementary to one or more messenger RNA (mRNA) molecules, and their main function is to downregulate gene expression. The identification of miRNA molecules is described, e.g., in Lagos-Quintana et al., *Science,* 294:853-858; Lau et al., *Science,* 294:858-862; and Lee et al., *Science,* 294:862-864.

The genes encoding miRNA are much longer than the processed mature miRNA molecule. miRNA are first transcribed as primary transcripts or pri-miRNA with a cap and poly-A tail and processed to short, ~70-nucleotide stem-loop structures known as pre-miRNA in the cell nucleus. This processing is performed in animals by a protein complex known as the Microprocessor complex, consisting of the nuclease Drosha and the double-stranded RNA binding protein Pasha (Denli et al., *Nature,* 432:231-235 (2004)). These pre-miRNA are then processed to mature miRNA in the cytoplasm by interaction with the endonuclease Dicer, which also initiates the formation of the RNA-induced silencing complex (RISC) (Bernstein et al., *Nature,* 409:363-366 (2001). Either the sense strand or antisense strand of DNA can function as templates to give rise to miRNA.

When Dicer cleaves the pre-miRNA stem-loop, two complementary short RNA molecules are formed, but only one is integrated into the RISC complex. This strand is known as the guide strand and is selected by the argonaute protein, the catalytically active RNase in the RISC complex, on the basis of the stability of the 5' end (Preall et al., *Curr. Biol.,* 16:530-535 (2006)). The remaining strand, known as the anti-guide or passenger strand, is degraded as a RISC complex substrate (Gregory et al., *Cell,* 123:631-640 (2005)). After integration into the active RISC complex, miRNAs base pair with their complementary mRNA molecules and induce target mRNA degradation and/or translational silencing.

Mammalian miRNA molecules are usually complementary to a site in the 3' UTR of the target mRNA sequence. In certain instances, the annealing of the miRNA to the target mRNA inhibits protein translation by blocking the protein translation machinery. In certain other instances, the annealing of the miRNA to the target mRNA facilitates the cleavage and degradation of the target mRNA through a process similar to RNA interference (RNAi). miRNA may also target methylation of genomic sites which correspond to targeted mRNA. Generally, miRNA function in association with a complement of proteins collectively termed the miRNP.

In certain aspects, the miRNA molecules described herein are about 15-100, 15-90, 15-80, 15-75, 15-70, 15-60, 15-50, or 15-40 nucleotides in length, more typically about 15-30, 15-25, or 19-25 nucleotides in length, and are preferably about 20-24, 21-22, or 21-23 nucleotides in length. In certain other aspects, miRNA molecules may comprise one or more modified nucleotides. As a non-limiting example, miRNA sequences may comprise one or more of the modified nucleotides described above for siRNA sequences. In a preferred embodiment, the miRNA molecule comprises 2'OMe nucleotides such as, for example, 2'OMe-guanosine nucleotides, 2'OMe-uridine nucleotides, or mixtures thereof.

In some embodiments, miRNA molecules may be used to silence one or more EBOV genes of interest, and preferably silence the expression of any combination of at least two of the EBOV L-pol, VP24, and VP35 genes. In particular embodiments, miRNAs are administered using a carrier system such as a nucleic acid-lipid particle (e.g., SNALP). In a preferred embodiment, the nucleic acid-lipid particle comprises: (a) a combination of miRNA molecules targeting at least two (or all three) of the following genes: EBOV L-pol, EBOV VP24, and/or EBOV VP35; (b) a cationic lipid of Formula I-XVI or a salt thereof; and (c) a non-cationic lipid (e.g., DPPC, DSPC, DSPE, and/or cholesterol). In certain instances, the nucleic acid-lipid particle may further comprise a conjugated lipid that prevents aggregation of particles (e.g., PEG-DAA).

In other embodiments, one or more agents that block the activity of an miRNA targeting EBOV RNA are administered using a lipid particle of the invention (e.g., a nucleic acid-lipid particle such as SNALP). Examples of blocking agents include, but are not limited to, steric blocking oligonucleotides, locked nucleic acid oligonucleotides, and Morpholino oligonucleotides. Such blocking agents may bind directly to the miRNA or to the miRNA binding site on the target RNA.

Additional embodiments related to the miRNA molecules of the invention are described in U.S. Patent Publication No.

20090291131 and PCT Publication No. WO 09/127060, the disclosures of which are herein incorporated by reference in their entirety for all purposes.

V. Lipid Particles

In certain aspects, the present invention provides lipid particles comprising one or more therapeutic nucleic acids (e.g., interfering RNA such as siRNA) and one or more cationic (amino) lipids or salts thereof. In some embodiments, the lipid particles of the invention further comprise one or more non-cationic lipids. In other embodiments, the lipid particles further comprise one or more conjugated lipids capable of reducing or inhibiting particle aggregation.

Lipid particles include, but are not limited to, lipid vesicles such as liposomes. As used herein, a lipid vesicle includes a structure having lipid-containing membranes enclosing an aqueous interior. In particular embodiments, lipid vesicles comprising one or more of the cationic lipids described herein are used to encapsulate nucleic acids within the lipid vesicles. In other embodiments, lipid vesicles comprising one or more of the cationic lipids described herein are complexed with nucleic acids to form lipoplexes.

The lipid particles of the invention preferably comprise a therapeutic nucleic acid such as an interfering RNA (e.g., siRNA), a cationic lipid, a non-cationic lipid, and a conjugated lipid that inhibits aggregation of particles. In some embodiments, the therapeutic nucleic acid is fully encapsulated within the lipid portion of the lipid particle such that the therapeutic nucleic acid in the lipid particle is resistant in aqueous solution to enzymatic degradation, e.g., by a nuclease. In other embodiments, the lipid particles described herein are substantially non-toxic to mammals such as humans. The lipid particles of the invention typically have a mean diameter of from about 30 nm to about 150 nm, from about 40 nm to about 150 nm, from about 50 nm to about 150 nm, from about 60 nm to about 130 nm, from about 70 nm to about 110 nm, or from about 70 to about 90 nm. The lipid particles of the invention also typically have a lipid:nucleic acid ratio (mass/mass ratio) of from about 1:1 to about 100:1, from about 1:1 to about 50:1, from about 2:1 to about 25:1, from about 3:1 to about 20:1, from about 5:1 to about 15:1, or from about 5:1 to about 10:1.

In preferred embodiments, the lipid particles of the invention are serum-stable nucleic acid-lipid particles (SNALP) which comprise an interfering RNA (e.g., dsRNA such as siRNA, Dicer-substrate dsRNA, shRNA, aiRNA, and/or miRNA), a cationic lipid (e.g., one or more cationic lipids of Formula I-XVI or salts thereof as set forth herein), a non-cationic lipid (e.g., mixtures of one or more phospholipids and cholesterol), and a conjugated lipid that inhibits aggregation of the particles (e.g., one or more PEG-lipid conjugates). The SNALP may comprise at least 1, 2, 3, 4, 5, 6, 7, 8, 9, 10, or more unmodified and/or modified interfering RNA molecules (e.g., siRNA) that target the EBOV genome and optionally target additional genes associated with viral infection and survival. Nucleic acid-lipid particles and their method of preparation are described in, e.g., U.S. Pat. Nos. 5,753,613; 5,785,992; 5,705,385; 5,976,567; 5,981,501; 6,110,745; and 6,320,017; and PCT Publication No. WO 96/40964, the disclosures of which are each herein incorporated by reference in their entirety for all purposes.

In the nucleic acid-lipid particles of the invention, the nucleic acid may be fully encapsulated within the lipid portion of the particle, thereby protecting the nucleic acid from nuclease degradation. In preferred embodiments, a SNALP comprising a nucleic acid such as an interfering RNA is fully encapsulated within the lipid portion of the particle, thereby protecting the nucleic acid from nuclease degradation. In certain instances, the nucleic acid in the SNALP is not substantially degraded after exposure of the particle to a nuclease at 37° C. for at least about 20, 30, 45, or 60 minutes. In certain other instances, the nucleic acid in the SNALP is not substantially degraded after incubation of the particle in serum at 37° C. for at least about 30, 45, or 60 minutes or at least about 2, 3, 4, 5, 6, 7, 8, 9, 10, 12, 14, 16, 18, 20, 22, 24, 26, 28, 30, 32, 34, or 36 hours. In other embodiments, the nucleic acid is complexed with the lipid portion of the particle. One of the benefits of the formulations of the present invention is that the nucleic acid-lipid particle compositions are substantially non-toxic to mammals such as humans.

The term "fully encapsulated" indicates that the nucleic acid in the nucleic acid-lipid particle is not significantly degraded after exposure to serum or a nuclease assay that would significantly degrade free DNA or RNA. In a fully encapsulated system, preferably less than about 25% of the nucleic acid in the particle is degraded in a treatment that would normally degrade 100% of free nucleic acid, more preferably less than about 10%, and most preferably less than about 5% of the nucleic acid in the particle is degraded. "Fully encapsulated" also indicates that the nucleic acid-lipid particles are serum-stable, that is, that they do not rapidly decompose into their component parts upon in vivo administration.

In the context of nucleic acids, full encapsulation may be determined by performing a membrane-impermeable fluorescent dye exclusion assay, which uses a dye that has enhanced fluorescence when associated with nucleic acid. Specific dyes such as OliGreen® and RiboGreen® (Invitrogen Corp.; Carlsbad, Calif.) are available for the quantitative determination of plasmid DNA, single-stranded deoxyribonucleotides, and/or single- or double-stranded ribonucleotides. Encapsulation is determined by adding the dye to a liposomal formulation, measuring the resulting fluorescence, and comparing it to the fluorescence observed upon addition of a small amount of nonionic detergent. Detergent-mediated disruption of the liposomal bilayer releases the encapsulated nucleic acid, allowing it to interact with the membrane-impermeable dye. Nucleic acid encapsulation may be calculated as $E=(I_o-I)/I_o$, where I and $I_o$ refer to the fluorescence intensities before and after the addition of detergent (see, Wheeler et al., *Gene Ther.,* 6:271-281 (1999)).

In other embodiments, the present invention provides a nucleic acid-lipid particle (e.g., SNALP) composition comprising a plurality of nucleic acid-lipid particles.

In some instances, the SNALP composition comprises nucleic acid that is fully encapsulated within the lipid portion of the particles, such that from about 30% to about 100%, from about 40% to about 100%, from about 50% to about 100%, from about 60% to about 100%, from about 70% to about 100%, from about 80% to about 100%, from about 90% to about 100%, from about 30% to about 95%, from about 40% to about 95%, from about 50% to about 95%, from about 60% to about 95%, from about 70% to about 95%, from about 80% to about 95%, from about 85% to about 95%, from about 90% to about 95%, from about 30% to about 90%, from about 40% to about 90%, from about 50% to about 90%, from about 60% to about 90%, from about 70% to about 90%, from about 80% to about 90%, or at least about 30%, 35%, 40%, 45%, 50%, 55%, 60%, 65%, 70%, 75%, 80%, 85%, 90%, 91%, 92%, 93%, 94%, 95%, 96%, 97%, 98%, or 99% (or any fraction thereof or range therein) of the particles have the nucleic acid encapsulated therein.

In other instances, the SNALP composition comprises nucleic acid that is fully encapsulated within the lipid portion of the particles, such that from about 30% to about 100%, from about 40% to about 100%, from about 50% to about 100%, from about 60% to about 100%, from about 70% to about 100%, from about 80% to about 100%, from about 90% to about 100%, from about 30% to about 95%, from about 40% to about 95%, from about 50% to about 95%, from about 60% to about 95%, from about 70% to about 95%, from about 80% to about 95%, from about 85% to about 95%, from about 90% to about 95%, from about 30% to about 90%, from about 40% to about 90%, from about 50% to about 90%, from about 60% to about 90%, from about 70% to about 90%, from about 80% to about 90%, or at least about 30%, 35%, 40%, 45%, 50%, 55%, 60%, 65%, 70%, 75%, 80%, 85%, 90%, 91%, 92%, 93%, 94%, 95%, 96%, 97%, 98%, or 99% (or any fraction thereof or range therein) of the input nucleic acid is encapsulated in the particles.

Depending on the intended use of the lipid particles of the invention, the proportions of the components can be varied and the delivery efficiency of a particular formulation can be measured using, e.g., an endosomal release parameter (ERP) assay.

In particular embodiments, the present invention provides a lipid particle (e.g., SNALP) composition comprising a plurality of lipid particles described herein and an antioxidant. In certain instances, the antioxidant in the lipid particle composition reduces, prevents, and/or inhibits the degradation of a cationic lipid present in the lipid particle. In instances wherein the active agent is a therapeutic nucleic acid such as an interfering RNA (e.g., siRNA), the antioxidant in the lipid particle composition reduces, prevents, and/or inhibits the degradation of the nucleic acid payload, e.g., by reducing, preventing, and/or inhibiting the formation of adducts between the nucleic acid and the cationic lipid. Non-limiting examples of antioxidants include hydrophilic antioxidants such as chelating agents (e.g., metal chelators such as ethylenediaminetetraacetic acid (EDTA), citrate, and the like), lipophilic antioxidants (e.g., vitamin E isomers, polyphenols, and the like), salts thereof; and mixtures thereof. If needed, the antioxidant is typically present in an amount sufficient to prevent, inhibit, and/or reduce the degradation of the cationic lipid and/or active agent present in the particle, e.g., at least about 20 mM EDTA or a salt thereof, or at least about 100 mM citrate or a salt thereof. An antioxidant such as EDTA and/or citrate may be included at any step or at multiple steps in the lipid particle formation process described in Section VI (e.g., prior to, during, and/or after lipid particle formation).

Additional embodiments related to methods of preventing the degradation of cationic lipids and/or active agents (e.g., therapeutic nucleic acids) present in lipid particles, compositions comprising lipid particles stabilized by these methods, methods of making these lipid particles, and methods of delivering and/or administering these lipid particles are described in U.S. Provisional Application No. 61/265,671, entitled "SNALP Formulations Containing Antioxidants," filed Dec. 1, 2009, the disclosure of which is herein incorporated by reference in its entirety for all purposes.

A. Cationic Lipids

Any of a variety of cationic lipids or salts thereof may be used in the lipid particles of the present invention (e.g., SNALP), either alone or in combination with one or more other cationic lipid species or non-cationic lipid species. In particular embodiments, one or more of the cationic lipids of Formula I-XVI or salts thereof as set forth herein may be used in the lipid particles of the present invention (e.g., SNALP), either alone or in combination with one or more other cationic lipid species or non-cationic lipid species. The cationic lipids include the (R) and/or (S) enantiomers thereof.

In some embodiments, the cationic lipid comprises a racemic mixture. In other embodiments, the cationic lipid comprises a mixture of one or more diastereomers. In certain embodiments, the cationic lipid is enriched in one enantiomer, such that the cationic lipid comprises at least about 55%, 60%, 65%, 70%, 75%, 80%, 85%, 90%, or 95% enantiomeric excess. In certain other embodiments, the cationic lipid is enriched in one diastereomer, such that the cationic lipid comprises at least about 55%, 60%, 65%, 70%, 75%, 80%, 85%, 90%, or 95% diastereomeric excess. In certain additional embodiments, the cationic lipid is chirally pure (e.g., comprises a single optical isomer). In further embodiments, the cationic lipid is enriched in one optical isomer (e.g., an optically active isomer), such that the cationic lipid comprises at least about 55%, 60%, 65%, 70%, 75%, 80%, 85%, 90%, or 95% isomeric excess. The present invention provides the synthesis of the cationic lipids of Formulas I-XVI as a racemic mixture or in optically pure form.

The terms "cationic lipid" and "amino lipid" are used interchangeably herein to include those lipids and salts thereof having one, two, three, or more fatty acid or fatty alkyl chains and a pH-titratable amino head group (e.g., an alkylamino or dialkylamino head group). The cationic lipid is typically protonated (i.e., positively charged) at a pH below the $pK_a$ of the cationic lipid and is substantially neutral at a pH above the $pK_a$. The cationic lipids of the invention may also be termed titratable cationic lipids.

The term "salts" includes any anionic and cationic complex, such as the complex formed between a cationic lipid disclosed herein and one or more anions. Non-limiting examples of anions include inorganic and organic anions, e.g., hydride, fluoride, chloride, bromide, iodide, oxalate (e.g., hemioxalate), phosphate, phosphonate, hydrogen phosphate, dihydrogen phosphate, oxide, carbonate, bicarbonate, nitrate, nitrite, nitride, bisulfite, sulfide, sulfite, bisulfate, sulfate, thiosulfate, hydrogen sulfate, borate, formate, acetate, benzoate, citrate, tartrate, lactate, acrylate, polyacrylate, fumarate, maleate, itaconate, glycolate, gluconate, malate, mandelate, tiglate, ascorbate, salicylate, polymethacrylate, perchlorate, chlorate, chlorite, hypochlorite, bromate, hypobromite, iodate, an alkylsulfonate, an arylsulfonate, arsenate, arsenite, chromate, dichromate, cyanide, cyanate, thiocyanate, hydroxide, peroxide, permanganate, and mixtures thereof. In particular embodiments, the salts of the cationic lipids disclosed herein are crystalline salts.

The term "alkyl" includes a straight chain or branched, noncyclic or cyclic, saturated aliphatic hydrocarbon containing from 1 to 24 carbon atoms. Representative saturated straight chain alkyls include, but are not limited to, methyl, ethyl, n-propyl, n-butyl, n-pentyl, n-hexyl, and the like, while saturated branched alkyls include, without limitation, isopropyl, sec-butyl, isobutyl, tert-butyl, isopentyl, and the like. Representative saturated cyclic alkyls include, but are not limited to, cyclopropyl, cyclobutyl, cyclopentyl, cyclohexyl, and the like, while unsaturated cyclic alkyls include, without limitation, cyclopentenyl, cyclohexenyl, and the like.

The term "alkenyl" includes an alkyl, as defined above, containing at least one double bond between adjacent carbon atoms. Alkenyls include both cis and trans isomers. Representative straight chain and branched alkenyls include, but are not limited to, ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like.

The term "alkynyl" includes any alkyl or alkenyl, as defined above, which additionally contains at least one triple bond between adjacent carbons. Representative straight chain and branched alkynyls include, without limitation, acetylenyl, propynyl, 1-butynyl, 2-butynyl, 1-pentynyl, 2-pentynyl, 3-methyl-1 butynyl, and the like.

The term "acyl" includes any alkyl, alkenyl, or alkynyl wherein the carbon at the point of attachment is substituted with an oxo group, as defined below. The following are non-limiting examples of acyl groups: —C(═O)alkyl, —C(═O)alkenyl, and —C(═O)alkynyl.

The term "heterocycle" includes a 5- to 7-membered monocyclic, or 7- to 10-membered bicyclic, heterocyclic ring which is either saturated, unsaturated, or aromatic, and which contains from 1 or 2 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring. The heterocycle may be attached via any heteroatom or carbon atom. Heterocycles include, but are not limited to, heteroaryls as defined below, as well as morpholinyl, pyrrolidinonyl, pyrrolidinyl, piperidinyl, piperizynyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

The terms "optionally substituted alkyl", "optionally substituted alkenyl", "optionally substituted alkynyl", "optionally substituted acyl", and "optionally substituted heterocycle" mean that, when substituted, at least one hydrogen atom is replaced with a substituent. In the case of an oxo substituent (═O), two hydrogen atoms are replaced. In this regard, substituents include, but are not limited to, oxo, halogen, heterocycle, —CN, —$OR^x$, —$NR^xR^y$, —$NR^x$(═O)$R^y$, —$NR^xSO_2R^y$, —C(═O)$R^x$, —C(═O)$OR^x$, —C(═O)$NR^xR^y$, —$SO_nR^x$, and —$SO_nNR^xR^y$, wherein n is 0, 1, or 2, $R^x$ and $R^y$ are the same or different and are independently hydrogen, alkyl, or heterocycle, and each of the alkyl and heterocycle substituents may be further substituted with one or more of oxo, halogen, —OH, —CN, alkyl, —$OR^x$, heterocycle, —$NR^xR^y$, —$NR^x$C(═O)$R^y$, —$NR^xSO_2R^y$, —C(═O)$R^x$, —C(═O)$OR^x$, —C(═O)$NR^xR^y$, —$SO_nR^x$, and —$SO_nNR^xR^y$. The term "optionally substituted," when used before a list of substituents, means that each of the substituents in the list may be optionally substituted as described herein.

The term "halogen" includes fluoro, chloro, bromo, and iodo.

In one aspect, cationic lipids of Formula I having the following structure (or salts thereof) are useful in the present invention:

(I)

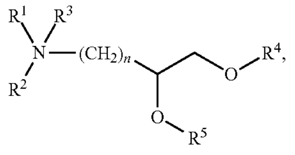

wherein $R^1$ and $R^2$ are either the same or different and are independently hydrogen (H) or an optionally substituted $C_1$-$C_6$ alkyl, $C_2$-$C_6$ alkenyl, or $C_2$-$C_6$ alkynyl, or $R^1$ and $R^2$ may join to form an optionally substituted heterocyclic ring of 4 to 6 carbon atoms and 1 or 2 heteroatoms selected from the group consisting of nitrogen (N), oxygen (O), and mixtures thereof;

$R^3$ is either absent or is hydrogen (H) or a $C_1$-$C_6$ alkyl to provide a quaternary amine;

$R^4$ and $R^5$ are either the same or different and are independently an optionally substituted $C_{10}$-$C_{24}$ alkyl, $C_{10}$-$C_{24}$ alkenyl, $C_{10}$-$C_{24}$ alkynyl, or $C_{10}$-$C_{24}$ acyl, wherein at least one of $R^4$ and $R^5$ comprises at least two sites of unsaturation; and n is 0, 1, 2, 3, or 4.

In some embodiments, $R^1$ and $R^2$ are independently an optionally substituted $C_1$-$C_4$ alkyl, $C_2$-$C_4$ alkenyl, or $C_2$-$C_4$ alkynyl. In one preferred embodiment, $R^1$ and $R^2$ are both methyl groups. In other preferred embodiments, n is 1 or 2. In other embodiments, $R^3$ is absent when the pH is above the $pK_a$ of the cationic lipid and $R^3$ is hydrogen when the pH is below the $pK_a$ of the cationic lipid such that the amino head group is protonated. In an alternative embodiment, $R^3$ is an optionally substituted $C_1$-$C_4$ alkyl to provide a quaternary amine. In further embodiments, $R^4$ and $R^5$ are independently an optionally substituted $C_{12}$-$C_{24}$, $C_{12}$-$C_{22}$, $C_{12}$-$C_{20}$, $C_{14}$-$C_{24}$, $C_{14}$-$C_{22}$, $C_{14}$-$C_{20}$, $C_{16}$-$C_{24}$, $C_{16}$-$C_{22}$, or $C_{16}$-$C_{20}$ alkyl, alkenyl, alkynyl, or acyl group (i.e., $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, or $C_{24}$ alkyl, alkenyl, alkynyl, or acyl group). In certain embodiments, at least one or both $R^4$ and $R^5$ independently comprises at least 2, 3, 4, 5, or 6 sites of unsaturation (e.g., 2, 3, 4, 5, 6, 2-3, 2-4, 2-5, or 2-6 sites of unsaturation).

In certain instances, $R^4$ and $R^5$ may independently comprise a dodecadienyl moiety, a tetradecadienyl moiety, a hexadecadienyl moiety, an octadecadienyl moiety, an icosadienyl moiety, a dodecatrienyl moiety, a tetradectrienyl moiety, a hexadecatrienyl moiety, an octadecatrienyl moiety, an icosatrienyl moiety, or an acyl derivative thereof (e.g., linoleoyl, linolenoyl, γ-linolenoyl, etc.). In some instances, the octadecadienyl moiety is a linoleyl moiety. In particular embodiments, $R^4$ and $R^5$ are both linoleyl moieties. In other instances, the octadecatrienyl moiety is a linolenyl moiety or a γ-linolenyl moiety. In particular embodiments, $R^4$ and $R^5$ are both linolenyl moieties or γ-linolenyl moieties. In certain instances, $R^4$ and $R^5$ are different, e.g., $R^4$ is a tetradectrienyl ($C_{14}$) and $R^5$ is linoleyl ($C_{18}$). In a preferred embodiment, the cationic lipid of Formula I is symmetrical, i.e., $R^4$ and $R^5$ are both the same. In further embodiments, the double bonds present in one or both $R^4$ and $R^5$ may be in the cis and/or trans configuration.

In some groups of embodiments to the cationic lipids of Formula I, $R^4$ and $R^5$ are either the same or different and are independently selected from the group consisting of:

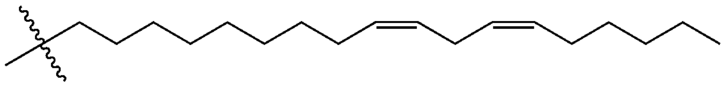
;

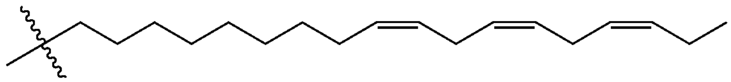
; and

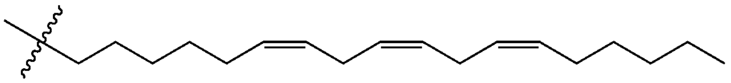
.

In particular embodiments, the cationic lipid of Formula I comprises 1,2-dilinoleyloxy-N,N-dimethylaminopropane (DLinDMA), 1,2-dilinolenyloxy-N,N-dimethylaminopropane (DLenDMA), or mixtures thereof.

In some embodiments, the cationic lipid of Formula I forms a salt (preferably a crystalline salt) with one or more anions. In one particular embodiment, the cationic lipid of Formula I is the oxalate (e.g., hemioxalate) salt thereof, which is preferably a crystalline salt.

In another aspect, cationic lipids of Formula II having the following structure (or salts thereof) are useful in the present invention:

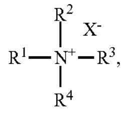
(II)

wherein $R^1$ and $R^2$ are independently selected and are H or $C_1$-$C_3$ alkyls, $R^3$ and $R^4$ are independently selected and are alkyl groups having from about 10 to about 20 carbon atoms, and at least one of $R^3$ and $R^4$ comprises at least two sites of unsaturation. In certain instances, $R^3$ and $R^4$ are both the same, i.e., $R^3$ and $R^4$ are both linoleyl ($C_{18}$), etc. In certain other instances, $R^3$ and $R^4$ are different, i.e., $R^3$ is tetradectrienyl ($C_{14}$) and $R^4$ is linoleyl ($C_{18}$). In a preferred embodiment, the cationic lipid of Formula II is symmetrical, i.e., $R^3$ and $R^4$ are both the same. In another preferred embodiment, both $R^3$ and $R^4$ comprise at least two sites of unsaturation. In some embodiments, $R^3$ and $R^4$ are independently selected from the group consisting of dodecadienyl, tetradecadienyl, hexadecadienyl, linoleyl, and icosadienyl. In a preferred embodiment, $R^3$ and $R^4$ are both linoleyl. In some embodiments, $R^3$ and $R^4$ comprise at least three sites of unsaturation and are independently selected from, e.g., dodecatrienyl, tetradectrienyl, hexadecatrienyl, linolenyl, and icosatrienyl.

In some embodiments, the cationic lipid of Formula II forms a salt (preferably a crystalline salt) with one or more anions. In one particular embodiment, the cationic lipid of Formula II is the oxalate (e.g., hemioxalate) salt thereof, which is preferably a crystalline salt.

The synthesis of cationic lipids such as DLinDMA and DLenDMA, as well as additional cationic lipids falling withinthe scope of Formulas I and II, is described in U.S. Patent Publication No. 20060083780, the disclosure of which is herein incorporated by reference in its entirety for all purposes.

In yet another aspect, cationic lipids of Formula III having the following structure (or salts thereof) are useful in the present invention:

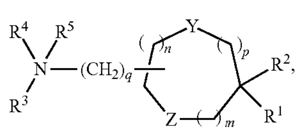
(III)

wherein $R^1$ and $R^2$ are either the same or different and are independently an optionally substituted $C_{12}$-$C_{24}$ alkyl, $C_{12}$-$C_{24}$ alkenyl, $C_{12}$-$C_{24}$ alkynyl, or $C_{12}$-$C_{24}$ acyl; $R^3$ and $R^4$ are either the same or different and are independently an optionally substituted $C_1$-$C_6$ alkyl, $C_2$-$C_6$ alkenyl, or $C_2$-$C_6$ alkynyl, or $R^3$ and $R^4$ may join to form an optionally substituted heterocyclic ring of 4 to 6 carbon atoms and 1 or 2 heteroatoms chosen from nitrogen and oxygen; $R^5$ is either absent or is hydrogen (H) or a $C_1$-$C_6$ alkyl to provide a quaternary amine; m, n, and p are either the same or different and are independently either 0, 1, or 2, with the proviso that m, n, and p are not simultaneously 0; q is 0, 1, 2, 3, or 4; and Y and Z are either the same or different and are independently O, S, or NH.

In some embodiments, $R^3$ and $R^4$ are independently an optionally substituted $C_1$-$C_4$ alkyl, $C_2$-$C_4$ alkenyl, or $C_2$-$C_4$ alkynyl. In a preferred embodiment, $R^3$ and $R^4$ are both methyl groups. In one embodiment, q is 1 or 2. In another embodiment, q is 1-2, 1-3, 1-4, 2-3, or 2-4. In further embodiments, $R^5$ is absent when the pH is above the $pK_a$ of the cationic lipid and $R^5$ is hydrogen when the pH is below the $pK_a$ of the cationic lipid such that the amino head group is protonated. In an alternative embodiment, $R^5$ is an optionally substituted $C_1$-$C_4$ alkyl to provide a quaternary amine. In additional embodiments, Y and Z are both O.

In other embodiments, $R^1$ and $R^2$ are independently an optionally substituted $C_{12}$-$C_{24}$, $C_{12}$-$C_{22}$, $C_{12}$-$C_{20}$, $C_{14}$-$C_{24}$, $C_{14}$-$C_{22}$, $C_{14}$-$C_{20}$, $C_{16}$-$C_{24}$, $C_{16}$-$C_{22}$, or $C_{16}$-$C_{20}$ alkyl, alkenyl, alkynyl, or acyl group (i.e., $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, or $C_{24}$ alkyl, alkenyl, alkynyl, or acyl group). In certain embodiments, at least one or both $R^1$ and $R^2$ independently comprises at least 1, 2, 3, 4, 5, or 6 sites of unsaturation (e.g., 1-2, 1-3, 1-4, 1-5, 1-6, 2-3, 2-4, 2-5, or 2-6 sites of unsaturation) or a substituted alkyl or acyl group. In certain instances, the unsaturated side-chain may comprise a myristoleyl moiety, a palmitoleyl moiety, an oleyl moiety, a dodecadienyl moiety, a tetradecadienyl moiety, a hexadecadienyl moiety, an octadecadienyl moiety, an icosadienyl moiety, a dodecatrienyl moiety, a tetradectrienyl moiety, a hexadecatrienyl moiety, an octadecatrienyl moiety, an icosatrienyl moiety, or an acyl derivative thereof (e.g., linoleoyl, linolenoyl, γ-linolenoyl, etc.). In some instances, the octadecadienyl moiety is a linoleyl moiety. In particular embodiments, $R^1$ and $R^2$ are both linoleyl moieties. In other instances, the octadecatrienyl moiety is a linolenyl moiety or a γ-linolenyl moiety. In particular embodiments, $R^1$ and $R^2$ are both linolenyl moieties or γ-linolenyl moieties.

In embodiments where one or both $R^1$ and $R^2$ independently comprises at least 1, 2, 3, 4, 5, or 6 sites of unsaturation, the double bonds present in one or both $R^1$ and $R^2$ may be in the cis and/or trans configuration. In certain instances, $R^1$ and $R^2$ are both the same, e.g., $R^1$ and $R^2$ are both linoleyl ($C_{18}$) moieties, etc. In certain other instances, $R^1$ and $R^2$ are different, e.g., $R^1$ is a tetradectrienyl ($C_{14}$) moiety and $R^2$ is a linoleyl ($C_{18}$) moiety. In a preferred embodiment, the cationic lipid of Formula III is symmetrical, i.e., $R^1$ and $R^2$ are both the same. In another preferred embodiment, at least one or both $R^1$ and $R^2$ comprises at least two sites of unsaturation (e.g., 2, 3, 4, 5, 6, 2-3, 2-4, 2-5, or 2-6 sites of unsaturation).

In embodiments where one or both $R^1$ and $R^2$ independently comprises a branched alkyl or acyl group (e.g., a substituted alkyl or acyl group), the branched alkyl or acyl group may comprise a $C_{12}$-$C_{24}$ alkyl or acyl having at least 1-6 (e.g., 1, 2, 3, 4, 5, 6, or more) $C_1$-$C_6$ alkyl substituents. In particular embodiments, the branched alkyl or acyl group comprises a $C_{12}$-$C_{20}$ or $C_{14}$-$C_{22}$ alkyl or acyl with 1-6 (e.g., 1, 2, 3, 4, 5, 6) $C_1$-$C_4$ alkyl (e.g., methyl, ethyl, propyl, or butyl) substituents. In some embodiments, the branched alkyl group comprises a phytanyl(3,7,11,15-tetramethyl-hexadecanyl) moiety and the branched acyl group comprises a phytanoyl(3,7,11,15-tetramethyl-hexadecanoyl) moiety. In particular embodiments, $R^1$ and $R^2$ are both phytanyl moieties.

In some groups of embodiments to the cationic lipids of Formula III, $R^1$ and $R^2$ are either the same or different and are independently selected from the group consisting of:

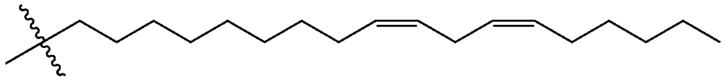

;

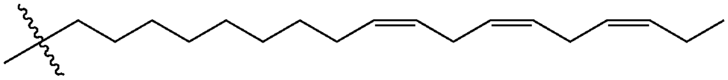

;

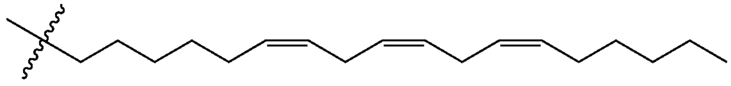

; and

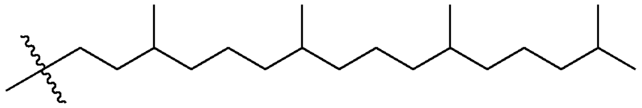

.

In certain embodiments, cationic lipids falling within the scope of Formula III include, but are not limited to, the following: 2,2-dilinoleyl-4-(2-dimethylaminoethyl)-[1,3]-dioxolane (DLin-K-C2-DMA; "XTC2" or "C2K"), 2,2-dilinoleyl-4-dimethylaminomethyl-[1,3]-dioxolane (DLin-K-DMA), 2,2-dilinoleyl-4-(3-dimethylaminopropyl)-[1,3]-dioxolane (DLin-K-C3-DMA; "C3K"), 2,2-dilinoleyl-4-(4-dimethylaminobutyl)-[1,3]-dioxolane (DLin-K-C4-DMA; "C4K"), 2,2-dilinoleyl-5-dimethylaminomethyl-[1,3]-dioxane (DLin-K6-DMA), 2,2-dilinoleyl-4-N-methylpepiazino-[1,3]-dioxolane (DLin-K-MPZ), 2,2-dioleoyl-4-dimethylaminomethyl-[1,3]-dioxolane (DO-K-DMA), 2,2-distearoyl-4-dimethylaminomethyl-[1,3]-dioxolane (DS-K-DMA), 2,2-dilinoleyl-4-N-morpholino-[1,3]-dioxolane (DLin-K-MA), 2,2-Dilinoleyl-4-trimethylamino-[1,3]-dioxolane chloride (DLin-K-TMA.C1), 2,2-dilinoleyl-4,5-bis(dimethylaminomethyl)-[1,3]-dioxolane (DLin-$K^2$-DMA), 2,2-dilinoleyl-4-methylpiperzine-[1,3]-dioxolane (D-Lin-K-N-methylpiperzine), DLen-C2K-DMA, γ-DLen-C2K-DMA, DPan-C2K-DMA, DPan-C3K-DMA, or mixtures thereof. In preferred embodiments, the cationic lipid of Formula III comprises DLin-K-C2-DMA and/or DLin-K-DMA.

In some embodiments, the cationic lipids of Formula III form a salt (preferably a crystalline salt) with one or more anions. In one particular embodiment, the cationic lipid of Formula III is the oxalate (e.g., hemioxalate) salt thereof, which is preferably a crystalline salt.

The synthesis of cationic lipids such as DLin-K-C2-DMA, DLin-K-C3-DMA, DLin-K-C4-DMA, DLin-K6-DMA, DLin-K-MPZ, DO-K-DMA, DS-K-DMA, DLin-K-MA, DLin-K-TMA.C1, DLin-$K^2$-DMA, D-Lin-K-N-methylpiperzine, as well as additional cationic lipids, is described in PCT Publication No. WO 2010/042877, the disclosure of which is incorporated herein by reference in its entirety for all purposes.

The synthesis of cationic lipids such as DLin-K-DMA, as well as additional cationic lipids, is described in PCT Publication No. WO 09/086558, the disclosure of which is herein incorporated by reference in its entirety for all purposes.

In a preferred embodiment, cationic lipids of Formula IV having the following structure (or salts thereof) are useful in the present invention:

(IV)

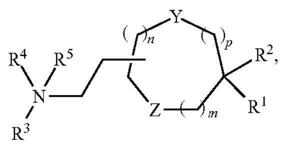

wherein $R^1$ and $R^2$ are either the same or different and are independently an optionally substituted $C_{12}$-$C_{24}$ alkyl, $C_{12}$-$C_{24}$ alkenyl, $C_{12}$-$C_{24}$ alkynyl, or $C_{12}$-$C_{24}$ acyl; $R^3$ and $R^4$ are either the same or different and are independently an optionally substituted $C_1$-$C_6$ alkyl, $C_2$-$C_6$ alkenyl, or $C_2$-$C_6$ alkynyl, or $R^3$ and $R^4$ may join to form an optionally substituted heterocyclic ring of 4 to 6 carbon atoms and 1 or 2 heteroatoms chosen from nitrogen and oxygen; $R^5$ is either absent or is hydrogen (H) or a $C_1$-$C_6$ alkyl to provide a quaternary amine; m, n, and p are either the same or different and are independently either 0, 1, or 2, with the proviso that m, n, and p are not simultaneously O; and Y and Z are either the same or different and are independently O, S, or NH.

In some embodiments, $R^3$ and $R^4$ are independently an optionally substituted $C_1$-$C_4$ alkyl, $C_2$-$C_4$ alkenyl, or $C_2$-$C_4$ alkynyl. In a preferred embodiment, $R^3$ and $R^4$ are both methyl groups. In further embodiments, $R^5$ is absent when the pH is above the $pK_a$ of the cationic lipid and $R^5$ is hydrogen when the pH is below the $pK_a$ of the cationic lipid such that the amino head group is protonated. In an alternative embodiment, $R^5$ is an optionally substituted $C_1$-$C_4$ alkyl to provide a quaternary amine. In additional embodiments, Y and Z are both O.

In other embodiments, $R^1$ and $R^2$ are independently an optionally substituted $C_{12}$-$C_{24}$, $C_{12}$-$C_{22}$, $C_{12}$-$C_{20}$, $C_{14}$-$C_{24}$, $C_{14}$-$C_{22}$, $C_{14}$-$C_{20}$, $C_{16}$-$C_{24}$, $C_{16}$-$C_{22}$, or $C_{16}$-$C_{20}$ alkyl, alkenyl, alkynyl, or acyl group (i.e., $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, or $C_{24}$ alkyl, alkenyl, alkynyl, or acyl group). In certain embodiments, at least one or both $R^1$ and $R^2$ independently comprises at least 1, 2, 3, 4, 5, or 6 sites of unsaturation (e.g., 1-2, 1-3, 1-4, 1-5, 1-6, 2-3, 2-4, 2-5, or 2-6 sites of unsaturation) or a substituted alkyl or acyl group. In certain instances, the unsaturated side-chain may comprise a myristoleyl moiety, a palmitoleyl moiety, an oleyl moiety, a dodecadienyl moiety, a tetradecadienyl moiety, a hexadecadienyl moiety, an octadecadienyl moiety, an icosadienyl moiety, a dodecatrienyl moiety, a tetradectrienyl moiety, a hexadecatrienyl moiety, an octadecatrienyl moiety, an icosatrienyl moiety, or an acyl derivative thereof (e.g., linoleoyl, linolenoyl, etc.). In some instances, the octadecadienyl moiety is a linoleyl moiety. In particular embodiments, $R^1$ and $R^2$ are both linoleyl moieties. In other instances, the octadecatrienyl moiety is a linolenyl moiety or a γ-linolenyl moiety. In particular embodiments, $R^1$ and $R^2$ are both linolenyl moieties or γ-linolenyl moieties.

In embodiments where one or both $R^1$ and $R^2$ independently comprises at least 1, 2, 3, 4, 5, or 6 sites of unsaturation, the double bonds present in one or both $R^1$ and $R^2$ may be in the cis and/or trans configuration. In certain instances, $R^1$ and $R^2$ are both the same, e.g., $R^1$ and $R^2$ are both linoleyl ($C_{18}$) moieties, etc. In certain other instances, $R^1$ and $R^2$ are different, e.g., $R^1$ is a tetradectrienyl ($C_{14}$) moiety and $R^2$ is a linoleyl ($C_{18}$) moiety. In a preferred embodiment, the cationic lipid of Formula IV is symmetrical, i.e., $R^1$ and $R^2$ are both the same. In another preferred embodiment, at least one or both $R^1$ and $R^2$ comprises at least two sites of unsaturation (e.g., 2, 3, 4, 5, 6, 2-3, 2-4, 2-5, or 2-6 sites of unsaturation).

In embodiments where one or both $R^1$ and $R^2$ independently comprises a branched alkyl or acyl group (e.g., a substituted alkyl or acyl group), the branched alkyl or acyl group may comprise a $C_{12}$-$C_{24}$ alkyl or acyl having at least 1-6 (e.g., 1, 2, 3, 4, 5, 6, or more) $C_1$-$C_6$ alkyl substituents. In particular embodiments, the branched alkyl or acyl group comprises a $C_{12}$-$C_{20}$ or $C_{14}$-$C_{22}$ alkyl or acyl with 1-6 (e.g., 1, 2, 3, 4, 5, 6) $C_1$-$C_4$ alkyl (e.g., methyl, ethyl, propyl, or butyl) substituents. In some embodiments, the branched alkyl group comprises a phytanyl(3,7,11,15-tetramethyl-hexadecanyl) moiety and the branched acyl group comprises a phytanoyl(3,7,11,15-tetramethyl-hexadecanoyl) moiety. In particular embodiments, $R^1$ and $R^2$ are both phytanyl moieties.

In some groups of embodiments to the cationic lipids of Formula IV, $R^1$ and $R^2$ are either the same or different and are independently selected from the group consisting of:

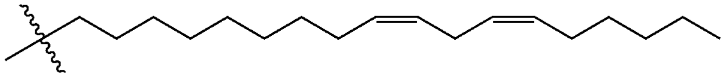
;

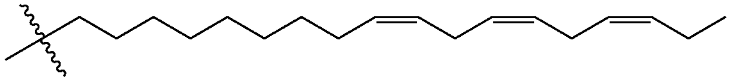
;

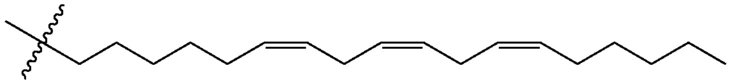
; and

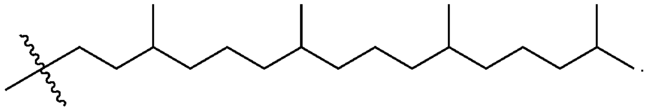
.

In certain embodiments, cationic lipids falling within the scope of Formula IV include, but are not limited to, the following: 2,2-dilinoleyl-4-(2-dimethylaminoethyl)-[1,3]-dioxolane (DLin-K-C2-DMA; "XTC2" or "C2K"), DLen-C2K-DMA, γ-DLen-C2K-DMA, DPan-C2K-DMA, or mixtures thereof. In preferred embodiments, the cationic lipid of Formula IV comprises DLin-K-C2-DMA.

In some embodiments, the cationic lipids of Formula IV form a salt (preferably a crystalline salt) with one or more anions. In one particular embodiment, the cationic lipid of Formula IV is the oxalate (e.g., hemioxalate) salt thereof, which is preferably a crystalline salt.

The synthesis of DLin-K-C2-DMA (C2K) is described in PCT Publication No. WO 2010/042877, the disclosure of which is incorporated herein by reference in its entirety for all purposes.

In a further aspect, cationic lipids of Formula V having the following structure are useful in the present invention:

In some embodiments, $R^1$ and $R^2$ are independently an optionally substituted $C_1$-$C_4$ alkyl, $C_2$-$C_4$ alkenyl, or $C_2$-$C_4$ alkynyl. In a preferred embodiment, $R^1$ and $R^2$ are both methyl groups. In another preferred embodiment, $R^4$ and $R^5$ are both butyl groups. In yet another preferred embodiment, n is 1. In other embodiments, $R^3$ is absent when the pH is above the $pK_a$ of the cationic lipid and $R^3$ is hydrogen when the pH is below the $pK_a$ of the cationic lipid such that the amino head group is protonated. In an alternative embodiment, $R^3$ is an optionally substituted $C_1$-$C_4$ alkyl to provide a quaternary amine. In further embodiments, $R^4$ and $R^5$ are independently an optionally substituted $C_2$-$C_6$ or $C_2$-$C_4$ alkyl or $C_2$-$C_6$ or $C_2$-$C_4$ alkenyl.

In an alternative embodiment, the cationic lipid of Formula V comprises ester linkages between the amino head group (V)

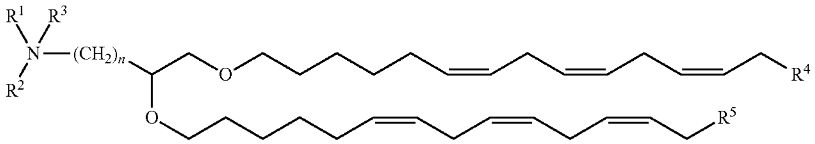

or salts thereof, wherein: $R^1$ and $R^2$ are either the same or different and are independently an optionally substituted $C_1$-$C_6$ alkyl, $C_2$-$C_6$ alkenyl, or $C_2$-$C_6$ alkynyl, or $R^1$ and $R^2$ may join to form an optionally substituted heterocyclic ring of 4 to 6 carbon atoms and 1 or 2 heteroatoms selected from the group consisting of nitrogen (N), oxygen (O), and mixtures thereof; $R^3$ is either absent or is hydrogen (H) or a $C_1$-$C_6$ alkyl to provide a quaternary amine; $R^4$ and $R^5$ are either absent or present and when present are either the same or different and are independently an optionally substituted $C_1$-$C_{10}$ alkyl or $C_2$-$C_{10}$ alkenyl; and n is 0, 1, 2, 3, or 4.

and one or both of the alkyl chains. In some embodiments, the cationic lipid of Formula V forms a salt (preferably a crystalline salt) with one or more anions. In one particular embodiment, the cationic lipid of Formula V is the oxalate (e.g., hemioxalate) salt thereof, which is preferably a crystalline salt.

Although each of the alkyl chains in Formula V contains cis double bonds at positions 6, 9, and 12 (i.e., cis,cis,cis-$\Delta^6$,$\Delta^9$,$\Delta^{12}$), in an alternative embodiment, one, two, or three of these double bonds in one or both alkyl chains may be in the trans configuration.

In a particularly preferred embodiment, the cationic lipid of Formula V has the structure:

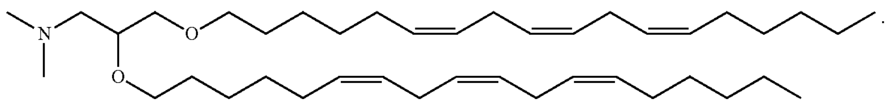

γ-DLenDMA

In another aspect, cationic lipids of Formula VI having the following structure are useful in the present invention:

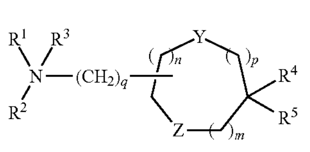

(VI)

or salts thereof, wherein: $R^1$ and $R^2$ are either the same or different and are independently an optionally substituted $C_1$-$C_6$ alkyl, $C_2$-$C_6$ alkenyl, or $C_2$-$C_6$ alkynyl, or $R^1$ and $R^2$ may join to form an optionally substituted heterocyclic ring of 4 to 6 carbon atoms and 1 or 2 heteroatoms selected from the group consisting of nitrogen (N), oxygen (O), and mixtures thereof; $R^3$ is either absent or is hydrogen (H) or a $C_1$-$C_6$ alkyl to provide a quaternary amine; $R^4$ and $R^5$ are either the same or different and are independently an optionally substituted $C_{12}$-$C_{24}$ alkyl, $C_{12}$-$C_{24}$ alkenyl, $C_{12}$-$C_{24}$ alkynyl, or $C_{12}$-$C_{24}$ acyl, wherein at least one of $R^4$ and $R^5$ comprises at least three sites of unsaturation or a substituted $C_{12}$-$C_{24}$ alkyl; m, n, and p are either the same or different and are independently either 0, 1, or 2, with the proviso that m, n, and p are not simultaneously 0; q is 0, 1, 2, 3, or 4; and Y and Z are either the same or different and are independently O, S, or NH.

In some embodiments, $R^1$ and $R^2$ are independently an optionally substituted $C_1$-$C_4$ alkyl, $C_2$-$C_4$ alkenyl, or $C_2$-$C_4$ alkynyl. In a preferred embodiment, $R^1$ and $R^2$ are both methyl groups. In another preferred embodiment, q is 2. In other embodiments, $R^3$ is absent when the pH is above the $pK_a$ of the cationic lipid and $R^3$ is hydrogen when the pH is below the $pK_a$ of the cationic lipid such that the amino head group is protonated. In an alternative embodiment, $R^3$ is an optionally substituted $C_1$-$C_4$ alkyl to provide a quaternary amine. In further embodiments, $R^4$ and $R^5$ are independently an optionally substituted $C_{12}$-$C_{20}$ or $C_{14}$-$C_{22}$ alkyl, $C_{12}$-$C_{20}$ or $C_{14}$-$C_{22}$ alkenyl, $C_{12}$-$C_{20}$ or $C_{14}$-$C_{22}$ alkynyl, or $C_{12}$-$C_{20}$ or $C_{14}$-$C_{22}$ acyl.

In embodiments where at least one of $R^4$ and $R^5$ comprises a branched alkyl group (e.g., a substituted $C_{12}$-$C_{24}$ alkyl group), the branched alkyl group may comprise a $C_{12}$-$C_{24}$ alkyl having at least 1-6 (e.g., 1, 2, 3, 4, 5, 6, or more) $C_1$-$C_6$ alkyl substituents. In particular embodiments, the branched alkyl group comprises a $C_{12}$-$C_{20}$ or $C_{14}$-$C_{22}$ alkyl with 1-6 (e.g., 1, 2, 3, 4, 5, 6) $C_1$-$C_4$ alkyl (e.g., methyl, ethyl, propyl, or butyl) substituents. Preferably, the branched alkyl group comprises a phytanyl(3,7,11,15-tetramethyl-hexadecanyl) moiety. In other preferred embodiments, $R^4$ and $R^5$ are both phytanyl moieties.

In alternative embodiments, at least one of $R^4$ and $R^5$ comprises a branched acyl group (e.g., a substituted $C_{12}$-$C_{24}$ acyl group). In certain instances, the branched acyl group may comprise a $C_{12}$-$C_{24}$ acyl having at least 1-6 (e.g., 1, 2, 3, 4, 5, 6, or more) $C_1$-$C_6$ alkyl substituents. In particular embodiments, the branched acyl group comprises a $C_{12}$-$C_{20}$ or $C_{14}$-$C_{22}$ acyl with 1-6 (e.g., 1, 2, 3, 4, 5, 6) $C_1$-$C_4$ alkyl (e.g., methyl, ethyl, propyl, or butyl) substituents. Preferably, the branched acyl group comprises a phytanoyl(3,7,11,15-tetramethyl-hexadecanoyl) moiety.

In embodiments where at least one of $R^4$ and $R^5$ comprises at least three sites of unsaturation, the double bonds present in one or both alkyl chains may be in the cis and/or trans configuration. In some embodiments, $R^4$ and $R^5$ are independently selected from the group consisting of a dodecatrienyl moiety, a tetradectrienyl moiety, a hexadecatrienyl moiety, an octadecatrienyl moiety, an icosatrienyl moiety, and a phytanyl moiety, as well as acyl derivatives thereof (e.g., linolenoyl, γ-linolenoyl, phytanoyl, etc.). In certain instances, the octadecatrienyl moiety is a linolenyl moiety or a γ-linolenyl moiety. In preferred embodiments, $R^4$ and $R^5$ are both linolenyl moieties or γ-linolenyl moieties. In particular embodiments, $R^4$ and $R^5$ independently comprise a backbone of from about 16 to about 22 carbon atoms, and one or both of $R^4$ and $R^5$ independently comprise at least three, four, five, or six sites of unsaturation.

In some embodiments, the cationic lipid of Formula VI forms a salt (preferably a crystalline salt) with one or more anions. In one particular embodiment, the cationic lipid of Formula VI is the oxalate (e.g., hemioxalate) salt thereof, which is preferably a crystalline salt.

In a particularly preferred embodiment, the cationic lipid of Formula VI has a structure selected from the group consisting of:

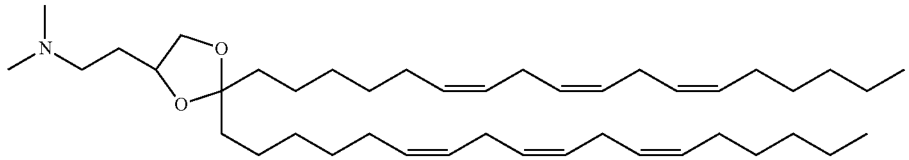
,

γ-DLen-C2K-DMA

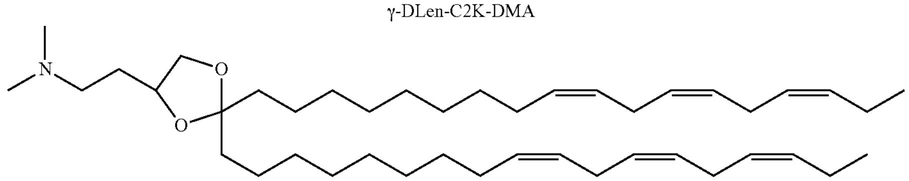
,

DLen-C2K-DMA

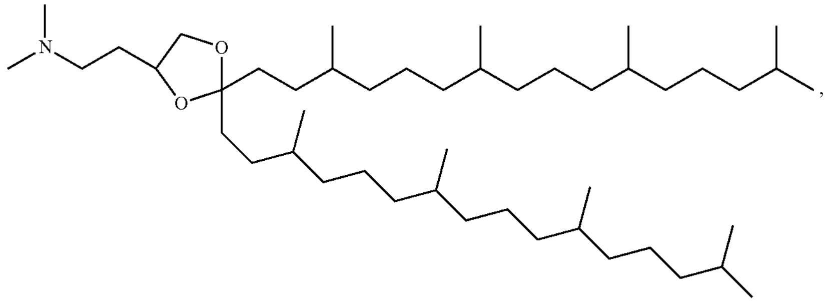
, and

DPan-C2K-DMA

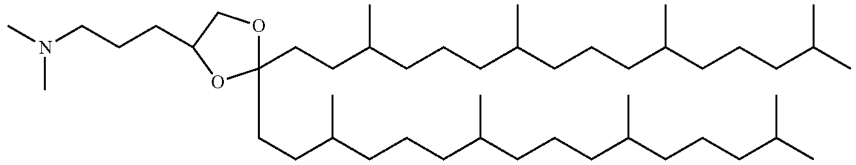
.

DPan-C3K-DMA

In yet another aspect, cationic lipids of Formula VII having the following structure are useful in the present invention:

(VII)

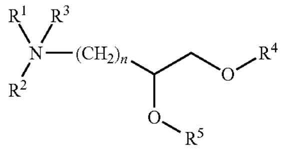

or salts thereof, wherein: $R^1$ and $R^2$ are joined to form an optionally substituted heterocyclic ring of 4 to 6 carbon atoms and 1 or 2 heteroatoms selected from the group consisting of nitrogen (N), oxygen (O), and mixtures thereof; $R^3$ is either absent or is hydrogen (H) or a $C_1$-$C_6$ alkyl to provide a quaternary amine; $R^4$ and $R^5$ are either the same or different and are independently an optionally substituted $C_{12}$-$C_{24}$ alkyl, $C_{12}$-$C_{24}$ alkenyl, $C_{12}$-$C_{24}$ alkynyl, or $C_{12}$-$C_{24}$ acyl; and n is 0, 1, 2, 3, or 4.

In some embodiments, $R^1$ and $R^2$ are joined to form a heterocyclic ring of 5 carbon atoms and 1 nitrogen atom. In certain instances, the heterocyclic ring is substituted with a substituent such as a hydroxyl group at the ortho, meta, and/or para positions. In a preferred embodiment, n is 1. In other embodiments, $R^3$ is absent when the pH is above the $pK_a$ of the cationic lipid and $R^3$ is hydrogen when the pH is below the $pK_a$ of the cationic lipid such that the amino head group is protonated. In an alternative embodiment, $R^3$ is an optionally substituted $C_1$-$C_4$ alkyl to provide a quaternary amine. In further embodiments, $R^4$ and $R^5$ are independently an optionally substituted $C_{12}$-$C_{20}$ or $C_{14}$-$C_{22}$ alkyl, $C_{12}$-$C_{20}$ or $C_{14}$-$C_{22}$ alkenyl, $C_{12}$-$C_{20}$ or $C_{14}$-$C_{22}$ alkynyl, or $C_{12}$-$C_{20}$ or $C_{14}$-$C_{22}$ acyl.

In certain embodiments, $R^4$ and $R^5$ are independently selected from the group consisting of a dodecadienyl moiety, a tetradecadienyl moiety, a hexadecadienyl moiety, an octadecadienyl moiety, an icosadienyl moiety, a dodecatrienyl moiety, a tetradectrienyl moiety, a hexadecatrienyl moiety, an octadecatrienyl moiety, an icosatrienyl moiety, and a branched alkyl group as described above (e.g., a phytanyl moiety), as well as acyl derivatives thereof (e.g., linoleoyl, linolenoyl, γ-linolenoyl, phytanoyl, etc.). In some instances, the octadecadienyl moiety is a linoleyl moiety. In other instances, the octadecatrienyl moiety is a linolenyl moiety or a γ-linolenyl moiety. In particular embodiments, $R^4$ and $R^5$ are both linoleyl moieties, linolenyl moieties, γ-linolenyl moieties, or phytanyl moieties.

In some embodiments, the cationic lipid of Formula VII forms a salt (preferably a crystalline salt) with one or more anions. In one particular embodiment, the cationic lipid of Formula VII is the oxalate (e.g., hemioxalate) salt thereof, which is preferably a crystalline salt.

In a particularly preferred embodiment, the cationic lipid of Formula VII has a structure selected from the group consisting of:

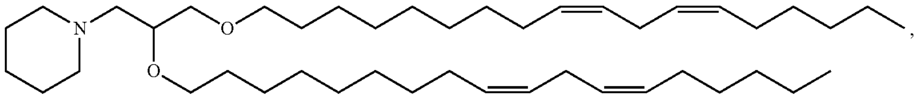

DLinPip

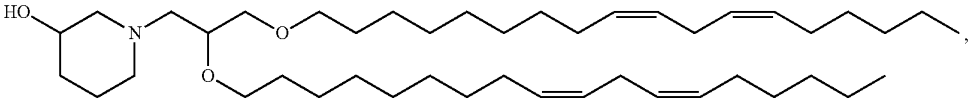

DLinPip (3-OH)

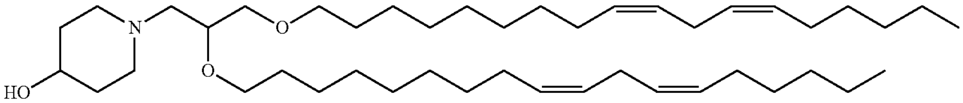

, and

DLinPip (4-OH)

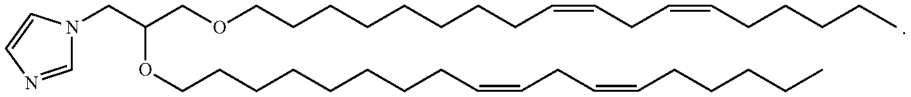

DLinIm

In still yet another aspect, cationic lipids of Formula VIII having the following structure are useful in the present invention:

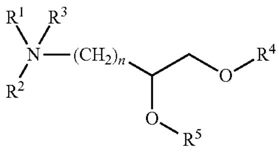

(VIII)

or salts thereof, wherein: $R^1$ and $R^2$ are either the same or different and are independently an optionally substituted $C_1$-$C_6$ alkyl, $C_2$-$C_6$ alkenyl, or $C_2$-$C_6$ alkynyl, or $R^1$ and $R^2$ may join to form an optionally substituted heterocyclic ring of 4 to 6 carbon atoms and 1 or 2 heteroatoms selected from the group consisting of nitrogen (N), oxygen (O), and mixtures thereof; $R^3$ is either absent or is hydrogen (H) or a $C_1$-$C_6$ alkyl to provide a quaternary amine; $R^4$ and $R^5$ are either the same or different and are independently an optionally substituted $C_{12}$-$C_{24}$ alkyl, $C_{12}$-$C_{24}$ alkenyl, $C_{12}$-$C_{24}$ alkynyl, or $C_{12}$-$C_{24}$ acyl; and n is 2, 3, or 4.

In some embodiments, $R^1$ and $R^2$ are independently an optionally substituted $C_1$-$C_4$ alkyl, $C_2$-$C_4$ alkenyl, or $C_2$-$C_4$ alkynyl. In a preferred embodiment, $R^1$ and $R^2$ are both methyl groups. In another preferred embodiment, n is 2. In other embodiments, $R^3$ is absent when the pH is above the $pK_a$ of the cationic lipid and $R^3$ is hydrogen when the pH is below the $pK_a$ of the cationic lipid such that the amino head group is protonated. In an alternative embodiment, $R^3$ is an optionally substituted $C_1$-$C_4$ alkyl to provide a quaternary amine. In further embodiments, $R^4$ and $R^5$ are independently an optionally substituted $C_{12}$-$C_{20}$ or $C_{14}$-$C_{22}$ alkyl, $C_{12}$-$C_{20}$ or $C_{14}$-$C_{22}$ alkenyl, $C_{12}$-$C_{20}$ or $C_{14}$-$C_{22}$ alkynyl, or $C_{12}$-$C_{20}$ or $C_{14}$-$C_{22}$ acyl.

In certain embodiments, $R^4$ and $R^5$ are independently selected from the group consisting of a dodecadienyl moiety, a tetradecadienyl moiety, a hexadecadienyl moiety, an octadecadienyl moiety, an icosadienyl moiety, a dodecatrienyl moiety, a tetradectrienyl moiety, a hexadecatrienyl moiety, an octadecatrienyl moiety, an icosatrienyl moiety, and a branched alkyl group as described above (e.g., a phytanyl moiety), as well as acyl derivatives thereof (e.g., linoleoyl, linolenoyl, γ-linolenoyl, phytanoyl, etc.). In some instances, the octadecadienyl moiety is a linoleyl moiety. In other instances, the octadecatrienyl moiety is a linolenyl moiety or a γ-linolenyl moiety. In particular embodiments, $R^4$ and $R^5$ are both linoleyl moieties, linolenyl moieties, γ-linolenyl moieties, or phytanyl moieties.

In some embodiments, the cationic lipid of Formula VIII forms a salt (preferably a crystalline salt) with one or more anions. In one particular embodiment, the cationic lipid of Formula VIII is the oxalate (e.g., hemioxalate) salt thereof, which is preferably a crystalline salt.

In a particularly preferred embodiment, the cationic lipid of Formula VIII has a structure selected from the group consisting of:

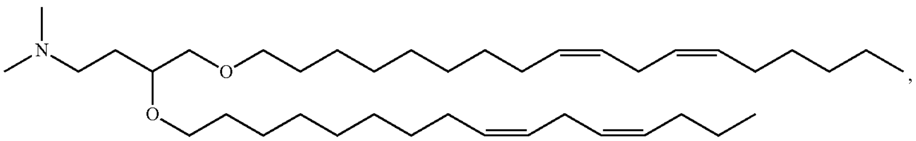

C2-DLinDMA

-continued

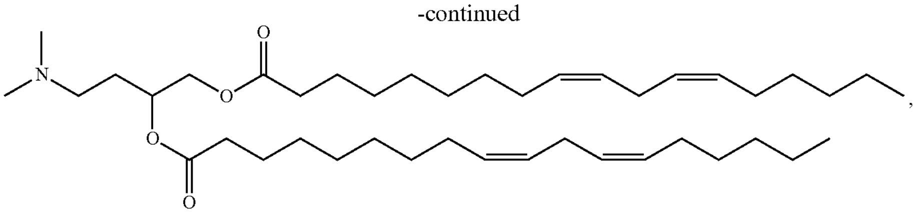

, and

C2-DLinDAP

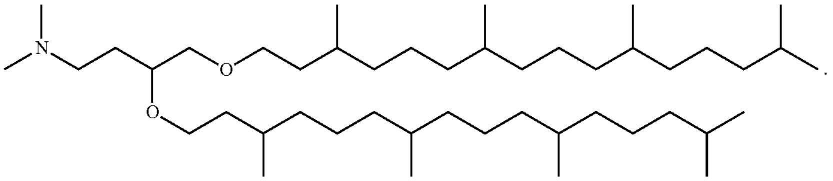

.

C2-DPanDMA

In another aspect, cationic lipids of Formula IX having the following structure are useful in the present invention:

(IX)

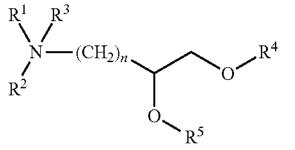

or salts thereof, wherein: $R^1$ and $R^2$ are either the same or different and are independently an optionally substituted $C_1$-$C_6$ alkyl, $C_2$-$C_6$ alkenyl, or $C_2$-$C_6$ alkynyl, or $R^1$ and $R^2$ may join to form an optionally substituted heterocyclic ring of 4 to 6 carbon atoms and 1 or 2 heteroatoms selected from the group consisting of nitrogen (N), oxygen (O), and mixtures thereof; $R^3$ is either absent or is hydrogen (H) or a $C_1$-$C_6$ alkyl to provide a quaternary amine; $R^4$ and $R^5$ are different and are independently an optionally substituted $C_1$-$C_{24}$ alkyl, $C_2$-$C_{24}$ alkenyl, $C_2$-$C_{24}$ alkynyl, or $C_1$-$C_{24}$ acyl; and n is 0, 1, 2, 3, or 4.

In some embodiments, $R^1$ and $R^2$ are independently an optionally substituted $C_1$-$C_4$ alkyl, $C_2$-$C_4$ alkenyl, or $C_2$-$C_4$ alkynyl. In a preferred embodiment, $R^1$ and $R^2$ are both methyl groups. In another preferred embodiment, n is 1. In other embodiments, $R^3$ is absent when the pH is above the $pK_a$ of the cationic lipid and $R^3$ is hydrogen when the pH is below the $pK_a$ of the cationic lipid such that the amino head group is protonated. In an alternative embodiment, $R^3$ is an optionally substituted $C_1$-$C_4$ alkyl to provide a quaternary amine. In further embodiments, $R^4$ and $R^5$ are different and are independently an optionally substituted $C_4$-$C_{20}$ alkyl, $C_4$-$C_{20}$ alkenyl, $C_4$-$C_{20}$ alkynyl, or $C_4$-$C_{20}$ acyl.

In some embodiments, $R^4$ is an optionally substituted $C_{12}$-$C_{24}$ alkyl, $C_{12}$-$C_{24}$ alkenyl, $C_{12}$-$C_{24}$ alkynyl, or $C_{12}$-$C_{24}$ acyl, and $R^5$ is an optionally substituted $C_4$-$C_{10}$ alkyl, $C_4$-$C_{10}$ alkenyl, $C_4$-$C_{10}$ alkynyl, or $C_4$-$C_{10}$ acyl. In certain instances, $R^4$ is an optionally substituted $C_{12}$-$C_{20}$ or $C_{14}$-$C_{22}$ alkyl, $C_{12}$-$C_{20}$ or $C_{14}$-$C_{22}$ alkenyl, $C_{12}$-$C_{20}$ or $C_{14}$-$C_{22}$ alkynyl, or $C_{12}$-$C_{20}$ or $C_{14}$-$C_{22}$ acyl, and $R^5$ is an optionally substituted $C_4$-$C_8$ or $C_6$ alkyl, $C_4$-$C_8$ or $C_6$ alkenyl, $C_4$-$C_8$ or $C_6$ alkynyl, or $C_4$-$C_8$ or $C_6$ acyl.

In other embodiments, $R^4$ is an optionally substituted $C_4$-$C_{10}$ alkyl, $C_4$-$C_{10}$ alkenyl, $C_4$-$C_{10}$ alkynyl, or $C_4$-$C_{10}$ acyl, and $R^5$ is an optionally substituted $C_{12}$-$C_{24}$ alkyl, $C_{12}$-$C_{24}$ alkenyl, $C_{12}$-$C_{24}$ alkynyl, or $C_{12}$-$C_{24}$ acyl. In certain instances, $R^4$ is an optionally substituted $C_4$-$C_8$ or $C_6$ alkyl, $C_4$-$C_8$ or $C_6$ alkenyl, $C_4$-$C_8$ or $C_6$ alkynyl, or $C_4$-$C_8$ or $C_6$ acyl, and $R^5$ is an optionally substituted $C_{12}$-$C_{20}$ or $C_{14}$-$C_{22}$ alkyl, $C_{12}$-$C_{20}$ or $C_{14}$-$C_{22}$ alkenyl, $C_{12}$-$C_{20}$ or $C_{14}$-$C_{22}$ alkynyl, or $C_{12}$-$C_{20}$ or $C_{14}$-$C_{22}$ acyl.

In particular embodiments, $R^4$ is a linoleyl moiety, and $R^5$ is a $C_6$ alkyl moiety, a $C_6$ alkenyl moiety, an octadecyl moiety, an oleyl moiety, a linolenyl moiety, a γ-linolenyl moiety, or a phytanyl moiety. In other embodiments, one of $R^4$ or $R^5$ is a phytanyl moiety.

In some embodiments, the cationic lipid of Formula IX forms a salt (preferably a crystalline salt) with one or more anions. In one particular embodiment, the cationic lipid of Formula IX is the oxalate (e.g., hemioxalate) salt thereof, which is preferably a crystalline salt.

In a particularly preferred embodiment, the cationic lipid of Formula IX is an asymmetric lipid having a structure selected from the group consisting of:

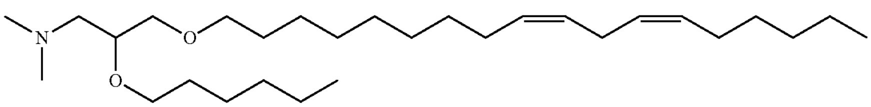

,

Linoleyl/$C_6$:0 DMA

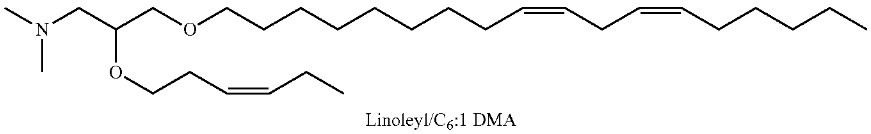

,

Linoleyl/$C_6$:1 DMA

-continued

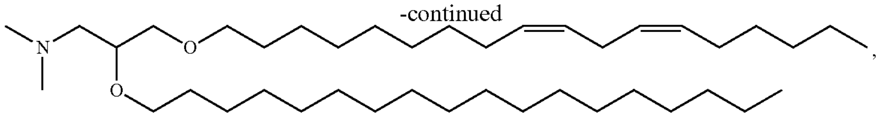,

Linoleyl/Stearyl DMA

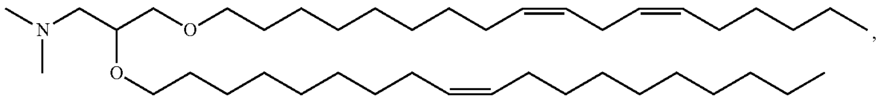,

Linoleyl/Oleyl DMA

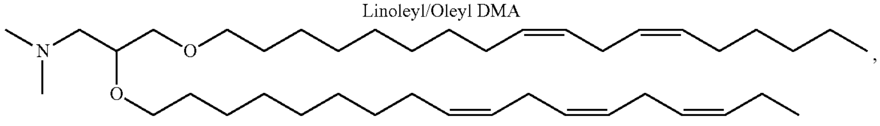, and

Linoleyl/Linolenyl DMA

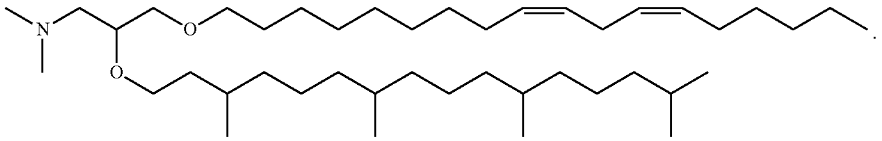.

Linoleyl/Phytanyl DMA

In yet another aspect, cationic lipids of Formula X having the following structure are useful in the present invention:

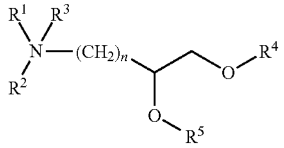

(X)

or salts thereof, wherein: $R^1$ and $R^2$ are either the same or different and are independently an optionally substituted $C_1$-$C_6$ alkyl, $C_2$-$C_6$ alkenyl, or $C_2$-$C_6$ alkynyl, or $R^1$ and $R^2$ may join to form an optionally substituted heterocyclic ring of 4 to 6 carbon atoms and 1 or 2 heteroatoms selected from the group consisting of nitrogen (N), oxygen (O), and mixtures thereof; $R^3$ is either absent or is hydrogen (H) or a $C_1$-$C_6$ alkyl to provide a quaternary amine; $R^4$ and $R^5$ are either the same or different and are independently an optionally substituted $C_{12}$-$C_{24}$ alkyl, $C_{12}$-$C_{24}$ alkenyl, $C_{12}$-$C_{24}$ alkynyl, or $C_{12}$-$C_{24}$ acyl, wherein at least one of $R^4$ and $R^5$ comprises at least four sites of unsaturation or a substituted $C_{12}$-$C_{24}$ alkyl; and n is 0, 1, 2, 3, or 4.

In some embodiments, $R^1$ and $R^2$ are independently an optionally substituted $C_1$-$C_4$ alkyl, $C_2$-$C_4$ alkenyl, or $C_2$-$C_4$ alkynyl. In a preferred embodiment, $R^1$ and $R^2$ are both methyl groups. In another preferred embodiment, n is 1. In other embodiments, $R^3$ is absent when the pH is above the $pK_a$ of the cationic lipid and $R^3$ is hydrogen when the pH is below the $pK_a$ of the cationic lipid such that the amino head group is protonated. In an alternative embodiment, $R^3$ is an optionally substituted $C_1$-$C_4$ alkyl to provide a quaternary amine. In further embodiments, $R^4$ and $R^5$ are independently an optionally substituted $C_{12}$-$C_{20}$ or $C_{14}$-$C_{22}$ alkyl, $C_{12}$-$C_{20}$ or $C_{14}$-$C_{22}$ alkenyl, $C_{12}$-$C_{20}$ or $C_{14}$-$C_{22}$ alkynyl, or $C_{12}$-$C_{20}$ or $C_{14}$-$C_{22}$ acyl.

In embodiments where at least one of $R^4$ and $R^5$ comprises a branched alkyl group (e.g., a substituted $C_{12}$-$C_{24}$ alkyl group), the branched alkyl group may comprise a $C_{12}$-$C_{24}$ alkyl having at least 1-6 (e.g., 1, 2, 3, 4, 5, 6, or more) $C_1$-$C_6$ alkyl substituents. In particular embodiments, the branched alkyl group comprises a $C_{12}$-$C_{20}$ or $C_{14}$-$C_{22}$ alkyl with 1-6 (e.g., 1, 2, 3, 4, 5, 6) $C_1$-$C_4$ alkyl (e.g., methyl, ethyl, propyl, or butyl) substituents. Preferably, the branched alkyl group comprises a phytanyl(3,7,11,15-tetramethyl-hexadecanyl) moiety.

In alternative embodiments, at least one of $R^4$ and $R^5$ comprises a branched acyl group (e.g., a substituted $C_{12}$-$C_{24}$ acyl group). In certain instances, the branched acyl group may comprise a $C_{12}$-$C_{24}$ acyl having at least 1-6 (e.g., 1, 2, 3, 4, 5, 6, or more) $C_1$-$C_6$ alkyl substituents. In particular embodiments, the branched acyl group comprises a $C_{12}$-$C_{20}$ or $C_{14}$-$C_{22}$ acyl with 1-6 (e.g., 1, 2, 3, 4, 5, 6) $C_1$-$C_4$ alkyl (e.g., methyl, ethyl, propyl, or butyl) substituents. Preferably, the branched acyl group comprises a phytanoyl(3,7,11,15-tetramethyl-hexadecanoyl) moiety.

In embodiments where at least one of $R^4$ and $R^5$ comprises at least four sites of unsaturation, the double bonds present in one or both alkyl chains may be in the cis and/or trans configuration. In a particular embodiment, $R^4$ and $R^5$ independently comprise four, five, or six sites of unsaturation. In some instances, $R^4$ comprises four, five, or six sites of unsaturation and $R^5$ comprises zero, one, two, three, four, five, or six sites of unsaturation. In other instances, $R^4$ comprises zero, one, two, three, four, five, or six sites of unsaturation and $R^5$ comprises four, five, or six sites of unsaturation. In a preferred embodiment, both $R^4$ and $R^5$ comprise four, five, or six sites of unsaturation. In particular embodiments, $R^4$ and $R^5$ independently comprise a backbone of from about 18 to about 24 carbon atoms, and one or both of $R^4$ and $R^5$ independently comprise at least four, five, or six sites of unsaturation.

In some embodiments, the cationic lipid of Formula X forms a salt (preferably a crystalline salt) with one or more anions. In one particular embodiment, the cationic lipid of Formula X is the oxalate (e.g., hemioxalate) salt thereof, which is preferably a crystalline salt.

In a particularly preferred embodiment, the cationic lipid of Formula X has a structure selected from the group consisting of

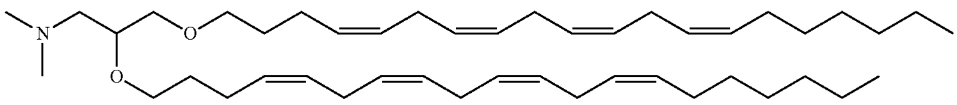,

DAraDMA

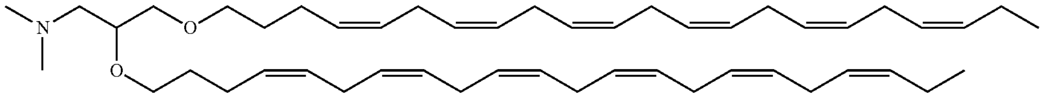, and

DDocDMA

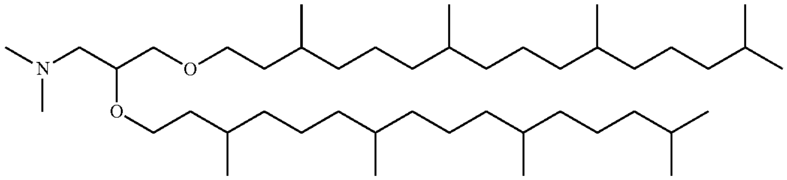.

DPanDMA

In still yet another aspect, cationic lipids of Formula XI having the following structure are useful in the present invention:

(XI)

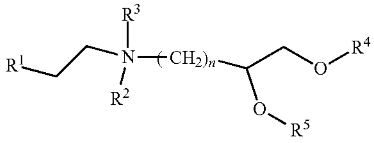

or salts thereof, wherein: $R^1$ is hydrogen (H) or $—(CH_2)_q—NR^6R^7R^8$, wherein: $R^6$ and $R^7$ are either the same or different and are independently an optionally substituted $C_1$-$C_6$ alkyl, $C_2$-$C_6$ alkenyl, or $C_2$-$C_6$ alkynyl, or $R^6$ and $R^7$ may join to form an optionally substituted heterocyclic ring of 4 to 6 carbon atoms and 1 or 2 heteroatoms selected from the group consisting of nitrogen (N), oxygen (O), and mixtures thereof; $R^8$ is either absent or is hydrogen (H) or a $C_1$-$C_6$ alkyl to provide a quaternary amine; and q is 0, 1, 2, 3, or 4; $R^2$ is an optionally substituted $C_1$-$C_6$ alkyl, $C_2$-$C_6$ alkenyl, or $C_2$-$C_6$ alkynyl; $R^3$ is either absent or is hydrogen (H) or a $C_1$-$C_6$ alkyl to provide a quaternary amine; $R^4$ and $R^5$ are either the same or different and are independently an optionally substituted $C_{12}$-$C_{24}$ alkyl, $C_{12}$-$C_{24}$ alkenyl, $C_{12}$-$C_{24}$ alkynyl, or $C_{12}$-$C_{24}$ acyl; and n is 0, 1, 2, 3, or 4.

In some embodiments, $R^2$ is an optionally substituted $C_1$-$C_4$ alkyl, $C_2$-$C_4$ alkenyl, or $C_2$-$C_4$ alkynyl. In other embodiments, $R^3$ is absent when the pH is above the $pK_a$ of the cationic lipid and $R^3$ is hydrogen when the pH is below the $pK_a$ of the cationic lipid such that the amino head group is protonated. In an alternative embodiment, $R^3$ is an optionally substituted $C_1$-$C_4$ alkyl to provide a quaternary amine. In certain embodiments, $R^4$ and $R^5$ are independently an optionally substituted $C_{12}$-$C_{20}$ or $C_{14}$-$C_{22}$ alkyl, $C_{12}$-$C_{20}$ or $C_{14}$-$C_{22}$ alkenyl, $C_{12}$-$C_{20}$ or $C_{14}$-$C_{22}$ alkynyl, or $C_{12}$-$C_{20}$ or $C_{14}$-$C_{22}$ acyl.

In further embodiments, $R^6$ and $R^7$ are independently an optionally substituted $C_1$-$C_4$ alkyl, $C_2$-$C_4$ alkenyl, or $C_2$-$C_4$ alkynyl. In other embodiments, $R^8$ is absent when the pH is above the $pK_a$ of the cationic lipid and $R^8$ is hydrogen when the pH is below the $pK_a$ of the cationic lipid such that the amino head group is protonated. In an alternative embodiment, $R^8$ is an optionally substituted $C_1$-$C_4$ alkyl to provide a quaternary amine.

In a preferred embodiment, $R^1$ is hydrogen and $R^2$ is an ethyl group. In another preferred embodiment, $R^6$ and $R^7$ are both methyl groups. In certain instances, n is 1. In certain other instances, q is 1.

In certain embodiments, $R^4$ and $R^5$ are independently selected from the group consisting of a dodecadienyl moiety, a tetradecadienyl moiety, a hexadecadienyl moiety, an octadecadienyl moiety, an icosadienyl moiety, a dodecatrienyl moiety, a tetradectrienyl moiety, a hexadecatrienyl moiety, an octadecatrienyl moiety, an icosatrienyl moiety, and a branched alkyl group as described above (e.g., a phytanyl moiety), as well as acyl derivatives thereof (e.g., linoleoyl, linolenoyl, γ-linolenoyl, phytanoyl, etc.). In some instances, the octadecadienyl moiety is a linoleyl moiety. In other instances, the octadecatrienyl moiety is a linolenyl moiety or a γ-linolenyl moiety. In particular embodiments, $R^4$ and $R^5$ are both linoleyl moieties, linolenyl moieties, γ-linolenyl moieties, or phytanyl moieties.

In some embodiments, the cationic lipid of Formula XI forms a salt (preferably a crystalline salt) with one or more anions. In one particular embodiment, the cationic lipid of Formula XI is the oxalate (e.g., hemioxalate) salt thereof, which is preferably a crystalline salt.

In a particularly preferred embodiment, the cationic lipid of Formula XI has a structure selected from the group consisting of:

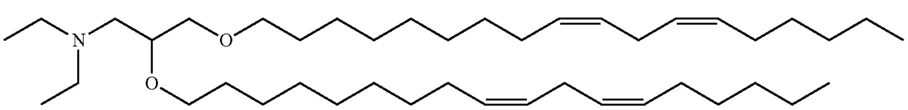 and

DLinDEA

-continued

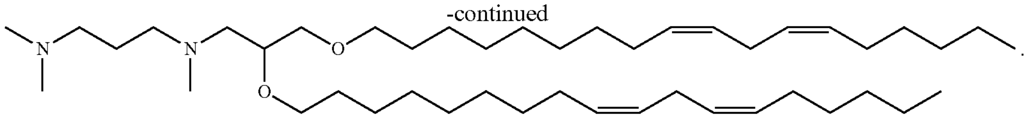

2N-DLinDMA

In another aspect, cationic lipids of Formula XII having the following structure are useful in the present invention:

(XII)

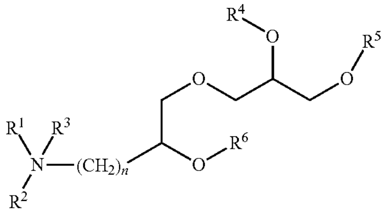

or salts thereof, wherein: $R^1$ and $R^2$ are either the same or different and are independently an optionally substituted $C_1$-$C_6$ alkyl, $C_2$-$C_6$ alkenyl, or $C_2$-$C_6$ alkynyl, or $R^1$ and $R^2$ may join to form an optionally substituted heterocyclic ring of 4 to 6 carbon atoms and 1 or 2 heteroatoms selected from the group consisting of nitrogen (N), oxygen (O), and mixtures thereof; $R^3$ is either absent or is hydrogen (H) or a $C_1$-$C_6$ alkyl to provide a quaternary amine; $R^4$, $R^5$, and $R^6$ are either the same or different and are independently an optionally substituted $C_{12}$-$C_{24}$ alkyl, $C_{12}$-$C_{24}$ alkenyl, $C_{12}$-$C_{24}$ alkynyl, or $C_{12}$-$C_{24}$ acyl; and n is 0, 1, 2, 3, or 4.

In some embodiments, $R^1$ and $R^2$ are independently an optionally substituted $C_1$-$C_4$ alkyl, $C_2$-$C_4$ alkenyl, or $C_2$-$C_4$ alkynyl. In a preferred embodiment, $R^1$ and $R^2$ are both methyl groups. In another preferred embodiment, n is 1. In other embodiments, $R^3$ is absent when the pH is above the $pK_a$ of the cationic lipid and $R^3$ is hydrogen when the pH is below the $pK_a$ of the cationic lipid such that the amino head group is protonated. In an alternative embodiment, $R^3$ is an optionally substituted $C_1$-$C_4$ alkyl to provide a quaternary amine. In further embodiments, $R^4$, $R^5$, and $R^6$ are independently an optionally substituted $C_{12}$-$C_{20}$ or $C_{14}$-$C_{22}$ alkyl, $C_{12}$-$C_{20}$ or $C_{14}$-$C_{22}$ alkenyl, $C_{12}$-$C_{20}$ or $C_{14}$-$C_{22}$ alkynyl, or $C_{12}$-$C_{20}$ or $C_{14}$-$C_{22}$ acyl.

In certain embodiments, $R^4$, $R^5$, and $R^6$ are independently selected from the group consisting of a dodecadienyl moiety, a tetradecadienyl moiety, a hexadecadienyl moiety, an octadecadienyl moiety, an icosadienyl moiety, a dodecatrienyl moiety, a tetradectrienyl moiety, a hexadecatrienyl moiety, an octadecatrienyl moiety, an icosatrienyl moiety, and a branched alkyl group as described above (e.g., a phytanyl moiety), as well as acyl derivatives thereof (e.g., linoleoyl, linolenoyl, γ-linolenoyl, phytanoyl, etc.). In some instances, the octadecadienyl moiety is a linoleyl moiety. In other instances, the octadecatrienyl moiety is a linolenyl moiety or a γ-linolenyl moiety. In particular embodiments, $R^4$, $R^5$, and $R^6$ are all linoleyl moieties, linolenyl moieties, γ-linolenyl moieties, or phytanyl moieties.

In some embodiments, the cationic lipid of Formula XII forms a salt (preferably a crystalline salt) with one or more anions. In one particular embodiment, the cationic lipid of Formula XII is the oxalate (e.g., hemioxalate) salt thereof, which is preferably a crystalline salt.

In a particularly preferred embodiment, the cationic lipid of Formula XII has a structure selected from the group consisting of:

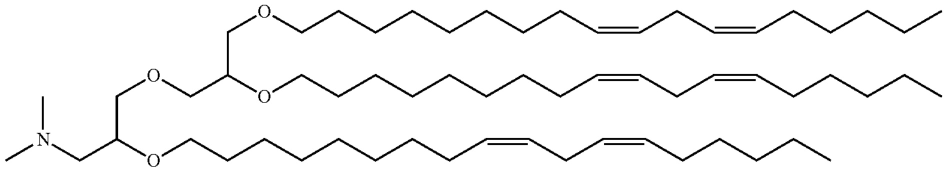

,

TLinDMA

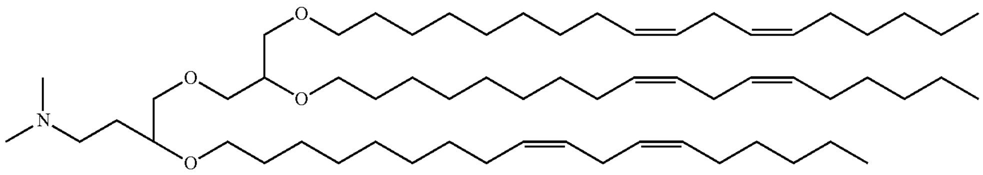

, and

C2-TLinDMA

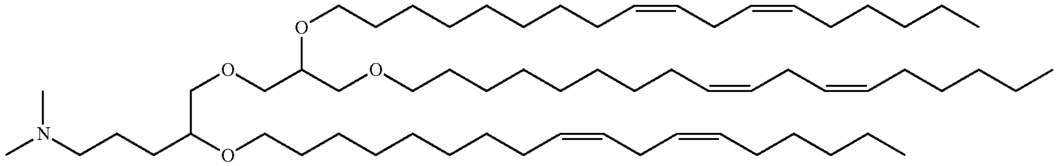

.

C3-TLinDMA

In yet another aspect, cationic lipids of Formula XIII having the following structure are useful in the present invention:

(XIII)

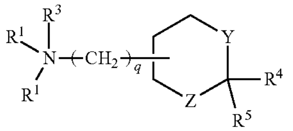

or salts thereof, wherein: $R^1$ and $R^2$ are either the same or different and are independently an optionally substituted $C_1$-$C_6$ alkyl, $C_2$-$C_6$ alkenyl, or $C_2$-$C_6$ alkynyl, or $R^1$ and $R^2$ may join to form an optionally substituted heterocyclic ring of 4 to 6 carbon atoms and 1 or 2 heteroatoms selected from the group consisting of nitrogen (N), oxygen (O), and mixtures thereof; $R^3$ is either absent or is hydrogen (H) or a $C_1$-$C_6$ alkyl to provide a quaternary amine; $R^4$ and $R^5$ are either the same or different and are independently an optionally substituted $C_{12}$-$C_{24}$ alkyl, $C_{12}$-$C_{24}$ alkenyl, $C_{12}$-$C_{24}$ alkynyl, or $C_{12}$-$C_{24}$ acyl; q is 0, 1, 2, 3, or 4; and Y and Z are either the same or different and are independently O, S, or NH, wherein if q is 1, $R^1$ and $R^2$ are both methyl groups, $R^4$ and $R^5$ are both linoleyl moieties, and Y and Z are both O, then the alkylamino group is attached to one of the two carbons adjacent to Y or Z (i.e., at the '4' or '6' position of the 6-membered ring).

In some embodiments, $R^1$ and $R^2$ are independently an optionally substituted $C_1$-$C_4$ alkyl, $C_2$-$C_4$ alkenyl, or $C_2$-$C_4$ alkynyl. In a preferred embodiment, $R^1$ and $R^2$ are both methyl groups. In another preferred embodiment, q is 2. In a particular embodiments, Y and Z are both oxygen (O). In other embodiments, $R^3$ is absent when the pH is above the $pK_a$ of the cationic lipid and $R^3$ is hydrogen when the pH is below the $pK_a$ of the cationic lipid such that the amino head group is protonated. In an alternative embodiment, $R^3$ is an optionally substituted $C_1$-$C_4$ alkyl to provide a quaternary amine. In further embodiments, $R^4$ and $R^5$ are independently an optionally substituted $C_{12}$-$C_{20}$ or $C_{14}$-$C_{22}$ alkyl, $C_{12}$-$C_{20}$ or $C_{14}$-$C_{22}$ alkenyl, $C_{12}$-$C_{20}$ or $C_{14}$-$C_{22}$ alkynyl, or $C_{12}$-$C_{20}$ or $C_{14}$-$C_{22}$ acyl.

In other embodiments, $R^4$ and $R^5$ are independently selected from the group consisting of a dodecadienyl moiety, a tetradecadienyl moiety, a hexadecadienyl moiety, an octadecadienyl moiety, an icosadienyl moiety, a dodecatrienyl moiety, a tetradectrienyl moiety, a hexadecatrienyl moiety, an octadecatrienyl moiety, an icosatrienyl moiety, and a branched alkyl group as described above (e.g., a phytanyl moiety), as well as acyl derivatives thereof (e.g., linoleoyl, linolenoyl, γ-linolenoyl, phytanoyl, etc.). In some instances, the octadecadienyl moiety is a linoleyl moiety. In other instances, the octadecatrienyl moiety is a linolenyl moiety or a γ-linolenyl moiety. In particular embodiments, $R^4$ and $R^5$ are both linoleyl moieties, linolenyl moieties, γ-linolenyl moieties, or phytanyl moieties.

The alkylamino head group of Formula XIII may be attached to the '4' or '5' position of the 6-membered ring as shown below in an exemplary embodiment wherein $R^1$ and $R^2$ are both methyl groups:

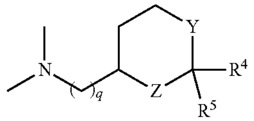

Head Group at '4' Position; or

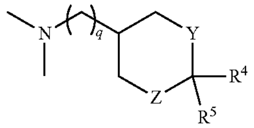

Head Group at '5' Position.

In further embodiments, the 6-membered ring of Formula XIII may be substituted with 1, 2, 3, 4, or 5 independently selected $C_1$-$C_6$ alkyl, $C_2$-$C_6$ alkenyl, $C_2$-$C_6$ alkynyl, $C_1$-$C_6$ alkoxyl, or hydroxyl substituents. In one particular embodiment, the 6-membered ring is substituted with 1, 2, 3, 4, or 5 independently selected $C_1$-$C_4$ alkyl (e.g., methyl, ethyl, propyl, or butyl) substituents. An exemplary embodiment of a cationic lipid of Formula XIII having a substituted 6-membered ring (methyl group attached to the '4' position) and wherein $R^1$ and $R^2$ are both methyl groups is shown below:

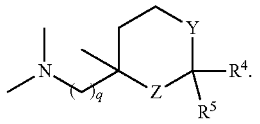

In particular embodiments, the cationic lipids of Formula XIII may be synthesized using 2-hydroxymethyl-1,4-butanediol and 1,3,5-pentanetriol (or 3-methyl-1,3,5-pentanetriol) as starting materials.

In some embodiments, the cationic lipid of Formula XIII forms a salt (preferably a crystalline salt) with one or more anions. In one particular embodiment, the cationic lipid of Formula XIII is the oxalate (e.g., hemioxalate) salt thereof, which is preferably a crystalline salt.

In a particularly preferred embodiment, the cationic lipid of Formula XIII has the structure:

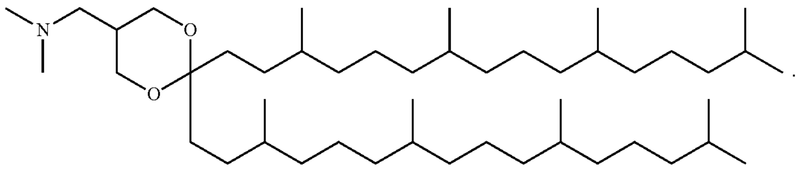

DPan-C1K6-DMA

In still yet another aspect, the present invention provides a cationic lipid of Formula XIV having the following structure:

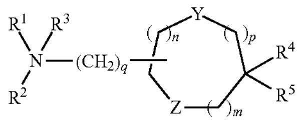

(XIV)

or salts thereof, wherein: $R^1$ and $R^2$ are either the same or different and are independently an optionally substituted $C_1$-$C_6$ alkyl, $C_2$-$C_6$ alkenyl, or $C_2$-$C_6$ alkynyl, or $R^1$ and $R^2$ may join to form an optionally substituted heterocyclic ring of 4 to 6 carbon atoms and 1 or 2 heteroatoms selected from the group consisting of nitrogen (N), oxygen (O), and mixtures thereof; $R^3$ is either absent or is hydrogen (H) or a $C_1$-$C_6$ alkyl to provide a quaternary amine; $R^4$ and $R^5$ are either the same or different and are independently an optionally substituted $C_{12}$-$C_{24}$ alkyl, $C_{12}$-$C_{24}$ alkenyl, $C_{12}$-$C_{24}$ alkynyl, or $C_{12}$-$C_{24}$ acyl, wherein at least one of $R^4$ and $R^5$ comprises at least one site of unsaturation in the trans (E) configuration; m, n, and p are either the same or different and are independently either 0, 1, or 2, with the proviso that m, n, and p are not simultaneously 0; q is 0, 1, 2, 3, or 4; and Y and Z are either the same or different and are independently O, S, or NH.

In some embodiments, $R^1$ and $R^2$ are independently an optionally substituted $C_1$-$C_4$ alkyl, $C_2$-$C_4$ alkenyl, or $C_2$-$C_4$ alkynyl. In a preferred embodiment, $R^1$ and $R^2$ are both methyl groups. In another preferred embodiment, q is 2. In other embodiments, $R^3$ is absent when the pH is above the $pK_a$ of the cationic lipid and $R^3$ is hydrogen when the pH is below the $pK_a$ of the cationic lipid such that the amino head group is protonated. In an alternative embodiment, $R^3$ is an optionally substituted $C_1$-$C_4$ alkyl to provide a quaternary amine. In further embodiments, $R^4$ and $R^5$ are independently an optionally substituted $C_{12}$-$C_{20}$ or $C_{14}$-$C_{22}$ alkyl, $C_{12}$-$C_{20}$ or $C_{14}$-$C_{22}$ alkenyl, $C_{12}$-$C_{20}$ or $C_{14}$-$C_{22}$ alkynyl, or $C_{12}$-$C_{20}$ or $C_{14}$-$C_{22}$ acyl.

In certain embodiments, at least one of $R^4$ and $R^5$ further comprises one, two, three, four, five, six, or more sites of unsaturation in the cis and/or trans configuration. In some instances, $R^4$ and $R^5$ are independently selected from any of the substituted or unsubstituted alkyl or acyl groups described herein, wherein at least one or both of $R^4$ and $R^5$ comprises at least one, two, three, four, five, or six sites of unsaturation in the trans configuration. In one particular embodiment, $R^4$ and $R^5$ independently comprise a backbone of from about 12 to about 22 carbon atoms (e.g., 12, 13, 14, 15, 16, 17, 18, 19, 20, 21, or 22 carbon atoms), and one or both of $R^4$ and $R^5$ independently comprise at least one, two, three, four, five, or six sites of unsaturation in the trans configuration. In some preferred embodiments, at least one of $R^4$ and $R^5$ comprises an (E)-heptadeceyl moiety. In other preferred embodiments, $R^4$ and $R^5$ are both (E)-8-heptadeceyl moieties.

In some embodiments, the cationic lipid of Formula XIV forms a salt (preferably a crystalline salt) with one or more anions. In one particular embodiment, the cationic lipid of Formula XIV is the oxalate (e.g., hemioxalate) salt thereof, which is preferably a crystalline salt.

In a particularly preferred embodiment, the cationic lipid of Formula XIV has the structure:

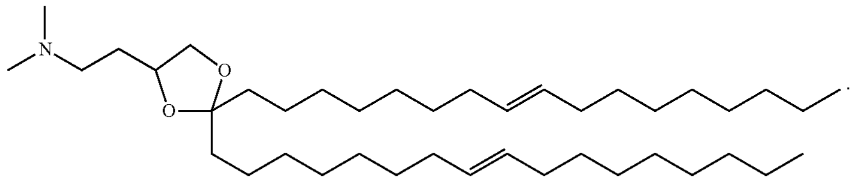

DHep-C2K-DMA

In another aspect, the present invention provides a cationic lipid of Formula XV having the following structure:

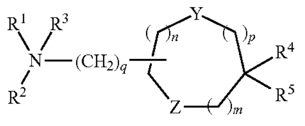

(XV)

or salts thereof, wherein: $R^1$ and $R^2$ are joined to form an optionally substituted heterocyclic ring of 4 to 6 carbon atoms and 1 or 2 heteroatoms selected from the group consisting of nitrogen (N), oxygen (O), and mixtures thereof; $R^3$ is either absent or is hydrogen (H) or a $C_1$-$C_6$ alkyl to provide a quaternary amine; $R^4$ and $R^5$ are either the same or different and are independently an optionally substituted $C_{12}$-$C_{24}$ alkyl, $C_{12}$-$C_{24}$ alkenyl, $C_{12}$-$C_{24}$ alkynyl, or $C_{12}$-$C_{24}$ acyl; m, n, and p are either the same or different and are independently either 0, 1, or 2, with the proviso that m, n, and p are not simultaneously 0; q is 0, 1, 2, 3, or 4; and Y and Z are either the same or different and are independently O, S, or NH.

In some embodiments, $R^1$ and $R^2$ are joined to form a heterocyclic ring of 5 carbon atoms and 1 nitrogen atom. In certain instances, the heterocyclic ring is substituted with a substituent such as a hydroxyl group at the ortho, meta, and/or para positions. In a preferred embodiment, q is 2. In other embodiments, $R^3$ is absent when the pH is above the $pK_a$ of the cationic lipid and $R^3$ is hydrogen when the pH is below the $pK_a$ of the cationic lipid such that the amino head group is protonated. In an alternative embodiment, $R^3$ is an optionally substituted $C_1$-$C_4$ alkyl to provide a quaternary amine. In further embodiments, $R^4$ and $R^5$ are independently an optionally substituted $C_{12}$-$C_{20}$ or $C_{14}$-$C_{22}$ alkyl, $C_{12}$-$C_{20}$ or $C_{14}$-$C_{22}$ alkenyl, $C_{12}$-$C_{20}$ or $C_{14}$-$C_{22}$ alkynyl, or $C_{12}$-$C_{20}$ or $C_{14}$-$C_{22}$ acyl.

In certain embodiments, $R^4$ and $R^5$ are independently selected from the group consisting of a dodecadienyl moiety, a tetradecadienyl moiety, a hexadecadienyl moiety, an octadecadienyl moiety, an icosadienyl moiety, a dodecatrienyl moiety, a tetradectrienyl moiety, a hexadecatrienyl moiety, an octadecatrienyl moiety, an icosatrienyl moiety, and a branched alkyl group as described above (e.g., a phytanyl moiety), as well as acyl derivatives thereof (e.g., linoleoyl, linolenoyl, γ-linolenoyl, phytanoyl, etc.). In some instances, the octadecadienyl moiety is a linoleyl moiety. In other instances, the octadecatrienyl moiety is a linolenyl moiety or a γ-linolenyl moiety. In particular embodiments, $R^4$ and $R^5$ are both linoleyl moieties, linolenyl moieties, γ-linolenyl moieties, or phytanyl moieties.

In some embodiments, the cationic lipid of Formula XV forms a salt (preferably a crystalline salt) with one or more anions. In one particular embodiment, the cationic lipid of Formula XV is the oxalate (e.g., hemioxalate) salt thereof, which is preferably a crystalline salt.

In a particularly preferred embodiment, the cationic lipid of Formula XV has the structure:

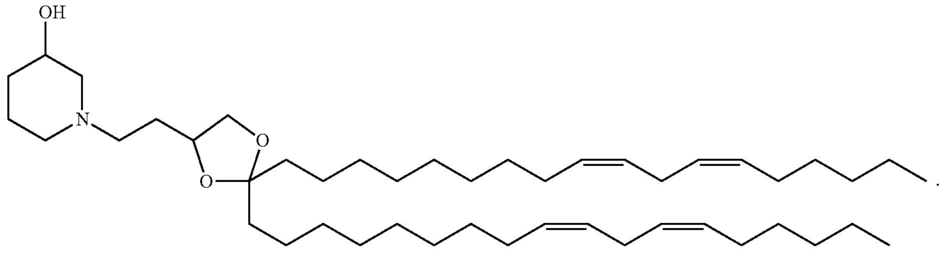

DLin-C2K-Pip-3OH

In yet another aspect, the present invention provides a cationic lipid of Formula XVI having the following structure:

(XVI)

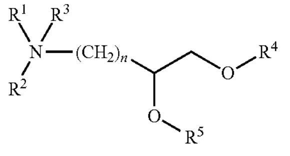

or salts thereof, wherein:

$R^1$ and $R^2$ are either the same or different and are independently an optionally substituted $C_1$-$C_6$ alkyl, $C_2$-$C_6$ alkenyl, or $C_2$-$C_6$ alkynyl, or $R^1$ and $R^2$ may join to form an optionally substituted heterocyclic ring of 4 to 6 carbon atoms and 1 or 2 heteroatoms selected from the group consisting of nitrogen (N), oxygen (O), and mixtures thereof;

$R^3$ is either absent or is hydrogen (H) or a $C_1$-$C_6$ alkyl to provide a quaternary amine;

$R^4$ and $R^5$ are either the same or different and are independently a substituted $C_{12}$-$C_{24}$ alkyl; and n is 0, 1, 2, 3, or 4.

In some embodiments, $R^1$ and $R^2$ are independently an optionally substituted $C_1$-$C_4$ alkyl, $C_2$-$C_4$ alkenyl, or $C_2$-$C_4$ alkynyl. In a preferred embodiment, $R^1$ and $R^2$ are both methyl groups. In one particular embodiment, n is 1. In another particular embodiment, n is 2. In other embodiments, $R^3$ is absent when the pH is above the $pK_a$ of the cationic lipid and $R^3$ is hydrogen when the pH is below the $pK_a$ of the cationic lipid such that the amino head group is protonated. In an alternative embodiment, $R^3$ is an optionally substituted $C_1$-$C_4$ alkyl to provide a quaternary amine.

In embodiments where at least one of $R^4$ and $R^5$ comprises a branched alkyl group (e.g., a substituted $C_{12}$-$C_{24}$ alkyl group), the branched alkyl group may comprise a $C_{12}$-$C_{24}$ alkyl having at least 1-6 (e.g., 1, 2, 3, 4, 5, 6, or more) $C_1$-$C_6$ alkyl substituents. In particular embodiments, the branched alkyl group comprises a $C_{12}$-$C_{20}$ or $C_{14}$-$C_{22}$ alkyl with 1-6 (e.g., 1, 2, 3, 4, 5, 6) $C_1$-$C_4$ alkyl (e.g., methyl, ethyl, propyl, or butyl) substituents. Preferably, the branched alkyl group comprises a phytanyl(3,7,11,15-tetramethyl-hexadecanyl) moiety. In particular embodiments, $R^4$ and $R^5$ are both phytanyl moieties.

In alternative embodiments, at least one of $R^4$ and $R^5$ comprises a branched acyl group (e.g., a substituted $C_{12}$-$C_{24}$ acyl group). In certain instances, the branched acyl group may comprise a $C_{12}$-$C_{24}$ acyl having at least 1-6 (e.g., 1, 2, 3, 4, 5, 6, or more) $C_1$-$C_6$ alkyl substituents. In particular embodiments, the branched acyl group comprises a $C_{12}$-$C_{20}$ or $C_{14}$-$C_{22}$ acyl with 1-6 (e.g., 1, 2, 3, 4, 5, 6) $C_1$-$C_4$ alkyl (e.g., methyl, ethyl, propyl, or butyl) substituents. Preferably, the branched acyl group comprises a phytanoyl(3,7,11,15-tetramethyl-hexadecanoyl) moiety. In particular embodiments, $R^4$ and $R^5$ are both phytanoyl moieties.

In some embodiments, the cationic lipid of Formula XVI forms a salt (preferably a crystalline salt) with one or more anions. In one particular embodiment, the cationic lipid of Formula XVI is the oxalate (e.g., hemioxalate) salt thereof, which is preferably a crystalline salt.

In a particularly preferred embodiment, the cationic lipid of Formula XVI has a structure selected from the group consisting of:

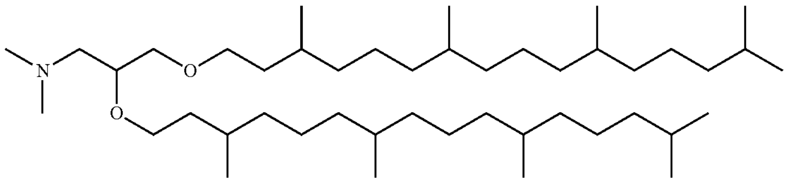

and

DPanDMA

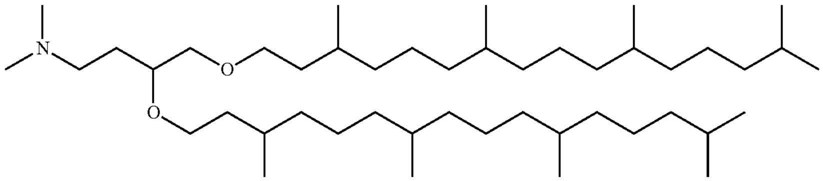

.

C2-DPanDMA

The synthesis of cationic lipids of Formulas V-XVI is described herein and in PCT Application No. PCT/CA2010/001029 entitled "Improved Cationic Lipids and Methods for the Delivery of Therapeutic Agents," filed Jun. 30, 2010, the disclosure of which is herein incorporated by reference in its entirety for all purposes.

Other cationic lipids or salts thereof which may be included in the lipid particles of the present invention include, but are not limited to, 1,2-dioeylcarbamoyloxy-3-dimethylaminopropane (DO-C-DAP), 1,2-dimyristoleoyl-3-dimethylaminopropane (DMDAP), 1,2-dioleoyl-3-trimethylaminopropane chloride (DOTAP.Cl), dilinoleylmethyl-3-dimethylaminopropionate (DLin-M-K-DMA; also known as DLin-M-DMA), N,N-dioleyl-N,N-dimethylammonium chloride (DODAC), 1,2-dioleyloxy-N,N-dimethylaminopropane (DODMA), 1,2-distearyloxy-N,N-dimethylaminopropane (DSDMA), N-(1-(2,3-dioleyloxyl)propyl)-N,N,N-trimethylammonium chloride (DOTMA), N,N-distearyl-N,N-dimethylammonium bromide (DDAB), N-(1-(2,3-dioleoyloxy)propyl)-N,N,N-trimethylammonium chloride (DOTAP), 3-(N—(N',N'-dimethylaminoethane)-carbamoyl) cholesterol (DC-Chol), N-(1,2-dimyristyloxyprop-3-yl)-N,N-dimethyl-N-hydroxyethyl ammonium bromide (DMRIE), 2,3-dioleyloxy-N-[2(spermine-carboxamido)ethyl]-N,N-dimethyl-1-propanaminiumtrifluoroacetate (DOSPA), dioctadecylamidoglycyl spermine (DOGS), 3-dimethylamino-2-(cholest-5-en-3-beta-oxybutan-4-oxy)-1-(cis,cis-9,12-octadecadienoxy)propane (CLinDMA), 2-[5'-(cholest-5-en-3-beta-oxy)-3'-oxapentoxy)-3-dimethy-1-(cis,cis-9',1-2'-octadecadienoxy)propane (CpLinDMA), N,N-dimethyl-3,4-dioleyloxybenzylamine (DMOBA), 1,2-N,N'-dioleylcarbamyl-3-dimethylaminopropane (DOcarbDAP), 1,2-N,N'-dilinoleylcarbamyl-3-dimethylaminopropane (DLincarbDAP), 1,2-dilinoleylcarbamoyloxy-3-dimethylaminopropane (DLin-C-DAP), 1,2-dilinoleyoxy-3-(dimethylamino)acetoxypropane (DLin-DAC), 1,2-dilinoleyoxy-3-morpholinopropane (DLin-MA), 1,2-dilinoleoyl-3-dimethylaminopropane (DLinDAP), 1,2-dilinoleylthio-3-dimethylaminopropane (DLin-S-DMA), 1-linoleoyl-2-linoleyloxy-3-dimethylaminopropane (DLin-2-DMAP), 1,2-dilinoleyloxy-3-trimethylaminopropane chloride salt (DLin-TMA.C1), 1,2-dilinoleoyl-3-trimethylaminopropane chloride salt (DLin-TAP.Cl), 1,2-dilinoleyloxy-3-(N-methylpiperazino)propane (DLin-MPZ), 3-(N,N-dilinoleylamino)-1,2-propanediol (DLinAP), 3-(N,N-dioleylamino)-1,2-propanedio (DOAP), 1,2-dilinoleyloxo-3-(2-N,N-dimethylamino)ethoxypropane (DLin-EG-DMA), and mixtures thereof.

Additional cationic lipids or salts thereof which may be included in the lipid particles of the present invention include, without limitation, cationic lipids such as (6Z,9Z,28Z,31Z)-heptatriaconta-6,9,28,31-tetraen-19-yl 4-(dimethylamino) butanoate (DLin-M-C3-DMA or "MC3") and certain analogs thereof as described in U.S. Provisional Patent Application No. 61/334,104, entitled "Novel Cationic Lipids and Methods of Use Thereof," filed May 12, 2010, and PCT Publication Nos. WO 2010/054401, WO 2010/054405, WO 2010/054406, and WO 2010/054384, the disclosures of which are herein incorporated by reference in their entirety for all purposes.

The synthesis of cationic lipids such as DO-C-DAP, DMDAP, DOTAP.Cl, DLin-M-K-DMA, as well as additional cationic lipids, is described in PCT Publication No. WO 2010/042877, the disclosure of which is incorporated herein by reference in its entirety for all purposes.

The synthesis of cationic lipids such as DLin-C-DAP, DLinDAC, DLinMA, DLinDAP, DLin-S-DMA, DLin-2-DMAP, DLinTMA.Cl, DLinTAP.Cl, DLinMPZ, DLinAP, DOAP, and DLin-EG-DMA, as well as additional cationic lipids, is described in PCT Publication No. WO 09/086558, the disclosure of which is herein incorporated by reference in its entirety for all purposes.

The synthesis of cationic lipids such as CLinDMA, as well as additional cationic lipids, is described in U.S. Patent Publication No. 20060240554, the disclosure of which is herein incorporated by reference in its entirety for all purposes.

The synthesis of a number of other cationic lipids and related analogs has been described in U.S. Pat. Nos. 5,208, 036; 5,264,618; 5,279,833; 5,283,185; 5,753,613; and 5,785,992; and PCT Publication No. WO 96/10390, the disclosures of which are each herein incorporated by reference in their entirety for all purposes. Additionally, a number of commercial preparations of cationic lipids can be used, such as, e.g., LIPOFECTIN® (including DOTMA and DOPE, available from GIBCO/BRL); LIPOFECTAMINE® (including DOSPA and DOPE, available from GIBCO/BRL); and TRANSFECTAM® (including DOGS, available from Promega Corp.).

In some embodiments, the cationic lipid comprises from about 45 mol % to about 90 mol %, from about 45 mol % to about 85 mol %, from about 45 mol % to about 80 mol %, from about 45 mol % to about 75 mol %, from about 45 mol % to about 70 mol %, from about 45 mol % to about 65 mol %, from about 45 mol % to about 60 mol %, from about 45 mol % to about 55 mol %, from about 50 mol % to about 90 mol %, from about 50 mol % to about 85 mol %, from about 50 mol % to about 80 mol %, from about 50 mol % to about 75 mol %, from about 50 mol % to about 70 mol %, from about 50 mol % to about 65 mol %, from about 50 mol % to about 60 mol %, from about 55 mol % to about 65 mol % or from about 55 mol % to about 70 mol % (or any fraction thereof or range therein) of the total lipid present in the particle.

In certain preferred embodiments, the cationic lipid comprises from about 50 mol % to about 58 mol %, from about 51 mol % to about 59 mol %, from about 51 mol % to about 58 mol %, from about 51 mol % to about 57 mol %, from about 52 mol % to about 58 mol %, from about 52 mol % to about 57 mol %, from about 52 mol % to about 56 mol %, or from about 53 mol % to about 55 mol % (or any fraction thereof or range therein) of the total lipid present in the particle. In particular embodiments, the cationic lipid comprises about 50 mol %, 51 mol %, 52 mol %, 53 mol %, 54 mol %, 55 mol %, 56 mol %, 57 mol %, 58 mol %, 59 mol %, 60 mol %, 61 mol %, 62 mol %, 63 mol %, 64 mol %, or 65 mol % (or any fraction thereof or range therein) of the total lipid present in the particle. In certain other embodiments, the cationic lipid comprises (at least) about 66, 67, 68, 69, 70, 71, 72, 73, 74, 75, 76, 77, 78, 79, 80, 81, 82, 83, 84, 85, 86, 87, 88, 89, or 90 mol % (or any fraction thereof or range therein) of the total lipid present in the particle.

In additional embodiments, the cationic lipid comprises from about 2 mol % to about 60 mol %, from about 5 mol % to about 50 mol %, from about 10 mol % to about 50 mol %, from about 20 mol % to about 50 mol %, from about 20 mol % to about 40 mol %, from about 30 mol % to about 40 mol %, or about 40 mol % (or any fraction thereof or range therein) of the total lipid present in the particle.

Additional percentages and ranges of cationic lipids suitable for use in the lipid particles of the present invention are described in PCT Publication No. WO 09/127060, U.S. application Ser. No. 12/794,701, filed Jun. 4, 2010, and U.S. application Ser. No. 12/828,189, filed Jun. 30, 2010, the disclosures of which are herein incorporated by reference in their entirety for all purposes.

It should be understood that the percentage of cationic lipid present in the lipid particles of the invention is a target amount, and that the actual amount of cationic lipid present in the formulation may vary, for example, by ±5 mol %. For example, in the 1:57 lipid particle (e.g., SNALP) formulation, the target amount of cationic lipid is 57.1 mol %, but the actual amount of cationic lipid may be ±5 mol %, +4 mol %, ±3 mol %, ±2 mol %, ±1 mol %, ±0.75 mol %, 0.5 mol %, ±0.25 mol %, or ±0.1 mol % of that target amount, with the balance of the formulation being made up of other lipid components (adding up to 100 mol % of total lipids present in the particle). Similarly, in the 7:54 lipid particle (e.g., SNALP) formulation, the target amount of cationic lipid is 54.06 mol %, but the actual amount of cationic lipid may be ±5 mol %, ±4 mol %, ±3 mol %, ±2 mol %, 1 mol %, 0.75 mol %, 0.5 mol %, ±0.25 mol %, or ±0.1 mol % of that target amount, with the balance of the formulation being made up of other lipid components (adding up to 100 mol % of total lipids present in the particle).

B. Non-Cationic Lipids

The non-cationic lipids used in the lipid particles of the invention (e.g., SNALP) can be any of a variety of neutral uncharged, zwitterionic, or anionic lipids capable of producing a stable complex.

Non-limiting examples of non-cationic lipids include phospholipids such as lecithin, phosphatidylethanolamine, lysolecithin, lysophosphatidylethanolamine, phosphatidylserine, phosphatidylinositol, sphingomyelin, egg sphingomyelin (ESM), cephalin, cardiolipin, phosphatidic acid, cerebrosides, dicetylphosphate, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoyl-phosphatidylcholine (POPC), palmitoyloleoyl-phosphatidylethanolamine (POPE), palmitoyloleyol-phosphatidylglycerol (POPG), dioleoylphosphatidylethanolamine 4-(N-maleimidomethyl)-cyclohexane-1-carboxylate (DOPE-mal), dipalmitoyl-phosphatidylethanolamine (DPPE), dimyristoyl-phosphatidylethanolamine (DMPE), distearoyl-phosphatidylethanolamine (DSPE), monomethyl-phosphatidylethanolamine, dimethyl-phosphatidylethanolamine, dielaidoyl-phosphatidylethanolamine (DEPE), stearoyloleoyl-phosphatidylethanolamine (SOPE), lysophosphatidylcholine, dilinoleoylphosphatidylcholine, and mixtures thereof. Other diacylphosphatidylcholine and diacylphosphatidylethanolamine phospholipids can also be used. The acyl groups in these lipids are preferably acyl groups derived from fatty acids having $C_{10}$-$C_{24}$ carbon chains, e.g., lauroyl, myristoyl, palmitoyl, stearoyl, or oleoyl.

Additional examples of non-cationic lipids include sterols such as cholesterol and derivatives thereof. Non-limiting examples of cholesterol derivatives include polar analogues such as 5α-cholestanol, 5β-coprostanol, cholesteryl-(2'-hydroxy)-ethyl ether, cholesteryl-(4'-hydroxy)-butyl ether, and 6-ketocholestanol; non-polar analogues such as 5α-cholestane, cholestenone, 5α-cholestanone, 5β-cholestanone, and cholesteryl decanoate; and mixtures thereof. In preferred embodiments, the cholesterol derivative is a polar analogue such as cholesteryl-(4'-hydroxy)-butyl ether. The synthesis of cholesteryl-(2'-hydroxy)-ethyl ether is described in PCT Publication No. WO 09/127060, the disclosure of which is herein incorporated by reference in its entirety for all purposes.

In some embodiments, the non-cationic lipid present in the lipid particles (e.g., SNALP) comprises or consists of a mixture of one or more phospholipids and cholesterol or a derivative thereof. In other embodiments, the non-cationic lipid present in the lipid particles (e.g., SNALP) comprises or consists of one or more phospholipids, e.g., a cholesterol-free lipid particle formulation. In yet other embodiments, the non-cationic lipid present in the lipid particles (e.g., SNALP) comprises or consists of cholesterol or a derivative thereof, e.g., a phospholipid-free lipid particle formulation.

Other examples of non-cationic lipids suitable for use in the present invention include nonphosphorous containing lipids such as, e.g., stearylamine, dodecylamine, hexadecylamine, acetyl palmitate, glycerolricinoleate, hexadecyl stereate, isopropyl myristate, amphoteric acrylic polymers, triethanolamine-lauryl sulfate, alkyl-aryl sulfate polyethyloxylated fatty acid amides, dioctadecyldimethyl ammonium bromide, ceramide, sphingomyelin, and the like.

In some embodiments, the non-cationic lipid comprises from about 10 mol % to about 60 mol %, from about 20 mol % to about 55 mol %, from about 20 mol % to about 45 mol %, from about 20 mol % to about 40 mol %, from about 25 mol % to about 50 mol %, from about 25 mol % to about 45 mol %, from about 30 mol % to about 50 mol %, from about 30 mol % to about 45 mol %, from about 30 mol % to about 40 mol %, from about 35 mol % to about 45 mol %, from about 37 mol % to about 42 mol %, or about 35 mol %, 36 mol %, 37 mol %, 38 mol %, 39 mol %, 40 mol %, 41 mol %, 42 mol %, 43 mol %, 44 mol %, or 45 mol % (or any fraction thereof or range therein) of the total lipid present in the particle.

In embodiments where the lipid particles contain a mixture of phospholipid and cholesterol or a cholesterol derivative, the mixture may comprise up to about 40 mol %, 45 mol %, 50 mol %, 55 mol %, or 60 mol % of the total lipid present in the particle.

In some embodiments, the phospholipid component in the mixture may comprise from about 2 mol % to about 20 mol %, from about 2 mol % to about 15 mol %, from about 2 mol % to about 12 mol %, from about 4 mol % to about 15 mol %, or from about 4 mol % to about 10 mol (or any fraction thereof or range therein) of the total lipid present in the particle. In certain preferred embodiments, the phospholipid component in the mixture comprises from about 5 mol % to about 10 mol %, from about 5 mol % to about 9 mol %, from about 5 mol % to about 8 mol %, from about 6 mol % to about 9 mol %, from about 6 mol % to about 8 mol %, or about 5 mol %, 6 mol %, 7 mol %, 8 mol %, 9 mol %, or 10 mol % (or any fraction thereof or range therein) of the total lipid present in the particle. As a non-limiting example, a 1:57 lipid particle formulation comprising a mixture of phospholipid and cholesterol may comprise a phospholipid such as DPPC or DSPC at about 7 mol % (or any fraction thereof), e.g., in a mixture with cholesterol or a cholesterol derivative at about 34 mol % (or any fraction thereof) of the total lipid present in the particle. As another non-limiting example, a 7:54 lipid particle formulation comprising a mixture of phospholipid and cholesterol may comprise a phospholipid such as DPPC or DSPC at about 7 mol % (or any fraction thereof), e.g., in a mixture with cholesterol or a cholesterol derivative at about 32 mol % (or any fraction thereof) of the total lipid present in the particle.

In other embodiments, the cholesterol component in the mixture may comprise from about 25 mol % to about 45 mol %, from about 25 mol % to about 40 mol %, from about 30 mol % to about 45 mol %, from about 30 mol % to about 40 mol %, from about 27 mol % to about 37 mol %, from about 25 mol % to about 30 mol %, or from about 35 mol % to about 40 mol (or any fraction thereof or range therein) of the total lipid present in the particle. In certain preferred embodiments, the cholesterol component in the mixture comprises from about 25 mol % to about 35 mol %, from about 27 mol % to about 35 mol %, from about 29 mol % to about 35 mol %, from about 30 mol % to about 35 mol %, from about 30 mol % to about 34 mol %, from about 31 mol % to about 33 mol %, or about 30 mol %, 31 mol %, 32 mol %, 33 mol %, 34 mol %, or 35 mol % (or any fraction thereof or range therein) of the total lipid present in the particle. In other embodiments, the cholesterol component in the mixture comprises about 36, 37, 38, 39, 40, 41, 42, 43, 44, or 45 mol % (or any fraction thereof or range therein) of the total lipid present in the particle. Typically, a 1:57 lipid particle formulation comprising a mixture of phospholipid and cholesterol may comprise cholesterol or a cholesterol derivative at about 34 mol % (or any fraction thereof), e.g., in a mixture with a phospholipid such as DPPC or DSPC at about 7 mol % (or any fraction thereof) of the total lipid present in the particle. Typically, a 7:54 lipid particle formulation comprising a mixture of phospholipid and cholesterol may comprise cholesterol or a cholesterol derivative at about 32 mol % (or any fraction thereof), e.g., in a mixture with a phospholipid such as DPPC or DSPC at about 7 mol % (or any fraction thereof) of the total lipid present in the particle.

In embodiments where the lipid particles are phospholipid-free, the cholesterol or derivative thereof may comprise up to about 25 mol %, 30 mol %, 35 mol %, 40 mol %, 45 mol %, 50 mol %, 55 mol %, or 60 mol % of the total lipid present in the particle.

In some embodiments, the cholesterol or derivative thereof in the phospholipid-free lipid particle formulation may comprise from about 25 mol % to about 45 mol %, from about 25 mol % to about 40 mol %, from about 30 mol % to about 45 mol %, from about 30 mol % to about 40 mol %, from about 31 mol % to about 39 mol %, from about 32 mol % to about 38 mol %, from about 33 mol % to about 37 mol %, from about 35 mol % to about 45 mol %, from about 30 mol % to about 35 mol %, from about 35 mol % to about 40 mol %, or about 30 mol %, 31 mol %, 32 mol %, 33 mol %, 34 mol %, 35 mol %, 36 mol %, 37 mol %, 38 mol %, 39 mol %, 40 mol %, 41 mol %, 42 mol %, 43 mol %, 44 mol %, or 45 mol % (or any fraction thereof or range therein) of the total lipid present in the particle. As a non-limiting example, a 1:62 lipid particle formulation may comprise cholesterol at about 37 mol % (or any fraction thereof) of the total lipid present in the particle. As another non-limiting example, a 7:58 lipid particle formulation may comprise cholesterol at about 35 mol % (or any fraction thereof) of the total lipid present in the particle.

In other embodiments, the non-cationic lipid comprises from about 5 mol % to about 90 mol %, from about 10 mol % to about 85 mol %, from about 20 mol % to about 80 mol %, about 10 mol % (e.g., phospholipid only), or about 60 mol % phospholipid and cholesterol or derivative thereof) (or any fraction thereof or range therein) of the total lipid present in the particle.

Additional percentages and ranges of non-cationic lipids suitable for use in the lipid particles of the present invention are described in PCT Publication No. WO 09/127060, U.S. application Ser. No. 12/794,701, filed Jun. 4, 2010, and U.S. application Ser. No. 12/828,189, filed Jun. 30, 2010, the disclosures of which are herein incorporated by reference in their entirety for all purposes.

It should be understood that the percentage of non-cationic lipid present in the lipid particles of the invention is a target amount, and that the actual amount of non-cationic lipid present in the formulation may vary, for example, by ±5 mol %. For example, in the 1:57 lipid particle (e.g., SNALP) formulation, the target amount of phospholipid is 7.1 mol % and the target amount of cholesterol is 34.3 mol %, but the actual amount of phospholipid may be ±2 mol %, ±1.5 mol %, ±1 mol %, ±0.75 mol %, ±0.5 mol %, ±0.25 mol %, or ±0.1 mol % of that target amount, and the actual amount of cholesterol may be ±3 mol %, ±2 mol %, ±1 mol %, ±0.75 mol %, ±0.5 mol %, ±0.25 mol %, or ±0.1 mol % of that target amount, with the balance of the formulation being made up of other lipid components (adding up to 100 mol % of total lipids present in the particle). Similarly, in the 7:54 lipid particle (e.g., SNALP) formulation, the target amount of phospholipid is 6.75 mol % and the target amount of cholesterol is 32.43 mol %, but the actual amount of phospholipid may be ±2 mol %, ±1.5 mol %, ±1 mol %, ±0.75 mol %, ±0.5 mol %, ±0.25 mol %, or ±0.1 mol % of that target amount, and the actual amount of cholesterol may be ±3 mol %, ±2 mol %, ±1 mol %, ±0.75 mol %, ±0.5 mol %, ±0.25 mol %, or ±0.1 mol % of that target amount, with the balance of the formulation being made up of other lipid components (adding up to 100 mol % of total lipids present in the particle).

C. Lipid Conjugates

In addition to cationic and non-cationic lipids, the lipid particles of the invention (e.g., SNALP) may further comprise a lipid conjugate. The conjugated lipid is useful in that it prevents the aggregation of particles. Suitable conjugated lipids include, but are not limited to, PEG-lipid conjugates, POZ-lipid conjugates, ATTA-lipid conjugates, cationic-polymer-lipid conjugates (CPLs), and mixtures thereof. In certain embodiments, the particles comprise either a PEG-lipid conjugate or an ATTA-lipid conjugate together with a CPL.

In a preferred embodiment, the lipid conjugate is a PEG-lipid. Examples of PEG-lipids include, but are not limited to, PEG coupled to dialkyloxypropyls (PEG-DAA) as described in, e.g., PCT Publication No. WO 05/026372, PEG coupled to diacylglycerol (PEG-DAG) as described in, e.g., U.S. Patent Publication Nos. 20030077829 and 2005008689, PEG coupled to phospholipids such as phosphatidylethanolamine (PEG-PE), PEG conjugated to ceramides as described in, e.g., U.S. Pat. No. 5,885,613, PEG conjugated to cholesterol or a derivative thereof, and mixtures thereof. The disclosures of these patent documents are herein incorporated by reference in their entirety for all purposes.

Additional PEG-lipids suitable for use in the invention include, without limitation, mPEG2000-1,2-di-O-alkyl-sn3-carbomoylglyceride (PEG-C-DOMG). The synthesis of PEG-C-DOMG is described in PCT Publication No. WO 09/086558, the disclosure of which is herein incorporated by reference in its entirety for all purposes. Yet additional suitable PEG-lipid conjugates include, without limitation, 1-[8'-(1,2-dimyristoyl-3-propanoxy)-carboxamido-3',6'-dioxaoctanyl]carbamoyl-ω-methyl-poly(ethylene glycol) (2KPEG-DMG). The synthesis of 2KPEG-DMG is described in U.S. Pat. No. 7,404,969, the disclosure of which is herein incorporated by reference in its entirety for all purposes.

PEG is a linear, water-soluble polymer of ethylene PEG repeating units with two terminal hydroxyl groups. PEGs are classified by their molecular weights; for example, PEG 2000 has an average molecular weight of about 2,000 daltons, and PEG 5000 has an average molecular weight of about 5,000 daltons. PEGs are commercially available from Sigma Chemical Co. and other companies and include, but are not limited to, the following: monomethoxypolyethylene glycol (MePEG-OH), monomethoxypolyethylene glycol-succinate (MePEG-S), monomethoxypolyethylene glycol-succinimidyl succinate (MePEG-S-NHS), monomethoxypolyethylene glycol-amine (MePEG-$NH_2$), monomethoxypolyethylene glycol-tresylate (MePEG-TRES), monomethoxypolyethylene glycol-imidazolyl-carbonyl (MePEG-IM), as well as such compounds containing a terminal hydroxyl group instead of a terminal methoxy group (e.g., HO-PEG-S, HO-PEG-S-NHS, HO-PEG-$NH_2$, etc.). Other PEGs such as those described in U.S. Pat. Nos. 6,774,180 and 7,053,150 (e.g., mPEG (20 KDa) amine) are also useful for preparing the PEG-lipid conjugates of the present invention. The disclosures of these patents are herein incorporated by reference in their entirety for all purposes. In addition, monomethoxypolyethyleneglycol-acetic acid (MePEG-$CH_2COOH$) is particularly useful for preparing PEG-lipid conjugates including, e.g., PEG-DAA conjugates.

The PEG moiety of the PEG-lipid conjugates described herein may comprise an average molecular weight ranging from about 550 daltons to about 10,000 daltons. In certain instances, the PEG moiety has an average molecular weight of from about 750 daltons to about 5,000 daltons (e.g., from about 1,000 daltons to about 5,000 daltons, from about 1,500 daltons to about 3,000 daltons, from about 750 daltons to about 3,000 daltons, from about 750 daltons to about 2,000 daltons, etc.). In other instances, the PEG moiety has an average molecular weight of from about 550 daltons to about 1000 daltons, from about 250 daltons to about 1000 daltons, from about 400 daltons to about 1000 daltons, from about 600 daltons to about 900 daltons, from about 700 daltons to about 800 daltons, or about 200, 250, 300, 350, 400, 450, 500, 550, 600, 650, 700, 750, 800, 850, 900, 950, or 1000 daltons. In preferred embodiments, the PEG moiety has an average molecular weight of about 2,000 daltons or about 750 daltons.

In certain instances, the PEG can be optionally substituted by an alkyl, alkoxy, acyl, or aryl group. The PEG can be conjugated directly to the lipid or may be linked to the lipid via a linker moiety. Any linker moiety suitable for coupling the PEG to a lipid can be used including, e.g., non-ester containing linker moieties and ester-containing linker moieties. In a preferred embodiment, the linker moiety is a non-ester containing linker moiety. As used herein, the term "non-ester containing linker moiety" refers to a linker moiety that does not contain a carboxylic ester bond (—OC(O)—). Suitable non-ester containing linker moieties include, but are not limited to, amido (—C(O)NH—), amino (—NR—), carbonyl (—C(O)—), carbamate (—NHC(O)O—), urea (—NHC(O)NH—), disulphide (—S—S—), ether (—O—), succinyl (—(O)CC$H_2$C$H_2$C(O)—), succinamidyl (—NHC(O)C$H_2$C$H_2$C(O)NH—), ether, disulphide, as well as combinations thereof (such as a linker containing both a carbamate linker moiety and an amido linker moiety). In a preferred embodiment, a carbamate linker is used to couple the PEG to the lipid.

In other embodiments, an ester containing linker moiety is used to couple the PEG to the lipid. Suitable ester containing linker moieties include, e.g., carbonate (—OC(O)O—), succinoyl, phosphate esters (—O—(O)POH—O—), sulfonate esters, and combinations thereof.

Phosphatidylethanolamines having a variety of acyl chain groups of varying chain lengths and degrees of saturation can be conjugated to PEG to form the lipid conjugate. Such phosphatidylethanolamines are commercially available, or can be isolated or synthesized using conventional techniques known to those of skilled in the art. Phosphatidylethanolamines containing saturated or unsaturated fatty acids with carbon chain lengths in the range of $C_{10}$ to $C_{20}$ are preferred. Phosphatidylethanolamines with mono- or diunsaturated fatty acids and mixtures of saturated and unsaturated fatty acids can also be used. Suitable phosphatidylethanolamines include, but are not limited to, dimyristoyl-phosphatidylethanolamine (DMPE), dipalmitoyl-phosphatidylethanolamine (DPPE), dioleoylphosphatidylethanolamine (DOPE), and distearoyl-phosphatidylethanolamine (DSPE).

The term "ATTA" or "polyamide" includes, without limitation, compounds described in U.S. Pat. Nos. 6,320,017 and 6,586,559, the disclosures of which are herein incorporated by reference in their entirety for all purposes. These compounds include a compound having the formula:

(XVII)

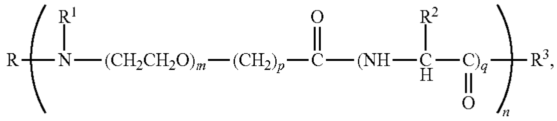

wherein R is a member selected from the group consisting of hydrogen, alkyl and acyl; $R^1$ is a member selected from the group consisting of hydrogen and alkyl; or optionally, R and $R^1$ and the nitrogen to which they are bound form an azido moiety; $R^2$ is a member of the group selected from hydrogen, optionally substituted alkyl, optionally substituted aryl and a side chain of an amino acid; $R^3$ is a member selected from the group consisting of hydrogen, halogen, hydroxy, alkoxy, mercapto, hydrazino, amino and $NR^4R^5$, wherein $R^4$ and $R^5$ are independently hydrogen or alkyl; n is 4 to 80; m is 2 to 6; p is 1 to 4; and q is 0 or 1. It will be apparent to those of skill in the art that other polyamides can be used in the compounds of the present invention.

The term "diacylglycerol" or "DAG" includes a compound having 2 fatty acyl chains, $R^1$ and $R^2$, both of which have independently between 2 and 30 carbons bonded to the 1- and 2-position of glycerol by ester linkages. The acyl groups can be saturated or have varying degrees of unsaturation. Suitable acyl groups include, but are not limited to, lauroyl ($C_{12}$), myristoyl ($C_{14}$), palmitoyl ($C_{16}$), stearoyl ($C_{18}$), and icosoyl ($C_{20}$). In preferred embodiments, $R^1$ and $R^2$ are the same, i.e., $R^1$ and $R^2$ are both myristoyl (i.e., dimyristoyl), $R^1$ and $R^2$ are both stearoyl (i.e., distearoyl), etc. Diacylglycerols have the following general formula:

(XVIII)

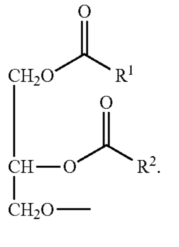

The term "dialkyloxypropyl" or "DAA" includes a compound having 2 alkyl chains, $R^1$ and $R^2$, both of which have independently between 2 and 30 carbons. The alkyl groups can be saturated or have varying degrees of unsaturation. Dialkyloxypropyls have the following general formula:

(XIX)

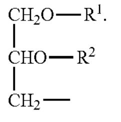

In a preferred embodiment, the PEG-lipid is a PEG-DAA conjugate having the following formula:

(XX)

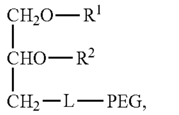

wherein $R^1$ and $R^2$ are independently selected and are long-chain alkyl groups having from about 10 to about 22 carbon atoms; PEG is a polyethyleneglycol; and L is a non-ester containing linker moiety or an ester containing linker moiety as described above. The long-chain alkyl groups can be saturated or unsaturated. Suitable alkyl groups include, but are not limited to, decyl ($C_{10}$), lauryl ($C_{12}$), myristyl ($C_{14}$), palmityl ($C_{16}$), stearyl ($C_{18}$), and icosyl ($C_{20}$). In preferred embodiments, $R^1$ and $R^2$ are the same, i.e., $R^1$ and $R^2$ are both myristyl (i.e., dimyristyl), $R^1$ and $R^2$ are both stearyl (i.e., distearyl), etc.

In Formula XX above, the PEG has an average molecular weight ranging from about 550 daltons to about 10,000 daltons. In certain instances, the PEG has an average molecular weight of from about 750 daltons to about 5,000 daltons (e.g., from about 1,000 daltons to about 5,000 daltons, from about 1,500 daltons to about 3,000 daltons, from about 750 daltons to about 3,000 daltons, from about 750 daltons to about 2,000 daltons, etc.). In other instances, the PEG moiety has an average molecular weight of from about 550 daltons to about 1000 daltons, from about 250 daltons to about 1000 daltons, from about 400 daltons to about 1000 daltons, from about 600 daltons to about 900 daltons, from about 700 daltons to about 800 daltons, or about 200, 250, 300, 350, 400, 450, 500, 550, 600, 650, 700, 750, 800, 850, 900, 950, or 1000 daltons. In preferred embodiments, the PEG has an average molecular weight of about 2,000 daltons or about 750 daltons. The PEG can be optionally substituted with alkyl, alkoxy, acyl, or aryl groups. In certain embodiments, the terminal hydroxyl group is substituted with a methoxy or methyl group.

In a preferred embodiment, "L" is a non-ester containing linker moiety. Suitable non-ester containing linkers include, but are not limited to, an amido linker moiety, an amino linker moiety, a carbonyl linker moiety, a carbamate linker moiety, a urea linker moiety, an ether linker moiety, a disulphide linker moiety, a succinamidyl linker moiety, and combinations thereof. In a preferred embodiment, the non-ester containing linker moiety is a carbamate linker moiety (i.e., a PEG-C-DAA conjugate). In another preferred embodiment, the non-ester containing linker moiety is an amido linker moiety (i.e., a PEG-A-DAA conjugate). In yet another preferred embodiment, the non-ester containing linker moiety is a succinamidyl linker moiety (i.e., a PEG-S-DAA conjugate).

In particular embodiments, the PEG-lipid conjugate is selected from:

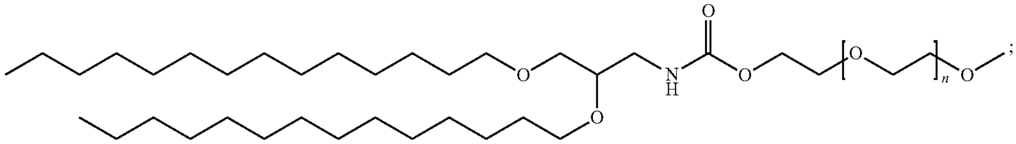

; and (PEG-C-DMA)

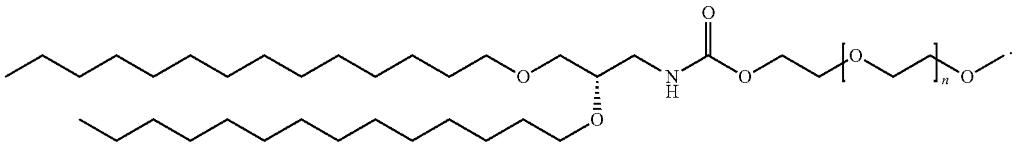

(PEG-C-DOMG)

The PEG-DAA conjugates are synthesized using standard techniques and reagents known to those of skill in the art. It will be recognized that the PEG-DAA conjugates will contain various amide, amine, ether, thio, carbamate, and urea linkages. Those of skill in the art will recognize that methods and reagents for forming these bonds are well known and readily available. See, e.g., March, ADVANCED ORGANIC CHEMISTRY (Wiley 1992); Larock, COMPREHENSIVE ORGANIC TRANSFORMATIONS (VCH 1989); and Furniss, VOGEL'S TEXTBOOK OF PRACTICAL ORGANIC CHEMISTRY, 5th ed. (Longman 1989). It will also be appreciated that any functional groups present may require protection and deprotection at different points in the synthesis of the PEG-DAA conjugates. Those of skill in the art will recognize that such techniques are well known. See, e.g., Green and Wuts, PROTECTIVE GROUPS IN ORGANIC SYNTHESIS (Wiley 1991).

Preferably, the PEG-DAA conjugate is a PEG-didecyloxypropyl ($C_{10}$) conjugate, a PEG-dilauryloxypropyl ($C_{12}$) conjugate, a PEG-dimyristyloxypropyl ($C_{14}$) conjugate, a PEG-dipalmityloxypropyl ($C_{16}$) conjugate, or a PEG-distearyloxypropyl ($C_{18}$) conjugate. In these embodiments, the PEG preferably has an average molecular weight of about 750 or about 2,000 daltons. In one particularly preferred embodiment, the PEG-lipid conjugate comprises PEG2000-C-DMA, wherein the "2000" denotes the average molecular weight of the PEG, the "C" denotes a carbamate linker moiety, and the "DMA" denotes dimyristyloxypropyl. In another particularly preferred embodiment, the PEG-lipid conjugate comprises PEG750-C-DMA, wherein the "750" denotes the average molecular weight of the PEG, the "C" denotes a carbamate linker moiety, and the "DMA" denotes dimyristyloxypropyl. In particular embodiments, the terminal hydroxyl group of the PEG is substituted with a methyl group. Those of skill in the art will readily appreciate that other dialkyloxypropyls can be used in the PEG-DAA conjugates of the present invention.

In addition to the foregoing, it will be readily apparent to those of skill in the art that other hydrophilic polymers can be used in place of PEG. Examples of suitable polymers that can be used in place of PEG include, but are not limited to, polyvinylpyrrolidone, polymethyloxazoline, polyethyloxazoline, polyhydroxypropyl methacrylamide, polymethacrylamide and polydimethylacrylamide, polylactic acid, polyglycolic acid, and derivatized celluloses such as hydroxymethylcellulose or hydroxyethylcellulose.

In addition to the foregoing components, the lipid particles (e.g., SNALP) of the present invention can further comprise cationic poly(ethylene glycol) (PEG) lipids or CPLs (see, e.g., Chen et al., *Bioconj. Chem.,* 11:433-437 (2000); U.S. Pat. No. 6,852,334; PCT Publication No. WO 00/62813, the disclosures of which are herein incorporated by reference in their entirety for all purposes).

Suitable CPLs include compounds of Formula XXI:

A-W—Y (XXI), wherein A, W, and Y are as described below.

With reference to Formula XXI, "A" is a lipid moiety such as an amphipathic lipid, a neutral lipid, or a hydrophobic lipid that acts as a lipid anchor. Suitable lipid examples include, but are not limited to, diacylglycerolyls, dialkylglycerolyls, N—N-dialkylaminos, 1,2-diacyloxy-3-aminopropanes, and 1,2-dialkyl-3-aminopropanes.

"W" is a polymer or an oligomer such as a hydrophilic polymer or oligomer. Preferably, the hydrophilic polymer is a biocompatible polymer that is nonimmunogenic or possesses low inherent immunogenicity. Alternatively, the hydrophilic polymer can be weakly antigenic if used with appropriate adjuvants. Suitable nonimmunogenic polymers include, but are not limited to, PEG, polyamides, polylactic acid, polyglycolic acid, polylactic acid/polyglycolic acid copolymers, and combinations thereof. In a preferred embodiment, the polymer has a molecular weight of from about 250 to about 7,000 daltons.

"Y" is a polycationic moiety. The term polycationic moiety refers to a compound, derivative, or functional group having a positive charge, preferably at least 2 positive charges at a selected pH, preferably physiological pH. Suitable polycationic moieties include basic amino acids and their derivatives such as arginine, asparagine, glutamine, lysine, and histidine; spermine; spermidine; cationic dendrimers; polyamines; polyamine sugars; and amino polysaccharides. The polycationic moieties can be linear, such as linear tetralysine, branched or dendrimeric in structure. Polycationic moieties have between about 2 to about 15 positive charges, preferably between about 2 to about 12 positive charges, and more preferably between about 2 to about 8 positive charges at selected pH values. The selection of which polycationic moiety to employ may be determined by the type of particle application which is desired.

The charges on the polycationic moieties can be either distributed around the entire particle moiety, or alternatively, they can be a discrete concentration of charge density in one particular area of the particle moiety e.g., a charge spike. If the charge density is distributed on the particle, the charge density can be equally distributed or unequally distributed. All variations of charge distribution of the polycationic moiety are encompassed by the present invention.

The lipid "A" and the nonimmunogenic polymer "W" can be attached by various methods and preferably by covalent attachment. Methods known to those of skill in the art can be used for the covalent attachment of "A" and "W." Suitable linkages include, but are not limited to, amide, amine, carboxyl, carbonate, carbamate, ester, and hydrazone linkages. It will be apparent to those skilled in the art that "A" and "W" must have complementary functional groups to effectuate the linkage. The reaction of these two groups, one on the lipid and the other on the polymer, will provide the desired linkage. For example, when the lipid is a diacylglycerol and the terminal hydroxyl is activated, for instance with NHS and DCC, to form an active ester, and is then reacted with a polymer which contains an amino group, such as with a polyamide (see, e.g., U.S. Pat. Nos. 6,320,017 and 6,586,559, the disclosures of which are herein incorporated by reference in their entirety for all purposes), an amide bond will form between the two groups.

In certain instances, the polycationic moiety can have a ligand attached, such as a targeting ligand or a chelating moiety for complexing calcium. Preferably, after the ligand is attached, the cationic moiety maintains a positive charge. In certain instances, the ligand that is attached has a positive charge. Suitable ligands include, but are not limited to, a compound or device with a reactive functional group and include lipids, amphipathic lipids, carrier compounds, bioaffinity compounds, biomaterials, biopolymers, biomedical devices, analytically detectable compounds, therapeutically active compounds, enzymes, peptides, proteins, antibodies, immune stimulators, radiolabels, fluorogens, biotin, drugs, haptens, DNA, RNA, polysaccharides, liposomes, virosomes, micelles, immunoglobulins, functional groups, other targeting moieties, or toxins.

In some embodiments, the lipid conjugate (e.g., PEG-lipid) comprises from about 0.1 mol % to about 2 mol %, from about 0.5 mol % to about 2 mol %, from about 1 mol % to about 2 mol %, from about 0.6 mol % to about 1.9 mol %, from about 0.7 mol % to about 1.8 mol %, from about 0.8 mol % to about 1.7 mol %, from about 0.9 mol % to about 1.6 mol %, from about 0.9 mol % to about 1.8 mol %, from about 1 mol % to about 1.8 mol %, from about 1 mol % to about 1.7 mol %, from about 1.2 mol % to about 1.8 mol %, from about 1.2 mol % to about 1.7 mol %, from about 1.3 mol % to about 1.6 mol %, from about 1.4 mol % to about 1.5 mol %, or about 1, 1.1, 1.2, 1.3, 1.4, 1.5, 1.6, 1.7, 1.8, 1.9, or 2 mol % (or any fraction thereof or range therein) of the total lipid present in the particle.

In other embodiments, the lipid conjugate (e.g., PEG-lipid) comprises from about 0 mol % to about 20 mol %, from about 0.5 mol % to about 20 mol %, from about 2 mol % to about 20 mol %, from about 1.5 mol % to about 18 mol %, from about 2 mol % to about 15 mol %, from about 4 mol % to about 15 mol %, from about 2 mol % to about 12 mol %, from about 5 mol % to about 12 mol %, or about 2 mol % (or any fraction thereof or range therein) of the total lipid present in the particle.

In further embodiments, the lipid conjugate (e.g., PEG-lipid) comprises from about 4 mol % to about 10 mol %, from about 5 mol % to about 10 mol %, from about 5 mol % to about 9 mol %, from about 5 mol % to about 8 mol %, from about 6 mol % to about 9 mol %, from about 6 mol % to about 8 mol %, or about 5 mol %, 6 mol %, 7 mol %, 8 mol %, 9 mol %, or 10 mol (or any fraction thereof or range therein) of the total lipid present in the particle.

Additional examples, percentages, and/or ranges of lipid conjugates suitable for use in the lipid particles of the invention are described in PCT Publication No. WO 09/127060, U.S. application Ser. No. 12/794,701, filed Jun. 4, 2010, U.S. application Ser. No. 12/828,189, filed Jun. 30, 2010, U.S. Provisional Application No. 61/294,828, filed Jan. 13, 2010, U.S. Provisional Application No. 61/295,140, filed Jan. 14, 2010, and PCT Publication No. WO 2010/006282, the disclosures of which are herein incorporated by reference in their entirety for all purposes.

It should be understood that the percentage of lipid conjugate (e.g., PEG-lipid) present in the lipid particles of the invention is a target amount, and that the actual amount of lipid conjugate present in the formulation may vary, for example, by ±2 mol %. For example, in the 1:57 lipid particle (e.g., SNALP) formulation, the target amount of lipid conjugate is 1.4 mol %, but the actual amount of lipid conjugate may be ±0.5 mol %, ±0.4 mol %, ±0.3 mol %, ±0.2 mol %, ±0.1 mol %, or ±0.05 mol % of that target amount, with the balance of the formulation being made up of other lipid components (adding up to 100 mol % of total lipids present in the particle). Similarly, in the 7:54 lipid particle (e.g., SNALP) formulation, the target amount of lipid conjugate is 6.76 mol %, but the actual amount of lipid conjugate may be ±2 mol %, ±1.5 mol %, ±1 mol %, ±0.75 mol %, ±0.5 mol %, ±0.25 mol %, or ±0.1 mol % of that target amount, with the balance of the formulation being made up of other lipid components (adding up to 100 mol % of total lipids present in the particle).

One of ordinary skill in the art will appreciate that the concentration of the lipid conjugate can be varied depending on the lipid conjugate employed and the rate at which the lipid particle is to become fusogenic.

By controlling the composition and concentration of the lipid conjugate, one can control the rate at which the lipid conjugate exchanges out of the lipid particle and, in turn, the rate at which the lipid particle becomes fusogenic. For instance, when a PEG-DAA conjugate is used as the lipid conjugate, the rate at which the lipid particle becomes fusogenic can be varied, for example, by varying the concentration of the lipid conjugate, by varying the molecular weight of the PEG, or by varying the chain length and degree of saturation of the alkyl groups on the PEG-DAA conjugate. In addition, other variables including, for example, pH, temperature, ionic strength, etc. can be used to vary and/or control the rate at which the lipid particle becomes fusogenic. Other methods which can be used to control the rate at which the lipid particle becomes fusogenic will become apparent to those of skill in the art upon reading this disclosure. Also, by controlling the composition and concentration of the lipid conjugate, one can control the lipid particle (e.g., SNALP) size.

VI. Preparation of Lipid Particles

The lipid particles of the present invention, e.g., SNALP, in which a nucleic acid such as an interfering RNA (e.g., siRNA) is entrapped within the lipid portion of the particle and is protected from degradation, can be formed by any method known in the art including, but not limited to, a continuous mixing method, a direct dilution process, and an in-line dilution process.

In particular embodiments, the cationic lipids may comprise one or more lipids of Formulas I-XVI or salts thereof, alone or in combination with other cationic lipid species. In other embodiments, the non-cationic lipids may comprise one or more lipids including egg sphingomyelin (ESM), distearoylphosphatidylcholine (DSPC), dioleoylphosphatidylcholine (DOPC), 1-palmitoyl-2-oleoyl-phosphatidylcholine (POPC), dipalmitoylphosphatidylcholine (DPPC), monomethyl-phosphatidylethanolamine, dimethyl-phosphatidylethanolamine, 14:0 PE (1,2-dimyristoyl-phosphatidylethanolamine (DMPE)), 16:0 PE (1,2-dipalmitoyl-phosphatidylethanolamine (DPPE)), 18:0 PE (1,2-distearoyl-phosphatidylethanolamine (DSPE)), 18:1 PE (1,2-dioleoyl-phosphatidylethanolamine (DOPE)), 18:1 trans PE (1,2-dielaidoyl-phosphatidylethanolamine (DEPE)), 18:0-18:1 PE (1-stearoyl-2-oleoyl-phosphatidylethanolamine (SOPE)), 16:0-18:1 PE (1-palmitoyl-2-oleoyl-phosphatidylethanolamine (POPE)), polyethylene glycol-based polymers (e.g., PEG 2000, PEG 5000, PEG-modified diacylglycerols, or PEG-modified dialkyloxypropyls), cholesterol, derivatives thereof, or combinations thereof.

In certain embodiments, the present invention provides nucleic acid-lipid particles (e.g., SNALP) produced via a continuous mixing method, e.g., a process that includes providing an aqueous solution comprising a nucleic acid (e.g., interfering RNA) in a first reservoir, providing an organic lipid solution in a second reservoir (wherein the lipids present in the organic lipid solution are solubilized in an organic solvent, e.g., a lower alkanol such as ethanol), and mixing the aqueous solution with the organic lipid solution such that the organic lipid solution mixes with the aqueous solution so as to substantially instantaneously produce a lipid vesicle (e.g., liposome) encapsulating the nucleic acid within the lipid vesicle. This process and the apparatus for carrying out this process are described in detail in U.S. Patent Publication No. 20040142025, the disclosure of which is herein incorporated by reference in its entirety for all purposes.

The action of continuously introducing lipid and buffer solutions into a mixing environment, such as in a mixing chamber, causes a continuous dilution of the lipid solution with the buffer solution, thereby producing a lipid vesicle substantially instantaneously upon mixing. As used herein, the phrase "continuously diluting a lipid solution with a buffer solution" (and variations) generally means that the lipid solution is diluted sufficiently rapidly in a hydration process with sufficient force to effectuate vesicle generation. By mixing the aqueous solution comprising a nucleic acid with the organic lipid solution, the organic lipid solution undergoes a continuous stepwise dilution in the presence of the buffer solution (i.e., aqueous solution) to produce a nucleic acid-lipid particle.

The nucleic acid-lipid particles formed using the continuous mixing method typically have a size of from about 30 nm to about 150 nm, from about 40 nm to about 150 nm, from about 50 nm to about 150 nm, from about 60 nm to about 130 nm, from about 70 nm to about 110 nm, from about 70 nm to about 100 nm, from about 80 nm to about 100 nm, from about 90 nm to about 100 nm, from about 70 to about 90 nm, from about 80 nm to about 90 nm, from about 70 nm to about 80 nm, less than about 120 nm, 110 nm, 100 nm, 90 nm, or 80 nm, or about 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, or 150 nm (or any fraction thereof or range therein). The particles thus formed do not aggregate and are optionally sized to achieve a uniform particle size.

In another embodiment, the present invention provides nucleic acid-lipid particles (e.g., SNALP) produced via a direct dilution process that includes forming a lipid vesicle (e.g., liposome) solution and immediately and directly introducing the lipid vesicle solution into a collection vessel containing a controlled amount of dilution buffer. In preferred aspects, the collection vessel includes one or more elements configured to stir the contents of the collection vessel to facilitate dilution. In one aspect, the amount of dilution buffer present in the collection vessel is substantially equal to the volume of lipid vesicle solution introduced thereto. As a non-limiting example, a lipid vesicle solution in 45% ethanol when introduced into the collection vessel containing an equal volume of dilution buffer will advantageously yield smaller particles.

In yet another embodiment, the present invention provides nucleic acid-lipid particles (e.g., SNALP) produced via an in-line dilution process in which a third reservoir containing dilution buffer is fluidly coupled to a second mixing region. In this embodiment, the lipid vesicle (e.g., liposome) solution formed in a first mixing region is immediately and directly mixed with dilution buffer in the second mixing region. In preferred aspects, the second mixing region includes a T-connector arranged so that the lipid vesicle solution and the dilution buffer flows meet as opposing 180° flows; however, connectors providing shallower angles can be used, e.g., from about 27° to about 180° (e.g., about 90°). A pump mechanism delivers a controllable flow of buffer to the second mixing region. In one aspect, the flow rate of dilution buffer provided to the second mixing region is controlled to be substantially equal to the flow rate of lipid vesicle solution introduced thereto from the first mixing region. This embodiment advantageously allows for more control of the flow of dilution buffer mixing with the lipid vesicle solution in the second mixing region, and therefore also the concentration of lipid vesicle solution in buffer throughout the second mixing process. Such control of the dilution buffer flow rate advantageously allows for small particle size formation at reduced concentrations.

These processes and the apparatuses for carrying out these direct dilution and in-line dilution processes are described in detail in U.S. Patent Publication No. 20070042031, the disclosure of which is herein incorporated by reference in its entirety for all purposes.

The nucleic acid-lipid particles formed using the direct dilution and in-line dilution processes typically have a size of from about 30 nm to about 150 nm, from about 40 nm to about 150 nm, from about 50 nm to about 150 nm, from about 60 nm to about 130 nm, from about 70 nm to about 110 nm, from about 70 nm to about 100 nm, from about 80 nm to about 100 nm, from about 90 nm to about 100 nm, from about 70 to about 90 nm, from about 80 nm to about 90 nm, from about 70 nm to about 80 nm, less than about 120 nm, 110 nm, 100 nm, 90 nm, or 80 nm, or about 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, or 150 nm (or any fraction thereof or range therein). The particles thus formed do not aggregate and are optionally sized to achieve a uniform particle size.

If needed, the lipid particles of the invention (e.g., SNALP) can be sized by any of the methods available for sizing liposomes. The sizing may be conducted in order to achieve a desired size range and relatively narrow distribution of particle sizes.

Several techniques are available for sizing the particles to a desired size. One sizing method, used for liposomes and equally applicable to the present particles, is described in U.S. Pat. No. 4,737,323, the disclosure of which is herein incorporated by reference in its entirety for all purposes. Sonicating a particle suspension either by bath or probe sonication produces a progressive size reduction down to particles of less than about 50 nm in size. Homogenization is another method which relies on shearing energy to fragment larger particles into smaller ones. In a typical homogenization procedure, particles are recirculated through a standard emulsion homogenizer until selected particle sizes, typically between about 60 and about 80 nm, are observed. In both methods, the particle size distribution can be monitored by conventional laser-beam particle size discrimination, or QELS.

Extrusion of the particles through a small-pore polycarbonate membrane or an asymmetric ceramic membrane is also an effective method for reducing particle sizes to a relatively well-defined size distribution. Typically, the suspension is cycled through the membrane one or more times until the desired particle size distribution is achieved. The particles may be extruded through successively smaller-pore membranes, to achieve a gradual reduction in size.

In some embodiments, the nucleic acids present in the particles are precondensed as described in, e.g., U.S. patent application Ser. No. 09/744,103, the disclosure of which is herein incorporated by reference in its entirety for all purposes.

In other embodiments, the methods may further comprise adding non-lipid polycations which are useful to effect the lipofection of cells using the present compositions. Examples of suitable non-lipid polycations include, hexadimethrine bromide (sold under the brand name POLYBRENE®, from Aldrich Chemical Co., Milwaukee, Wis., USA) or other salts of hexadimethrine. Other suitable polycations include, for example, salts of poly-L-ornithine, poly-L-arginine, poly-L-lysine, poly-D-lysine, polyallylamine, and polyethyleneimine. Addition of these salts is preferably after the particles have been formed.

In some embodiments, the nucleic acid to lipid ratios (mass/mass ratios) in a formed nucleic acid-lipid particle (e.g., SNALP) will range from about 0.01 to about 0.2, from about 0.05 to about 0.2, from about 0.02 to about 0.1, from about 0.03 to about 0.1, or from about 0.01 to about 0.08. The ratio of the starting materials (input) also falls within this range. In other embodiments, the particle preparation uses about 400 μg nucleic acid per 10 mg total lipid or a nucleic acid to lipid mass ratio of about 0.01 to about 0.08 and, more preferably, about 0.04, which corresponds to 1.25 mg of total lipid per 50 μg of nucleic acid. In other preferred embodiments, the particle has a nucleic acid:lipid mass ratio of about 0.08.

In other embodiments, the lipid to nucleic acid ratios (mass/mass ratios) in a formed nucleic acid-lipid particle (e.g., SNALP) will range from about 1 (1:1) to about 100 (100:1), from about 5 (5:1) to about 100 (100:1), from about 1 (1:1) to about 50 (50:1), from about 2 (2:1) to about 50 (50:1), from about 3 (3:1) to about 50 (50:1), from about 4 (4:1) to about 50 (50:1), from about 5 (5:1) to about 50 (50:1), from about 1 (1:1) to about 25 (25:1), from about 2 (2:1) to about 25 (25:1), from about 3 (3:1) to about 25 (25:1), from about 4 (4:1) to about 25 (25:1), from about 5 (5:1) to about 25 (25:1), from about 5 (5:1) to about 20 (20:1), from about 5 (5:1) to about 15 (15:1), from about 5 (5:1) to about 10 (10:1), or about 5 (5:1), 6 (6:1), 7 (7:1), 8 (8:1), 9 (9:1), 10 (10:1), 11 (11:1), 12 (12:1), 13 (13:1), 14 (14:1), 15 (15:1), 16 (16:1), 17 (17:1), 18 (18:1), 19 (19:1), 20 (20:1), 21 (21:1), 22 (22:1), 23 (23:1), 24 (24:1), or 25 (25:1), or any fraction thereof or range therein. The ratio of the starting materials (input) also falls within this range.

As previously discussed, the conjugated lipid may further include a CPL. A variety of general methods for making SNALP-CPLs (CPL-containing SNALP) are discussed herein. Two general techniques include the "post-insertion" technique, that is, insertion of a CPL into, for example, a pre-formed SNALP, and the "standard" technique, wherein the CPL is included in the lipid mixture during, for example, the SNALP formation steps. The post-insertion technique results in SNALP having CPLs mainly in the external face of the SNALP bilayer membrane, whereas standard techniques provide SNALP having CPLs on both internal and external faces. The method is especially useful for vesicles made from phospholipids (which can contain cholesterol) and also for vesicles containing PEG-lipids (such as PEG-DAAs and PEG-DAGs). Methods of making SNALP-CPLs are taught, for example, in U.S. Pat. Nos. 5,705,385; 6,586,410; 5,981,501; 6,534,484; and 6,852,334; U.S. Patent Publication No. 20020072121; and PCT Publication No. WO 00/62813, the disclosures of which are herein incorporated by reference in their entirety for all purposes.

VII. Kits

The present invention also provides lipid particles (e.g., SNALP) in kit form. In some embodiments, the kit comprises a container which is compartmentalized for holding the various elements of the lipid particles (e.g., the active agents or therapeutic agents such as nucleic acids and the individual lipid components of the particles). Preferably, the kit comprises a container (e.g., a vial or ampoule) which holds the lipid particles of the invention (e.g., SNALP), wherein the particles are produced by one of the processes set forth herein. In certain embodiments, the kit may further comprise an endosomal membrane destabilizer (e.g., calcium ions). The kit typically contains the particle compositions of the invention, either as a suspension in a pharmaceutically acceptable carrier or in dehydrated form, with instructions for their rehydration (if lyophilized) and administration.

As explained herein, it has surprisingly been found that the SNALP formulations of the present invention containing a combination of siRNA molecules targeting at least two or all three of the EBOV L-pol, VP24, and VP35 genes were capable of providing complete postexposure protection of nonhuman primates against a lethal EBOV challenge. In certain embodiments, the SNALP formulations of the present invention comprising a cocktail of siRNAs targeting any combination of at least two (or all three) of the EBOV L-pol, VP24, and VP35 genes demonstrate an increased potency (i.e., increased silencing activity) and an increased tolerability (e.g., a more favorable toxicity profile), e.g., when compared to other nucleic acid-lipid particle compositions previously described. In preferred embodiments, the kits of the invention comprise these lipid particles, wherein the particles are present in a container as a suspension or in dehydrated form. Such kits are particularly advantageous for use in providing effective postexposure treatment strategies for combating EBOV infections.

In certain instances, it may be desirable to have a targeting moiety attached to the surface of the lipid particle to further enhance the targeting of the particle. Methods of attaching targeting moieties (e.g., antibodies, proteins, etc.) to lipids (such as those used in the present particles) are known to those of skill in the art.

VIII. Administration of Lipid Particles

Once formed, the lipid particles of the invention (e.g., SNALP) are particularly useful for introducing interfering RNA (e.g., siRNA) targeting one or more EBOV genes (such as L-pol, VP24, VP30, VP35, VP40, NP, GP, or combinations thereof) into cells. As noted, it has surprisingly been found that the SNALP formulations of the present invention containing a pool of siRNA molecules targeting at least two or all three of the EBOV L-pol, VP24, and VP35 genes unexpectedly provided complete postexposure protection against a lethal EBOV challenge in a nonhuman primate model. Accordingly, the present invention also provides methods for introducing one or more interfering RNA (e.g., siRNA) into a cell infected by EBOV. EBOV is capable of infecting and replicating in virtually all cell types. In particular embodiments, the interfering RNA is introduced into reticuloendothelial cells (such as, e.g., macrophages, monocytes, etc.) as well as other cell types, including fibroblasts, endothelial cells (such as those lining the interior surface of blood vessels), and/or platelet cells infected with EBOV. The methods may be carried out in vitro or in vivo by first forming the particles as described above and then contacting the particles with the cells for a period of time sufficient for delivery of the interfering RNA to the cells to occur.

The lipid particles of the invention (e.g., SNALP) can be adsorbed to almost any cell type with which they are mixed or contacted. Once adsorbed, the particles can either be endocytosed by a portion of the cells, exchange lipids with cell membranes, or fuse with the cells. Transfer or incorporation of the nucleic acid (e.g., interfering RNA) portion of the particle can take place via any one of these pathways. In particular, when fusion takes place, the particle membrane is integrated into the cell membrane and the contents of the particle combine with the intracellular fluid.

The lipid particles of the invention (e.g., SNALP) can be administered either alone or in a mixture with a pharmaceutically acceptable carrier (e.g., physiological saline or phosphate buffer) selected in accordance with the route of administration and standard pharmaceutical practice. Generally, normal buffered saline (e.g., 135-150 mM NaCl) will be employed as the pharmaceutically acceptable carrier. Other suitable carriers include, e.g., water, buffered water, 0.4% saline, 0.3% glycine, and the like, including glycoproteins for enhanced stability, such as albumin, lipoprotein, globulin, etc. Additional suitable carriers are described in, e.g., REMINGTON'S PHARMACEUTICAL SCIENCES, Mack Publishing Company, Philadelphia, Pa., 17th ed. (1985). As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The phrase "pharmaceutically acceptable" refers to molecular entities and compositions that do not produce an allergic or similar untoward reaction when administered to a human.

The pharmaceutically acceptable carrier is generally added following lipid particle formation. Thus, after the lipid particle (e.g., SNALP) is formed, the particle can be diluted into pharmaceutically acceptable carriers such as normal buffered saline.

The concentration of particles in the pharmaceutical formulations can vary widely, i.e., from less than about 0.05%, usually at or at least about 2 to 5%, to as much as about 10 to 90% by weight, and will be selected primarily by fluid volumes, viscosities, etc., in accordance with the particular mode of administration selected. For example, the concentration may be increased to lower the fluid load associated with treatment. This may be particularly desirable in patients having atherosclerosis-associated congestive heart failure or severe hypertension. Alternatively, particles composed of irritating lipids may be diluted to low concentrations to lessen inflammation at the site of administration.

The pharmaceutical compositions of the present invention may be sterilized by conventional, well-known sterilization techniques. Aqueous solutions can be packaged for use or filtered under aseptic conditions and lyophilized, the lyophilized preparation being combined with a sterile aqueous solution prior to administration. The compositions can contain pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, and calcium chloride. Additionally, the particle suspension may include lipid-protective agents which protect lipids against free-radical and lipid-peroxidative damages on storage. Lipophilic free-radical quenchers, such as alphatocopherol, and water-soluble iron-specific chelators, such as ferrioxamine, are suitable.

In some embodiments, the lipid particles of the invention (e.g., SNALP) are particularly useful in methods for the therapeutic delivery of one or more nucleic acids comprising an interfering RNA sequence (e.g., siRNA). In particular, it is an object of this invention to provide in vitro and in vivo methods for treatment of EBOV infections in a mammal (e.g., a rodent such as a mouse or a primate such as a human, chimpanzee, or monkey) by downregulating or silencing the transcription and/or translation of one or more target nucleic acid sequences or genes of interest (such as EBOV L-pol, VP24, VP30, VP35, VP40, NP, GP, or combinations thereof). As a non-limiting example, the methods of the invention are useful for the in vivo delivery of interfering RNA (e.g., siRNA) to EBOV-infected cells of a mammalian subject for the treatment of an EBOV infection. In certain embodiments, the EBOV infection is associated with expression and/or overexpression of an EBOV gene and expression or overexpression of the gene is reduced by the interfering RNA (e.g., siRNA). In certain other embodiments, a therapeutically effective amount of the lipid particle may be administered to the mammal. In some instances, one, two, three, or more interfering RNA molecules (e.g., siRNA) are formulated into a SNALP, and the particles are administered to patients requiring such treatment. In other instances, cells are removed from a patient, the interfering RNA is delivered in vitro (e.g., using a SNALP described herein), and the cells are reinjected into the patient.

A. In Vivo Administration

Systemic delivery for in vivo therapy, e.g., delivery of a therapeutic nucleic acid to a distal target cell via body systems such as the circulation, has been achieved using nucleic acid-lipid particles such as those described in PCT Publication Nos. WO 05/007196, WO 05/121348, WO 05/120152, and WO 04/002453, the disclosures of which are herein incorporated by reference in their entirety for all purposes. The present invention also provides fully encapsulated lipid particles that protect the nucleic acid from nuclease degradation in serum, are non-immunogenic, are small in size, and are suitable for repeat dosing.

For in vivo administration, administration can be in any manner known in the art, e.g., by injection, oral administration, inhalation (e.g., intransal or intratracheal), transdermal application, or rectal administration. Administration can be accomplished via single or divided doses. The pharmaceutical compositions can be administered parenterally, i.e., intraarticularly, intravenously, intraperitoneally, subcutaneously, or intramuscularly. In some embodiments, the pharmaceutical compositions are administered intravenously or intraperitoneally by a bolus injection (see, e.g., U.S. Pat. No. 5,286,634). Intracellular nucleic acid delivery has also been discussed in Straubringer et al., *Methods Enzymol.,* 101:512 (1983); Mannino et al., *Biotechniques,* 6:682 (1988); Nicolau et al., *Crit. Rev. Ther. Drug Carrier Syst.,* 6:239 (1989); and Behr, *Acc. Chem. Res.,* 26:274 (1993). Still other methods of administering lipid-based therapeutics are described in, for example, U.S. Pat. Nos. 3,993,754; 4,145,410; 4,235,871; 4,224,179; 4,522,803; and 4,588,578. The lipid particles can be administered by direct injection at the site of disease or by injection at a site distal from the site of disease (see, e.g., Culver, HUMAN GENE THERAPY, MaryAnn Liebert, Inc., Publishers, New York. pp. 70-71(1994)). The disclosures of the above-described references are herein incorporated by reference in their entirety for all purposes.

In embodiments where the lipid particles of the present invention (e.g., SNALP) are administered intravenously, at least about 5%, 10%, 15%, 20%, or 25% of the total injected dose of the particles is present in plasma about 8, 12, 24, 36, or 48 hours after injection. In other embodiments, more than about 20%, 30%, 40% and as much as about 60%, 70% or 80% of the total injected dose of the lipid particles is present in plasma about 8, 12, 24, 36, or 48 hours after injection. In certain instances, more than about 10% of a plurality of the particles is present in the plasma of a mammal about 1 hour after administration. In certain other instances, the presence of the lipid particles is detectable at least about 1 hour after administration of the particle. In some embodiments, the presence of a therapeutic nucleic acid such as an interfering RNA molecule is detectable in cells (e.g., EBOV-infected cells) at about 8, 12, 24, 36, 48, 60, 72 or 96 hours after administration. In other embodiments, downregulation of expression of a target sequence, such as an EBOV sequence, by an interfering RNA (e.g., siRNA) is detectable at about 8, 12, 24, 36, 48, 60, 72 or 96 hours after administration. In yet other embodiments, downregulation of expression of a target sequence, such as an EBOV sequence, by an interfering RNA (e.g., siRNA) occurs preferentially in EBOV-infected cells and/or cells capable of being infected by EBOV. In further embodiments, the presence or effect of an interfering RNA (e.g., siRNA) in cells at a site proximal or distal to the site of administration is detectable at about 12, 24, 48, 72, or 96 hours, or at about 6, 8, 10, 12, 14, 16, 18, 19, 20, 22, 24, 26, or 28 days after administration. In additional embodiments, the lipid particles (e.g., SNALP) of the present invention are administered parenterally or intraperitoneally.

The compositions of the present invention, either alone or in combination with other suitable components, can be made into aerosol formulations (i.e., they can be "nebulized") to be administered via inhalation (e.g., intranasally or intratracheally) (see, Brigham et al., *Am. J. Sci.,* 298:278 (1989)). Aerosol formulations can be placed into pressurized acceptable propellants, such as dichlorodifluoromethane, propane, nitrogen, and the like.

In certain embodiments, the pharmaceutical compositions may be delivered by intranasal sprays, inhalation, and/or other aerosol delivery vehicles. Methods for delivering nucleic acid compositions directly to the lungs via nasal aerosol sprays have been described, e.g., in U.S. Pat. Nos. 5,756,353 and 5,804,212. Likewise, the delivery of drugs using intranasal microparticle resins and lysophosphatidyl-glycerol compounds (U.S. Pat. No. 5,725,871) are also well-known in the pharmaceutical arts. Similarly, transmucosal drug delivery in the form of a polytetrafluoroetheylene support matrix is described in U.S. Pat. No. 5,780,045. The disclosures of the above-described patents are herein incorporated by reference in their entirety for all purposes.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions are preferably administered, for example, by intravenous infusion, orally, topically, intraperitoneally, intravesically, or intrathecally.

Generally, when administered intravenously, the lipid particle formulations are formulated with a suitable pharmaceutical carrier. Many pharmaceutically acceptable carriers may be employed in the compositions and methods of the present invention. Suitable formulations for use in the present invention are found, for example, in REMINGTON'S PHARMACEUTICAL SCIENCES, Mack Publishing Company, Philadelphia, Pa., 17th ed. (1985). A variety of aqueous carriers may be used, for example, water, buffered water, 0.4% saline, 0.3% glycine, and the like, and may include glycoproteins for enhanced stability, such as albumin, lipoprotein, globulin, etc. Generally, normal buffered saline (135-150 mM NaCl) will be employed as the pharmaceutically acceptable carrier, but other suitable carriers will suffice. These compositions can be sterilized by conventional liposomal sterilization techniques, such as filtration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc. These compositions can be sterilized using the techniques referred to above or, alternatively, they can be produced under sterile conditions. The resulting aqueous solutions may be packaged for use or filtered under aseptic conditions and lyophilized, the lyophilized preparation being combined with a sterile aqueous solution prior to administration.

In certain applications, the lipid particles disclosed herein may be delivered via oral administration to the individual. The particles may be incorporated with excipients and used in the form of ingestible tablets, buccal tablets, troches, capsules, pills, lozenges, elixirs, mouthwash, suspensions, oral sprays, syrups, wafers, and the like (see, e.g., U.S. Pat. Nos. 5,641,515, 5,580,579, and 5,792,451, the disclosures of which are herein incorporated by reference in their entirety for all purposes). These oral dosage forms may also contain the following: binders, gelatin; excipients, lubricants, and/or flavoring agents. When the unit dosage form is a capsule, it may contain, in addition to the materials described above, a liquid carrier. Various other materials may be present as coatings or to otherwise modify the physical form of the dosage unit. Of course, any material used in preparing any unit dosage form should be pharmaceutically pure and substantially non-toxic in the amounts employed.

Typically, these oral formulations may contain at least about 0.1% of the lipid particles or more, although the percentage of the particles may, of course, be varied and may conveniently be between about 1% or 2% and about 60% or 70% or more of the weight or volume of the total formulation. Naturally, the amount of particles in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

Formulations suitable for oral administration can consist of: (a) liquid solutions, such as an effective amount of a packaged therapeutic nucleic acid (e.g., interfering RNA) suspended in diluents such as water, saline, or PEG 400; (b) capsules, sachets, or tablets, each containing a predetermined amount of a therapeutic nucleic acid (e.g., interfering RNA), as liquids, solids, granules, or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise a therapeutic nucleic acid (e.g., interfering RNA) in a flavor, e.g., sucrose, as well as pastilles comprising the therapeutic nucleic acid in an inert base, such as gelatin and glycerin or sucrose and acacia emulsions, gels, and the like containing, in addition to the therapeutic nucleic acid, carriers known in the art.

In another example of their use, lipid particles can be incorporated into a broad range of topical dosage forms. For instance, a suspension containing nucleic acid-lipid particles such as SNALP can be formulated and administered as gels, oils, emulsions, topical creams, pastes, ointments, lotions, foams, mousses, and the like.

When preparing pharmaceutical preparations of the lipid particles of the invention, it is preferable to use quantities of the particles which have been purified to reduce or eliminate empty particles or particles with therapeutic agents such as nucleic acid associated with the external surface.

The methods of the present invention may be practiced in a variety of hosts. Preferred hosts include mammalian species, such as primates (e.g., humans and chimpanzees as well as other nonhuman primates), canines, felines, equines, bovines, ovines, caprines, rodents (e.g., rats and mice), lagomorphs, and swine.

The amount of particles administered will depend upon the ratio of therapeutic nucleic acid (e.g., interfering RNA) to lipid, the particular therapeutic nucleic acid used, the disease or disorder being treated, the age, weight, and condition of the patient, and the judgment of the clinician, but will generally be between about 0.01 and about 50 mg per kilogram of body weight, preferably between about 0.1 and about 5 mg/kg of body weight, or about $10^8$-$10^{10}$ particles per administration (e.g., injection).

B. In Vitro Administration

For in vitro applications, the delivery of therapeutic nucleic acids (e.g., interfering RNA) can be to any cell grown in culture, whether of plant or animal origin, vertebrate or invertebrate, and of any tissue or type. In preferred embodiments, the cells are animal cells, more preferably mammalian cells, and most preferably human cells.

Contact between the cells and the lipid particles, when carried out in vitro, takes place in a biologically compatible medium. The concentration of particles varies widely depending on the particular application, but is generally between about 1 μmol and about 10 mmol. Treatment of the cells with the lipid particles is generally carried out at physiological temperatures (about 37° C.) for periods of time of from about 1 to 48 hours, preferably of from about 2 to 4 hours.

In one group of preferred embodiments, a lipid particle suspension is added to 60-80% confluent plated cells having a cell density of from about $10^3$ to about $10^5$ cells/ml, more preferably about $2\times10^4$ cells/ml. The concentration of the suspension added to the cells is preferably of from about 0.01 to 0.2 μg/ml, more preferably about 0.1 μg/ml.

To the extent that tissue culture of cells may be required, it is well-known in the art. For example, Freshney, Culture of Animal Cells, a Manual of Basic Technique, 3rd Ed., Wiley-Liss, New York (1994), Kuchler et al., Biochemical Methods in Cell Culture and Virology, Dowden, Hutchinson and Ross, Inc. (1977), and the references cited therein provide a general guide to the culture of cells. Cultured cell systems often will be in the form of monolayers of cells, although cell suspensions are also used.

Using an Endosomal Release Parameter (ERP) assay, the delivery efficiency of the SNALP or other lipid particle of the invention can be optimized. An ERP assay is described in detail in U.S. Patent Publication No. 20030077829, the disclosure of which is herein incorporated by reference in its entirety for all purposes. More particularly, the purpose of an ERP assay is to distinguish the effect of various cationic lipids and helper lipid components of SNALP or other lipid particle based on their relative effect on binding/uptake or fusion with/destabilization of the endosomal membrane. This assay allows one to determine quantitatively how each component of the SNALP or other lipid particle affects delivery efficiency, thereby optimizing the SNALP or other lipid particle. Usually, an ERP assay measures expression of a reporter protein (e.g., luciferase, β-galactosidase, green fluorescent protein (GFP), etc.), and in some instances, a SNALP formulation optimized for an expression plasmid will also be appropriate for encapsulating an interfering RNA. In other instances, an ERP assay can be adapted to measure down-regulation of transcription or translation of a target sequence in the presence or absence of an interfering RNA (e.g., siRNA). By comparing the ERPs for each of the various SNALP or other lipid particles, one can readily determine the optimized system, e.g., the SNALP or other lipid particle that has the greatest uptake in the cell.

C. Cells for Delivery of Lipid Particles

The compositions and methods of the present invention are particularly well suited for treating EBOV infections by targeting, e.g., EBOV gene expression in vivo. The present invention can be practiced on a wide variety of cell types from any vertebrate species, including mammals, such as, e.g., canines, felines, equines, bovines, ovines, caprines, rodents (e.g., mice, rats, and guinea pigs), lagomorphs, swine, and primates (e.g. monkeys, chimpanzees, and humans). Suitable cells include, but are not limited to, any cell infected with EBOV or capable of becoming infected with EBOV, such as, e.g., reticuloendothelial cells (e.g., monocytes, macrophages, Kupffer cells, tissue histiocytes, etc.), fibroblast cells, endothelial cells, platelet cells, and the like.

D. Detection of Lipid Particles

In some embodiments, the lipid particles of the present invention (e.g., SNALP) are detectable in the subject at about 1, 2, 3, 4, 5, 6, 7, 8 or more hours. In other embodiments, the lipid particles of the present invention (e.g., SNALP) are detectable in the subject at about 8, 12, 24, 48, 60, 72, or 96 hours, or about 6, 8, 10, 12, 14, 16, 18, 19, 22, 24, 25, or 28 days after administration of the particles. The presence of the particles can be detected in the cells, tissues, or other biological samples from the subject. The particles may be detected, e.g., by direct detection of the particles, detection of a therapeutic nucleic acid such as an interfering RNA (e.g., siRNA) sequence, detection of the target sequence of interest (i.e., by detecting expression or reduced expression of the sequence of interest), detection of a compound modulated by an EBOV protein (e.g., interferon), detection of viral load in the subject, or a combination thereof.

1. Detection of Particles

Lipid particles of the invention such as SNALP can be detected using any method known in the art. For example, a label can be coupled directly or indirectly to a component of the lipid particle using methods well-known in the art. A wide variety of labels can be used, with the choice of label depending on sensitivity required, ease of conjugation with the lipid particle component, stability requirements, and available instrumentation and disposal provisions. Suitable labels include, but are not limited to, spectral labels such as fluorescent dyes (e.g., fluorescein and derivatives, such as fluorescein isothiocyanate (FITC) and Oregon Green™; rhodamine and derivatives such Texas red, tetrarhodimine isothiocynate (TRITC), etc., digoxigenin, biotin, phycoerythrin, AMCA, CyDyes™, and the like; radiolabels such as $^3H$, $^{125}I$, $^{35}S$, $^{14}C$, $^{32}P$, $^{33}P$, etc.; enzymes such as horse radish peroxidase, alkaline phosphatase, etc.; spectral colorimetric labels such as colloidal gold or colored glass or plastic beads such as polystyrene, polypropylene, latex, etc. The label can be detected using any means known in the art.

2. Detection of Nucleic Acids

Nucleic acids (e.g., interfering RNA) are detected and quantified herein by any of a number of means well-known to those of skill in the art. The detection of nucleic acids may proceed by well-known methods such as Southern analysis, Northern analysis, gel electrophoresis, PCR, radiolabeling, scintillation counting, and affinity chromatography. Additional analytic biochemical methods such as spectrophotometry, radiography, electrophoresis, capillary electrophoresis, high performance liquid chromatography (HPLC), thin layer chromatography (TLC), and hyperdiffusion chromatography may also be employed.

The selection of a nucleic acid hybridization format is not critical. A variety of nucleic acid hybridization formats are known to those skilled in the art. For example, common formats include sandwich assays and competition or displacement assays. Hybridization techniques are generally described in, e.g., "Nucleic Acid Hybridization, A Practical Approach," Eds. Hames and Higgins, IRL Press (1985).

The sensitivity of the hybridization assays may be enhanced through the use of a nucleic acid amplification system which multiplies the target nucleic acid being detected. In vitro amplification techniques suitable for amplifying sequences for use as molecular probes or for generating nucleic acid fragments for subsequent subcloning are known. Examples of techniques sufficient to direct persons of skill through such in vitro amplification methods, including the polymerase chain reaction (PCR), the ligase chain reaction (LCR), Qβ-replicase amplification, and other RNA polymerase mediated techniques (e.g., NASBA™) are found in Sambrook et al., In *Molecular Cloning: A Laboratory Manual*, Cold Spring Harbor Laboratory Press (2000); and Ausubel et al., Short Protocols in Molecular Biology, eds., Current Protocols, Greene Publishing Associates, Inc. and John Wiley & Sons, Inc. (2002); as well as U.S. Pat. No. 4,683,202; PCR Protocols, A Guide to Methods and Applications (Innis et al. eds.) Academic Press Inc. San Diego, Calif. (1990); Arnheim & Levinson (Oct. 1, 1990), C&EN 36; The *Journal Of NIH Research,* 3:81 (1991); Kwoh et al., *Proc. Natl. Acad. Sci. USA,* 86:1173 (1989); Guatelli et al., *Proc. Natl. Acad. Sci. USA,* 87:1874 (1990); Lomeli et al., *J. Clin. Chem.,* 35:1826 (1989); Landegren et al., *Science,* 241: 1077 (1988); Van Brunt, *Biotechnology,* 8:291 (1990); Wu and Wallace, *Gene,* 4:560 (1989); Barringer et al., *Gene,* 89:117 (1990); and Sooknanan and Malek, *Biotechnology,* 13:563 (1995). Improved methods of cloning in vitro amplified nucleic acids are described in U.S. Pat. No. 5,426,039. Other methods described in the art are the nucleic acid sequence based amplification (NASBA™, Cangene, Mississauga, Ontario) and Qβ-replicase systems. These systems can be used to directly identify mutants where the PCR or LCR primers are designed to be extended or ligated only when a select sequence is present. Alternatively, the select sequences can be generally amplified using, for example, nonspecific PCR primers and the amplified target region later probed for a specific sequence indicative of a mutation. The disclosures of the above-described references are herein incorporated by reference in their entirety for all purposes.

Nucleic acids for use as probes, e.g., in in vitro amplification methods, for use as gene probes, or as inhibitor components are typically synthesized chemically according to the solid phase phosphoramidite triester method described by Beaucage et al., *Tetrahedron Letts.,* 22:1859 1862 (1981), e.g., using an automated synthesizer, as described in Needham VanDevanter et al., *Nucleic Acids Res.,* 12:6159 (1984). Purification of polynucleotides, where necessary, is typically performed by either native acrylamide gel electrophoresis or by anion exchange HPLC as described in Pearson et al., *J. Chrom.,* 255:137 149 (1983). The sequence of the synthetic polynucleotides can be verified using the chemical degradation method of Maxam and Gilbert (1980) in Grossman and Moldave (eds.) Academic Press, New York, *Methods in Enzymology,* 65:499.

An alternative means for determining the level of transcription is in situ hybridization. In situ hybridization assays are well-known and are generally described in Angerer et al., *Methods Enzymol.,* 152:649 (1987). In an in situ hybridization assay, cells are fixed to a solid support, typically a glass slide. If DNA is to be probed, the cells are denatured with heat or alkali. The cells are then contacted with a hybridization solution at a moderate temperature to permit annealing of specific probes that are labeled. The probes are preferably labeled with radioisotopes or fluorescent reporters.

3. Detection of Ebola Virus Load

EBOV load can be detected using any means known in the art. Typically, EBOV load is detected in a biological sample from the subject. For example, viral load in the subject's blood can be detected by measuring EBOV antigens using an immunoassay such as an ELISA (see, e.g., Meissner et al., *Virology,* 300:236-43 (2002); and Ksiazek et al., *J. Clin. Microbiol.,* 30:947-950 (1992)). Viral load can also be detected by amplifying EBOV nucleic acids (see, e.g., Drosten et al., *J Clin. Microbiol.,* 40: 2323-2330 (2002)) or by conventional plaque assay using monolayers of Vero or Vero E6 cells (see, e.g., Jahrling, Filoviruses and Arenaviruses, In *Manual of Clinical Microbiology*, Eds. Baron, Pfaller, Tenover, and Yolken, ASM Press, Washington, D.C. (1999)).

IX. Examples

The present invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

Example 1

Postexposure Protection of Nonhuman Primates Against a Lethal Ebola Virus Challenge by RNA Interference For more than 30 years, EBOV has been associated with periodic episodes of hemorrhagic fever in Central Africa that produce severe disease in infected patients. Mortality rates in outbreaks have ranged from 50% for the Sudan species of EBOV (SEBOV) to up to 90% for the Zaire species of EBOV (ZEBOV) (2). An outbreak late in 2007 caused by an apparently new species of EBOV in Uganda resulted in a fatality rate of about 25% (3).

EBOV particles contain an approximately 19-kb noninfectious RNA genome that encodes seven structural proteins and one nonstructural protein with the following gene order: 3' leader, nucleoprotein (NP), virion protein (VP) 35 (VP35), VP40, glycoprotein (GP), VP30, VP24, polymerase L protein (L-pol), and 5' trailer (4). Four of these proteins are associated with the viral genomic RNA in the ribonucleoprotein complex: NP, VP30, VP35, and L-pol. The L-pol and VP35 proteins together comprise the polymerase complex that is responsible for transcribing and replicating the EBOV genome. The L-pol protein provides the RNA-dependent RNA polymerase activity of the complex. The L-pol protein offers an ideal target for antiviral approaches not only because suppression should lead to a nearly total loss of all RNA synthesis, but also because of the absence of similar proteins in mammalian cells. In addition to the L-pol protein, the VP24 and VP35 proteins are also promising targets for antiviral interventions as both have been shown to have inhibitory effects on the host type I interferon (IFN) response. Specifically, VP35 was shown to function as a type I IFN antagonist (5-7) by blocking IFN regulatory factor (IRF)-3 activation and possibly preventing transcription of IFN-0 (6). VP24 expression was shown to interfere with type I IFN signaling (8) and mutations in VP24 have been linked to adaptation of ZEBOV to produce a lethal infection in mice (8) and guinea pigs (9).

While there are no vaccines or postexposure treatment modalities available for preventing or managing EBOV infections, remarkable progress has been made over the last few years in developing candidate preventive vaccines that can protect nonhuman primates against EBOV (10-17). However, progress in developing antiviral drugs and other postexposure interventions has been much slower. In a previous study, an siRNA targeting the ZEBOV L-pol gene (designated "EK-1") was identified that inhibited the replication of ZEBOV in vitro and completely protected ZEBOV-infected guinea pigs (1). Although EK-1 was highly effective, a cocktail approach was selected for the present study using three siRNAs, one targeting each of the L-pol (i.e., EK-1), VP24, and VP35 genes. This cocktail of multiple siRNAs enables the targeting of potential RNAi escape mutants. The use of multiple siRNAs for targeting potential RNAi escape mutants has been shown for HIV-1 and polio (18). By targeting three different viral gene products, the Ebola virus is inactivated in three different areas of its life cycle.

Lead siRNAs to VP24 (i.e., VP24-1160) and VP35 (i.e., VP35-855) were identified using a nonviral plasmid-based expression system. Non-saturating concentrations of siRNA were used in this system so that relative differences in siRNA potency could be determined. FIG. 1 shows that VP24-1160 was the most efficacious siRNA targeting ZEBOV VP24, while VP35-855 had the best efficacy against ZEBOV VP35. EK-1, VP24-1160, and VP35-855 were selected as siRNA components of the ZEBOV SNALP cocktail. These lead siRNAs were selectively modified by substituting 2'O-methyl (2'OMe) guanosine and/or uridines in the sense and antisense strands to eliminate immune stimulatory capacity of the siRNA in SNALP (19-21). The RNAi activity of the modified siRNAs was then confirmed in vitro using the plasmid-based system. In particular, modified VP24-1160 siRNA showed similar efficacy to unmodified VP24-1160 siRNA in reducing VP24 gene expression (FIG. 2). Modified VP35-855 siRNA and modified EK-1 siRNA also maintained significant efficacy against VP35 and L polymerase-expressing plasmids, respectively (FIG. 2).

It is important to ensure that formulated siRNA do not activate an immune stimulatory response, as these responses can have significant antiviral activity (32). The immune stimulatory activity of ZEBOV SNALP was tested in vivo in mice (19). FIG. 3 shows that IFN-α and IL-6 were not induced in plasma of mice 4 h after injection of ZEBOV SNALP at 5 mg total siRNA per kg body weight. A positive control, chemically unmodified Luc SNALP, induced high levels of both proteins in plasma. A more sensitive measure of localized IFN production is IFN-induced protein with tetratricopeptide repeats (IFIT1) mRNA in the liver (19). QuantiGene branched DNA analysis of liver IFIT1 mRNA 4 h after injection of SNALP showed no significant differences from the PBS negative control for the 2'OMe-modified Luc or ZEBOV cocktail SNALP, whereas the unmodified Luc SNALP induced significant levels of IFIT1 mRNA (1180-fold over PBS treatment) (FIG. 3).

The immune stimulatory activity of ZEBOV SNALP on human peripheral blood mononuclear cell (PBMC) cultures was also tested. As shown in FIG. 4, native (chemically unmodified) Luc, EK-1, VP24-1160, and VP35-855 siRNAs induced strong IFN-α in culture supernatants even at 100 nM concentrations, whereas no IFN-α could be detected following exposure to the 2'OMe-modified versions at up to 400 nM. These data show that 2'OMe modification of bases in the sense and antisense strand of these siRNAs was sufficient to eliminate measurable IFN-α production in human immune cells. Taken together, these data indicate that any differences observed in survival between the Luc mod and ZEBOV SNALP-treated animals are due to RNAi rather than non-specific stimulation of the innate immune system.

FIG. 5A shows that SNALPs containing ZEBOV siRNAs substantially reduced ZEBOV produced in supernatants of Vero E6 cells 48 h after infection. To determine whether L-pol, VP35, and VP24 mRNA are cleaved by the specific mechanism of RNAi, 5' RACE (Rapid Amplification of cDNA Ends) was performed on total RNA from Vero E6 cells treated with SNALP followed by ZEBOV infection. FIG. 5B shows that EK-1-mod, VP35-855-mod, and VP24-1160-mod all induced specific mRNA cleavage only for their target mRNA in cells treated with SNALP containing either siRNA alone (FIG. 5B, lanes 3, 8, and 13), whereas all three RACE bands can be seen in cells treated with ZEBOV cocktail SNALP (FIG. 5B, lanes 4, 9, and 14), producing the specific RACE PCR product of the correct size. No RACE PCR products of the appropriate size were observed for PBS (FIG. 5B, lanes 2, 7, and 12) or Luc mod (FIG. 5B, lanes 5, 10, and 15) SNALP-treated cells, further showing the specificity of the RACE results. The RACE PCR products were sequenced and found to correspond to the specific predicted cleavage site of their respective siRNA, confirming the specific mechanism of RNAi.

Figure 6A:
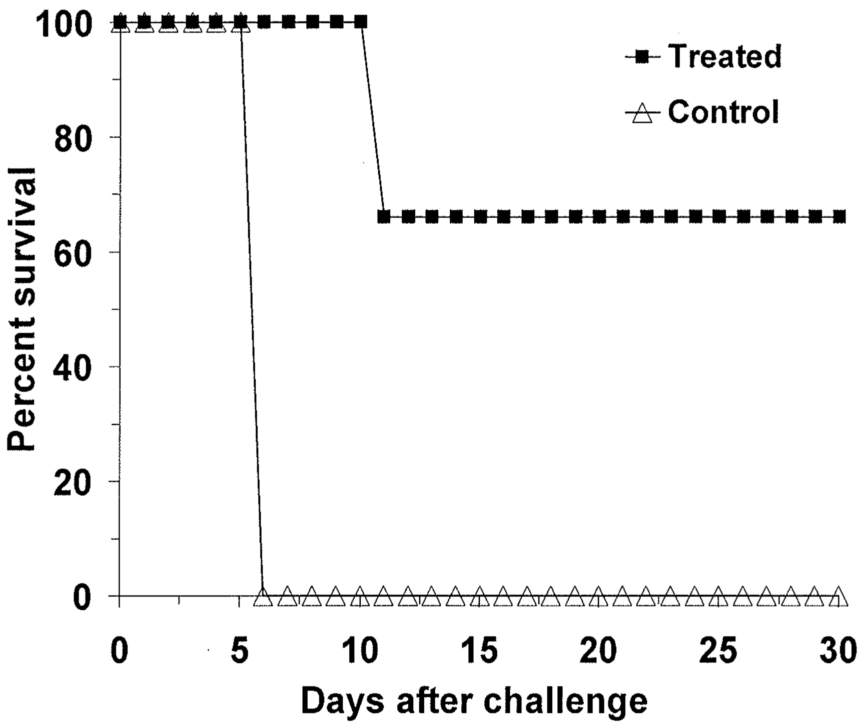
FIGS. 6A-B illustrate Kaplan-Meier survival curves for ZEBOV-infected rhesus macaques treated after challenge with a cocktail of anti-ZEBOV siRNAs targeting L-pol, VP24, and VP35. (6A) Animals treated 30 minutes and on days 1, 3, and 5 after ZEBOV challenge. (6B) Animals treated 30 minutes and on days 1, 2, 3, 4, 5, and 6 after ZEBOV challenge.

The protective efficacy of the lead anti-ZEBOV siRNAs was determined in an established rhesus macaque model of ZEBOV HF (22). Importantly, this is a rapid and uniformly lethal model (death in 26 of 26 rhesus macaques challenged with the same ZEBOV seed stock by the same dose and route as in the current study) where animals typically succumb 6-10 days after challenge. A combination of modified siRNAs targeting the ZEBOV L-pol gene (EK-1 mod), VP24 (VP24-1160-mod), and VP35 (VP35-855-mod) were formulated in SNALP. One group of three rhesus monkeys was treated 30 minutes after a lethal ZEBOV challenge with the pooled siRNAs (2 mg/kg total siRNA/dose), and again at the same dose on days 1, 3, and 5 after ZEBOV challenge (four treatments), while a control animal received no treatment. All four animals developed clinical symptoms consistent with ZEBOV HF by day 6 (Table 7). The control animal succumbed to ZEBOV infection before blood collection on day 6 (FIG. 6A). One treated animal (Subject 3) developed a high ZEBOV viremia at day 6 (Table 8) and succumbed on day 10 (FIG. 6A). ZEBOV was detected in the plasma of one of the remaining treated animals (Subject 2) at day 6, but was not detected in the plasma of the other remaining treated animal (Subject 1) (Table 8). Both of these animals (Subjects 1 and 2) survived.

Figure 6B:
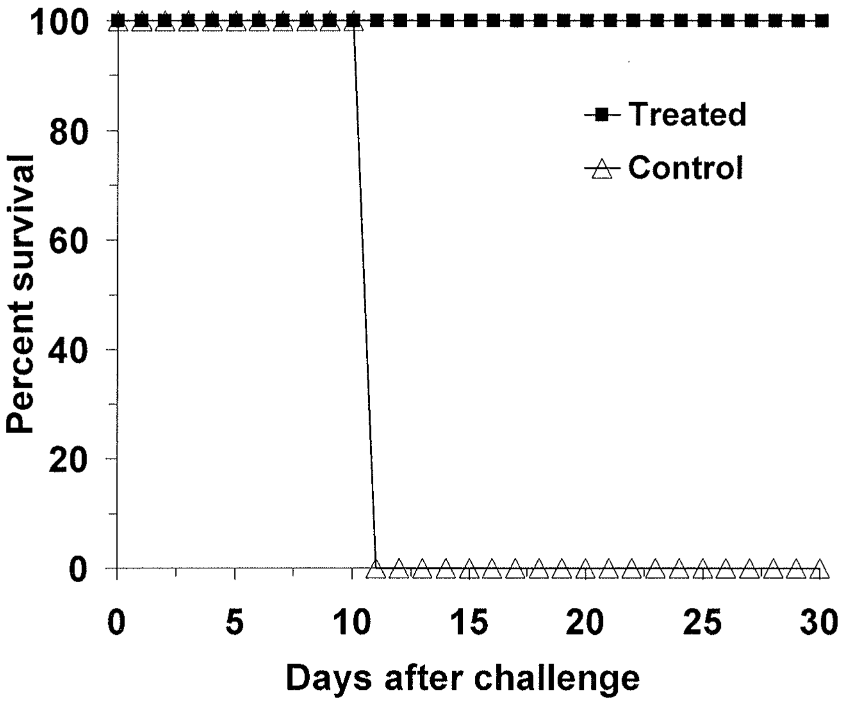

The question of whether increasing the frequency of treatments could improve outcome was then studied. In this subsequent study, four rhesus monkeys were treated 30 minutes after a lethal ZEBOV challenge with the pool of anti-ZEBOV siRNAs at 2 mg/kg/dose and again daily at this dose on days 1 through 6 after ZEBOV challenge (seven treatments), while a control animal was treated in parallel with an equal dose of nonspecific modified siRNA (Luc mod) in SNALP. This treatment regimen proved more effective, as clinical symptoms of ZEBOV infection in the specifically treated macaques were less severe (Table 7). The Luc mod SNALP-treated control animal succumbed on day 10, while all four animals receiving the pooled anti-ZEBOV siRNAs survived (FIG. 6B). ZEBOV was detected in the plasma of the control animal on days 3, 6, and 10 (Table 8). Low levels of ZEBOV were detected in the plasma of all four ZEBOV siRNA treated macaques on day 6 and one of these animals at day 10 (Subject 6), but ZEBOV was not detected in any of these animals at day 14 (Table 8). It has been shown that ZEBOV-infected rhesus monkeys succumb when viremia levels on days 6 to 10 after exposure exceed 4.5 log 10 pfu/ml, while animals survive when levels fail to reach this level. Peak viremia in surviving siRNA-treated macaques in this study never exceeded 2.4 log 10 pfu/ml (Table 8).

Clinical assessments also demonstrated that this aggressive SNALP treatment regimen was well tolerated with only minor changes in liver enzyme levels (alanine aminotransferase (ALT)<2-fold, aspartate aminotransferase (AST)<6-fold increase), potentially related to viral infection. All six animals that survived ZEBOV challenge (two from the initial study and four from the second study) were healthy on day 40 and were euthanized on days 40-43.

TABLE 7

Clinical findings in rhesus monkeys infected with ZEBOV and given postexposure treatment with anti-ZEBOV siRNAs (Subjects 1-3, 4-7), a nonspecific siRNA (Control 2), or no treatment (Control 1).

| Animal | Treatment | Days 1-35 after ZEBOV challenge | Day of death |
|---|---|---|---|
| Subject 1 | Anti-ZEBOV siRNAs 30 min, days 1, 3, 5 | Anorexia (7-9), Lymphopenia (6) AST↑↑↑ (10) | Survived |
| Subject 2 | Anti-ZEBOV siRNAs 30 min, days 1, 3, 5 | Fever (6), Mild rash (8, 11, 12), Moderate rash (9, 10), Depression (7-11), Anorexia (7-11), Diarrhea (12), Lymphopenia (6, 14), Thrombocytopenia (6) ALP↑ (10), ALT↑ (10), AST↑ (6), AST↑↑↑ (10), GGT↑↑↑ (10) | Survived |
| Subject 3 | Anti-ZEBOV siRNAs 30 min, days 1, 3, 5 | Mild rash (6-10), Depression (6-10), Anorexia (6-10), Bleeding at venipuncture site (10), Recumbency (10), Thrombocytopenia (6) ALP↑ (6), ALP↑↑↑ (10), ALT↑↑ (10), AST↑ (3), AST↑↑↑ (6, 10), BUN↑↑↑ (10), CRE↑↑↑ (10), GGT↑↑↑ (10) | Day 10 |
| Control 1 | None | Mild rash (5), Anorexia (5), Depression (5) | Day 6 |
| Subject 4 | Anti-ZEBOV siRNAs 30 min, days 1-6 | Thrombocytopenia (6, 10) AST↑↑ (6) | Survived |
| Subject 5 | Anti-ZEBOV siRNAs 30 min, days 1-6 | AST↑↑↑ (6), AST↑ (10) | Survived |
| Subject 6 | Anti-ZEBOV siRNAs 30 min, days 1-6 | Fever (10), Lymphopenia (6), Thrombocytopenia (6, 10, 14) AST↑ (10) | Survived |
| Subject 7 | Anti-ZEBOV siRNAs 30 min, days 1-6 | Fever (10), Lymphopenia (6), Thrombocytopenia (6) AST↑↑↑ (10) | Survived |
| Control 2 | Nonspecific siRNA 30 min, days 1-6 | Fever (6), Recumbency (10), Thrombocytopenia (6) ALT↑ (6), ALT↑↑↑ (10), AST↑↑↑ (6, 10), BUN↑↑↑ (10), CRE↑ (10) | Day 10 |

Fever is defined as a temperature more than 2.5° F. over baseline or at least 1.5° F. over baseline and ≥103.5° F.
Mild rash: focal areas of petechiae covering less than 10% of the skin;
Moderate rash: areas of petechiae covering between 10% and 40% of the skin;
severe rash: areas of petechiae and/or echymosis covering more than 40% of the skin.
Lymphopenia and thrombocytopenia defined by ≥35% drop in numbers of lymphocytes and platelets, respectively.
Alkaline phosphatase (ALP),
alanine aminotransferase (ALT),
aspartate aminotransferase (AST),
gamma-glutamyltransferase (GGT),
blood urea nitrogen (BUN),
creatinine (CRE)
↑ = 2-3 fold increase;
↑↑ = 4-5 fold increase;
↑↑↑ = >5 fold increase Days after filovirus challenge are shown in parentheses ( )

TABLE 8

Plasma viral load in rhesus monkeys infected with ZEBOV and given postexposure treatment with anti-ZEBOV siRNAs (Subjects 1-3, 4-7), a nonspecific siRNA (Control 2), or no treatment (Control 1).

| Animal No. | Treatment | Plasma viral load Day 3 | Day 6 | Day 10 | Day 14 |
|---|---|---|---|---|---|
| Subject 1 | Anti-ZEBOV siRNAs 30 min, days 1, 3, 5 | 0* | 0 | 0 | 0 |
| Subject 2 | Anti-ZEBOV siRNAs 30 min, days 1, 3, 5 | 0 | 0 | 22 | 0 |
| Subject 3 | Anti-ZEBOV siRNAs 30 min, days 1, 3, 5 | 0 | 3.7 | 6.8 | |
| Control 1** | None | 0 | | | |
| Subject 4 | Anti-ZEBOV siRNAs 30 min, days 1-6 | 0 | 2.0 | 0 | 0 |
| Subject 5 | Anti-ZEBOV siRNAs 30 min, days 1-6 | 0 | 2.4 | 0 | 0 |
| Subject 6 | Anti-ZEBOV siRNAs 30 min, days 1-6 | 0 | 2.0 | 2.1 | 0 |
| Subject 7 | Anti-ZEBOV siRNAs 30 min, days 1-6 | 0 | 2.1 | 0 | 0 |
| Control 2 | Nonspecific siRNA 30 min, days 1-6 | 0 | 4.1 | 6.7 | |

*Log10 plaque-forming units (pfu) of ZEBOV per ml of plasma

**Control 1 was found dead on day 6 and no blood was collected for viral load

RNAi represents a promising new approach for combating human diseases, including those caused by bacterial and viral pathogens. Indeed, RNAi has been employed in cell culture systems and rodents to inhibit the replication of a number of pathogens that cause disease in humans. However, only two studies have examined the utility of RNAi as an effective therapeutic modality in nonhuman primate models of human infectious diseases. One study showed that siRNAs inhibited the replication of GB virus B in a nonlethal marmoset surrogate model of human hepatitis C (23), while a second study showed that siRNAs against SARS coronavirus inhibited SARS coronavirus replication in a nonlethal rhesus monkey model (24). However, both of these studies used unmodified, accordingly immune stimulatory, siRNA, potentially confounding the interpretation of these results. To date, there has been no evaluation of the utility of RNAi as a postexposure treatment in a lethal model of a human infectious disease in nonhuman primates. This example shows that siRNAs against ZEBOV inhibited replication of ZEBOV and completely protected rhesus monkeys against death.

Figure 7:
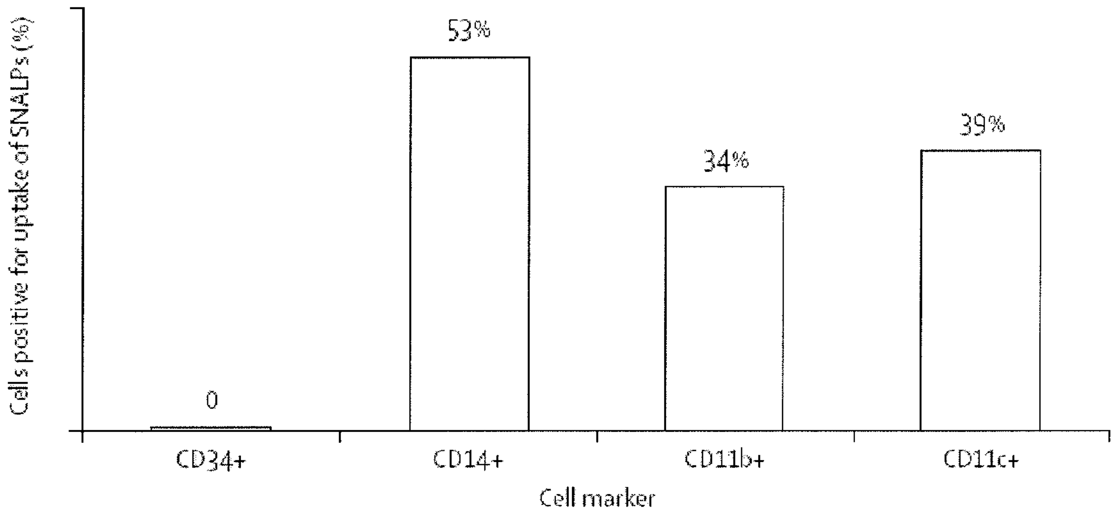
FIG. 7 illustrates that CD34+ cord blood cells which differentiated into CD14+ monocytes show uptake of FITC-labelled siRNA SNALP into cells of the reticuloendothelial system. Uptake of SNALP containing FITC-labeled Luc mod siRNA by CD11c-, CD11b-, CD14-, and CD34-positive cells following 4 hour incubation at a concentration of 150 nM SNALP. Results are expressed as the percent of cells positive for uptake as determined by flow cytometry.

As noted above, the development of treatments for EBOV HF has been slow and no previous candidate treatment has shown complete protection against ZEBOV HF in nonhuman primates. Some measure of success has been achieved using approaches that mitigate the coagulation disorders that characterize EBOV infection (25,26). Recently, 50% of nonhuman primates were protected against ZEBOV by administering a live-attenuated recombinant vesicular stomatitis virus vaccine vector expressing the ZEBOV GP shortly after a high dose ZEBOV challenge (27). Several new postexposure treatment approaches based on siRNA (1) and antisense oligomers (28,29) have shown promising results in rodent models, but there have been no reports of either treatment strategy being evaluated after EBOV challenge in nonhuman primates, which more faithfully reproduce human EBOV infections (2,22). While RNAi-mediated treatment strategies show potential for combating EBOV infections, systemic administration of synthetically manufactured siRNA duplexes can activate the innate immune response, inducing high levels of inflammatory cytokines such as tumor necrosis factor-alpha, interleukin (IL)-6, and IFNs, particularly IFN-alpha (IFN-$\alpha$), which may contribute to the observed antiviral activity in vivo (30-32). Off-target effects can be toxic to the host and also confound interpretation of results. This SNALP formulation enters cells of the reticuloendothelial system as shown by uptake of fluorescent SNALP into Kupffer cells in the murine liver and in 53% of CD14+ monocytes from human cord blood CD34+ cell culture (FIG. 7). These data show that SNALP can be taken up by the reticuloendothelial cell population relevant to EBOV infection. It is imperative that siRNA be modified to prevent immune activation in vivo (19). When tested in vitro on human PBMC and in vivo in mice, the ZEBOV cocktail was nonimmunostimulatory to the limit of sensitivity of the assays used. These data and the 5'RACE PCR data indicate that the observed antiviral effects in non-human primates are the result of specific RNAi in reticuloendothelial cells and not due to immunostimulation or other off-target effects.

Figure 8A:
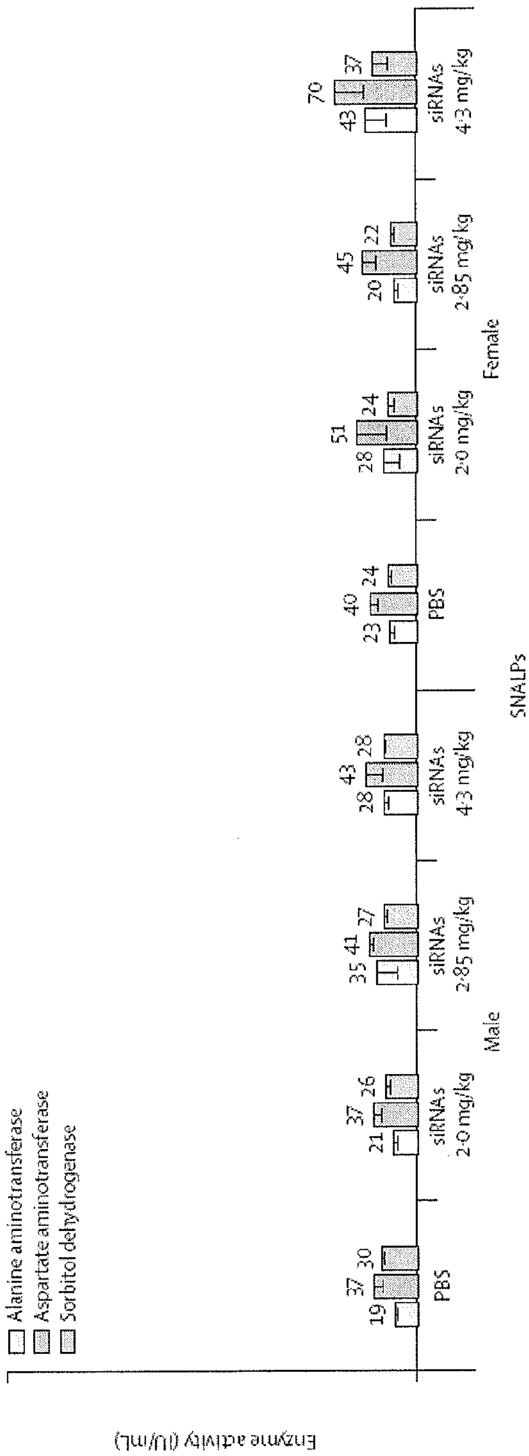
FIGS. 8A-B illustrate the effect of daily administration of stable nucleic acid-lipid particles (SNALPs) containing Zaire Ebola virus (ZEBOV) small interfering RNAs on activities of alanine aminotransferase (ALT), aspartate aminotransferase (AST), and sorbitol dehydrogenase (8A), and blood cell counts (8B) in mice.
Figure 8B:
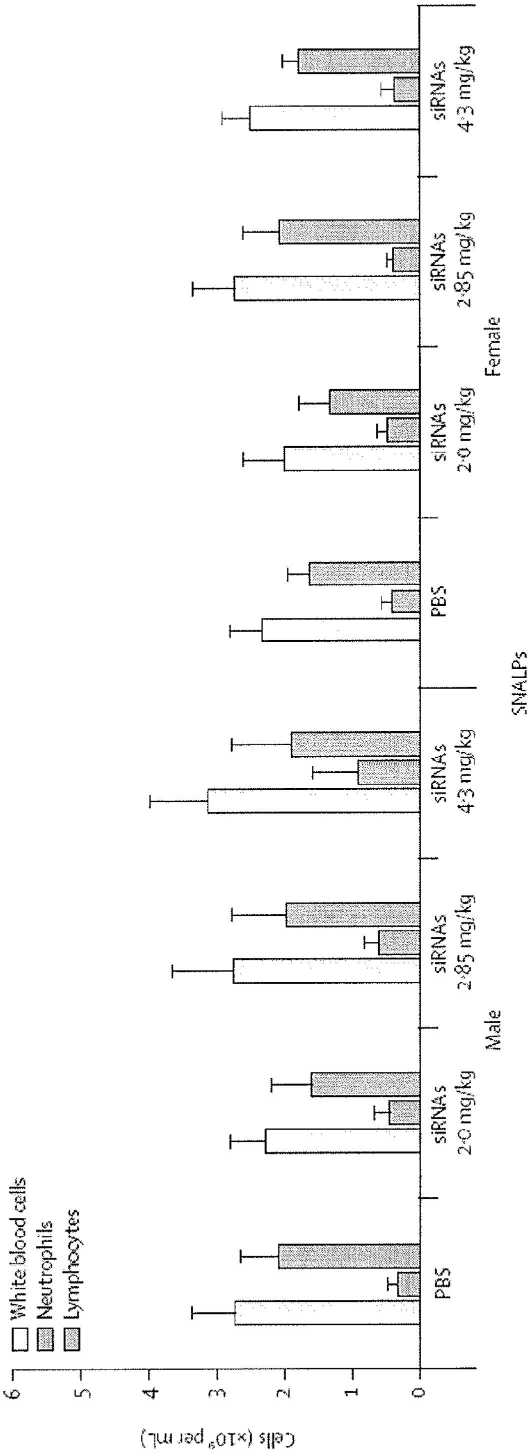

In the tolerability studies, activities of alanine aminotransferase (ALT), aspartate aminotransferase (AST), and sorbitol dehydrogenase remained unchanged 48 h after the mice were given the final dose of SNALPs containing ZEBOV siRNAs, even at the highest cumulative dose (FIG. 8A). Complete blood cell and differential counts were also unaffected at the doses tested in the mice (FIG. 8B).

The rhesus macaque model employed in these studies represents a worse-case scenario such as an accidental needle-stick exposure of a laboratory worker or first responder to a high infectious dose of ZEBOV as has occurred several times over the past 5 years (33-35). ZEBOV infection of humans normally progresses slower than ZEBOV infection of macaques, with case fatality rates in humans ranging from 70-90% (2), indicating that the therapeutic window may be larger than in experimentally infected macaques. Nonetheless, anti-ZEBOV siRNA treatment can be beneficial if administered at the onset of symptoms or at a pre-symptomatic stage of the disease course. The results described herein demonstrate a significant advance in treating ZEBOV infections of nonhuman primates over previously described postexposure methods.

Methods siRNA Design and In Vitro siRNA Screening Using psiCHECK2 Dual-Luciferase Assay in HepG2 Cells.

siRNAs were designed to target individual regions of the ZEBOV L-pol, VP24, or VP35 genes following the Tuschl siRNA user guide as previously described. The siRNA duplexes were chemically synthesized by Dharmacon Inc. (Chicago, Ill.) or Integrated DNA Technologies BVBA (Leuven, Belgium). EK-1 siRNA targeting the L-pol gene of ZEBOV was previously described (1). VP24-1160 and VP35-855 siRNAs targeting the VP24 and VP35 genes of ZEBOV were identified by screening in vitro for reduction of either the ZEBOV VP24 or ZEBOV VP35 viral transgene expressed under the control of the SV40 promoter in the psiCHECK2 dual-luciferase plasmid system (Promega, Madison, Wis.) in HepG2 cells. Briefly, 100 of Lipofectamine 2000 (LF2000) complexes containing 0.75 μg of plasmid and 100 of siRNA at various concentrations were added to a 96-well plate followed by 800 of HepG2 cells (15,000 cells/well). 48 h after transfection, cells were lysed. The dual-luciferase reporter assay system (Promega) and a Berthold luminometer were used to measure both *Renilla* luciferase (fused to either the ZEBOV-VP24 or ZEBOV-VP35 transgene) and firefly luciferase signals. The *Renilla* luciferase signal was normalized to the firefly-luciferase signal and expressed as percent gene expression relative to a plasmid-only control assigned a value of 100%. Sequences of siRNAs are shown in Table 9.

TABLE 9

| Sequences of siRNAs targeting the ZEBOV VP24 and VP35 genes. | | | | |
|---|---|---|---|---|
| siRNA | Target or Sense Strand Sequence (5' → 3') | SEQ ID NO. | Antisense Strand Sequence (5' → 3') | SEQ ID NO. |
| VP24-775 | GCUGAUUGACCAGUCUUUG***AU*** | 1 | CAAAGACUGGUCAAUCAGC***UG*** | 2 |
| VP24-978 | ACGGAUUGUUGAGCAGUAU***UG*** | 3 | AUACUGCUCAACAAUCCGU***UG*** | 4 |
| VP24-1160 | UCCUCGACACGAAUGCAAA***GU*** | 5 | UUUGCAUUCGUGUCGAGGA***UC*** | 6 |
| VP24-1160-mod | UCCUCGACACGAAUGCAAA***GU*** | 7 | UUUGCAUUCGUGUCGAGGA***UC*** | 8 |
| Luc | GAUUAUGUCCGGUUAUGUA***AA*** | 9 | UACAUAACCGGACAUAAUC***AU*** | 10 |
| VP35-219 | GCGACAUCUUCUGUGAUAU***UG*** | 11 | AUAUCACAGAAGAUGUCGC***UU*** | 12 |
| VP35-349 | GGAGGUAGUACAAACAUUG***dTdT*** | 13 | CAAUGUUUGUACUACCUCC***dTdT*** | 14 |
| VP35-687 | GGGAGGCAUUCAACAAUCU***AG*** | 15 | AGAUUGUUGAAUGCCUCCC***UA*** | 16 |
| VP35-855 | GCAACUCAUUGGACAUCAU***UC*** | 17 | AUGAUGUCCAAUGAGUUGC***UA*** | 18 |

2'OMe nucleotides are indicated in bold and underlined.
3'-overhangs are indicated in bold and italicized.
The 3'-overhangs on one or both strands of the siRNA molecule may alternatively comprise 1-4 deoxythymidine (dT) nucleotides, 1-4 modified and/or unmodified uridine (U) ribonucleotides, or 1-4 modified and/or unmodified ribonucleotides having complementarity to the target sequence or the complementary strand thereof.

ZEBOV Infection of Vero E6 Cells.

Vero E6 cells were plated at $1\times10^5$ cells/ml (2 ml/well of a 6 well plate) and 24 h later treated with 50 nM of SNALP containing either EK-1-mod, VP24-1160-mod, VP35-855-mod, or ZEBOV cocktail (EK-1-mod, VP24-1160-mod, and VP35-855-mod in 1:1:1 ratio) or Luc mod SNALP for 16 h followed by infection with 1.0 MOI of ZEBOV virus. Twenty-four hours after virus infection, cell monolayers were lysed with Trizol Reagent (Invitrogen) for total RNA isolation and 5'RACE assays.

Quantitative RT-PCR.

Viral RNA was purified using the Qiagen QIAmp viral RNA mini kit (Qiagen, Valencia, Calif., USA) according to the manufacturer's protocol. One-step quantitative real-time RT-PCR reactions were done on a LightCycler 480 (Roche, Indianapolis, Ind., USA) in 20 μL volumes with 5 μL of purified RNA and the Superscript III One-Step RT-PCR System (Invitrogen). Primers (forward 5'-CGGACCTGGTTTGGTTGTG-3'; reverse 5'-GCTGCAGTGTCGCATCTGA-3') and TaqMan probe (6-carboxyfluorescein-5'-CCCTTGCCACAATCT-minor groove binder nonfluorescent quencher-3') from Applied Biosystems (Foster City, Calif., USA) were specific for the ZEBOV glycoprotein gene. Cycling conditions were reverse transcription at 50° C. for 20 min, and initial denaturation at 95° C. for 5 min; followed by 45 cycles of denaturation at 95° C. for 5 s, and annealing, synthesis, and single acquisition at 60° C. for 20 s; and final cooling at 40° C. for 30 s. Absolute quantification of viral gene expression was based on a viral RNA standard by use of the LC480 software (version 1.50).

5'RACE Assays.

Total RNA was extracted from cell lysates following the Trizol method as described by the manufacturer. Total RNA (3.6 μg) was ligated to 0.52 μg of the GeneRacer RNA oligo adaptor (5'-CGACUGGAGCACGAGGACACUGACAUGGACUGAAGGAGUAGAAA-3') according to the GeneRacer Kit (Invitrogen) without prior treatment. Ligated RNA was reverse transcribed using a gene-specific primer, either to the L-pol (EK-1 GSP: 5'-TTIGTGATTCGTCCTTTTGCAGT-3'), VP24 (VP24-1160 GSP 5'-AGCAATTCTATGATGTTGTCTTGGA-3'), or VP35 (VP35-855 GSP 5'-CATCACTTTTGGTTTGGGTTACTT-3'). To detect cleavage products, PCR was performed using primers, designed according to the Invitrogen GeneRacer manual, complementary to the RNA adaptor (GR5: 5-CGACTGGAGCACGAGGACACTGA-3') and either L-pol mRNA to detect EK-1 cleavage (EK-1 Rev2: 5'-TGAGATGGTTTTGGTGTGGCATCT-3'), VP24 mRNA to detect VP24-1160 cleavage (VP24-1160 Rev2: 5'-CCTGGTTTTTGTAAGGGTGTCAACT-3'), or VP35 mRNA to detect VP35-855 cleavage (VP35-855 Rev2: 5'-TTTCTGGCAAGCTCGGGGAATGT-3'). Amplification products were resolved by agarose gel electrophoresis using 2% Agarose 1000/TBE gels (Invitrogen) and visualized by ethidium bromide staining. The identity of specific PCR products was confirmed by direct sequencing of the excised bands using a primer from within the GeneRacer sequence (GR5 5': 5'-ACTGGAGCACGAGGACAC-3') and a primer downstream of either the EK-1 cleavage site (EK-1 3'seq: 5'-AGCCATAACATACCCTCAGT-3'), VP24-1160 cleavage site (VP24-1160 3'seq: 5'-ATGAAAGCAGAGATGTCAAG-3'), or VP35-855 cleavage site (VP35-855 3'seq: ATTAGGGCACATTGAGGAG-3').

In Vitro Immune Stimulation Assays.

Human PBMC were isolated from whole blood from healthy donors by a standard Ficoll-Hypaque density centrifugation technique. Immune stimulation assays were performed as previously described (21). In brief, PBMC were resuspended in RPMI 1640 media supplemented with 10% FBS and plated in 96 well plates at $2.5\times10^5$ cells/well. SNALP-formulated siRNAs were immediately added to cells and cultured for 24 h. IFN-α was measured in culture supernatants by ELISA (PBL Biomedical Piscataway, N.J.).

Differentiation and SNALP Uptake in CD34+ Cells from Cord Blood.

Human cord blood stem cells (Stem Cell Technologies, Vancouver, BC) were cultured for 5 days in Iscove's Modified Dulbecco's Media (IMDM) with Glutamax (Invitrogen, Carlsbad, Calif.), 20% BIT 9500 serum substitute (Stem Cell Technologies, Vancouver, BC), 40 μg/ml human LDL (Calbiochem), 55 μM β-mercaptoethanol, 100 ng/ml each of hFlt3L and hSCF and 10 ng/ml hTPO (Peprotech, Rocky Hill, N.J.). Cells were given fresh media every 3 days. To prime cells for differentiation, on day 6 cells were supplemented with 20 ng/ml each of rhIL-3 and rhIL-6 (R&D Systems, Minneapolis, Minn.). At day 10, cells were differentiated into dendritic cells and monocytes by the further addition of 50 ng/ml of rhM-CSF and 20 ng/ml rhGM-CSF (Peprotech).

Fully differentiated CD34 cells were incubated with 150 nM FITC labelled Luc mod modified SNALP for 4 hrs after which cells were harvested, washed in 2% FBS in PBS and stained with fluorescently labelled antibodies (BD Biosciences) against cell phenotype markers (CD11c, CD11b, CD14, and CD34). Cell uptake by phenotype was acquired and analyzed on a 3 laser, 8 color LSRII using FACSDiva software V 6.0.

Mouse Studies.

Animal studies were completed in accordance with the Canadian Council on Animal Care guidelines following approval by the local Animal Care and Use Committee at Tekmira Pharmaceuticals. Six to eight-week-old female CD1 ICR mice were subjected to a one week quarantine and acclimation period prior to use. SNALP were administered by standard intravenous injection in the lateral tail vein in 0.2 mL PBS. To measure in vivo cytokine induction, blood was collected by cardiac puncture 4 h after siRNA administration and processed as plasma for cytokine analysis. Liver tissues were also collected into RNALater solution (Sigma Aldrich Co.; St Louis, Mo.) for IFIT1 mRNA analysis.

Cytokine ELISA.

All cytokines were quantified using sandwich ELISA kits according to the manufacturer's instructions. These were mouse IFN-α (PBL Biomedical; Piscataway, N.J.), and mouse IL-6 (eBioscience; San Diego, Calif.).

Measurement of IFIT1 mRNA in Mouse Liver.

Livers of mice were homogenized in Tissue and Lysis Solution (EpiCentre Biotechnologies; Madison, Wis.) containing 50 mg/ml proteinase K (EpiCentre) in a Fastprep tissue homogenizer using the Lysis Matrix A tubes containing garnet sand and 1 bead (MP Biomedicals). Tissues were homogenized three times at a speed of 5.5 for 15 sec each followed by incubation in a 65° C. water bath for 15 min and centrifugation for 5 min at 16,000×g at 16° C. The QuantiGene branched DNA assay (Affymetrix) was performed as per the manufacturer's instructions (Quantigene 1.0 Manual) to determine induction of IFIT1 mRNA relative to the house keeping gene GAPDH in liver lysates. The IFIT1 probe set was specific to mouse IFIT1 (positions 4-499, NM_008331) and the GAPDH probe set was specific to mouse GAPDH (positions 9-319, NM_008084). Data is shown as the ratio of IFIT1 relative light units (RLU) to GAPDH RLU.

siRNAs Used in Nonhuman Primate Studies.

siRNAs used for nonhuman primate studies were selected based on RNAi activity assays and immunostimulatory studies. The siRNA duplexes were chemically synthesized by Dharmacon Inc. or Integrated DNA Technologies BVBA (Leuven, Belgium). Sequences used in the nonhuman primate studies are shown in Table 10. The ZEBOV siRNA cocktail was a 1:1:1 mixture (by mass) of the EK-1-mod, VP24-1160-mod, and VP35-855-mod siRNAs.

TABLE 10

Sequences of siRNAs targeting the ZEBOV L-pol, VP24, and VP35 genes.

| siRNA | Target or Sense Strand Sequence (5' → 3') | SEQ ID NO. | Antisense Strand Sequence (5' → 3') | SEQ ID NO. |
|---|---|---|---|---|
| Luc | GAUUAUGUCCGGUUAUGUA***AA*** | 9 | UACAUAACCGGACAUAAUC***AU*** | 10 |
| Luc-mod | GA**UU**A**U**G**U**CCGG**UU**A**U**G**U**A***AA*** | 19 | UACA**U**AACCGGACA**U**AA**U**C***AU*** | 20 |
| EK-1 | GUACGAAGCUGUAUAUAAA***UU*** | 21 | UUUAUAUACAGCUUCGUAC***AA*** | 22 |
| EK-1-mod | G**U**ACGAAGCU**G**UAUA**U**AAA***UU*** | 23 | UUUA**U**AUACAGCUUCG**U**AC***AA*** | 24 |
| VP24-1160 | UCCUCGACACGAAUGCAAA***GU*** | 5 | UUUGCAUUCGUGUCGAGGA***UC*** | 6 |
| VP24-1160-mod | UCC**U**CGACACGAA**U**GCAAA***GU*** | 7 | UU**U**GCAUUCGUGUC**G**AG**G**A***UC*** | 8 |
| VP35-855 | GCAACUCAUUGGACAUCAU***UC*** | 17 | AUGAUGUCCAAUGAGUUGC***UA*** | 18 |
| VP35-855-mod | GCAAC**U**CAUUG**G**ACA**U**CAU***UC*** | 25 | AUGAU**G**UCCAAUGA**G**U**U**GC***UA*** | 26 |

2'OMe nucleotides are indicated in bold and underlined.

3'-overhangs are indicated in bold and italicized.

The 3'-overhangs on one or both strands of the siRNA molecule may alternatively comprise 1-4 deoxythymidine (dT) nucleotides, 1-4 modified and/or unmodified uridine (U) ribonucleotides, or 1-4 modified and/or unmodified ribonucleotides having complementarity to the target sequence or the complementary strand thereof.

Lipid Encapsulation of siRNA.

siRNA were encapsulated by the process of spontaneous vesicle formation reported by Jeffs and colleagues (36). ZEBOV siRNA were formulated as a cocktail in the same lipid particle. SNALP were comprised of synthetic cholesterol (Sigma, St. Louis, Mo.), the phospholipid DPPC (dipalmitoylphosphatidylcholine; Avanti Polar Lipids, Alabaster, Ala.), the PEG-lipid PEG-C-DMA (3-N-[(ω-methoxy poly(ethylene glycol)2000)carbamoyl]-1,2-dimyrestyloxypropylamine) (37), and the cationic lipid DLinDMA (1,2-dilinoleyloxy-3-N,N-dimethylaminopropane) (37). The resulting SNALP were dialyzed in PBS and filter sterilized through a 0.2 μM filter before use. Particle sizes ranged from 81 to 85 nm (for example, the average size of ZEBOV SNALP particles used in the first nonhuman primate was 81.7 nm) and typically 90-95% of the siRNA was encapsulated within these lipid particles. Particle size is consistent batch to batch with a tight size and polydispersity within each batch. Endotoxin is less than 3 EU/ml for all batches. No sample aggregation is observed as shown through particle size testing.

Rhesus Macaques.

Nine healthy, filovirus-seronegative rhesus macaques (*Macaca mulatta*) of Chinese origin (5-8 kg) were used for these studies. Four animals were employed in study 1 and 5 animals were employed in study 2. Hickman, Leonard, Broviac Central Venous Catheters (BARD Access Systems; Salt Lake City, Utah) were placed into the lumen of the jugular vein of each animal and advanced so that the tip lay in the superior vena cava above the right atrium. The catheters were tunneled subcutaneously from the cervical surgery site over the right shoulder and to the point in the center of the back. After closure of the last skin incision, monkeys were placed in Lomir primate jackets (Lomir Biomedical Inc.; Malone, N.Y.), returned to their cages, and tethered. A continuous i.v. infusion of saline at a rate of 2 ml/h was provided using a basic single syringe KDS100 infusion pump (KDS Scientific; Holliston, Mass.). Seven days after insertion of the catheters and placement in Lomir primate jackets, animals were inoculated intramuscularly (i.m.) with 1000 pfu of ZEBOV (Kikwit strain). In the first study employing four macaques, the pool of SNALP-formulated anti-ZEBOV siRNAs (2 mg/kg) was administered to three of the macaques by bolus i.v. infusion 30 minutes after the ZEBOV challenge, while the control animal received no treatment. The three animals received additional treatments of the SNALP-formulated anti-ZEBOV siRNAs on days 1, 3, and 5 after the ZEBOV challenge. In the second study employing five macaques, the pool of SNALP-formulated anti-ZEBOV siRNAs was administered to four of the macaques by bolus i.v. infusion 30 minutes after the ZEBOV challenge, while the control animal received an equal dose of SNALP-formulated nonspecific siRNAs. The animals received additional treatments of the SNALP-formulated anti-ZEBOV siRNAs or the SNALP-formulated nonspecific siRNA (control) on days 1, 2, 3, 4, 5, and 6 after the ZEBOV challenge. Animals were given physical exams and blood was collected at the time of challenge and on days 3, 6, 10, 14, 22, and 40-43 after filovirus challenge.

Animal studies performed in BSL-4 biocontainment at USAMRIID were approved by the USAMRIID Laboratory Animal Use Committee. Animal research was conducted in compliance with the Animal Welfare Act and other Federal statutes and regulations relating to animals and experiments involving animals and adheres to the principles stated in the *Guide for the Care and Use of Laboratory Animals*, National Research Council, 1996. The facilities used are fully accredited by the Association for Assessment and Accreditation of Laboratory Animal Care International.

Hematology and Serum Biochemistry.

Total white blood cell counts, white blood cell differentials, red blood cell counts, platelet counts, hematocrit values, total hemoglobin, mean cell volume, mean corpuscular volume, and mean corpuscular hemoglobin concentration were determined from blood samples collected in tubes containing EDTA, by using a laser-based hematologic Analyzer (Coulter Electronics; Hialeah, Fla., USA). The white blood cell differentials were performed manually on Wright-stained blood smears. Serum samples were tested for concentrations of albumin (ALB), amylase (AMY), alanine aminotransferase (ALT), aspartate aminotransferase (AST), alkaline phosphatase (ALP), gamma-glutamyltransferase (GGT), glucose (GLU), cholesterol (CHOL), total protein (TP), total bilirubin (TBIL), blood urea nitrogen (BUN), and creatinine (CRE) by using a Piccolo Point-Of-Care Blood Analyzer (Abaxis; Sunnyvale, Calif., USA).

Virus Detection by Plaque Assay.

Virus titration was performed by conventional plaque assay on Vero E6 cells from cell culture fluids of blood collected from rhesus monkeys as previously described (38).

REFERENCES

1. Geisbert, T. W. et al. Postexposure protection of guinea pigs against a lethal Ebola virus challenge is conferred by RNA interference. *J. Infect. Dis.* 193, 1650-1657 (2006).
2. Sanchez, A., Geisbert, T. W. & Feldmann, H. Filoviridae: Marburg and Ebola Viruses. in *Fields Virology* (eds. Knipe, D. M. & Howley, P. M.) 1409-1448 (Lippincott Williams & Wilkins, Philadelphia).
3. Towner, J. S. et al. Newly discovered Ebola virus associated with hemorrhagic fever outbreak in Uganda. *PLoS Pathog.* 4, e1000212 (2008).
4. Sanchez, A., Kiley, M. P., Holloway, B. P. & Auperin, D. D. Sequence analysis of the Ebola virus genome: organization, genetic elements, and comparison with the genome of Marburg virus. *Virus Res.* 29, 215-240 (1993).
5. Basler, C. F. et al. The Ebola virus VP35 protein functions as a type I IFN antagonist. *Proc. Natl. Acad. Sci. USA* 97, 12289-12294 (2000).
6. Basler, C. F. et al. The Ebola virus VP35 protein inhibits activation of interferon regulatory factor 3. *J. Virol.* 77, 7945-7956 (2003).
7. Basler, C. F. and Palese, P. Modulation of innate immunity by filoviruses. in *Ebola and Marburg viruses: molecular and cellular biology* (eds. Klenk, H. D. & Feldmann, H) (Horizon Bioscience, Norfolk, UK, 2004).
8. Ebihara, H. et al. Molecular determinants of Ebola virus virulence in mice. *PLoS Pathog.* 2, e73 (2006).
9. Volchkov, V. E., Chepurnov, A. A., Volchkova. V. A., Ternovoj. V. A. & Klenk, H. D. Molecular characterization of guinea pig-adapted variants of Ebola virus. *Virology* 277, 147-155 (2000).
10. Sullivan, N. J., Sanchez, A., Rollin, P. E., Yang, Z. Y. & and G. J. Nabel. Development of a preventive vaccine for Ebola virus infection in primates. *Nature* 408, 605-609 (2000).
11. Sullivan, N. J. et al. Accelerated vaccination for Ebola virus haemorrhagic fever in non-human primates. *Nature* 424, 681-684 (2003).
12. Jones, S. M. et al. Live attenuated recombinant vaccine protects nonhuman primates against Ebola and Marburg viruses. *Nat. Med.* 11, 786-790 (2005).
13. Sullivan, N. J. et al. Immune protection of nonhuman primates against Ebola virus with single low-dose adenovirus vectors encoding modified GPs. *PLoS Med.* 3, e177 (2006).
14. Bukreyev, A. et al. Successful topical respiratory tract immunization of primates against Ebola virus. *J. Virol.* 81, 6379-88 (2007).
15. Warfield, K. L., Swenson, D. L., Olinger, G. G., Kalina, W. V., Aman, M. J. & Bavari, S. 2007. Ebola virus-like particle-based vaccine protects nonhuman primates against lethal Ebola virus challenge. *J. Infect. Dis.* 196 Suppl 2, S430-437 (2007).
16. Geisbert, T. W. et al. Vesicular stomatitis virus-based vaccines protect nonhuman primates against aerosol challenge with Ebola and Marburg viruses. *Vaccine* 26, 6894-6900 (2008).

17. Swenson, D. L. et al. Complete protection of nonhuman primates against multi-strain Ebola and Marburg virus infections. *Clin. Vaccine Immunol.* 15, 460-467 (2008).
18. Grimm, D. & Kay, M. Combinatorial RNAi: A winning strategy for the race against evolving targets? *Mol. Ther.* 15, 878-888 (2007).
19. Robbins, M. A., Judge, A. D. & MacLachlan, I. siRNA and innate immunity. *Oligonucleotides* 19, 89-101 (2009).
20. Judge, A. et al. Confirming the RNAi-mediated mechanism of action of siRNA-based cancer therapeutics in mice. *J. Clin. Invest.* 119, 661-673 (2009).
21. Judge, A. D., Bola, G., Lee, A. C. H. & MacLachlan, I. Design of noninflammatory synthetic siRNA mediating potent gene silencing in vivo. *Mol. Ther.* 13, 494-505 (2006).
22. Geisbert, T. W., Jahrling, P. B., Larsen, T., Davis, K. J. & Hensley, L. E. Filovirus Pathogenesis in Nonhuman Primates. in *Ebola and Marburg Viruses: Molecular and Cellular Biology* (eds. Klenk, H. D. & Feldmann, H.) 203-238 (Horizon Bioscience, Norfolk, UK, 2004).
23. Yokota, T. et al. Efficient regulation of viral replication by siRNA in a non-human primate surrogate model for hepatitis C. *Biochem. Biophys. Res. Commun.* 361, 294-300 (2007).
24. Tang, Q., Li, B., Woodle, M. & Lu, P. Y. Application if siRNA against SARS in the rhesus macaque model. *Methods Mol. Biol.* 442, 139-158 (2008).
25. Geisbert, T. W. et al. Treatment of Ebola virus infection with a recombinant inhibitor of factor VIIa/tissue factor: a study in rhesus monkeys. *Lancet* 362, 1953-1958 (2003).
26. Hensley, L. E. et al. Recombinant human activated protein C for the postexposure treatment of Ebola hemorrhagic fever. *J Infect. Dis.* 196 Suppl 2, S390-S399 (2007).
27. Feldmann, H. et al. Effective post-exposure treatment of Ebola infection. *PLoS Pathog.* 3, e2 (2007).
28. Enterlein, S. et al. VP35 knockdown inhibits Ebola virus amplification and protects against lethal infection in mice. *Antimicrob. Agents Chemother.* 50, 984-993 (2006).
29. Warfield, K. L. et al. Gene-specific countermeasures against Ebola virus based on antisense phosphorodiamidate morpholino oligomers. *PLoS Pathog.* 2, e1 (2006).
30. Hornung, V, et al. Sequence-specific potent induction of IFN-alpha by short interfering RNA in plasmacytoid dendritic cells through TLR7. *Nat. Med.* 11, 263-270 (2005).
31. Judge, A. D., Sood, V., Shaw, J. R., Fang, D., McClintock, K. & MacLachlan, I. Sequence-dependent stimulation of the mammalian innate immune response by synthetic siRNA. *Nat. Biotechnol.* 23, 457-462 (2005).
32. Robbins, M, et al. Misinterpreting the therapeutic effects of siRNA caused by immune stimulation. *Hum. Gene Ther.* 19, 991-999 (2008).
33. Kortepeter, M. G., et al. Managing potential laboratory exposure to Ebola virus by using a patient biocontainment care unit. *Emerg. Infect. Dis.* 14, 881-887 (2008).
34. International Society for Infectious Diseases. Ebola virus, needlestick injury—Germany: (Hamburg). Archive number 20090317.1084
35. International Society for Infectious Diseases. Ebola, lab accident death—Russia (Siberia). Archive number 20040522.1377
36. Jeffs, L. B., Palmer, L. R., Ambegia, E. G., Giesbrecht, C., Ewanick, S. & MacLachlan, I. A scalable, extrusion-free method for efficient liposomal encapsulation of plasmid DNA. *Pharm. Res.* 22, 362-372 (2005).
37. Heyes, J., Palmer, L., Bremner, K. & MacLachlan, I. Cationic lipid saturation influences intracellular delivery of encapsulated nucleic acids. *J. Control Release* 107, 276-287 (2005).
38. Jahrling, P. B. et al. Evaluation of immune globulin and recombinant interferon α-2b for treatment of experimental Ebola virus infections. *J. Infect. Dis.* 179 Suppl 1, S224-S234 (1999).

Example 2

Characterization of Inflammatory Response to SNALP Formulations in Human Whole Blood Inflammatory response to SNALPs containing one or more interfering RNAs (e.g., siRNAs) targeting one or more genes of interest such as one, two, or all three of the EBOV L-pol, VP24, and VP35 genes can be evaluated by measuring cytokine induction ex vivo in whole blood samples taken from human subjects. In certain instances, the SNALPs can contain either no siRNA payload ("empty") or an siRNA payload comprising one or a pool of siRNAs. The siRNAs tested can include, e.g., any of the EBOV siRNA molecules described herein, whether alone or in combination (e.g., L-pol+VP35 siRNAs, L-pol+VP24 siRNAs, VP24+VP35 siRNAs, or L-pol+VP24+VP35 siRNAs). Briefly, fresh blood is isolated, immediately diluted 1:1 with 0.9% saline solution, and plated 0.45 mL/well into 48 well tissue culture treated plates. SNALPs are diluted in formulation PBS and added to the plated blood samples at a concentration of either 300 nM or 1200 nM. After 24 hours, the plates are centrifuged at 1200 rpm for 20 minutes and the supernatant (plasma) is collected. Cytokine induction (e.g., TNFα, IL-8, etc.) can be measured by ELISA and/or Cytometric Bead Array.

In particular embodiments, increasing the number of selective 2'OMe modifications to an siRNA sequence (e.g., 2'OMe modifications at G's and/or U's in the double-stranded and/or 3' overhang regions of the siRNA sequence) can decrease the immunostimulatory response to the siRNA.

Example 3

In Vitro and In Vivo Activity Screen of Modified EBOV siRNAs in SNALP Formulations EBOV L-pol siRNAs of the same nucleotide sequence were modified to incorporate an increasing number and alternate patterns of 2'OMe nucleotides. 307 different sense strands (S-1 to S-307) and 331 different antisense strands (AS-1 to AS-331) were designed (see, Tables 1-2). EBOV L-pol double-stranded siRNAs were generated by mix and match annealing of all possible combinations of sense strands and antisense strands. The number of modifications for double-stranded L-pol siRNAs ranged from 5 to 11 2'OMe nucleotides in the double-stranded region. In certain embodiments, the pattern of modification can include 2'OMe-modified nucleotides in the 3' overhang of one or both strands of the siRNA, such that the number of modifications is further increased in the entire siRNA molecule. Table 11 shows exemplary modified double-stranded L-pol siRNAs that resulted from the mix and match annealing of sense strands S-1 to S-3 with antisense strands AS-1 to AS-6.

TABLE 11

| siRNA | EBOV L-pol siRNA Sequence | % 2'OMe-Modified | % AModified in DS Region |
|---|---|---|---|
| EK-1 S1/AS1 | 5'-GUACGAAGCUGUAUAUAAATT-3'<br>3'-TTCAUGCUUCGACAUAUAUUU-5' | 5/42 = 11.9% | 5/38 = 13.2% |
| EK-1 S1/AS2 | 5'-GUACGAAGCUGUAUAUAAATT-3'<br>3'-TTCAUGCUUCGACAUAUAUUU-5' | 6/42 = 14.3% | 6/38 = 15.8% |
| EK-1 S1/AS3 | 5'-GUACGAAGCUGUAUAUAAATT-3'<br>3'-TTCAUGCUUCGACAUAUAUUU-5' | 6/42 = 14.3% | 6/38 = 15.8% |
| EK-1 S1/AS4 | 5'-GUACGAAGCUGUAUAUAAATT-3'<br>3'-TTCAUGCUUCGACAUAUAUUU-5' | 6/42 = 14.3% | 6/38 = 15.8% |
| EK-1 S1/AS5 | 5'-GUACGAAGCUGUAUAUAAATT-3'<br>3'-TTCAUGCUUCGACAUAUAUUU-5' | 7/42 = 16.7% | 7/38 = 18.4% |
| EK-1 S1/AS6 | 5'-GUACGAAGCUGUAUAUAAATT-3'<br>3'-TTCAUGCUUCGACAUAUAUUU-5' | 6/42 = 14.3% | 6/38 = 15.8% |
| EK-1 S2/AS1 | 5'-GUACGAAGCUGUAUAUAAATT-3'<br>3'-TTCAUGCUUCGACAUAUAUUU-5' | 9/42 = 21.4% | 9/38 = 23.7% |
| EK-1 S2/AS2 | 5'-GUACGAAGCUGUAUAUAAATT-3'<br>3'-TTCAUGCUUCGACAUAUAUUU-5' | 10/42 = 23.8% | 10/38 = 26.3% |
| EK-1 S2/AS3 | 5'-GUACGAAGCUGUAUAUAAATT-3'<br>3'-TTCAUGCUUCGACAUAUAUUU-5' | 10/42 = 23.8% | 10/38 = 26.3% |
| EK-1 S2/AS4 | 5'-GUACGAAGCUGUAUAUAAATT-3'<br>3'-TTCAUGCUUCGACAUAUAUUU-5' | 10/42 = 23.8% | 10/38 = 26.3% |
| EK-1 S2/AS5 | 5'-GUACGAAGCUGUAUAUAAATT-3'<br>3'-TTCAUGCUUCGACAUAUAUUU-5' | 11/42 = 26.2% | 11/38 = 28.9% |
| EK-1 S2/AS6 | 5'-GUACGAAGCUGUAUAUAAATT-3'<br>3'-TTCAUGCUUCGACAUAUAUUU-5' | 10/42 = 23.8% | 10/38 = 26.3% |
| EK-1 S3/AS1 | 5'-GUACGAAGCUGUAUAUAAATT-3'<br>3'-TTCAUGCUUCGACAUAUAUUU-5' | 6/42 = 14.3% | 6/38 = 15.8% |
| EK-1 S3/AS2 | 5'-GUACGAAGCUGUAUAUAAATT-3'<br>3'-TTCAUGCUUCGACAUAUAUUU-5' | 7/42 = 16.7% | 7/38 = 18.4% |
| EK-1 S3/AS3 | 5'-GUACGAAGCUGUAUAUAAATT-3'<br>3'-TTCAUGCUUCGACAUAUAUUU-5' | 7/42 = 16.7% | 7/38 = 18.4% |
| EK-1 S3/AS4 | 5'-GUACGAAGCUGUAUAUAAATT-3'<br>3'-TTCAUGCUUCGACAUAUAUUU-5' | 7/42 = 16.7% | 7/38 = 18.4% |
| EK-1 S3/AS5 | 5'-GUACGAAGCUGUAUAUAAATT-3'<br>3'-TTCAUGCUUCGACAUAUAUUU-5' | 8/42 = 19% | 8/38 = 21.1% |
| EK-1 S3/AS6 | 5'-GUACGAAGCUGUAUAUAAATT-3'<br>3'-TTCAUGCUUCGACAUAUAUUU-5' | 7/42 = 16.7% | 7/38 = 18.4% |

EBOV VP35 siRNAs of the same nucleotide sequence were modified to incorporate an increasing number and alternate patterns of 2'OMe nucleotides. 37 different sense strands (S-1 to S-37) and 50 different antisense strands (AS-1 to AS-50) were designed (see, Tables 5-6). EBOV VP35 double-stranded siRNAs were generated by mix and match annealing of all possible combinations of sense strands and antisense strands. The number of modifications for double-stranded VP35 siRNAs ranged from 6 to 11 2'OMe nucleotides in the double-stranded region. In certain embodiments, the pattern of modification included 2'OMe-modified nucleotides in the 3' overhang of one or both strands of the siRNA, such that the number of modifications was further increased in the entire siRNA molecule. Table 12 shows exemplary modified double-stranded VP35 siRNAs that resulted from the mix and match annealing of sense strands S-1 to S-3 with antisense strands AS-1 to AS-5.

TABLE 12

| siRNA | EBOV VP35 siRNA Sequence | % 2'OMe-Modified | % Modified in DS Region |
|---|---|---|---|
| VP35-855 S1/AS1 | 5'-GCAACUCAUUGGACAUCAUUC-3'<br>3'-AUCGUUGAGUAACCUGUAGUA-5' | 6/42 = 14.3% | 6/38 = 15.8% |

TABLE 12-continued

| siRNA | EBOV VP35 siRNA Sequence | % 2'OMe-Modified | % Modified in DS Region |
|---|---|---|---|
| VP35-855 S1/AS2 | 5'-GCAACUCAUUGGACAUCAUUC-3'<br>3'-AUCGUUGAGUAACCUGUAGUA-5' | 7/42 = 16.7% | 6/38 = 15.8% |
| VP35-855 S1/AS3 | 5'-GCAACUCAUUGGACAUCAUUC-3'<br>3'-AUCGUUGAGUAACCUGUAGUA-5' | 8/42 = 19% | 7/38 = 18.4% |
| VP35-855 S1/AS4 | 5'-GCAACUCAUUGGACAUCAUUC-3'<br>3'-AUCGUUGAGUAACCUGUAGUA-5' | 8/42 = 19% | 7/38 = 18.4% |
| VP35-855 S1/AS5 | 5'-GCAACUCAUUGGACAUCAUUC-3'<br>3'-AUCGUUGAGUAACCUGUAGUA-5' | 9/42 = 21.4% | 8/38 = 21.1% |
| VP35-855 S2/AS1 | 5'-GCAACUCAUUGGACAUCAUUC-3'<br>3'-AUCGUUGAGUAACCUGUAGUA-5' | 10/42 = 23.8% | 9/38 = 23.7% |
| VP35-855 S2/AS2 | 5'-GCAACUCAUUGGACAUCAUUC-3'<br>3'-AUCGUUGAGUAACCUGUAGUA-5' | 11/42 = 26.2% | 9/38 = 23.7% |
| VP35-855 S2/AS3 | 5'-GCAACUCAUUGGACAUCAUUC-3'<br>3'-AUCGUUGAGUAACCUGUAGUA-5' | 12/42 = 28.6% | 10/38 = 26.3% |
| VP35-855 S2/AS4 | 5'-GCAACUCAUUGGACAUCAUUC-3'<br>3'-AUCGUUGAGUAACCUGUAGUA-5' | 12/42 = 28.6% | 10/38 = 26.3% |
| VP35-855 S2/AS5 | 5'-GCAACUCAUUGGACAUCAUUC-3'<br>3'-AUCGUUGAGUAACCUGUAGUA-5' | 13/42 = 31% | 11/38 = 28.9% |
| VP35-855 S3/AS1 | 5'-GCAACUCAUUGGACAUCAUUC-3'<br>3'-AUCGUUGAGUAACCUGUAGUA-5' | 8/42 = 19% | 7/38 = 18.4% |
| VP35-855 S3/AS2 | 5'-GCAACUCAUUGGACAUCAUUC-3'<br>3'-AUCGUUGAGUAACCUGUAGUA-5' | 9/42 = 21.4% | 7/38 = 18.4% |
| VP35-855 S3/AS3 | 5'-GCAACUCAUUGGACAUCAUUC-3'<br>3'-AUCGUUGAGUAACCUGUAGUA-5' | 10/42 = 23.8% | 8/38 = 21.1% |
| VP35-855 S3/AS4 | 5'-GCAACUCAUUGGACAUCAUUC-3'<br>3'-AUCGUUGAGUAACCUGUAGUA-5' | 10/42 = 23.8% | 8/38 = 21.1% |
| VP35-855 S3/AS5 | 5'-GCAACUCAUUGGACAUCAUUC-3'<br>3'-AUCGUUGAGUAACCUGUAGUA-5' | 11/42 = 26.2% | 9/38 = 23.7% |

In certain embodiments, EBOV L-pol and VP35 siRNA duplexes can be prepared and tested in vitro and in vivo as follows: (1) siRNA sense strand (e.g., at 2×1 μmol scale) and antisense strand (e.g., at 1×1 μmol scale) sequences are synthesized; (2) the sense and antisense sequences are hydrated in RNA buffer to, e.g., 5 mg/ml, and quantitated at OD260 using a nanodrop; (3) the sense and antisense sequences (e.g., 600 jug of each) are annealed and formulated into SNALP as described herein (e.g., as a 1:57 SNALP using a syringe press method) at, e.g., a 250 μg scale, and tested on human whole blood for immunostimulation as described, e.g., in Example 2 above; (4) non-immunostimulatory siRNAs are formulated into SNALP (e.g., as a 1:57 SNALP formulation using a pH loading method) and tested on cells such as Vero E6 cells against ZEBOV as described, e.g., in Example 1 above; and (5) lead modified siRNAs are scaled up (e.g., at a 500 mg scale) and tested in vivo in an animal model such as monkeys for assessment of non-human primate (NHP) efficacy as described, e.g., in Example 1 above.

In particular embodiments, increasing the number of selective 2'OMe modifications to the siRNA sequence (e.g., 2'OMe modifications at G's and/or U's in the double-stranded and/or 3' overhang regions of the siRNA sequence) does not decrease activity, and in some cases increases silencing activity.

Example 4

Synthesis of 1,2-Di-γ-linolenyloxy-N,N-dimethylaminopropane (γ-DLenDMA

γ-DLenDMA having the structure shown below was synthesized as described below.

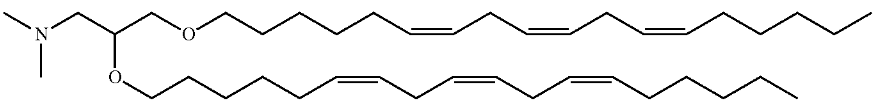

$C_{41}H_{73}O_2N$
Mol. Wt.: 612.04

A 250 mL round bottom flask was charged with 3-(dimethylamino)-1,2-propanediol (0.8 g, 6.7 mmol), tetrabutylammonium hydrogen sulphate (1 g), gamma linolenyl mesylate (cis-6,9,12-octadecatriene sulphonic acid) (5 g, 14.6 mmol), and 30 mL toluene. After stirring for 15 minutes, the reaction was cooled to 0-5° C. A solution of 40% sodium hydroxide (15 mL) was added slowly. The reaction was left to stir for approximately 48 hours. An additional 15 mL of toluene was then added to the reaction vessel, along with 40% sodium hydroxide (15 mL). After the reaction was stirred for an additional 12 hours, water (50 mL) and isopropyl acetate (50 mL) were added and stirred for 15 minutes. The mixture was then transferred to a 500 mL separatory funnel and allowed to separate. The lower aqueous phase was run off and the organic phase was washed with saturated sodium chloride (2×50 mL). Since the aqueous and organic phases resulting from the saturated sodium chloride washes could not be completely separated after 20 minutes, the lower aqueous phase (slightly yellow) was run off and back extracted with chloroform (~45 mL). The organic phase was dried with $MgSO_4$, filtered, and the solvent evaporated.

The crude product, an orange liquid, was purified on column chromatography using silica gel (60 g) with 0-3% methanol gradient in dichloromethane to yield 3.19 g. The product was further purified via column chromatography on silica gel (50 g) with 10-30% ethyl acetate gradient in hexanes to yield 1.26 g pure product.

Example 5

Synthesis of 1,2-Diphytanyloxy-3-(N,N-dimethyl)-propylamine (DPanDMA)

DPanDMA having the structure shown below was synthesized as described below.

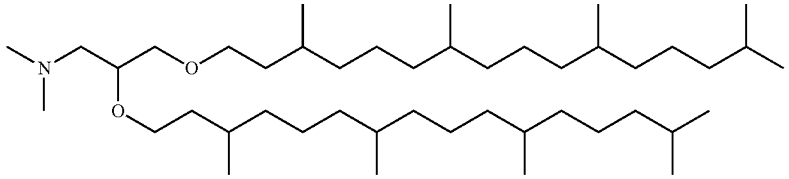

$C_{45}H_{93}NO_2$
Exact Mass: 679.72
Mol. Wt.: 680.23
C, 79.46; H, 13.78; N, 2.06; O, 4.70

Step 1: Synthesis of Phytanol

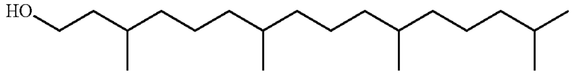

$C_{20}H_{42}O$
Exact Mass: 298.32
Mol. Wt.: 298.55
C, 80.46; H, 14.18; O, 5.36

Phytol (21.0 g, 70.8 mmol), ethanol (180 mL) and a stir bar were added to a 500 mL round bottom flask. Raney Nickel 2800 (as purchased, a 50% by weight solution in water if used as purchased, Nickel >89% metal present) (6.8 g, 51.5 mmol) was added, and the flask sealed and flushed with hydrogen. A 12" needle was used to bubble hydrogen through the solution for 10 minutes. The reaction was stirred for 5 days, using a balloon as a hydrogen reservoir. Hydrogen was also bubbled through the reaction mixture at 24 h and 48 h, 5 minutes each time. The metal catalyst was then removed by filtering through Celite. The ethanolic solution was concentrated, and 200 mL of DCM added to the resulting oil. The solution was washed with water (2×100 mL), dried over $MgSO_4$, and concentrated. TLC indicated formation of the phytanol product, yield 20.0 g.

Step 2: Synthesis of Phytanyl Mesylate

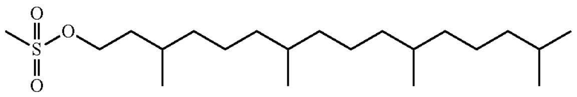

$C_{21}H_{44}O_3S$
Exact Mass: 376.30
Mol. Wt.: 376.64
C, 66.97; H, 11.78; O, 12.74; S, 8.51

Phytanol (20.0 g, 66.7 mmol), triethylamine (18.6 mL, 133 mmol), and a stir bar were added to a 1000 mL round bottom flask. The flask was sealed and flushed with nitrogen. Anhydrous DCM (250 mL) was added, and the mixture cooled to −15° C. (ice and NaCl). Mesyl Chloride (10.4 mL, 133 mmol) was added slowly via syringe over a 30 minute period, and the reaction stirred at −15° C. for a further 1.5 hours. At this point TLC showed that the starting material had been used up. The solution was diluted with DCM (250 mL) and washed with saturated $NaHCO_3$ (2×200 mL). The organic phase was then dried ($MgSO_4$), filtered, and concentrated (rotovap). The crude product was purified by column chromatography. Yield: 21.5 g, 85.7%.

Step 3: Synthesis of DPanDMA

Sodium hydride (2.5 g, 100 mmol) was added to a 250 mL round bottom flask, along with benzene (40 mL) and a stir bar. In a 50 mL beaker, a solution was made from the N,N-Dimethyl-3-aminopropane-1,2-diol (1.42 g, 12 mmol) and benzene (60 mL). This was added to the reaction vessel and the reaction stirred for 10 minutes (effervescence). Phytanyl Mesylate (10.52 g, 28 mmol) was added and the flask fitted with a condenser, flushed with nitrogen, and heated to reflux. After 18 hours, the flask was removed from the heat and allowed to cool. The volume was made up to 200 mL with benzene. EtOH was added slowly to quench unreacted sodium hydride. Once quenching was complete, the reaction mixture was washed twice with EtOH/$H_2O$, in a ratio to the benzene of 1:1:0.6 benzene:water:ethanol. The aqueous phases were combined and extracted with $CHCl_3$ (2×100 mL). Finally, the organic phase was dried ($MgSO_4$), filtered, and concentrated (rotovap). Purification by column chromatography yielded DPanDMA as a pale yellow oil (6.1 g, 8.97 mmol, 74.7%).

Example 6

Synthesis of Cationic Lipids of the TLinDMA Family

The following diagram provides a general scheme for synthesizing members of the C(n)-TLinDMA family of cationic lipids:

was added via cannula. The resulting mixture was stirred at room temperature for 48 hours. The progress of the reaction was monitored using TLC. The crude product was used without further purification.

Synthesis of TLinDMA (Compound III)

A 100 mL round bottom flask was charged with a stir bar, NaH (0.6 g, 24 mmol), and 25 mL benzene. Subsequently, Compound II (0.4 g, 2 mmol) was added followed immediately by linoleyl methane sulfonate (2.8 g, 8 mmol). The reaction was flushed with nitrogen and refluxed overnight. Progress of the reaction was monitored via TLC. The reaction mixture was transferred to a 250 mL separatory funnel and diluted with benzene to a final volume of 50 mL. The reaction was quenched with ethanol (30 mL) and then washed with water (50 mL). The lower aqueous phase was run off and the reaction mixture was washed again with ethanol (30 mL) and water (50 mL). The organic phase was dried with $MgSO_4$,

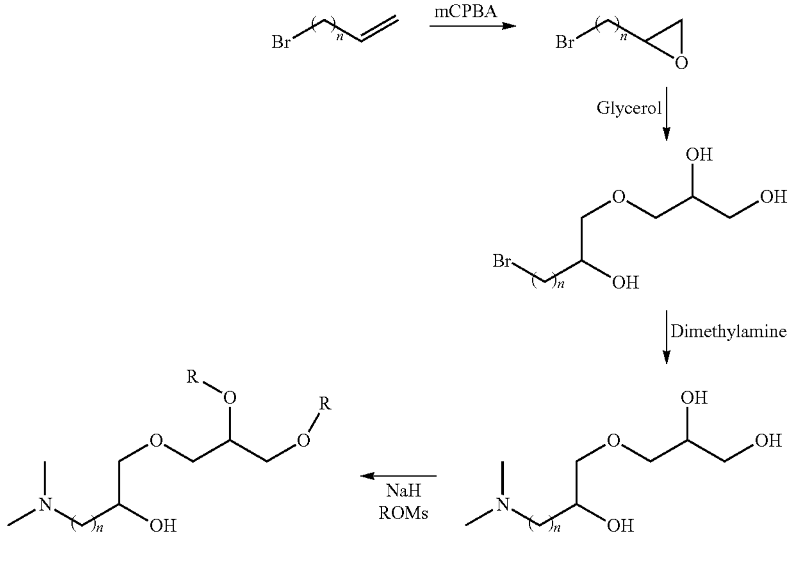

R = Linoleyl; *n* is 0, 1, 2, 3, or 4

TLinDMA (1-(2,3-linoleyloxypropoxy)-2-(linoleyloxy)-(N,N-dimethyl)-propyl-3-amine) (Compound III) was synthesized as follows:

Synthesis of Compound I

A 1000 ml round bottom flask was charged with epibromohydrin (5 g, 37 mmol), glycerol (10 g, 110 mmol), a stir bar and then flushed with nitrogen. Anhydrous chloroform (350 mL) was added via cannula, followed by $BF_3.Et_2O$ (0.5 mL, 3.7 mmol) and refluxed for 3 hours under nitrogen. The reaction mixture was cooled and subsequently stirred at room temperature overnight. Upon completion of the reaction, the reaction mixture was concentrated and the crude product (15 g) was purified via column chromatography using silica gel (150 g).

Synthesis of Compound II

A 500 mL round bottom flask was charged with Compound I (3.8 g, 17 mmol) and a stir bar. After flushing with nitrogen, dimethylamine in a 2.0 M methyl alcohol solution (170 mL)

filtered, and solvent removed. The crude product (2.3 g) was purified via column chromatography on silica gel (60 g) with 0-3% methanol gradient in dichloromethane.

C2-TLinDMA (Compound VII) was synthesized as follows:

Synthesis of Compound IV

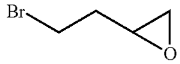

Chemical Formula: $C_4H_7BrO$
Exact Mass: 150.0
Molecular Weight: 151.0
Elemental Analysis: C, 31.82; H, 4.67; Br, 52.92; O, 10.60

A solution of 4-bromo-1-butene (11.5 g, 85 mmol) in $CH_2Cl_2$ (anh., 120 ml) was prepared under nitrogen in a 1000 ml RBF with a magnetic stirrer. In a separate flask, a solution of 3-chloroperbenzoic acid (77%, MW 173, 44.05 g, 196 mmol) in $CH_2Cl_2$ (anh., 250 ml) prepared and added to the reaction mixture by canulla. The reaction was stirred for 3 days, and then concentrated. The product (oil/white solid mixture) was re-dissolved in THF (300 mL) and a solution of 4% sodium dithionite (180 mL) added to remove excess per-acid. The mixture (now cloudy) was stirred for 20 minutes and then EtOAc (750 mL) added. The mixture was transferred to a separating funnel and the organic was washed with water (100 mL), sat. $NaHCO_3$ (2×300 mL, EFFERVESCENCE), water again (300 mL) and brine (300 mL). The solution was concentrated and the product purified by chromatography.

Synthesis of Compound V

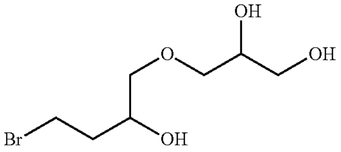

Chemical Formula: $C_7H_{15}BrO_4$
Exact Mass: 242.0
Molecular Weight: 243.1

A 250 ml round bottom flask was charged with Compound IV (1.3 g, 9 mmol), glycerol (2.5 g, 27 mmol), a stir bar and then flushed with nitrogen. Anhydrous chloroform (100 mL) was added via cannula, followed by $BF_3.Et_2O$ (0.15 mL, 1.1 mmol) and refluxed for 3 hours under nitrogen. The reaction mixture was subsequently stirred at room temperature overnight.

Synthesis of Compound VI

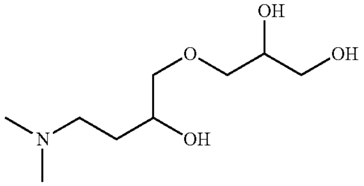

Chemical Formula: $C_9H_{21}NO_4$
Exact Mass: 207.1
Molecular Weight: 207.3

A 50 mL round bottom flask was charged with Compound V (0.3 g, 1.2 mmol) and a stir bar. After flushing with nitrogen, dimethylamine in a 2.0 M methyl alcohol solution (25 mL) was added via syringe. The resulting mixture was stirred at room temperature for 48 hours. The progress of the reaction was monitored using t.l.c. The reaction mixture was concentrated and the crude product used without further purification.

Synthesis of C2-TLinDMA (Compound VII)

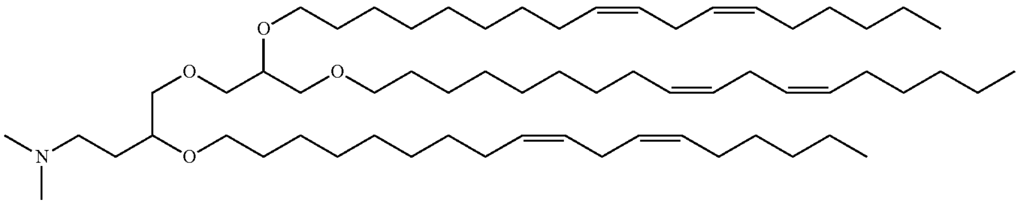

Chemical Formula: $C_{63}H_{117}NO_4$
Exact Mass: 951.9
Molecular Weight: 952.6

A 100 mL round bottom flask was charged with a stir bar, NaH (0.6 g, 24 mmol), and 25 mL benzene. Compound VI (0.37 g, 1.8 mmol) was added followed immediately by linoleyl methane sulfonate (2.8 g, 8 mmol). The reaction was refluxed overnight and progress of the reaction was monitored via t.l.c. The reaction mixture was transferred to a 250 mL separatory funnel and diluted with benzene to a final volume of 50 mL. The reaction was quenched with ethanol (30 mL) and then washed with water (50 mL). The lower aqueous phase was run off and the reaction mixture washed again with ethanol (30 mL) and water (50 mL). The organic phase was dried with $MgSO_4$, filtered, and solvent removed. The crude product, 2.5 g, was purified using column chromatography on silica gel (60 g), eluted with 0-3% methanol gradient in DCM.

C3-TLinDMA (Compound XI) was synthesized as follows:

Synthesis of Compound VIII

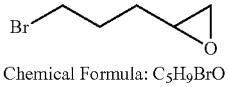

Chemical Formula: $C_5H_9BrO$
Exact Mass: 164.0
Molecular Weight: 165.0
Elemental Analysis: C, 36.39; H, 5.50; Br, 48.42; O, 9.69

A solution of 5-bromo-1-pentene (85 mmol) in $CH_2Cl_2$ (anh., 120 ml) is prepared under nitrogen in a 1000 ml RBF with a magnetic stirrer. In a separate flask, a solution of 3-chloroperbenzoic acid (77%, MW 173, 44.05 g, 196 mmol) in $CH_2Cl_2$ (anh., 250 ml) is prepared and added to the reaction mixture by canulla. The reaction is stirred for 3 days, and then concentrated. The product (oil/white solid mixture) is re-dissolved in THF (300 mL) and a solution of 4% sodium dithionite (180 mL) added to remove excess peracid. The mixture (now cloudy) is stirred for 20 minutes and then EtOAc (750 mL) added. The mixture is transferred to a separating funnel and the organic is washed with water (100 mL), sat. $NaHCO_3$ (2×300 mL, EFFERVESCENCE), water again (300 mL) and brine (300 mL). The solution is concentrated and the product purified by chromatography.

Synthesis of Compound IX

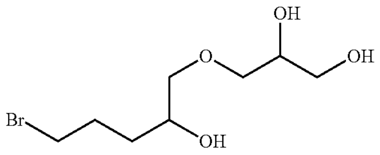

Chemical Formula: $C_8H_{17}BrO_4$
Exact Mass: 256.0
Molecular Weight: 257.1

A 250 ml round bottom flask is charged with Compound VIII (1.3 g, 9 mmol), glycerol (2.5 g, 27 mmol), a stir bar and then flushed with nitrogen. Anhydrous chloroform (100 mL) is added via cannula, followed by $BF_3.Et_2O$ (0.15 mL, 1.1 mmol) and refluxed for 3 hours under nitrogen. The reaction mixture is subsequently stirred at room temperature overnight.

Synthesis of Compound X

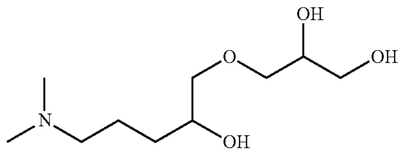

Chemical Formula: $C_{10}H_{23}NO_4$
Exact Mass: 221.2
Molecular Weight: 221.3

A 50 mL round bottom flask is charged with Compound IX (0.3 g, 1.2 mmol) and a stir bar. After flushing with nitrogen, dimethylamine in a 2.0 M methyl alcohol solution (25 mL) is added via syringe. The resulting mixture is stirred at room temperature for 48 hours. The progress of the reaction is monitored using t.l.c. The reaction mixture is concentrated and the crude product used without further purification.

Synthesis of C3-TLinDMA (Compound XI)

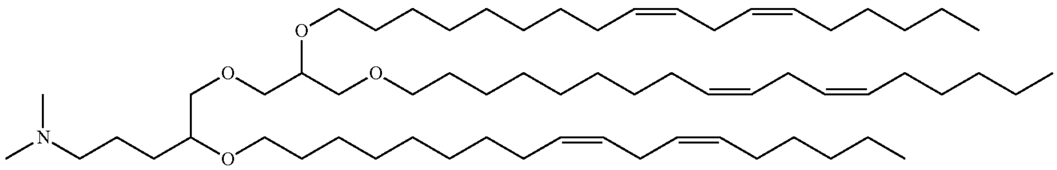

Chemical Formula: $C_{64}H_{119}NO_4$
Exact Mass: 965.9
Molecular Weight: 966.6

A 100 mL round bottom flask is charged with a stir bar, NaH (0.6 g, 24 mmol), and 25 mL benzene. Compound X (0.37 g, 1.8 mmol) is added followed immediately by linoleyl methane sulfonate (2.8 g, 8 mmol). The reaction is refluxed overnight and progress of the reaction monitored via t.l.c. The reaction mixture is transferred to a 250 mL separatory funnel and diluted with benzene to a final volume of 50 mL. The reaction is quenched with ethanol (30 mL) and then washed with water (50 mL). The lower aqueous phase is run off and the reaction mixture washed again with ethanol (30 mL) and water (50 mL). The organic phase is dried with $MgSO_4$, filtered, and solvent removed. The crude product, 2.5 g, is purified using column chromatography on silica gel (60 g), eluted with 0-3% methanol gradient in DCM.

Example 7

Synthesis of Novel C2 Lipids

Novel C2 lipids (Compounds V-VII) having the structures shown below were synthesized as shown in the following schematic diagram.

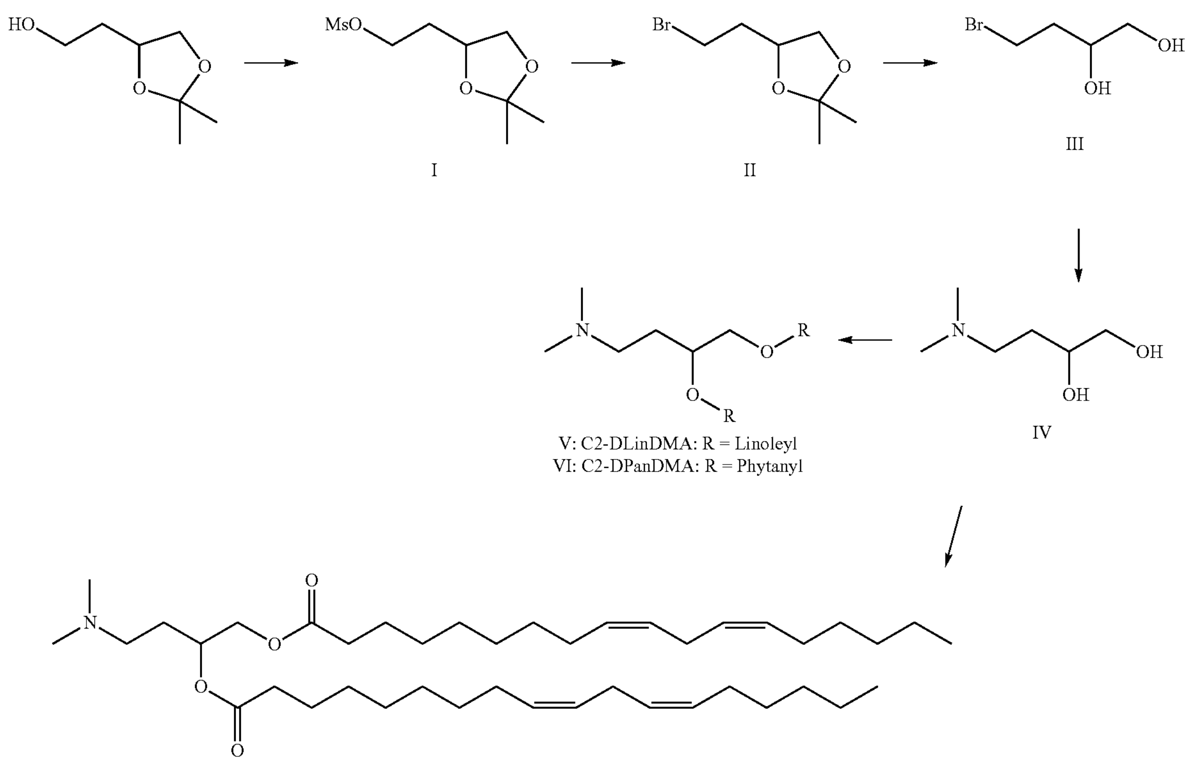

I

II

III

IV

V: C2-DLinDMA: R = Linoleyl
VI: C2-DPanDMA: R = Phytanyl

VII: C2-DLinDAP

Step 1: Synthesis of 4-(2-Methanesulfonylethyl)-2,2-dimethyl-1,3-dioxolane (Compound I)

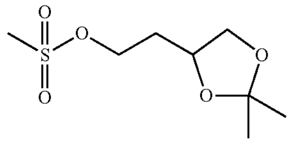

$C_8H_{16}O_5S$
Exact Mass: 224.07
Molecular Weight: 224.28
C, 42.84; H, 7.19; O, 35.67; S, 14.30

4-(2-Hydroxylethyl)-2,2-dimethyl-1,3-dioxolane (25 g, 170 mmol), triethylamine (55.9 mL, 400 mmol), and a stir bar were added to a 1000 mL round bottom flask. The flask was sealed and flushed with nitrogen. Anhydrous DCM (600 mL) was added, and the mixture cooled to approx −5° C. (ice and NaCl). Mesyl chloride (19.9 mL, 255 mmol, 1.5 eq) was added slowly via syringe over a 60 minute period, and the reaction stirred at −5° C. for a further 1.5 hours. At this point TLC showed that the starting material had been consumed. The solution was diluted with DCM (350 mL), divided into two (~500 mL) portions, and each portion worked up as follows: the solution was transferred to a 1000-mL separating funnel and washed with saturated $NaHCO_3$ (2×200 mL). The organic phase was then dried ($MgSO_4$), filtered, and concentrated (rotovap). The crude product was purified by column chromatography. Final yield: 32.0 g, 84.1%.

Step 2: Synthesis of 4-(2-Bromoethyl)-2,2-dimethyl-1,3-dioxolane (Compound II)

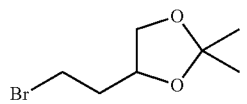

$C_7H_{13}BrO_2$
Exact Mass: 208.01
Mol. Wt.: 209.08
C, 40.21; H, 6.27; Br, 38.22; O, 15.30

Magnesium bromide etherate (40 g, 130 mmol) and a stir bar were added to a 2000 mL round bottom flask and flushed with nitrogen. A solution of 4-(2-methanesulfonylethyl)-2,2-dimethyl-1,3-dioxolane (I) (17.5 g, 78 mmol) in anhydrous diethyl ether (900 mL) was added via canulla, and the suspension stirred overnight. The ether was first decanted into a beaker. Water (200 mL) and ether (300 mL) were added to the precipitate and stirred for 5 minutes. The precipitate was dissolved, and the ether phase was then collected and added to the ether solution from the reaction. The organic phase was then washed, concentrated to about 500 mL, washed with water, dried over anhydrous $Mg_2SO_4$, filtered, and concentrated to yield a yellow oil (16.0 g). This was purified by flash chromatography to yield 10.6 g of product (50.7 mmol, 65%).

Step 3: Synthesis of 4-Bromobutane-1,2-diol (Compound III)

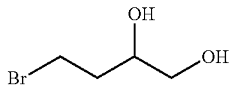

$C_4H_9O_2$
Exact Mass: 167.98
Mol. Wt.: 169.02
C, 28.42; H, 5.37; Br, 47.28; O, 18.93

4-(2-Bromoethyl)-2,2-dimethyl-1,3-dioxolane (II) (9 g, 43 mmol) was added to a 500 mL RBF with a stirbar. 100 mL of $MeOH:H_2O:HCl$ in a ratio of (60:20:5) were added. After 30 minutes, sat. $NaHCO_3$ (~75 mL) was added (effervescence), until pH paper indicated solution was basic. At this point the mixture was slightly cloudy. Ether (300 mL) was added (while stirring) and the cloudiness disappeared. The reaction mixture was transferred to a 1000 mL sep funnel and the 2 phases separated. The extraction of the aqueous phase was repeated two more times (2×300 mL ether). Organics were combined, dried over $MgSO_4$ and concentrated to yield a colorless oil (7.0 g), which was purified by column chromatography.

Step 4: Synthesis of 4-(Dimethylamino)-1,2-butanediol (Compound IV)

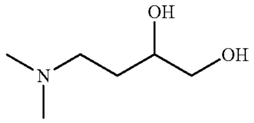

Chemical Formula: $C_6H_{15}NO_2$
Exact Mass: 133.1
Molecular Weight: 133.2
Elemental Analysis: C, 54.11; H, 11.35; N, 10.52; O, 24.03

4-Bromobutane-1,2-diol (III) (1 g, 6.0 mmol) was added to a 50 mL RBF with a stir bar, sealed, and flushed with nitrogen. 30 mL of Dimethylamine (2.0M solution in MeOH) was delivered by canulla and the reaction stirred overnight. TLC indicated all the starting material had disappeared. The solvent (and DMA) were removed by evaporation and the crude product used without further purification.

Synthesis of 1,2-Dilinoleyloxy-(N,N-dimethyl)-butyl-4-amine (C2-DLinDMA) (Compound V)

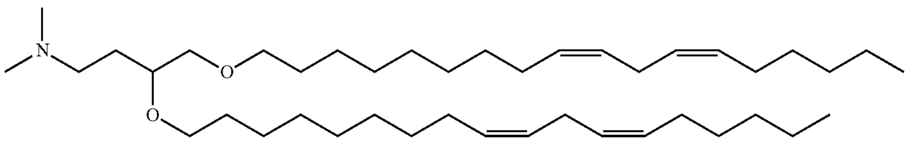

$C_{43}H_{79}NO_3$
Exact Mass: 657.61
Mol. Wt.: 658.09
C, 78.48; H, 12.10; N, 2.13; O, 7.29

4-(Dimethylamino)-1,2-butanediol (IV) (1.3 g, 3.4 mmol), linoleyl mesylate (2.0 g, 5.8 mmol), tetrabutylammonium hydrogen sulphate (0.5 g, 1.5 mmol), toluene (30 mL), and a stir bar were added to a 100 mL RBF. 30 mL of 40% NaOH was made and added to the reaction mixture. The resulting mixture was stirred at room temperature, under nitrogen for 60 hours. Deionized water (50 mL) and isopropyl acetate (50 mL) were added and the mixture stirred vigorously for a further 10-15 min. The mixture was transferred to a 250 mL separating funnel and allowed to separate and the aqueous phase removed. The organic phase was washed twice with water (2×30 mL) using MeOH to aid the separation, and the organic phase was dried ($MgSO_4$), filtered, and concentrated to obtain a dark yellow oil. The oil was purified by column chromatography.

Synthesis of 1,2-Diphytanyloxy-(N,N-dimethyl)-butyl-4-amine (C2-DPanDMA) (Compound VI)

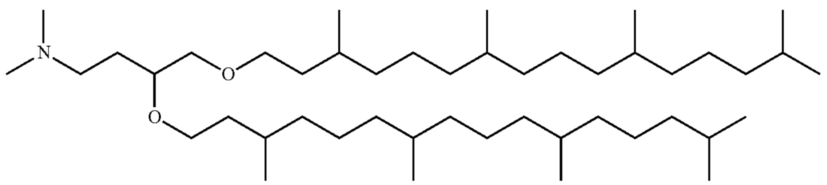

Chemical Formula: $C_{46}H_{95}NO_2$
Exact Mass: 693.7
Molecular Weight: 694.3
Elemental Analysis: C, 79.58; H, 13.79; N, 2.02, O, 4.61

Sodium hydride (360 mg, 15 mmol), benzene (40 mL), and a stir bar were added to a 50 mL round bottom flask. 4-(Dimethylamino)-1,2-butanediol (IV) (200 mg, 1.5 mmol) was added and the reaction stirred for 10 minutes (effervescence). Phytanyl Mesylate (1.07 g, 2.92 mmol) was then added and the flask fitted with a condenser, flushed with nitrogen, and heated to reflux. After 18 hours, the flask was allowed to cool to room temperature. The volume was made up to 40 mL with benzene. EtOH was added slowly to quench unreacted sodium hydride. Once quenching was complete, the reaction mixture was washed twice with an EtOH/$H_2O$, in a ratio to the benzene of 1:1:0.6 benzene:water:ethanol. The aqueous washes were combined and extracted with $CHCl_3$ (2×20 mL). Finally, the organics were combined, dried ($MgSO_4$), filtered, and concentrated (rotovap). Purification by column chromatography yielded a pale yellow oil (250 mg, 0.145 mmol, 25%).

Synthesis of 1,2-Dilinoleoyloxy-(N,N-dimethyl)-butyl-4-amine (C2-DLinDAP) (Compound VII)

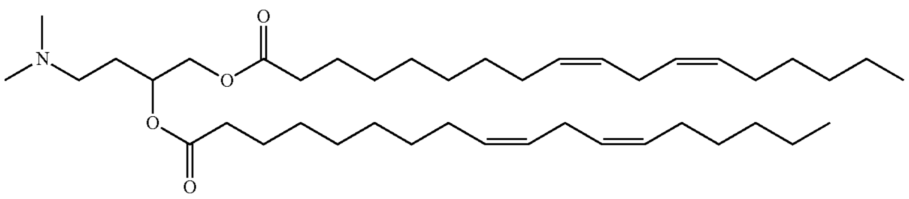

Chemical Formula: $C_{42}H_{75}NO_4$
Exact Mass: 657.6
Molecular Weight: 658.0
Elemental Analysis: C, 76.66; H, 11.49; N, 2.13, O, 9.73

A flask containing 4-(Dimethylamino)-1,2-butanediol (IV) (crude, 266 mg, 2 mmol (max)), TEA (0.84 mL, 6 mmol), and DMAP (24 mg, 0.2 mmol) was flushed with nitrogen before the addition of anhydrous $CH_2Cl_2$ (50 ml). Linoleoyl chloride (1.2 g, 4 mmol) was added and the solution stirred overnight. The solution was rinsed into a 250 mL separatory funnel with DCM (~70 mL) and washed with water (2×50 mL). The organic was dried ($MgSO_4$), concentrated, and purified by chromatography.

Example 8

Synthesis of Novel Phytanyl Cationic Lipids

DPan-C2K-DMA, DPan-C1K6-DMA, and DPan-C3K-DMA having the structures shown below were synthesized as shown in the following schematic diagram.

Synthesis of Phytanol

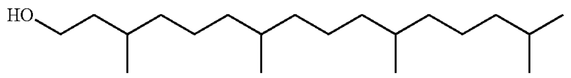

$C_{20}H_{42}O$
Exact Mass: 298.32
Mol. Wt.: 298.55
C, 80.46; H, 14.18; O, 5.36

Phytol (21.0 g, 70.8 mmol), ethanol (180 mL) and a stir bar were added to a 500 mL round bottom flask. Raney Nickel 2800 (as purchased, a 50% by weight solution in water if used as purchased, Nickel >89% metal present) (6.8 g, 51.5 mmol) was added, and the flask sealed and flushed with hydrogen. A 12" needle was used to bubble hydrogen through the solution for 10 minutes. The reaction was stirred for 5 days, using a balloon as a hydrogen reservoir. Hydrogen was also bubbled through the reaction mixture at 24 h and 48 h, 5 minutes each time. The metal catalyst was then removed by filtering through Celite. The ethanolic solution was concentrated, and 200 mL of DCM added to the resulting oil. The solution was washed with water (2×100 mL), dried over $MgSO_4$, and concentrated. TLC indicated formation of the phytanol product, yield 20.0 g.

Synthesis of Phytanyl Mesylate

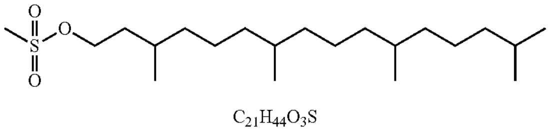

$C_{21}H_{44}O_3S$
Exact Mass: 376.30
Mol. Wt.: 376.64
C, 66.97; H, 11.78; O, 12.74; S, 8.51

Phytanol (20.0 g, 66.7 mmol), triethylamine (18.6 mL, 133 mmol) and a stir bar were added to a 1000 mL round bottom flask. The flask was sealed and flushed with nitrogen. Anhydrous DCM (250 mL) was added, and the mixture cooled to −15° C. (Ice and NaCl). Mesyl Chloride (10.4 mL, 133 mmol) was added slowly via syringe over a 30 minute period, and the reaction stirred at −15° C. for a further 1.5 hours. At this point TLC showed that the starting material had been used up. The solution was diluted with DCM (250 mL) and washed with saturated $NaHCO_3$ (2×200 mL). The organic phase was then dried ($MgSO_4$), filtered and concentrated (rotovap). The crude product was purified by column chromatography. Yield 21.5 g, 85.7%.

Synthesis of Phytanyl Bromide

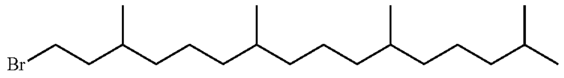

Chemical Formula: $C_{20}H_{41}Br$
Exact Mass: 360.2
Molecular Weight: 361.4
Elemental Analysis: C, 66.46; H, 11.43; Br, 22.11

Magnesium bromide etherate (17 g, 55 mmol) and a stir bar were added to a 500 mL round bottom flask. The flask was sealed and flushed with nitrogen and anhydrous diethyl ether (200 mL) added via cannula. A solution of phytanyl mesylate (10.9 g, 28.9 mmol (FW=377)) in anhydrous ether (50 mL) was also added via canulla, and the suspension stirred overnight. The following morning a precipitate had formed on the side of the flask. Chilled water (200 mL) was added (ppte dissolved) and the mixture transferred to a 1000-mL separating funnel. After shaking, the organic phase was separated. The aqueous phase was then extracted with ether (2×150 mL) and all ether phases combined. The ether phase was washed with water (2×150 mL), brine (150 mL) and dried over anhydrous $Mg_2SO_4$. The solution was filtered, concentrated, and purified by flash chromatography. Final yield 9.5 g (26.3 mmol, 91.1%).

Synthesis of Compound A

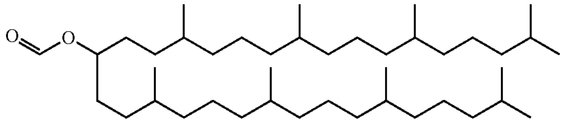

Chemical Formula: $C_{42}H_{84}O_2$
Exact Mass: 620.65
Molecular Weight: 621.12
Elemental Analysis: C, 81.22; H, 13.63; O, 5.15

Magnesium turnings (720 mg, 30 mmol), a crystal of iodine, and a stirbar were added to a 500 mL round-bottom flask. The flask was flushed with nitrogen and anhydrous diethyl ether (200 mL) added via cannula. A solution of phytanyl bromide (9.5 g, 26.3 mmol) in anhydrous ether (20 mL) was added and the resulting cloudy mixture refluxed overnight. The mixture was cooled to RT and, without removing the subaseal or condenser, ethyl formate (2.2 g, 2.41 mL, 30 mmol) added via syringe and 12" needle. The addition was made dropwise, directly into the reaction mixture, and the cloudy suspension again stirred overnight. R.M. was transferred to a 500-mL sep. funnel with ether (50 mL), and washed with 10% $H_2SO_4$ (100 mL—the cloudy R.M. now clarified upon shaking), water (2×100 mL) and brine. The organic was dried over anhydrous $Mg_2SO_4$, filtered, and concentrated. Yield (crude) was 8 g. TLC indicated that the majority of product was the diphytanylmethyl formate, which was purified by chromatography (0-6% ether in hexane).

Synthesis of Compound B

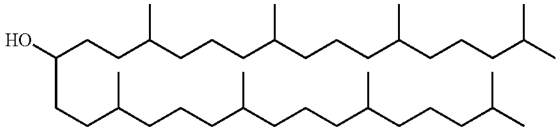

Chemical Formula: $C_{41}H_{84}O$
Exact Mass: 592.65
Molecular Weight: 593.11
Elemental Analysis: C, 83.03; H, 14.28; O, 2.70

The purified formate (A) (5.5 g, 8.86 mmol) was then transferred to a 1000 mL round bottom flask with stirbar and 90% EtOH (500 mL) and KOH (2.0 g, 35.7 mmol) added. The reaction mixture was clear, and was stirred overnight. The following day the mixture was concentrated by rotovap to 50% of its volume and then poured into 200 mL of 5% HCl. The aqueous phase was extracted with ether (3×100 mL). The combined ether extracts were washed with water (3×200 mL), dried ($MgSO_4$), and concentrated. TLC (DCM) revealed reaction to have gone cleanly to completion, and the product (5.5 g, 100%) was used without further purification.

Synthesis of Compound C

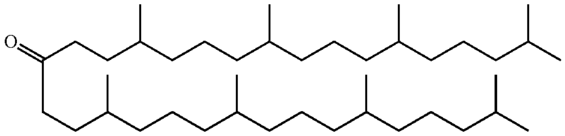

Chemical Formula: $C_{41}H_{82}O$
Exact Mass: 590.6
Molecular Weight: 591.1
Elemental Analysis: C, 83.31; H, 13.98; O, 2.71

To a mixture of Compound B (5.5 g, 9.3 mmol), pyridinium chlorochromate (PCC) (5.5 g, 25.5 mmol) and anhydrous sodium carbonate (0.6 g, 5.66 mmol) in DCM were added. The resulting suspension was stirred for 1 h, but TLC indicated still some starting material (SM) remaining. The suspension was stirred another hour, and appeared to have progressed slightly, but not to completion. Further PCC (1.0 g) and sodium carbonate (0.2 g) were added and the reaction stirred overnight. Reaction had now gone to completion. Ether (300 mL) was then added to the mixture and the resulting brown suspension filtered through a pad of silica (300 mL), washing the pad with ether (3×100 mL). The ether phases were combined, concentrated, and purified to yield 5.0 g (90%) of ketone.

Synthesis of Compound D

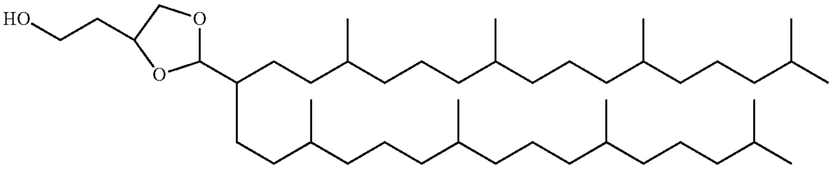

Chemical Formula: $C_{45}H_{90}O_3$
Exact Mass: 678.69
Molecular Weight: 679.19
Elemental Analysis: C, 79.58; H, 13.36; O, 7.07

A 100 mL round bottom flask was charged with Compound C (1.4 g, 2.4 mmol), 1, 2, 4-butanetriol (0.51 g, 4.8 mmol), pyridinium p-toluenesulfonate (0.06 g, 0.24 mmol), and a stir bar. The reaction vessel was flushed with nitrogen and anhydrous toluene (30 mL) added via cannula. The flask was equipped with a Dean-Stark tube and condenser and flushed with nitrogen. The reaction was refluxed under nitrogen overnight and progress of the reaction monitored via TLC. After refluxing for three hours, reaction solution deposited in the Dean-Stark tube was removed via syringe (20 mL) and the reaction vessel immediately replenished with fresh toluene (20 mL). This was repeated every hour, for a total of three times, and then left to reflux mildly overnight. After cooling to room temperature, the reaction mixture was transferred to a 250 mL separatory funnel with toluene (2×5 mL), washed with 5% aqueous $Na_2CO_3$ (2×50 mL), water (50 mL), and dried over $MgSO_4$. Evaporation of the solvent gave 1.67 g of crude product which was purified via column chromatography on silica gel (50 g) using dichloromethane as eluent. Yield: 1.4 g, 2.06 mmol, 86%.

Synthesis of Compound E

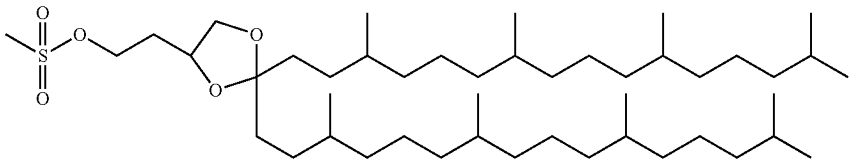

Chemical Formula: $C_{46}H_{92}O_5S$
Exact Mass: 756.67
Molecular Weight: 757.28
Elemental Analysis: C, 72.96; H, 12.25; O, 10.56; S, 4.23

A 100 mL round bottom flask was charged with Compound D (1.4 g, 2.06 mmol) and a stir bar. The vessel was flushed with nitrogen and DCM (25 mL) added. Subsequently, triethylamine (0.72 g, 7.1 mmol, 0.99 mL) was added via syringe and the resulting solution cooled to −15° C. (NaCl, ice). In a separate 50 mL round bottom flask, a solution of methanesulfonic anhydride (0.74 g, 4.1 mmol) and DCM (20 mL) was prepared. This solution was added drop wise to the above solution over a 30 minute period. The reaction vessel was maintained at −15° C. The reaction mixture was stirred at room temperature overnight and monitored via TLC. The reaction mixture was then diluted with DCM (25 mL), and washed with $NaHCO_3$ (2×30 mL), then dried over anhydrous $MgSO_4$. The crude product (1.7 g) was used in the next step without further purification.

Synthesis of DPan-C2K-DMA

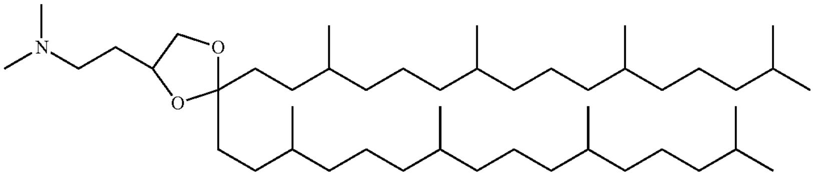

Chemical Formula: $C_{47}H_{95}NO_2$
Exact Mass: 705.74
Molecular Weight: 706.26
Elemental Analysis: C, 79.93; H, 13.56; N, 1.98: O, 4.53

A 500 mL round bottom flask was charged with crude Compound E (1.7 g, 2.5 mmol) and a stir bar. The reaction vessel was flushed with nitrogen and dimethylamine in THF (2.0 M, 65 mL) subsequently added via syringe. The resulting mixture was stirred for three days at room temperature. The reaction was concentrated and the crude product purified by column chromatography using silica gel (40 g) with a gradient of 0-5% methanol in dichloromethane.

Synthesis of Compound F

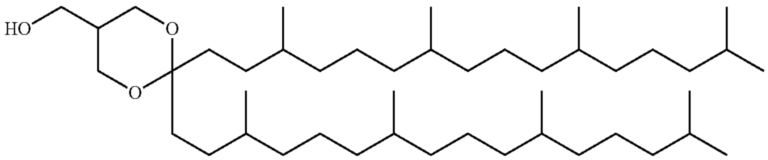

Chemical Formula: $C_{45}H_{90}O_3$
Exact Mass: 678.69
Molecular Weight: 679.19
Elemental Analysis: C, 79.58; H, 13.36; O, 7.07

A 100 mL round bottom flask was charged with Compound C (1.2 g, 2.1 mmol), 2-hydroxymethyl-1,3-propanediol (0.45 g, 4.2 mmol), pyridinium p-toluenesulfonate (0.05 g, 0.21 mmol), and a stir bar. The reaction vessel was flushed with nitrogen and anhydrous toluene (45 mL) subsequently added via cannula. The flask was equipped with a Dean-Stark tube and condenser and flushed with nitrogen. The reaction was refluxed under nitrogen overnight and progress of the reaction monitored via TLC. After refluxing for three hours, reaction solution deposited in the Dean-Stark tube was removed via syringe (20 mL) and the reaction vessel immediately replenished with fresh toluene (20 mL). This was repeated every hour, for a total of three times, and then left to reflux mildly overnight. After cooling to room temperature, the reaction mixture was transferred to a 250 mL separatory funnel with toluene (2×5 mL), washed with 5% aqueous $Na_2CO_3$ (2×50 mL), water (50 mL), and dried over $MgSO_4$. Evaporation of the solvent gave 1.44 g of crude product which was then purified via column chromatography on silica gel (35 g) with 0-3% methanol gradient in dichloromethane.

Synthesis of Compound G

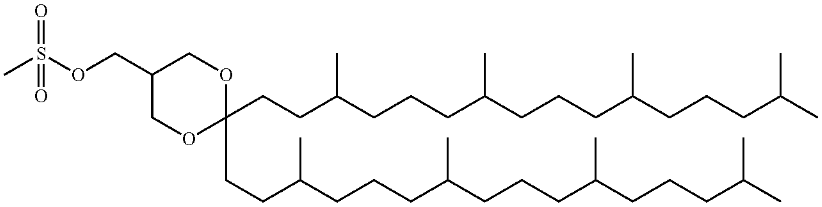

Chemical Formula: $C_{46}H_{92}O_5S$
Exact Mass: 756.67
Molecular Weight: 757.28
Elemental Analysis: C, 72.96; H, 12.25; O, 10.56 S, 4.23

A 250 mL round bottom flask was charged with Compound F (1.2 g, 1.8 mmol) and a stir bar. The vessel was flushed with nitrogen and DCM (25 mL) added. Subsequently, triethylamine (0.62 g, 6.1 mmol, 0.85 mL) was added via syringe and the resulting solution cooled to −15° C. (NaCl, ice). In a separate 50 mL round bottom flask, a solution of methanesulfonic anhydride (0.67 g, 3.7 mmol) and DCM (20 mL) was prepared. This solution was added drop wise to the above solution over a 30 minute period. The reaction vessel was maintained at −15° C. during the addition. The reaction mixture was stirred at room temperature overnight and monitored via TLC. The reaction mixture was then diluted with DCM (25 mL) and washed with $NaHCO_3$ (2×30 mL), then dried over anhydrous $MgSO_4$. The crude product (1.6 g) was used in the following step without further purification.

Synthesis of DPan-C1K6-DMA

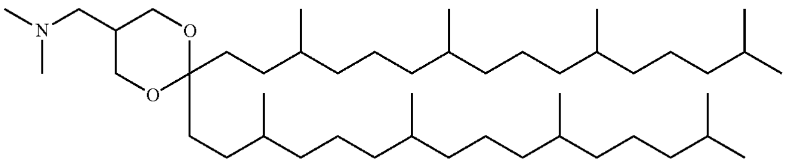

Chemical Formula: $C_{47}H_{95}NO_2$
Exact Mass: 705.74
Molecular Weight: 706.26
Elemental Analysis: C, 79.93; H, 13.56; N, 1.98; O, 4.53

A 250 mL round bottom flask was charged with crude Compound G (1.6 g, 2.1 mmol) and a stir bar. The reaction vessel was flushed with nitrogen and dimethylamine in THF (2.0 M, 60 mL) subsequently added via syringe. The resulting mixture was stirred for six days at room temperature. After solvent was evaporated, the crude product was purified using column chromatography on silica gel (30 g) with 0-30% ethyl acetate gradient in hexanes.

Synthesis of Compound H

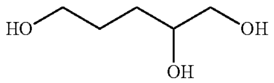

Chemical Formula: $C_5H_{12}O_3$
Exact Mass: 120.08
Molecular Weight: 120.15
Elemental Analysis: C, 49.98; H, 10.07; H, 10.07; O, 39.95

A 50 mL round bottom flask was charged with (R)-γ-hydroxymethyl-γ-butyrolactone (1.0 g, 8.6 mmol), flushed with nitrogen, and sealed with a rubber septum. Anhydrous THF (40 mL) was subsequently added via syringe. The (R)-γ-hydroxymethyl-γ-butyrolactone solution was then added drop wise under nitrogen to a prepared solution containing $LiAlH_4$ (3.5 g, 92 mmol) in 160 mL anhydrous THF. During the addition, the reaction vessel was maintained at 0° C. The resulting suspension was stirred at room temperature overnight. The reaction mixture was cooled to 0° C. and brine (10-22 mL) added very slowly using a Pasteur pipette. The mixture was stirred under nitrogen at room temperature overnight. The white solid was filtered and washed with THF (3×25 mL). The organics were combined and concentrated. After solvent was removed, the crude product seemed to contain water along with an oily residue; therefore, the crude product was azeotroped within ethanol (100 mL) resulting in a yellow oil. The crude product (0.45 g) was used in the next step without further purification.

Synthesis of Compound I

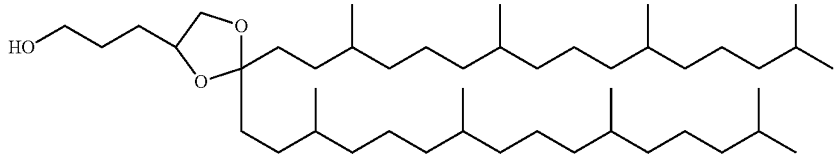

Chemical Formula: $C_{46}H_{92}O_3$
Exact Mass: 692.70
Molecular Weight: 693.22
Elemental Analysis: C, 79.70; H, 13.38; O, 6.92

A 100 mL round bottom flask was charged with Compound C (1.0 g, 1.8 mmol), Compound H (crude, 0.450 g, 3.6 mmol), pyridinium p-toluenesulfonate (0.05 g, 0.24 mmol), and a stir bar. The reaction vessel was flushed with nitrogen and anhydrous toluene (45 mL) subsequently added via cannula. The flask was equipped with a Dean-Stark tube and condenser and flushed with nitrogen. The reaction was refluxed under nitrogen overnight and progress of reaction monitored via TLC. After refluxing for three hours, reaction solution deposited in the Dean-Stark tube was removed via syringe (20 mL) and the reaction vessel immediately replenished with fresh toluene (20 mL). This was repeated every hour, for a total of five times, and then left to reflux mildly overnight. After cooling to room temperature, the reaction mixture was transferred to a 250 mL separatory funnel with toluene (2×5 mL), washed with 5% aqueous $Na_2CO_3$ (2×50 mL), water (50 mL), and dried over $MgSO_4$. Evaporation of the solvent gave 1.13 g of crude product which was then purified via column chromatography on silica gel (30 g) using dichloromethane as eluent. Yield, 1.0 g.

Synthesis of Compound J

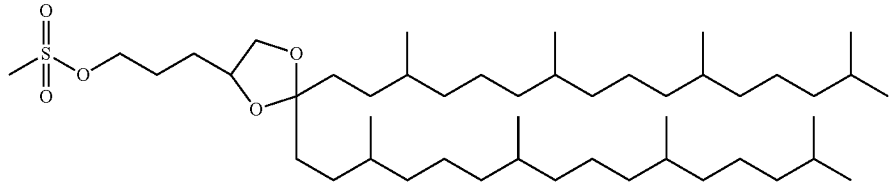

Chemical Formula: $C_{47}H_{94}O_5S$
Exact Mass: 770.68
Molecular Weight: 771.31
Elemental Analysis: C, 73.19; H, 12.28; O, 10.37; S, 4.16

A 250 mL round bottom flask was charged with Compound I (1.0 g, 1.44 mmol) and a stir bar. The vessel was flushed with nitrogen and DCM (25 mL) added. Subsequently, triethylamine (0.51 g, 5 mmol, and 0.7 mL) was added via syringe and the resulting solution cooled to −15° C. (NaCl, ice). In a separate 50 mL round bottom flask, a solution of methanesulfonic anhydride (0.54 g, 3.0 mmol) and anhydrous DCM (20 mL) was prepared. This solution was added drop wise to the above solution over a 30 minute period. The reaction vessel was maintained at −15° C. The reaction mixture was stirred at room temperature overnight and monitored via TLC. The reaction mixture was then diluted with DCM (25 mL) and washed with $NaHCO_3$ (2×30 mL), then dried over anhydrous $MgSO_4$. The crude product (1.2 g) was used in the next step without further purification.

Synthesis of DPan-C3K-DMA

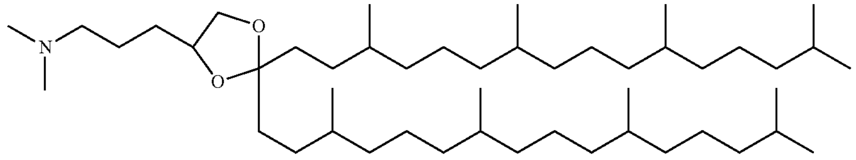

Chemical Formula: $C_{48}H_{97}NO_2$
Exact Mass: 719.75
Molecular Weight: 720.29
Elemental Analysis: C, 80.04; H, 13.57; N, 1.94; O, 4.44

A 100 mL round bottom flask was charged with crude Compound J (1.2 g, 1.6 mmol) and a stir bar. The reaction vessel was flushed with nitrogen and dimethylamine in THF (2.0 M, 45 mL) subsequently added via syringe. The resulting mixture was stirred for four days at room temperature. After solvent was evaporated, the crude product was purified using column chromatography on silica gel (30 g) with 0-30% ethyl acetate gradient in hexanes.

Example 9

Synthesis of DLen-C2K-DMA

DLen-C2K-DMA having the structure shown below was synthesized as shown in the following schematic diagram.

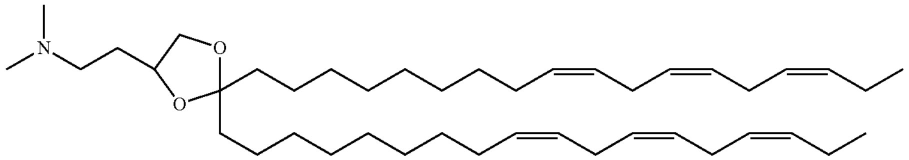

DLen-C2K-DMA

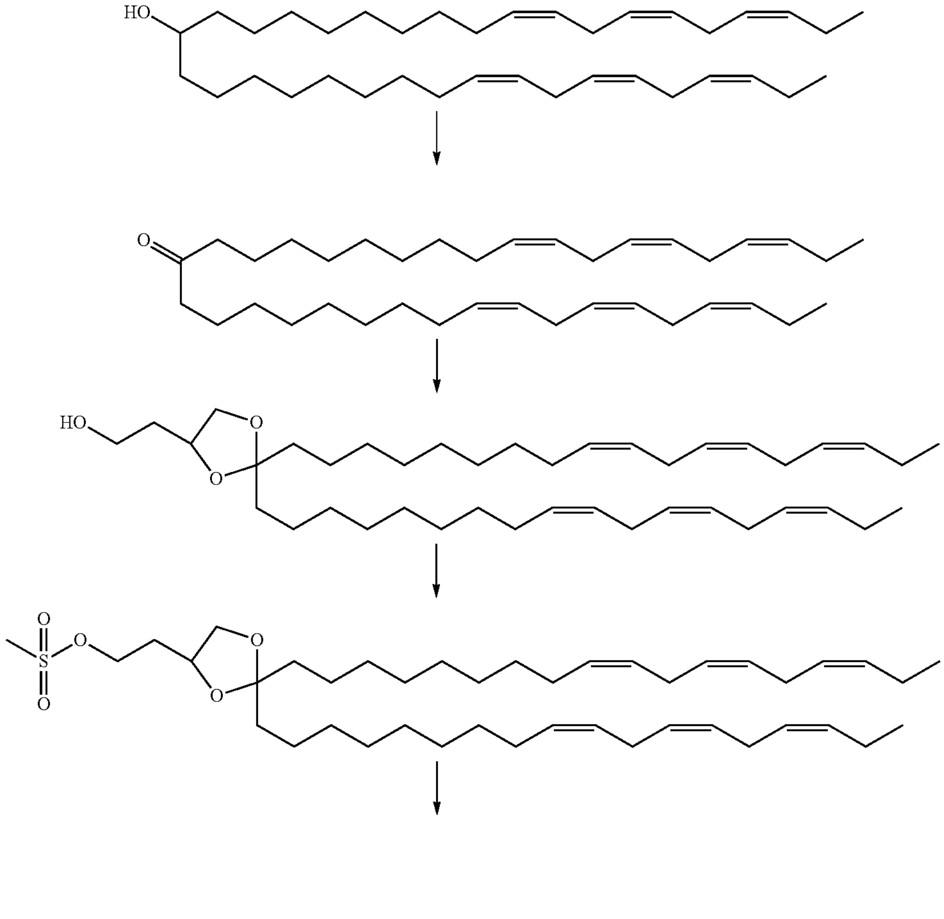

-continued

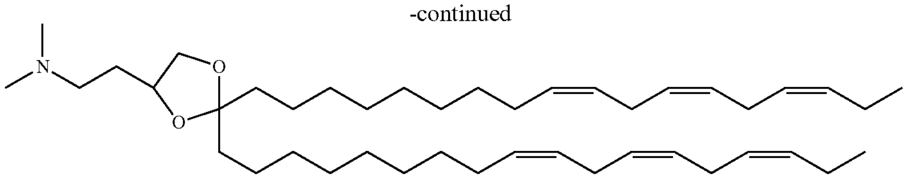

Synthesis of Dilinolenyl Ketone

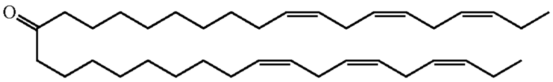 [SMILES: CC/C=C\C/C=C\C/C=C\CCCCCCCCC(=O)CCCCCCCC/C=C\C/C=C\C/C=C\CC]

To a 1000 mL RBF containing a solution of dilinolenyl methanol (6.0 g, 11.4 mmol) in anh. DCM (200 mL) was added pyridinium chlorochromate (7.39 g, 34.2 mmol), anh. sodium carbonate (1.0 g, 5.66 mmol) and a stirbar. The resulting suspension was stirred under nitrogen at RT for 3 h, after which time TLC indicated all SM to have been consumed. Ether (300 mL) was then added to the mixture and the resulting brown suspension filtered through a pad of silica (300 mL), washing the pad with ether (3×100 mL). The ether phases were combined, concentrated and purified to yield 4.2 g (8.0 mmol, 70%) of the ketone.

Synthesis of Linolenyl Ketal

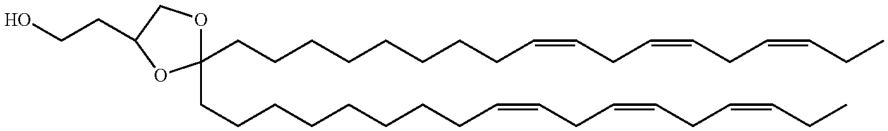 [SMILES: CC/C=C\C/C=C\C/C=C\CCCCCCCCC1(CCCCCCCC/C=C\C/C=C\C/C=C\CC)OCC(CCO)O1]

A 100 mL RBF was charged with dilinolenyl ketone (4.2 g, 8.2 mmol), 1,2,4-butanetriol (3.4 g, 32 mmol), PPTS (200 mg, 0.8 mmol) and a stir bar. The flask was flushed with nitrogen and anhydrous toluene (60 mL) added. The reaction vessel was fitted with a Dean Stark tube and condenser and brought to reflux and the reaction was left overnight. After cooling to room temperature, the reaction mixture diluted with toluene (50 mL), and washed with 5% aq. $Na_2CO_3$ (2×50 mL), water (50 mL), dried ($MgSO_4$) and purified by chromatography to yield 3.0 g (4.9 mmol, 59%) of the ketal.

Mesylate Formation

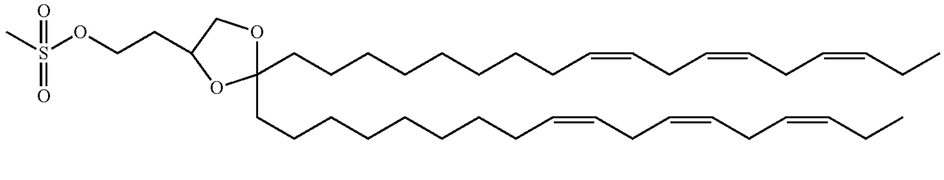 [SMILES: CC/C=C\C/C=C\C/C=C\CCCCCCCCC1(CCCCCCCC/C=C\C/C=C\C/C=C\CC)OCC(CCOS(C)(=O)=O)O1]

A 250 mL RBF was charged with the linolenyl ketal (3.0 g, 4.9 mmol), TEA (2.2 mL, 15.6 mmol) and a stir bar. The flask was flushed with nitrogen, anh. DCM (20 mL) added, and the solution cooled to −15° C. In a separate 50 mL flask, a solution of MsCl (9.7 mmol, 2 eqv.) in anhydrous DCM (30 mL) was prepared, then transferred to the reaction vessel by syringe over 20 minutes. The reaction was stirred for 90 minutes at −15° C., at which point starting material had been consumed. The reaction mixture was diluted with a further 50 mL of DCM, washed with $NaHCO_3$ (2×50 mL), dried ($MgSO_4$) and purified by chromatography. Final yield 3.1 g, 4.5 mmol, 92%.

Synthesis of DLen-C2K-DMA

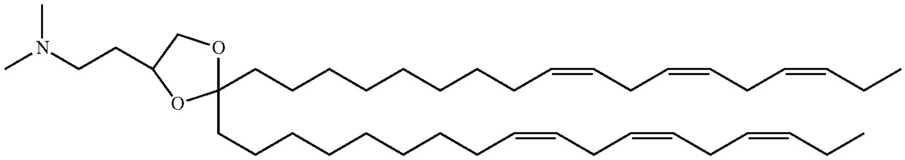 [SMILES: CC/C=C\C/C=C\C/C=C\CCCCCCCCC1(CCCCCCCC/C=C\C/C=C\C/C=C\CC)OCC(CCN(C)C)O1]

A 250 mL RBF was charged with the mesylate (3.0 g, 4.35 mmol), isopropanol (25 mL) and a stir bar. The flask was flushed with nitrogen, sealed, and a 2.0 M solution of dimethylamine in methanol (120 mL) added via canulla. The reaction was stirred at room temperature for 3 days. The solution was concentrated and purified by chromatography. Final yield 2.49 g, 3.9 mmol, 90%.

Example 10

Synthesis of γ-DLen-C2K-DMA

γ-DLen-C2K-DMA having the structure shown below was synthesized as shown in the following schematic diagram.

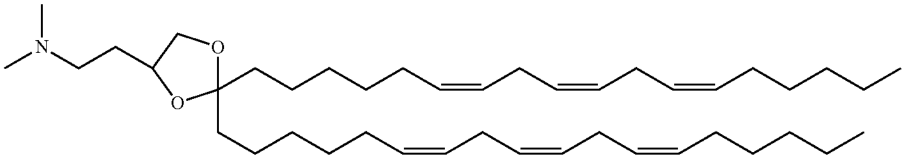

γ-DLen-C2K-DMA

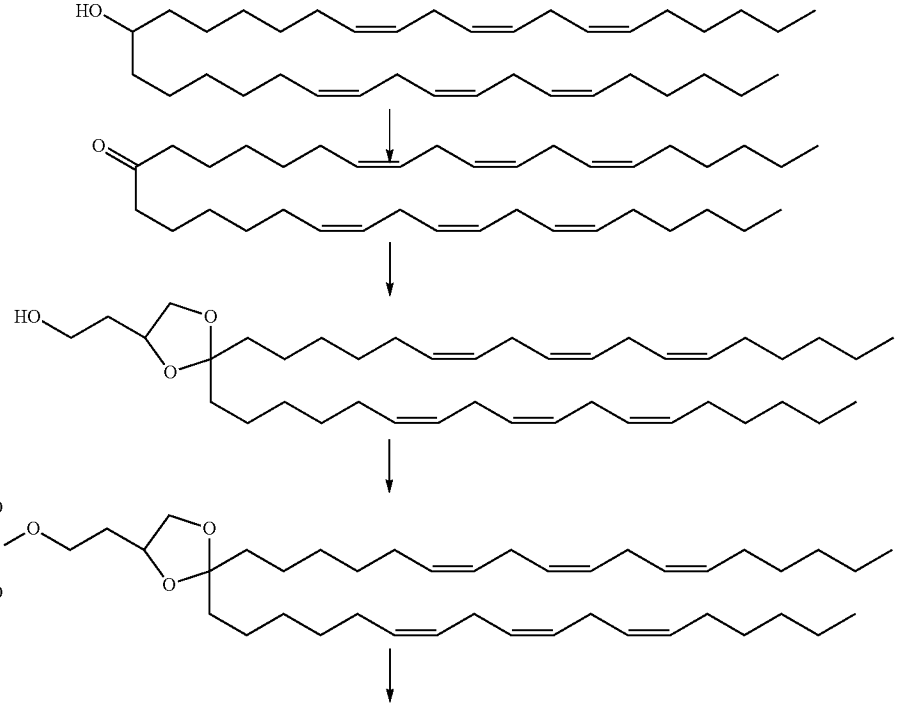

-continued

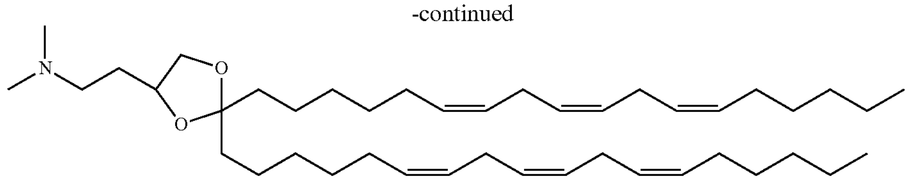

Synthesis of Di-γ-Linolenyl Ketone

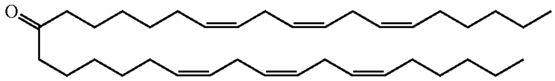

To a 1000 mL RBF containing a solution of di-γ-linolenyl methanol (6.0 g, 11.4 mmol) in anh. DCM (200 mL) was added pyridinium chlorochromate (7.39 g, 34.2 mmol), anh. sodium carbonate (1.0 g, 5.66 mmol) and a stirbar. The resulting suspension was stirred under nitrogen at RT for 3 h, after which time TLC indicated all SM to have been consumed. Ether (300 mL) was then added to the mixture and the resulting brown suspension filtered through a pad of silica (300 mL), washing the pad with ether (3×100 mL). The ether phases were combined, concentrated and purified to yield 5.5 g (10.5 mmol, 92%) of ketone.

Synthesis of γ-Linolenyl Ketal

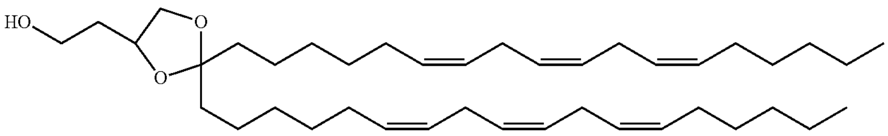 [SMILES: CCCCC/C=C\C/C=C\C/C=C\CCCCCC1(CCCCC/C=C\C/C=C\C/C=C\CCCCC)OCC(CCO)O1]

A 100 mL RBF was charged with di-γ-linolenyl ketone (2.14 g, 4.1 mmol), 1,2,4-butanetriol (1.7 g, 16.0 mmol), PPTS (100 mg, 0.4 mmol) and a stir bar. The flask was flushed with nitrogen and anhydrous toluene (30 mL) added. The reaction vessel was fitted with a Dean Stark tube and condenser and brought to reflux and the reaction was left overnight. After cooling to room temperature, the reaction mixture was washed with 5% aq. $Na_2CO_3$ (2×50 mL), water (50 mL), dried ($MgSO_4$) and purified by chromatography to yield 1.34 g (2.2 mmol, 53%) of the ketal.

Mesylate Formation

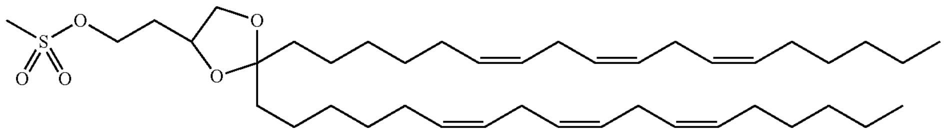 [SMILES: CCCCC/C=C\C/C=C\C/C=C\CCCCCC1(CCCCC/C=C\C/C=C\C/C=C\CCCCC)OCC(CCOS(C)(=O)=O)O1]

A 250 mL RBF was charged with the γ-linolenyl ketal (1.34 g, 2.19 mmol), TEA (1 mL, 7.1 mmol) and a stir bar. The flask was flushed with nitrogen, anh. DCM (10 mL) added, and the solution cooled to −15° C. In a separate 50 mL flask, a solution of MsCl (342 μL, 4.4 mmol, 2 eqv.) in anhydrous DCM (15 mL) was prepared, then transferred to the reaction vessel by syringe over 20 minutes. The reaction was stirred for 90 minutes at −15° C., at which point starting material had been consumed. The reaction mixture was diluted with a further 50 mL of DCM, washed with $NaHCO_3$ (2×50 mL), dried ($MgSO_4$) and purified by chromatography. Final yield 1.31 g, 1.90 mmol, 87%.

Synthesis of γ-DLen-C2K-DMA

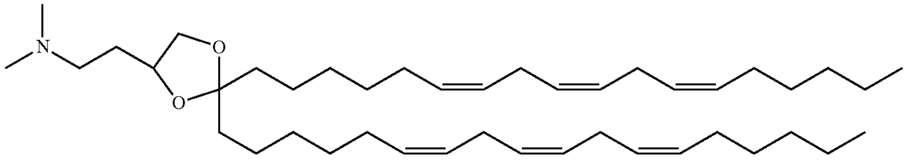 [SMILES: CCCCC/C=C\C/C=C\C/C=C\CCCCCC1(CCCCC/C=C\C/C=C\C/C=C\CCCCC)OCC(CCN(C)C)O1]

A 250 mL RBF was charged with the mesylate (1.31 g, 1.9 mmol), isopropanol (10 mL) and a stir bar. The flask was flushed with nitrogen, sealed, and a 2.0 M solution of dimethylamine in methanol (60 mL) added via canulla. The reaction was stirred at room temperature for 3 days. The solution was concentrated and purified by chromatography. Final yield 1.1 g, 1.72 mmol, 91%.

It is to be understood that the above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications, patents, PCT publications, and Genbank Accession Nos., are incorporated herein by reference for all purposes.

What is claimed is:

1. A composition comprising an siRNA that silences Ebola virus VP24 expression consisting of the following sense and antisense strand sequences:

5'-UCCUCGACACGAAUGCAAAGU-3'
(SEQ ID NO. 10)

3'-CUAGGAGCUGUGCUUACGUUU-5',
(SEQ ID NO. 17)

wherein the bolded and underlined nucleotides are 2'OMe nucleotides.

2. The composition of claim 1, wherein the composition further comprises an siRNA that silences Ebola virus L-pol expression consisting of the following sense and antisense strand sequences:

5'-GUACGAAGCUGUAUAUAAATT-3'
(SEQ ID NO. 2)

3'-TTCAUGCUUCGACAUAUAUUU-5',
(SEQ ID NO. 6)

wherein the bolded and underlined nucleotides are 2'OMe nucleotides.

3. The composition of claim 1, wherein the composition further comprises an siRNA that silences Ebola virus VP35 expression consisting of the following sense and antisense strand sequences:

5'-GCAACUCAUUGGACAUCAUUC-3'
(SEQ ID NO. 26)

3'-AUCGUUGAGUAACCUGUAGUA-5',
(SEQ ID NO. 30)

wherein the bolded and underlined nucleotides are 2'OMe nucleotides.

4. The composition of claim 1, wherein the composition further comprises:

(a) an siRNA that silences Ebola virus L-pol expression consisting of the following sense and antisense strand sequences:

5'-GUACGAAGCUGUAUAUAAATT-3'
(SEQ ID NO. 2)

3'-TTCAUGCUUCGACAUAUAUUU-5',
(SEQ ID NO. 6)

wherein the bolded and underlined nucleotides are 2'OMe nucleotides; and (b) an siRNA that silences Ebola virus VP35 expression consisting of the following sense and antisense strand sequences:

5'-GCAACUCAUUGGACAUCAUUC-3'
(SEQ ID NO. 26)

3'-AUCGUUGAGUAACCUGUAGUA-5',
(SEQ ID NO. 30)

wherein the bolded and underlined nucleotides are 2'OMe nucleotides.

5. The composition of claim 1, further comprising a pharmaceutically acceptable carrier.

6. A nucleic acid-lipid particle comprising:

(a) a composition of claim 1;

(b) a cationic lipid; and (c) a non-cationic lipid.

7. The nucleic acid-lipid particle of claim 6, wherein the particle further comprises a conjugated lipid that inhibits aggregation of particles.

8. The nucleic acid-lipid particle of claim 6, wherein the cationic lipid comprises 1,2-dilinoleyloxy-N,N-dimethylaminopropane (DLinDMA), 1,2-dilinolenyloxy-N,N-dimethylaminopropane (DLenDMA), 1,2-γ-dimlinolenyloxy-N,N-dimethylaminopropane (γ-DLenDMA), 2,2-dilinoleyl-4-(2-dimethylaminoethyl)[1,3]-dioxolane (DLin-K-C2-DMA), 2,2-dilinoleyl-4-dimethylaminomethyl-[1,3]-dioxolane (DLin-K-DMA), or a mixture thereof.

9. The nucleic acid-lipid particle of claim 6, wherein the non-cationic lipid is selected from the group consisting of a phospholipid, cholesterol, or a mixture of a phospholipid and cholesterol.

10. The nucleic acid-lipid particle of claim 9, wherein the phospholipid comprises dipalmitoylphosphatidylcholine (DPPC), distearoylphosphatidylcholine (DSPC), or a mixture thereof.

11. The nucleic acid-lipid particle of claim 9, wherein the cholesterol is a cholesterol derivative.

12. The nucleic acid-lipid particle of claim 7, wherein the conjugated lipid that inhibits aggregation of particles comprises a polyethyleneglycol (PEG)-lipid conjugate.

13. The nucleic acid-lipid particle of claim 12, wherein the PEG-lipid conjugate is member selected from the group consisting of a PEG-diacylglycerol (PEG-DAG) conjugate, a PEG dialkyloxypropyl (PEG-DAA) conjugate, a PEG-phospholipid conjugate, a PEG-ceramide (PEG-Cer) conjugate, and a mixture thereof.

14. The nucleic acid-lipid particle of claim 13, wherein the PEG-lipid conjugate is a PEG-DAA conjugate.

15. The nucleic acid-lipid particle of claim 14, wherein the PEG-DAA conjugate is selected from the group consisting of a PEG-didecyloxypropyl ($C_{10}$) conjugate, a PEG-dilauryloxypropyl ($C_{12}$) conjugate, a PEG-dimyristyloxypropyl ($C_{14}$) conjugate, a PEG-dipalmityloxypropyl ($C_{16}$) conjugate, a PEG-distearyloxypropyl ($C_{18}$) conjugate, and a mixture thereof.

16. The nucleic acid-lipid particle of claim 6, wherein the composition is fully encapsulated in the nucleic acid-lipid particle.

17. A pharmaceutical composition comprising a nucleic acid-lipid particle of claim 6 and a pharmaceutically acceptable carrier.

18. A method for introducing an siRNA that silences Ebola virus gene expression into a cell, the method comprising:

contacting the cell with a nucleic acid-lipid particle of claim 6.

19. A method for silencing Ebola virus gene expression in a mammal in need thereof, the method comprising:

administering to the mammal a nucleic acid-lipid particle of claim 6.

20. A method for the in vivo delivery of an siRNA that silences Ebola virus gene expression, the method comprising:

administering to a mammal a nucleic acid-lipid particle of claim 6.

21. A method for treating and/or ameliorating one or more symptoms associated with an Ebola virus infection in a mammal in need thereof, the method comprising:

administering to the mammal a therapeutically effective amount of a nucleic acid-lipid particle of claim 6.

22. A method for inactivating and/or inhibiting the replication of Ebola virus in a mammal in need thereof, the method comprising:

administering to the mammal a therapeutically effective amount of a nucleic acid-lipid particle of claim 6.

23. A method for preventing and/or treating hemorrhagic fever in a mammal in need thereof, the method comprising:

administering to the mammal a therapeutically effective amount of a nucleic acid-lipid particle of claim 6.

* * * * *

SEQUENCE LISTING

```
<160> NUMBER OF SEQ ID NOS: 86

<210> SEQ ID NO 1
<211> LENGTH: 21
<212> TYPE: DNA
<213> ORGANISM: Artificial Sequence
<220> FEATURE:
<223> OTHER INFORMATION: synthetic first interfering RNA (siRNA) sense
      strand S-1 for Ebola virus polymerase L (L-pol)
<220> FEATURE:
<223> OTHER INFORMATION: Description of Combined DNA/RNA Molecule:
      synthetic first interfering RNA (siRNA) sense strand S-1 for
      Ebola virus polymerase L (L-pol)
<220> FEATURE:
<221> NAME/KEY: modified_base
<222> LOCATION: (2)...(2)
<223> OTHER INFORMATION: n = um
<220> FEATURE:
<221> NAME/KEY: modified_base
<222> LOCATION: (11)...(11)
<223> OTHER INFORMATION: n = gm
<220> FEATURE:
<221> NAME/KEY: modified_base
<222> LOCATION: (16)...(16)
<223> OTHER INFORMATION: n = um

<400> SEQUENCE: 1

gnacgaagcu nuauanaaat t                                               21


<210> SEQ ID NO 2
<211> LENGTH: 21
<212> TYPE: DNA
<213> ORGANISM: Artificial Sequence
<220> FEATURE:
<223> OTHER INFORMATION: synthetic first interfering RNA (siRNA) sense
      strand S-2 for Ebola virus polymerase L (L-pol)
<220> FEATURE:
<223> OTHER INFORMATION: Description of Combined DNA/RNA Molecule:
      synthetic first interfering RNA (siRNA) sense strand S-2 for
      Ebola virus polymerase L (L-pol)
<220> FEATURE:
<221> NAME/KEY: modified_base
<222> LOCATION: (2)...(2)
<223> OTHER INFORMATION: n = um
<220> FEATURE:
<221> NAME/KEY: modified_base
<222> LOCATION: (5)...(5)
<223> OTHER INFORMATION: n = ug
<220> FEATURE:
```

```
<221> NAME/KEY: modified_base
<222> LOCATION: (10)...(10)
<223> OTHER INFORMATION: n = um
<220> FEATURE:
<221> NAME/KEY: modified_base
<222> LOCATION: (11)...(11)
<223> OTHER INFORMATION: n = gm
<220> FEATURE:
<221> NAME/KEY: modified_base
<222> LOCATION: (12)...(16)
<223> OTHER INFORMATION: n = um

<400> SEQUENCE: 2

gnacnaagcn nnananaaat t                                                21


<210> SEQ ID NO 3
<211> LENGTH: 21
<212> TYPE: DNA
<213> ORGANISM: Artificial Sequence
<220> FEATURE:
<223> OTHER INFORMATION: synthetic first interfering RNA (siRNA) sense
      strand S-3 for Ebola virus polymerase L (L-pol)
<220> FEATURE:
<223> OTHER INFORMATION: Description of Combined DNA/RNA Molecule:
      synthetic first interfering RNA (siRNA) sense strand S-3 for
      Ebola virus polymerase L (L-pol)
<220> FEATURE:
<221> NAME/KEY: modified_base
<222> LOCATION: (2)...(2)
<223> OTHER INFORMATION: n = um
<220> FEATURE:
<221> NAME/KEY: modified_base
<222> LOCATION: (11)...(11)
<223> OTHER INFORMATION: n = gm
<220> FEATURE:
<221> NAME/KEY: modified_base
<222> LOCATION: (14)...(16)
<223> OTHER INFORMATION: n = um

<400> SEQUENCE: 3

gnacgaagcu nuananaaat t                                                21


<210> SEQ ID NO 4
<211> LENGTH: 21
<212> TYPE: DNA
<213> ORGANISM: Artificial Sequence
<220> FEATURE:
<223> OTHER INFORMATION: synthetic first interfering RNA (siRNA)
      antisense strand AS-1 for Ebola virus polymerase L (L-pol)
<220> FEATURE:
<223> OTHER INFORMATION: Description of Combined DNA/RNA Molecule:
      synthetic first interfering RNA (siRNA) antisense strand AS-1 for
      Ebola virus polymerase L (L-pol)
<220> FEATURE:
<221> NAME/KEY: modified_base
<222> LOCATION: (5)...(17)
<223> OTHER INFORMATION: n = um

<400> SEQUENCE: 4

uuuanauaca gcuucgnact t                                                21


<210> SEQ ID NO 5
<211> LENGTH: 21
<212> TYPE: DNA
<213> ORGANISM: Artificial Sequence
<220> FEATURE:
<223> OTHER INFORMATION: synthetic first interfering RNA (siRNA)
      antisense strand AS-2 for Ebola virus polymerase L (L-pol)
<220> FEATURE:
<223> OTHER INFORMATION: Description of Combined DNA/RNA Molecule:
      synthetic first interfering RNA (siRNA) antisense strand AS-2 for
      Ebola virus polymerase L (L-pol)
<220> FEATURE:
```

<221> NAME/KEY: modified_base
<222> LOCATION: (5)...(17)
<223> OTHER INFORMATION: n = um

<400> SEQUENCE: 5
uuuanauaca gcuncgnact t 21

<210> SEQ ID NO 6
<211> LENGTH: 21
<212> TYPE: DNA
<213> ORGANISM: Artificial Sequence
<220> FEATURE:
<223> OTHER INFORMATION: synthetic first interfering RNA (siRNA) antisense strand AS-3 for Ebola virus polymerase L (L-pol)
<220> FEATURE:
<223> OTHER INFORMATION: Description of Combined DNA/RNA Molecule: synthetic first interfering RNA (siRNA) antisense strand AS-3 for Ebola virus polymerase L (L-pol)
<220> FEATURE:
<221> NAME/KEY: modified_base
<222> LOCATION: (5)...(17)
<223> OTHER INFORMATION: n = um

<400> SEQUENCE: 6
uuuanauaca gcnucgnact t 21

<210> SEQ ID NO 7
<211> LENGTH: 21
<212> TYPE: DNA
<213> ORGANISM: Artificial Sequence
<220> FEATURE:
<223> OTHER INFORMATION: synthetic first interfering RNA (siRNA) antisense strand AS-4 for Ebola virus polymerase L (L-pol)
<220> FEATURE:
<223> OTHER INFORMATION: Description of Combined DNA/RNA Molecule: synthetic first interfering RNA (siRNA) antisense strand AS-4 for Ebola virus polymerase L (L-pol)
<220> FEATURE:
<221> NAME/KEY: modified_base
<222> LOCATION: (5)...(5)
<223> OTHER INFORMATION: n = um
<220> FEATURE:
<221> NAME/KEY: modified_base
<222> LOCATION: (11)...(11)
<223> OTHER INFORMATION: n = gm
<220> FEATURE:
<221> NAME/KEY: modified_base
<222> LOCATION: (17)...(17)
<223> OTHER INFORMATION: n = um

<400> SEQUENCE: 7
uuuanauaca ncuucgnact t 21

<210> SEQ ID NO 8
<211> LENGTH: 21
<212> TYPE: DNA
<213> ORGANISM: Artificial Sequence
<220> FEATURE:
<223> OTHER INFORMATION: synthetic first interfering RNA (siRNA) antisense strand AS-5 for Ebola virus polymerase L (L-pol)
<220> FEATURE:
<223> OTHER INFORMATION: Description of Combined DNA/RNA Molecule: synthetic first interfering RNA (siRNA) antisense strand AS-5 for Ebola virus polymerase L (L-pol)
<220> FEATURE:
<221> NAME/KEY: modified_base
<222> LOCATION: (2)...(17)
<223> OTHER INFORMATION: n = um

<400> SEQUENCE: 8
unuanauaca gcnucgnact t 21

<210> SEQ ID NO 9
<211> LENGTH: 21
<212> TYPE: DNA
<213> ORGANISM: Artificial Sequence
<220> FEATURE:
<223> OTHER INFORMATION: synthetic first interfering RNA (siRNA) antisense strand AS-6 for Ebola virus polymerase L (L-pol)
<220> FEATURE:
<223> OTHER INFORMATION: Description of Combined DNA/RNA Molecule: synthetic first interfering RNA (siRNA) antisense strand AS-6 for Ebola virus polymerase L (L-pol)
<220> FEATURE:
<221> NAME/KEY: modified_base
<222> LOCATION: (3)...(17)
<223> OTHER INFORMATION: n = um

<400> SEQUENCE: 9
uunanauaca gcuucgnact t 21

<210> SEQ ID NO 10
<211> LENGTH: 21
<212> TYPE: RNA
<213> ORGANISM: Artificial Sequence
<220> FEATURE:
<223> OTHER INFORMATION: synthetic second interfering RNA (siRNA) sense strand for Ebola virus virion protein 24 (VP24)
<220> FEATURE:
<221> NAME/KEY: modified_base
<222> LOCATION: (4)...(14)
<223> OTHER INFORMATION: n = um

<400> SEQUENCE: 10
uccncgacac gaangcaaag u 21

<210> SEQ ID NO 11
<211> LENGTH: 21
<212> TYPE: RNA
<213> ORGANISM: Artificial Sequence
<220> FEATURE:
<223> OTHER INFORMATION: synthetic second interfering RNA (siRNA) sense strand for Ebola virus virion protein 24 (VP24)
<220> FEATURE:
<221> NAME/KEY: modified_base
<222> LOCATION: (4)...(14)
<223> OTHER INFORMATION: n = um
<220> FEATURE:
<221> NAME/KEY: modified_base
<222> LOCATION: (20)...(20)
<223> OTHER INFORMATION: n = gm

<400> SEQUENCE: 11
uccncgacac gaangcaaan u 21

<210> SEQ ID NO 12
<211> LENGTH: 21
<212> TYPE: RNA
<213> ORGANISM: Artificial Sequence
<220> FEATURE:
<223> OTHER INFORMATION: synthetic second interfering RNA (siRNA) sense strand for Ebola virus virion protein 24 (VP24)
<220> FEATURE:
<221> NAME/KEY: modified_base
<222> LOCATION: (4)...(21)
<223> OTHER INFORMATION: n = um

<400> SEQUENCE: 12
uccncgacac gaangcaaag n 21

<210> SEQ ID NO 13
<211> LENGTH: 21

<212> TYPE: RNA
<213> ORGANISM: Artificial Sequence
<220> FEATURE:
<223> OTHER INFORMATION: synthetic second interfering RNA (siRNA) sense strand for Ebola virus virion protein 24 (VP24)
<220> FEATURE:
<221> NAME/KEY: modified_base
<222> LOCATION: (4)...(14)
<223> OTHER INFORMATION: n = um
<220> FEATURE:
<221> NAME/KEY: modified_base
<222> LOCATION: (20)...(20)
<223> OTHER INFORMATION: n = gm
<220> FEATURE:
<221> NAME/KEY: modified_base
<222> LOCATION: (21)...(21)
<223> OTHER INFORMATION: n = um

<400> SEQUENCE: 13
uccncgacac gaangcaaan n 21

<210> SEQ ID NO 14
<211> LENGTH: 21
<212> TYPE: RNA
<213> ORGANISM: Artificial Sequence
<220> FEATURE:
<223> OTHER INFORMATION: synthetic second interfering RNA (siRNA) sense strand for Ebola virus virion protein 24 (VP24)
<220> FEATURE:
<221> NAME/KEY: modified_base
<222> LOCATION: (1)...(14)
<223> OTHER INFORMATION: n = um

<400> SEQUENCE: 14
nccncgacac gaangcaaag u 21

<210> SEQ ID NO 15
<211> LENGTH: 21
<212> TYPE: RNA
<213> ORGANISM: Artificial Sequence
<220> FEATURE:
<223> OTHER INFORMATION: synthetic second interfering RNA (siRNA) sense strand for Ebola virus virion protein 24 (VP24)
<220> FEATURE:
<221> NAME/KEY: modified_base
<222> LOCATION: (1)...(14)
<223> OTHER INFORMATION: n = um
<220> FEATURE:
<221> NAME/KEY: modified_base
<222> LOCATION: (20)...(20)
<223> OTHER INFORMATION: n = gm

<400> SEQUENCE: 15
nccncgacac gaangcaaan u 21

<210> SEQ ID NO 16
<211> LENGTH: 21
<212> TYPE: RNA
<213> ORGANISM: Artificial Sequence
<220> FEATURE:
<223> OTHER INFORMATION: synthetic second interfering RNA (siRNA) sense strand for Ebola virus virion protein 24 (VP24)
<220> FEATURE:
<221> NAME/KEY: modified_base
<222> LOCATION: (1)...(21)
<223> OTHER INFORMATION: n = um

<400> SEQUENCE: 16
nccncgacac gaangcaaag n 21

<210> SEQ ID NO 17

```
<211> LENGTH: 21
<212> TYPE: RNA
<213> ORGANISM: Artificial Sequence
<220> FEATURE:
<223> OTHER INFORMATION: synthetic second interfering RNA (siRNA)
      antisense strand for Ebola virus virion protein 24 (VP24)
<220> FEATURE:
<221> NAME/KEY: modified_base
<222> LOCATION: (3)...(3)
<223> OTHER INFORMATION: n = um
<220> FEATURE:
<221> NAME/KEY: modified_base
<222> LOCATION: (15)...(18)
<223> OTHER INFORMATION: n = gm

<400> SEQUENCE: 17

uungcauucg ugucnagnau c                                             21


<210> SEQ ID NO 18
<211> LENGTH: 21
<212> TYPE: RNA
<213> ORGANISM: Artificial Sequence
<220> FEATURE:
<223> OTHER INFORMATION: synthetic second interfering RNA (siRNA)
      antisense strand for Ebola virus virion protein 24 (VP24)
<220> FEATURE:
<221> NAME/KEY: modified_base
<222> LOCATION: (3)...(3)
<223> OTHER INFORMATION: n = um
<220> FEATURE:
<221> NAME/KEY: modified_base
<222> LOCATION: (15)...(18)
<223> OTHER INFORMATION: n = gm
<220> FEATURE:
<221> NAME/KEY: modified_base
<222> LOCATION: (20)...(20)
<223> OTHER INFORMATION: n = um

<400> SEQUENCE: 18

uungcauucg ugucnagnan c                                             21


<210> SEQ ID NO 19
<211> LENGTH: 21
<212> TYPE: RNA
<213> ORGANISM: Artificial Sequence
<220> FEATURE:
<223> OTHER INFORMATION: synthetic second interfering RNA (siRNA)
      antisense strand for Ebola virus virion protein 24 (VP24)
<220> FEATURE:
<221> NAME/KEY: modified_base
<222> LOCATION: (2)...(13)
<223> OTHER INFORMATION: n = um

<400> SEQUENCE: 19

unugcauncg ugncgaggau c                                             21


<210> SEQ ID NO 20
<211> LENGTH: 21
<212> TYPE: RNA
<213> ORGANISM: Artificial Sequence
<220> FEATURE:
<223> OTHER INFORMATION: synthetic second interfering RNA (siRNA)
      antisense strand for Ebola virus virion protein 24 (VP24)
<220> FEATURE:
<221> NAME/KEY: modified_base
<222> LOCATION: (2)...(20)
<223> OTHER INFORMATION: n = um

<400> SEQUENCE: 20

unugcauncg ugncgaggan c                                             21
```

<210> SEQ ID NO 21
<211> LENGTH: 21
<212> TYPE: RNA
<213> ORGANISM: Artificial Sequence
<220> FEATURE:
<223> OTHER INFORMATION: synthetic second interfering RNA (siRNA) antisense strand for Ebola virus virion protein 24 (VP24)
<220> FEATURE:
<221> NAME/KEY: modified_base
<222> LOCATION: (1)...(13)
<223> OTHER INFORMATION: n = um

<400> SEQUENCE: 21
nungcauucg ugncgaggau c 21

<210> SEQ ID NO 22
<211> LENGTH: 21
<212> TYPE: RNA
<213> ORGANISM: Artificial Sequence
<220> FEATURE:
<223> OTHER INFORMATION: synthetic second interfering RNA (siRNA) antisense strand for Ebola virus virion protein 24 (VP24)
<220> FEATURE:
<221> NAME/KEY: modified_base
<222> LOCATION: (1)...(20)
<223> OTHER INFORMATION: n = um

<400> SEQUENCE: 22
nungcauucg ugncgaggan c 21

<210> SEQ ID NO 23
<211> LENGTH: 21
<212> TYPE: RNA
<213> ORGANISM: Artificial Sequence
<220> FEATURE:
<223> OTHER INFORMATION: synthetic second interfering RNA (siRNA) antisense strand for Ebola virus virion protein 24 (VP24)
<220> FEATURE:
<221> NAME/KEY: modified_base
<222> LOCATION: (2)...(11)
<223> OTHER INFORMATION: n = um

<400> SEQUENCE: 23
unugcanucg ngucgaggau c 21

<210> SEQ ID NO 24
<211> LENGTH: 21
<212> TYPE: RNA
<213> ORGANISM: Artificial Sequence
<220> FEATURE:
<223> OTHER INFORMATION: synthetic second interfering RNA (siRNA) antisense strand for Ebola virus virion protein 24 (VP24)
<220> FEATURE:
<221> NAME/KEY: modified_base
<222> LOCATION: (2)...(20)
<223> OTHER INFORMATION: n = um

<400> SEQUENCE: 24
unugcanucg ngucgaggan c 21

<210> SEQ ID NO 25
<211> LENGTH: 21
<212> TYPE: RNA
<213> ORGANISM: Artificial Sequence
<220> FEATURE:
<223> OTHER INFORMATION: synthetic third interfering RNA (siRNA) sense strand for Ebola virus virion protein 35 (VP35)
<220> FEATURE:
<221> NAME/KEY: modified_base
<222> LOCATION: (6)...(6)
<223> OTHER INFORMATION: n = um
<220> FEATURE:
<221> NAME/KEY: modified_base
<222> LOCATION: (12)...(12)
<223> OTHER INFORMATION: n = gm
<220> FEATURE:
<221> NAME/KEY: modified_base
<222> LOCATION: (16)...(16)
<223> OTHER INFORMATION: n = um

<400> SEQUENCE: 25
gcaacncauu gnacancauu c 21

<210> SEQ ID NO 26
<211> LENGTH: 21
<212> TYPE: RNA
<213> ORGANISM: Artificial Sequence
<220> FEATURE:
<223> OTHER INFORMATION: synthetic third interfering RNA (siRNA) sense strand for Ebola virus virion protein 35 (VP35)
<220> FEATURE:
<221> NAME/KEY: modified_base
<222> LOCATION: (1)...(1)
<223> OTHER INFORMATION: n = gm
<220> FEATURE:
<221> NAME/KEY: modified_base
<222> LOCATION: (6)...(10)
<223> OTHER INFORMATION: n = um
<220> FEATURE:
<221> NAME/KEY: modified_base
<222> LOCATION: (12)...(12)
<223> OTHER INFORMATION: n = gm
<220> FEATURE:
<221> NAME/KEY: modified_base
<222> LOCATION: (16)...(20)
<223> OTHER INFORMATION: n = um

<400> SEQUENCE: 26
ncaacncaun gnacancann c 21

<210> SEQ ID NO 27
<211> LENGTH: 21
<212> TYPE: RNA
<213> ORGANISM: Artificial Sequence
<220> FEATURE:
<223> OTHER INFORMATION: synthetic third interfering RNA (siRNA) sense strand for Ebola virus virion protein 35 (VP35)
<220> FEATURE:
<221> NAME/KEY: modified_base
<222> LOCATION: (6)...(10)
<223> OTHER INFORMATION: n = um
<220> FEATURE:
<221> NAME/KEY: modified_base
<222> LOCATION: (12)...(12)
<223> OTHER INFORMATION: n = gm
<220> FEATURE:
<221> NAME/KEY: modified_base
<222> LOCATION: (16)...(20)
<223> OTHER INFORMATION: n = um

<400> SEQUENCE: 27
gcaacncaun gnacancaun c 21

<210> SEQ ID NO 28
<211> LENGTH: 21
<212> TYPE: RNA
<213> ORGANISM: Artificial Sequence
<220> FEATURE:
<223> OTHER INFORMATION: synthetic third interfering RNA (siRNA) antisense strand for Ebola virus virion protein 35 (VP35)
<220> FEATURE:
<221> NAME/KEY: modified_base
<222> LOCATION: (6)...(15)
<223> OTHER INFORMATION: n = gm
<220> FEATURE:
<221> NAME/KEY: modified_base
<222> LOCATION: (17)...(17)
<223> OTHER INFORMATION: n = um

<400> SEQUENCE: 28
augaunucca auganungcu a 21

<210> SEQ ID NO 29
<211> LENGTH: 21
<212> TYPE: RNA
<213> ORGANISM: Artificial Sequence
<220> FEATURE:
<223> OTHER INFORMATION: synthetic third interfering RNA (siRNA)
antisense strand for Ebola virus virion protein 35 (VP35)
<220> FEATURE:
<221> NAME/KEY: modified_base
<222> LOCATION: (6)...(15)
<223> OTHER INFORMATION: n = gm
<220> FEATURE:
<221> NAME/KEY: modified_base
<222> LOCATION: (17)...(20)
<223> OTHER INFORMATION: n = um

<400> SEQUENCE: 29
augaunucca auganungcn a 21

<210> SEQ ID NO 30
<211> LENGTH: 21
<212> TYPE: RNA
<213> ORGANISM: Artificial Sequence
<220> FEATURE:
<223> OTHER INFORMATION: synthetic third interfering RNA (siRNA)
antisense strand for Ebola virus virion protein 35 (VP35)
<220> FEATURE:
<221> NAME/KEY: modified_base
<222> LOCATION: (2)...(2)
<223> OTHER INFORMATION: n = um
<220> FEATURE:
<221> NAME/KEY: modified_base
<222> LOCATION: (6)...(15)
<223> OTHER INFORMATION: n = gm
<220> FEATURE:
<221> NAME/KEY: modified_base
<222> LOCATION: (17)...(20)
<223> OTHER INFORMATION: n = um

<400> SEQUENCE: 30
angaunucca auganungcn a 21

<210> SEQ ID NO 31
<211> LENGTH: 21
<212> TYPE: RNA
<213> ORGANISM: Artificial Sequence
<220> FEATURE:
<223> OTHER INFORMATION: synthetic third interfering RNA (siRNA)
antisense strand for Ebola virus virion protein 35 (VP35)
<220> FEATURE:
<221> NAME/KEY: modified_base
<222> LOCATION: (6)...(6)
<223> OTHER INFORMATION: n = gm
<220> FEATURE:
<221> NAME/KEY: modified_base
<222> LOCATION: (12)...(12)
<223> OTHER INFORMATION: n = um
<220> FEATURE:
<221> NAME/KEY: modified_base
<222> LOCATION: (15)...(15)
<223> OTHER INFORMATION: n = gm
<220> FEATURE:
<221> NAME/KEY: modified_base
<222> LOCATION: (17)...(20)
<223> OTHER INFORMATION: n = um

<400> SEQUENCE: 31
augaunucca anganungcn a 21

<210> SEQ ID NO 32
<211> LENGTH: 21
<212> TYPE: RNA
<213> ORGANISM: Artificial Sequence
<220> FEATURE:
<223> OTHER INFORMATION: synthetic third interfering RNA (siRNA) antisense strand for Ebola virus virion protein 35 (VP35)
<220> FEATURE:
<221> NAME/KEY: modified_base
<222> LOCATION: (2)...(2)
<223> OTHER INFORMATION: n = um
<220> FEATURE:
<221> NAME/KEY: modified_base
<222> LOCATION: (6)...(6)
<223> OTHER INFORMATION: n = gm
<220> FEATURE:
<221> NAME/KEY: modified_base
<222> LOCATION: (12)...(12)
<223> OTHER INFORMATION: n = um
<220> FEATURE:
<221> NAME/KEY: modified_base
<222> LOCATION: (15)...(15)
<223> OTHER INFORMATION: n = gm
<220> FEATURE:
<221> NAME/KEY: modified_base
<222> LOCATION: (17)...(20)
<223> OTHER INFORMATION: n = um

<400> SEQUENCE: 32
angaunucca anganungcn a 21

<210> SEQ ID NO 33
<211> LENGTH: 21
<212> TYPE: RNA
<213> ORGANISM: Artificial Sequence
<220> FEATURE:
<223> OTHER INFORMATION: synthetic siRNA target or sense strand for Ebola virus virion protein 24 (VP24-775)

<400> SEQUENCE: 33
gcugauugac cagucuuuga u 21

<210> SEQ ID NO 34
<211> LENGTH: 21
<212> TYPE: RNA
<213> ORGANISM: Artificial Sequence
<220> FEATURE:
<223> OTHER INFORMATION: synthetic siRNA antisense strand for Ebola virus virion protein 24 (VP24-775)

<400> SEQUENCE: 34
caaagacugg ucaaucagcu g 21

<210> SEQ ID NO 35
<211> LENGTH: 21
<212> TYPE: RNA
<213> ORGANISM: Artificial Sequence
<220> FEATURE:
<223> OTHER INFORMATION: synthetic siRNA target or sense strand for Ebola virus virion protein 24 (VP24-978)

<400> SEQUENCE: 35
acggauuguu gagcaguauu g 21

<210> SEQ ID NO 36

<211> LENGTH: 21
<212> TYPE: RNA
<213> ORGANISM: Artificial Sequence
<220> FEATURE:
<223> OTHER INFORMATION: synthetic siRNA antisense strand for Ebola virus virion protein 24 (VP24-978)

<400> SEQUENCE: 36
auacugcuca acaauccguu g 21

<210> SEQ ID NO 37
<211> LENGTH: 21
<212> TYPE: RNA
<213> ORGANISM: Artificial Sequence
<220> FEATURE:
<223> OTHER INFORMATION: synthetic siRNA target or sense strand for Ebola virus virion protein 24 (VP24-1160)

<400> SEQUENCE: 37
uccucgacac gaaugcaaag u 21

<210> SEQ ID NO 38
<211> LENGTH: 21
<212> TYPE: RNA
<213> ORGANISM: Artificial Sequence
<220> FEATURE:
<223> OTHER INFORMATION: synthetic siRNA antisense strand for Ebola virus virion protein 24 (VP24-1160)

<400> SEQUENCE: 38
uuugcauucg ugucgaggau c 21

<210> SEQ ID NO 39
<211> LENGTH: 21
<212> TYPE: RNA
<213> ORGANISM: Artificial Sequence
<220> FEATURE:
<223> OTHER INFORMATION: synthetic siRNA target or sense strand for Ebola virus virion protein 24 (VP24-1160-mod)
<220> FEATURE:
<221> NAME/KEY: modified_base
<222> LOCATION: (4)...(14)
<223> OTHER INFORMATION: n = um

<400> SEQUENCE: 39
uccncgacac gaangcaaag u 21

<210> SEQ ID NO 40
<211> LENGTH: 21
<212> TYPE: RNA
<213> ORGANISM: Artificial Sequence
<220> FEATURE:
<223> OTHER INFORMATION: synthetic siRNA antisense strand for Ebola virus virion protein 24 (VP24-1160-mod)
<220> FEATURE:
<221> NAME/KEY: modified_base
<222> LOCATION: (3)...(3)
<223> OTHER INFORMATION: n = um
<220> FEATURE:
<221> NAME/KEY: modified_base
<222> LOCATION: (15)...(18)
<223> OTHER INFORMATION: n = gm

<400> SEQUENCE: 40
uungcauucg ugucnagnau c 21

<210> SEQ ID NO 41
<211> LENGTH: 21
<212> TYPE: RNA

```
<213> ORGANISM: Artificial Sequence
<220> FEATURE:
<223> OTHER INFORMATION: synthetic siRNA target or sense strand for
      Renilla firefly luciferase (Luc)

<400> SEQUENCE: 41

gauuaugucc gguuauguaa a                                               21

<210> SEQ ID NO 42
<211> LENGTH: 21
<212> TYPE: RNA
<213> ORGANISM: Artificial Sequence
<220> FEATURE:
<223> OTHER INFORMATION: synthetic siRNA antisense strand for Renilla
      firefly luciferase (Luc)

<400> SEQUENCE: 42

uacauaaccg gacauaauca u                                               21

<210> SEQ ID NO 43
<211> LENGTH: 21
<212> TYPE: RNA
<213> ORGANISM: Artificial Sequence
<220> FEATURE:
<223> OTHER INFORMATION: synthetic siRNA target or sense strand for
      Ebola virus virion protein 35 (VP35-219)

<400> SEQUENCE: 43

gcgacaucuu cugugauauu g                                               21

<210> SEQ ID NO 44
<211> LENGTH: 21
<212> TYPE: RNA
<213> ORGANISM: Artificial Sequence
<220> FEATURE:
<223> OTHER INFORMATION: synthetic siRNA antisense strand for Ebola
      virus virion protein 35 (VP35-219)

<400> SEQUENCE: 44

auaucacaga agaugucgcu u                                               21

<210> SEQ ID NO 45
<211> LENGTH: 21
<212> TYPE: DNA
<213> ORGANISM: Artificial Sequence
<220> FEATURE:
<223> OTHER INFORMATION: synthetic siRNA target or sense strand for
      Ebola virus virion protein 35 (VP35-349)
<220> FEATURE:
<223> OTHER INFORMATION: Description of Combined DNA/RNA Molecule:
      synthetic siRNA target or sense strand for Ebola virus virion
      protein 35 (VP35-349)

<400> SEQUENCE: 45

ggagguagua caaacauugt t                                               21

<210> SEQ ID NO 46
<211> LENGTH: 21
<212> TYPE: DNA
<213> ORGANISM: Artificial Sequence
<220> FEATURE:
<223> OTHER INFORMATION: synthetic siRNA antisense strand for Ebola
      virus virion protein 35 (VP35-349)
<220> FEATURE:
<223> OTHER INFORMATION: Description of Combined DNA/RNA Molecule:
      synthetic siRNA antisense strand for Ebola virus virion
      protein 35 (VP35-349)

<400> SEQUENCE: 46
```

caauguuugu acuaccucct t 21

<210> SEQ ID NO 47
<211> LENGTH: 21
<212> TYPE: RNA
<213> ORGANISM: Artificial Sequence
<220> FEATURE:
<223> OTHER INFORMATION: synthetic siRNA target or sense strand for Ebola virus virion protein 35 (VP35-687)

<400> SEQUENCE: 47
gggaggcauu caacaaucua g 21

<210> SEQ ID NO 48
<211> LENGTH: 21
<212> TYPE: RNA
<213> ORGANISM: Artificial Sequence
<220> FEATURE:
<223> OTHER INFORMATION: synthetic siRNA antisense strand for Ebola virus virion protein 35 (VP35-687)

<400> SEQUENCE: 48
agauuguuga augccucccu a 21

<210> SEQ ID NO 49
<211> LENGTH: 21
<212> TYPE: RNA
<213> ORGANISM: Artificial Sequence
<220> FEATURE:
<223> OTHER INFORMATION: synthetic siRNA target or sense strand for Ebola virus virion protein 35 (VP35-855)

<400> SEQUENCE: 49
gcaacucauu ggacaucauu c 21

<210> SEQ ID NO 50
<211> LENGTH: 21
<212> TYPE: RNA
<213> ORGANISM: Artificial Sequence
<220> FEATURE:
<223> OTHER INFORMATION: synthetic siRNA antisense strand for Ebola virus virion protein 35 (VP35-855)

<400> SEQUENCE: 50
augaugucca augaguugcu a 21

<210> SEQ ID NO 51
<211> LENGTH: 21
<212> TYPE: RNA
<213> ORGANISM: Artificial Sequence
<220> FEATURE:
<223> OTHER INFORMATION: synthetic siRNA target or sense strand for Renilla firefly luciferase (Luc-mod)
<220> FEATURE:
<221> NAME/KEY: modified_base
<222> LOCATION: (3)...(18)
<223> OTHER INFORMATION: n = um

<400> SEQUENCE: 51
gannangncc ggnnangnaa a 21

<210> SEQ ID NO 52
<211> LENGTH: 21
<212> TYPE: RNA
<213> ORGANISM: Artificial Sequence
<220> FEATURE:
<223> OTHER INFORMATION: synthetic siRNA antisense strand for Renilla firefly luciferase (Luc-mod)
<220> FEATURE:
<221> NAME/KEY: modified_base
<222> LOCATION: (5)...(18)
<223> OTHER INFORMATION: n = um

<400> SEQUENCE: 52
uacanaaccg gacanaanca u 21

<210> SEQ ID NO 53
<211> LENGTH: 21
<212> TYPE: RNA
<213> ORGANISM: Artificial Sequence
<220> FEATURE:
<223> OTHER INFORMATION: synthetic siRNA target or sense strand for Ebola virus polymerase L (L-pol) EK-1

<400> SEQUENCE: 53
guacgaagcu guauauaaau u 21

<210> SEQ ID NO 54
<211> LENGTH: 21
<212> TYPE: RNA
<213> ORGANISM: Artificial Sequence
<220> FEATURE:
<223> OTHER INFORMATION: synthetic siRNA antisense strand for Ebola virus polymerase L (L-pol) EK-1

<400> SEQUENCE: 54
uuuauauaca gcuucguaca a 21

<210> SEQ ID NO 55
<211> LENGTH: 21
<212> TYPE: RNA
<213> ORGANISM: Artificial Sequence
<220> FEATURE:
<223> OTHER INFORMATION: synthetic siRNA target or sense strand for Ebola virus polymerase L (L-pol) EK-1-mod
<220> FEATURE:
<221> NAME/KEY: modified_base
<222> LOCATION: (2)...(2)
<223> OTHER INFORMATION: n = um
<220> FEATURE:
<221> NAME/KEY: modified_base
<222> LOCATION: (11)...(11)
<223> OTHER INFORMATION: n = gm
<220> FEATURE:
<221> NAME/KEY: modified_base
<222> LOCATION: (16)...(16)
<223> OTHER INFORMATION: n = um

<400> SEQUENCE: 55
gnacgaagcu nuauanaaau u 21

<210> SEQ ID NO 56
<211> LENGTH: 21
<212> TYPE: RNA
<213> ORGANISM: Artificial Sequence
<220> FEATURE:
<223> OTHER INFORMATION: synthetic siRNA antisense strand for Ebola virus polymerase L (L-pol) EK-1-mod
<220> FEATURE:
<221> NAME/KEY: modified_base
<222> LOCATION: (5)...(17)
<223> OTHER INFORMATION: n = um

<400> SEQUENCE: 56
uuuanauaca gcuucgnaca a 21

<210> SEQ ID NO 57
<211> LENGTH: 21
<212> TYPE: RNA
<213> ORGANISM: Artificial Sequence
<220> FEATURE:
<223> OTHER INFORMATION: synthetic siRNA target or sense strand for Ebola virus virion protein 35 (VP35-855-mod)
<220> FEATURE:
<221> NAME/KEY: modified_base
<222> LOCATION: (6)...(6)
<223> OTHER INFORMATION: n = um
<220> FEATURE:
<221> NAME/KEY: modified_base
<222> LOCATION: (12)...(12)
<223> OTHER INFORMATION: n = gm
<220> FEATURE:
<221> NAME/KEY: modified_base
<222> LOCATION: (16)...(16)
<223> OTHER INFORMATION: n = um

<400> SEQUENCE: 57
gcaacncauu gnacancauu c 21

<210> SEQ ID NO 58
<211> LENGTH: 21
<212> TYPE: RNA
<213> ORGANISM: Artificial Sequence
<220> FEATURE:
<223> OTHER INFORMATION: synthetic siRNA antisense strand for Ebola virus virion protein 35 (VP35-855-mod)
<220> FEATURE:
<221> NAME/KEY: modified_base
<222> LOCATION: (6)...(15)
<223> OTHER INFORMATION: n = gm
<220> FEATURE:
<221> NAME/KEY: modified_base
<222> LOCATION: (17)...(17)
<223> OTHER INFORMATION: n = um

<400> SEQUENCE: 58
augaunucca auganungcu a 21

<210> SEQ ID NO 59
<211> LENGTH: 19
<212> TYPE: RNA
<213> ORGANISM: Artificial Sequence
<220> FEATURE:
<223> OTHER INFORMATION: synthetic siRNA antisense strand for Ebola virus polymerase L (L-pol)

<400> SEQUENCE: 59
uuuauauaca gcuucguac 19

<210> SEQ ID NO 60
<211> LENGTH: 19
<212> TYPE: RNA
<213> ORGANISM: Artificial Sequence
<220> FEATURE:
<223> OTHER INFORMATION: synthetic siRNA antisense strand for Ebola virus virion protein 24 (VP24)

<400> SEQUENCE: 60
uuugcauucg ugucgagga 19

<210> SEQ ID NO 61
<211> LENGTH: 19
<212> TYPE: RNA
<213> ORGANISM: Artificial Sequence
<220> FEATURE:
<223> OTHER INFORMATION: synthetic siRNA antisense strand for Ebola virus virion protein 35 (VP35)

<400> SEQUENCE: 61
augaugucca augaguugc 19

<210> SEQ ID NO 62
<211> LENGTH: 19
<212> TYPE: RNA
<213> ORGANISM: Artificial Sequence
<220> FEATURE:
<223> OTHER INFORMATION: synthetic first interfering RNA (siRNA) sense strand for Ebola virus polymerase L (L-pol)

<400> SEQUENCE: 62
guacgaagcu guauauaaa 19

<210> SEQ ID NO 63
<211> LENGTH: 19
<212> TYPE: RNA
<213> ORGANISM: Artificial Sequence
<220> FEATURE:
<223> OTHER INFORMATION: synthetic second interfering RNA (siRNA) modified sense strand for Ebola virus virion protein 24 (VP24)
<220> FEATURE:
<221> NAME/KEY: modified_base
<222> LOCATION: (1)...(4)
<223> OTHER INFORMATION: n = um
<220> FEATURE:
<221> NAME/KEY: modified_base
<222> LOCATION: (6)...(11)
<223> OTHER INFORMATION: n = gm
<220> FEATURE:
<221> NAME/KEY: modified_base
<222> LOCATION: (14)...(14)
<223> OTHER INFORMATION: n = um
<220> FEATURE:
<221> NAME/KEY: modified_base
<222> LOCATION: (15)...(15)
<223> OTHER INFORMATION: n = gm

<400> SEQUENCE: 63
nccncnacac naanncaaa 19

<210> SEQ ID NO 64
<211> LENGTH: 19
<212> TYPE: RNA
<213> ORGANISM: Artificial Sequence
<220> FEATURE:
<223> OTHER INFORMATION: synthetic second interfering RNA (siRNA) modified antisense strand for Ebola virus virion protein 24 (VP24)
<220> FEATURE:
<221> NAME/KEY: modified_base
<222> LOCATION: (1)...(3)
<223> OTHER INFORMATION: n = um
<220> FEATURE:
<221> NAME/KEY: modified_base
<222> LOCATION: (4)...(4)
<223> OTHER INFORMATION: n = gm
<220> FEATURE:
<221> NAME/KEY: modified_base
<222> LOCATION: (7)...(8)
<223> OTHER INFORMATION: n = um
<220> FEATURE:
<221> NAME/KEY: modified_base
<222> LOCATION: (10)...(10)
<223> OTHER INFORMATION: n = gm
<220> FEATURE:
<221> NAME/KEY: modified_base
<222> LOCATION: (11)...(11)
<223> OTHER INFORMATION: n = um
<220> FEATURE:
<221> NAME/KEY: modified_base
<222> LOCATION: (12)...(12)
<223> OTHER INFORMATION: n = gm
<220> FEATURE:
<221> NAME/KEY: modified_base
<222> LOCATION: (13)...(13)
<223> OTHER INFORMATION: n = um
<220> FEATURE:
<221> NAME/KEY: modified_base
<222> LOCATION: (15)...(18)
<223> OTHER INFORMATION: n = gm

<400> SEQUENCE: 64
nnnncanncn nnncnanna 19

<210> SEQ ID NO 65
<211> LENGTH: 19
<212> TYPE: RNA
<213> ORGANISM: Artificial Sequence
<220> FEATURE:
<223> OTHER INFORMATION: synthetic second interfering RNA (siRNA) antisense strand for Ebola virus virion protein 24 (VP24)
<220> FEATURE:
<221> NAME/KEY: modified_base
<222> LOCATION: (3)...(3)
<223> OTHER INFORMATION: n = um
<220> FEATURE:
<221> NAME/KEY: modified_base
<222> LOCATION: (15)...(18)
<223> OTHER INFORMATION: n = gm

<400> SEQUENCE: 65
uungcauucg ugucnagna 19

<210> SEQ ID NO 66
<211> LENGTH: 19
<212> TYPE: RNA
<213> ORGANISM: Artificial Sequence
<220> FEATURE:
<223> OTHER INFORMATION: synthetic second interfering RNA (siRNA) antisense strand for Ebola virus virion protein 24 (VP24)

<400> SEQUENCE: 66
uuugcauucg ugucgagga 19

<210> SEQ ID NO 67
<211> LENGTH: 21
<212> TYPE: RNA
<213> ORGANISM: Artificial Sequence
<220> FEATURE:
<223> OTHER INFORMATION: synthetic second interfering RNA (siRNA) sense strand for Ebola virus virion protein 24 (VP24)

<400> SEQUENCE: 67
uccucgacac gaaugcaaag u 21

<210> SEQ ID NO 68
<211> LENGTH: 21
<212> TYPE: RNA
<213> ORGANISM: Artificial Sequence
<220> FEATURE:
<223> OTHER INFORMATION: synthetic second interfering RNA (siRNA) sense strand for Ebola virus virion protein 24 (VP24-1160 mod)
<220> FEATURE:
<221> NAME/KEY: modified_base
<222> LOCATION: (4)...(14)
<223> OTHER INFORMATION: n = um

<400> SEQUENCE: 68
uccncgacac gaangcaaag u 21

<210> SEQ ID NO 69
<211> LENGTH: 19
<212> TYPE: RNA
<213> ORGANISM: Artificial Sequence
<220> FEATURE:
<223> OTHER INFORMATION: synthetic third interfering RNA (siRNA) sense strand for Ebola virus virion protein 35 (VP35)

<400> SEQUENCE: 69
gcaacucauu ggacaucau 19

<210> SEQ ID NO 70
<211> LENGTH: 19
<212> TYPE: RNA
<213> ORGANISM: Artificial Sequence
<220> FEATURE:
<223> OTHER INFORMATION: synthetic third interfering RNA (siRNA) antisense strand for Ebola virus virion protein 35 (VP35)

<400> SEQUENCE: 70
augaugucca augaguugc 19

<210> SEQ ID NO 71
<211> LENGTH: 19
<212> TYPE: RNA
<213> ORGANISM: Artificial Sequence
<220> FEATURE:
<223> OTHER INFORMATION: synthetic third interfering RNA (siRNA) sense strand for Ebola virus virion protein 35 (VP35)

<400> SEQUENCE: 71
gcaacucauu ggacaucau 19

<210> SEQ ID NO 72
<211> LENGTH: 19
<212> TYPE: DNA
<213> ORGANISM: Artificial Sequence
<220> FEATURE:
<223> OTHER INFORMATION: synthetic quantitative real-time PCR (RT-PCR) forward primer for Zaire species of Ebola virus (ZEBOV) glycoprotein gene

<400> SEQUENCE: 72
cggacctggt ttggttgtg 19

<210> SEQ ID NO 73
<211> LENGTH: 19
<212> TYPE: DNA
<213> ORGANISM: Artificial Sequence
<220> FEATURE:
<223> OTHER INFORMATION: synthetic quantitative real-time PCR (RT-PCR) reverse primer for Zaire species of Ebola virus (ZEBOV) glycoprotein gene

<400> SEQUENCE: 73
gctgcagtgt cgcatctga 19

<210> SEQ ID NO 74
<211> LENGTH: 15
<212> TYPE: DNA
<213> ORGANISM: Artificial Sequence
<220> FEATURE:
<223> OTHER INFORMATION: synthetic quantitative real-time PCR (RT-PCR) TaqMan probe for Zaire species of Ebola virus (ZEBOV) glycoprotein gene
<220> FEATURE:
<221> NAME/KEY: modified_base
<222> LOCATION: (1)...(1)
<223> OTHER INFORMATION: c modified by 6-carboxy fluorescein
<220> FEATURE:
<221> NAME/KEY: modified_base
<222> LOCATION: (15)...(15)
<223> OTHER INFORMATION: t modified by minor groove binder nonfluorescent quencher

<400> SEQUENCE: 74
cccttgccac aatct 15

<210> SEQ ID NO 75
<211> LENGTH: 44
<212> TYPE: RNA
<213> ORGANISM: Artificial Sequence
<220> FEATURE:
<223> OTHER INFORMATION: synthetic GeneRacer RNA oligo adaptor

<400> SEQUENCE: 75
cgacuggagc acgaggacac ugacauggac ugaaggagua gaaa 44

<210> SEQ ID NO 76
<211> LENGTH: 23
<212> TYPE: DNA
<213> ORGANISM: Artificial Sequence
<220> FEATURE:
<223> OTHER INFORMATION: synthetic Ebola virus polymerase L (L-pol) gene-specific primer EK-1 GSP

<400> SEQUENCE: 76
tttgtgattc gtccttttgc agt 23

<210> SEQ ID NO 77
<211> LENGTH: 25
<212> TYPE: DNA
<213> ORGANISM: Artificial Sequence
<220> FEATURE:
<223> OTHER INFORMATION: synthetic Ebola virus virion protein 24 (VP24) gene-specific primer VP24-1160 GSP

<400> SEQUENCE: 77
agcaattcta tgatgttgtc ttgga 25

<210> SEQ ID NO 78
<211> LENGTH: 24
<212> TYPE: DNA
<213> ORGANISM: Artificial Sequence
<220> FEATURE:
<223> OTHER INFORMATION: synthetic Ebola virus virion protein 35 (VP35) gene-specific primer VP35-855 GSP

<400> SEQUENCE: 78
catcactttt ggtttgggtt actt 24

<210> SEQ ID NO 79
<211> LENGTH: 23
<212> TYPE: DNA
<213> ORGANISM: Artificial Sequence
<220> FEATURE:
<223> OTHER INFORMATION: synthetic RNA adaptor GR5

<400> SEQUENCE: 79
cgactggagc acgaggacac tga 23

<210> SEQ ID NO 80
<211> LENGTH: 24
<212> TYPE: DNA

<213> ORGANISM: Artificial Sequence
<220> FEATURE:
<223> OTHER INFORMATION: synthetic PCR primer EK-1 Rev2 for Ebola virus polymerase L (L-pol)

<400> SEQUENCE: 80
tgagatggtt ttggtgtggc atct 24

<210> SEQ ID NO 81
<211> LENGTH: 25
<212> TYPE: DNA
<213> ORGANISM: Artificial Sequence
<220> FEATURE:
<223> OTHER INFORMATION: synthetic PCR primer VP24-1160 Rev2 for Ebola virus virion protein 24 (VP24)

<400> SEQUENCE: 81
cctggttttt gtaagggtgt caact 25

<210> SEQ ID NO 82
<211> LENGTH: 23
<212> TYPE: DNA
<213> ORGANISM: Artificial Sequence
<220> FEATURE:
<223> OTHER INFORMATION: synthetic PCR primer VP35-855 Rev2 for Ebola virus virion protein 35 (VP35)

<400> SEQUENCE: 82
tttctggcaa gctcggggaa tgt 23

<210> SEQ ID NO 83
<211> LENGTH: 18
<212> TYPE: DNA
<213> ORGANISM: Artificial Sequence
<220> FEATURE:
<223> OTHER INFORMATION: synthetic sequencing primer from within GeneRacer GR5 sequence

<400> SEQUENCE: 83
actggagcac gaggacac 18

<210> SEQ ID NO 84
<211> LENGTH: 20
<212> TYPE: DNA
<213> ORGANISM: Artificial Sequence
<220> FEATURE:
<223> OTHER INFORMATION: synthetic EK-1 3'seq primer

<400> SEQUENCE: 84
agccataaca taccctcagt 20

<210> SEQ ID NO 85
<211> LENGTH: 20
<212> TYPE: DNA
<213> ORGANISM: Artificial Sequence
<220> FEATURE:
<223> OTHER INFORMATION: synthetic VP24-1160 3'seq primer

<400> SEQUENCE: 85
atgaaagcag agatgtcaag 20

<210> SEQ ID NO 86
<211> LENGTH: 19
<212> TYPE: DNA
<213> ORGANISM: Artificial Sequence
<220> FEATURE:
<223> OTHER INFORMATION: synthetic VP35-855 3'seq primer -continued

<400> SEQUENCE: 86
attagggcac attgaggag 19